(12) United States Patent
McKim

(10) Patent No.: US 7,615,361 B2
(45) Date of Patent: *Nov. 10, 2009

(54) TOXICITY SCREENING METHODS

(75) Inventor: James M. McKim, Kalamazoo, MI (US)

(73) Assignee: Ceetox, Inc., Kalamazoo, MI (US)

( * ) Notice: Subject to any disclaimer, the term of this patent is extended or adjusted under 35 U.S.C. 154(b) by 74 days.

This patent is subject to a terminal disclaimer.

(21) Appl. No.: 11/714,526

(22) Filed: Mar. 6, 2007

(65) Prior Publication Data

US 2007/0218457 A1 Sep. 20, 2007

Related U.S. Application Data

(60) Provisional application No. 60/743,599, filed on Mar. 21, 2006, provisional application No. 60/779,660, filed on Mar. 6, 2006.

(51) Int. Cl.
*C12Q 1/02* (2006.01)
*C12Q 1/00* (2006.01)

(52) U.S. Cl. .......................................... 435/29

(58) Field of Classification Search ........................ None
See application file for complete search history.

(56) References Cited

U.S. PATENT DOCUMENTS 4,882,270 A 11/1989 Moroz
6,998,249 B1 2/2006 McKim et al.

FOREIGN PATENT DOCUMENTS

| DK | 171085 | 12/1995 |
|----|--------|---------|
| GB | 2271772 | 4/1994 |
| WO | WO 95/32184 | 11/1995 |
| WO | WO 95/35278 | 12/1995 |
| WO | WO 97/49653 | 12/1997 |

OTHER PUBLICATIONS

Renwick et al.; Regulatory and Pharmacology 18:463-480 (1993).
Eisenbrandt et al.; Fd. Chem. Toxic. 32(7): 655-669 (1994).
Generaly & Applied Toxicology, vol. 1, Stockton Press, New York, 1993, pp. 11-20.
Fricker; Toxic. In Vitro 8(4): 879-881 (1994).
Yao et al.; Toxicology Methods 2(3): 199-218 (1992) Abstract.
Chung et al.; Chonnam J Med Sci 1(2): 128-138 (1988) Abstract.
Morrison et al.; Biomaterials 16(13): 987-992 (Sep 1995) Abstract.
Garza-Ocanas et al.; Toxicology 73(2): 191-201 (1992) Abstract.
Conners et al.; (Biochem Pharmacol 24:2217-24), 1975.
Burkhardt, John E. et al.; "Commentary: A View on Discovery Pathology," *Toxicologic Pathology*, 27(4):472-473 (1999).
Car, B.D. et al.; "Commentary: Discovery Toxicology—A Nascent Science," *Toxicologic Pathology*, 27(4):481-483 (1999).
Cockerell, Gary L. et al.; "Focua On: Discovery Pathology," *Toxicologic Pathology*, 27(4):471 (1999).
Cockerell, G.L. et al.; "Commentary: Redesigning the Preclinical Paradigm: The Role of Pathology and Toxicology in Supporting Discovery Research," *Toxicologic Pathology*, 27(4):477-478 (1999).
Denizot, F. et al.; "Rapid colorimetric assay for cell growth and survival Modifications to the tetrazolium dye procedure giving improved sensitivity and reliability," *J. Immunol. Methods*, 89:271-277 (1986).
Drug Discovery Using Combichem's Drug Discovery Engine©; htp://www.combichem.com/Publication/Papers/Discovery.htm, pp. 1-6 (1997).
Essig—Marcello, J. et al.; "A Double—Label *in Situ* Cytotoxicity Assay Using the Fluorescent Probes Neutral Red and BCECF- AM," In vitro *toxicol*, 3(3):219-532 (1986).
Feinfield, D.A. et al.; "Urinary Glutathione—S—Transferase in Cisplatin Nephrotoxicity in the Rat," *J Clin Chem Clin Biochem.* 24:529-532 (1986).
Goegan, P. et al.; "Effects of Serum Protein and Colloid on the AlamarBlue Assay in Cell Cultures," *Toxicol.* In Vitro 9(3):257-266 (1995).
Harleman, J.H.; "Commentary Contribution of Pathology to Drug Research and Development in the Next Decade," *Toxicologic Pathology*, 27(4):479-480 (1999).
Kangas, L. et al.; "Bioluminescence of Cellular ATP: A New Method for Evaluating Cytotoxic Agents In Vitro," *Med Biol*, 62:338-343 (1984).
Lowik, C.W.G.M. et al.; "Quantification of Adherent and Nonadherent Cells Cultured in 96-Well Plates Using the Supravital Stain Neutral Red," *Anal. Biochem.* 213:426-433 (1993).
Mossman, T.; "Rapid Colorimeric Assay for Cellular Growth and Survival: Application to Proliferation and Cytotoxicity Assays," *J. Immunol. Methods*, 65:55-63 (1983).
Myers, P.L.; "Re-engineering Of The Drug Discovery Process, Utilizing A Unique Combination Of Library Design And Parallel Synthesis," http://combichem.com/Publication/Papers/reengineering.htm pp. 1-4 (1997).
Oberly, T. et al.; "Effects of Lead Administration on Developing Rat Kidney II. Functional, Morphologic, and Immunohistochemical Studies," *Toxicol. Appl. Pharmacol.* 131:94-107 (1995).

*Primary Examiner*—Vera Afremova
(74) *Attorney, Agent, or Firm*—Dunlap Codding, P.C.

(57) ABSTRACT

The present invention provides methods of determining a level of toxicity of a given compound based on in vitro assays. The present invention provides particular methods of determining organ-specific toxicity and species-specific toxicity of a given compound based on in vitro assays. In addition, the present invention provides methods of determining a level of toxicity in normal tissue for an anti-tumor compound. The methods include providing at least one cell type and culturing the cell type in the presence of at least one concentration of the chemical compound, measuring at least one indicator of cell health at the at least one concentration of compound for the at least one cell type, and performing a concentration response analysis, from which a toxic concentration can be determined.

14 Claims, 104 Drawing Sheets

FIGURE 3
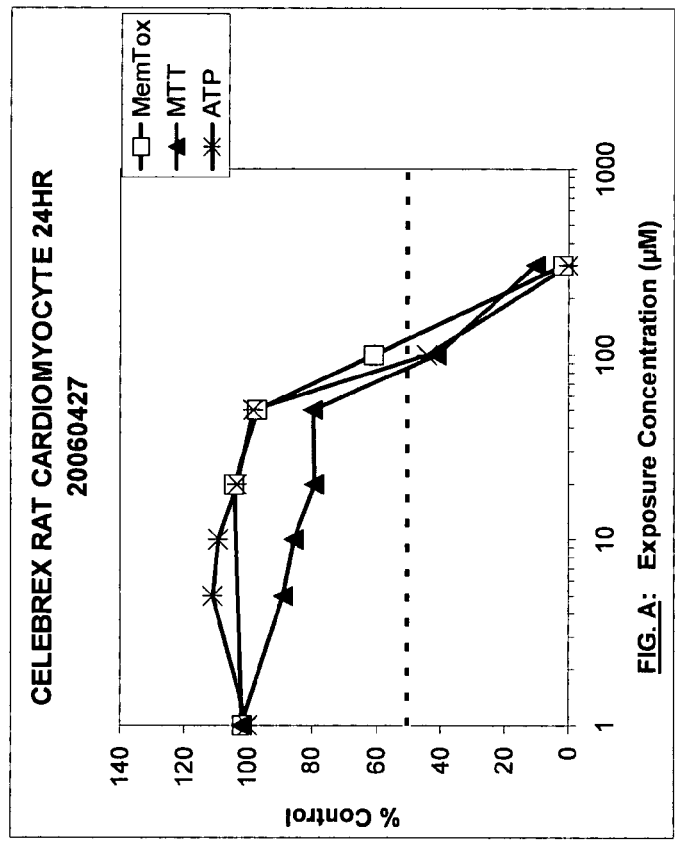
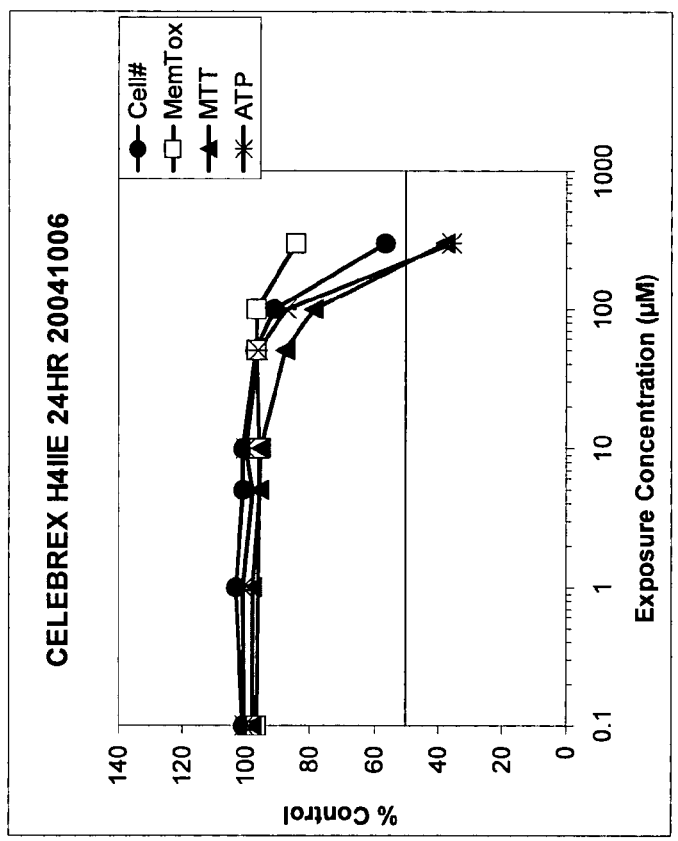
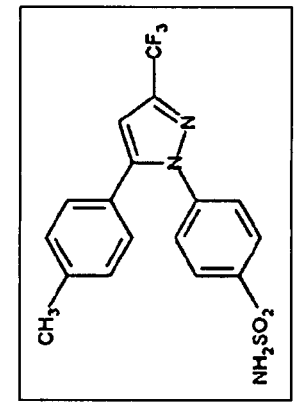

FIGURE 9
METHOTREXATE
H4IIE
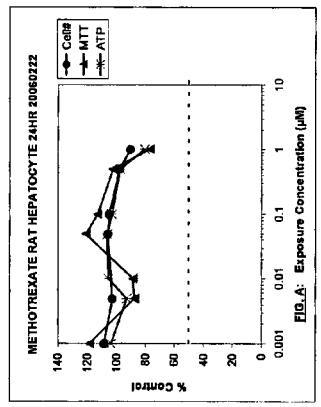
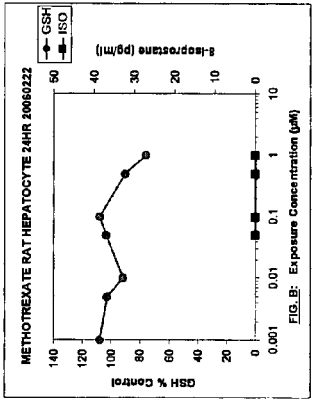
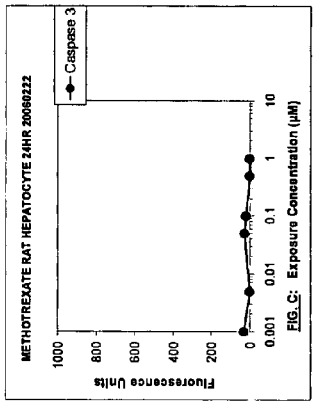
NRK
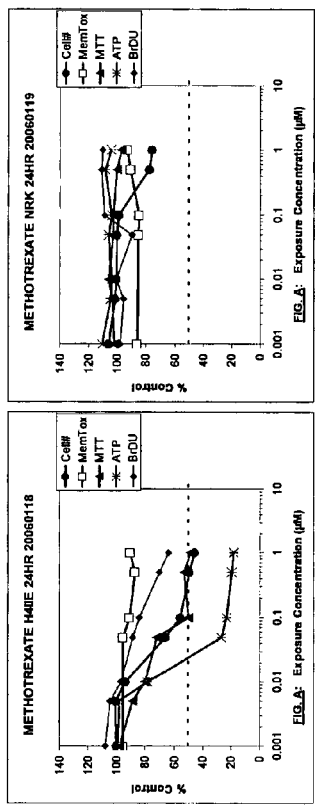
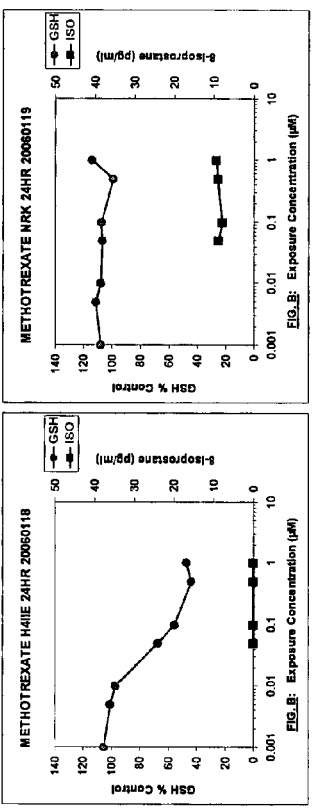
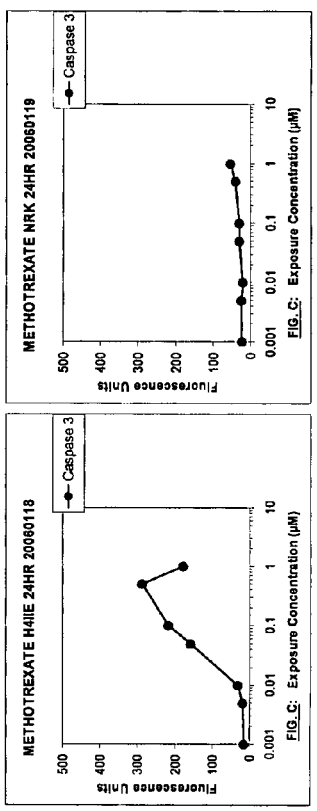
RAT PRIMARY

FIGURE 10
DOXORUBICIN (ADRIAMYCIN)
RAT PRIMARY
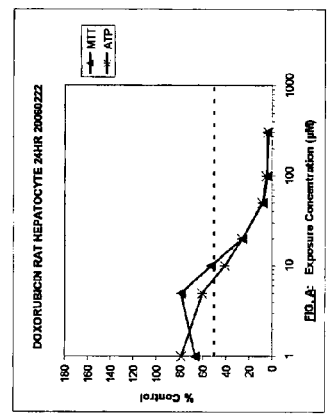
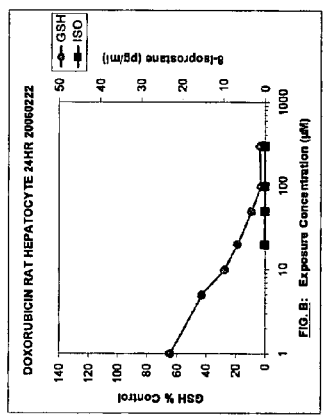
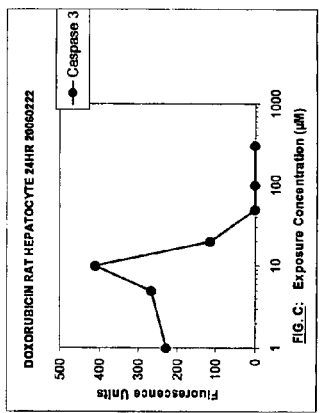
NRK
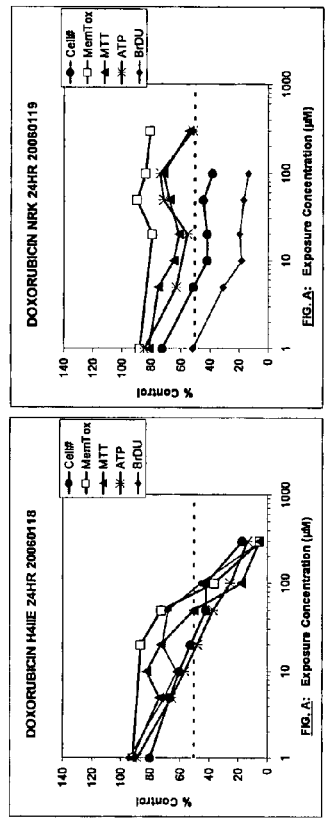
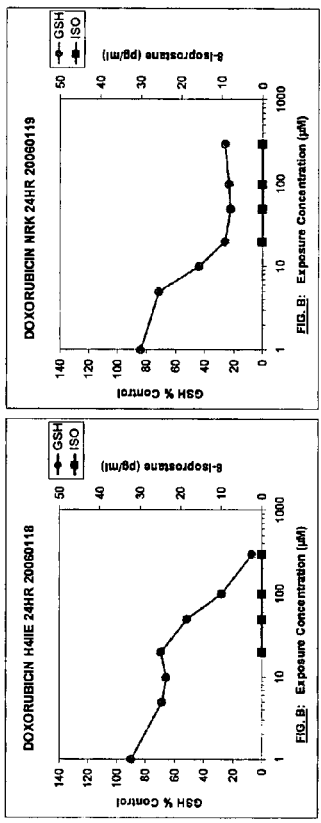
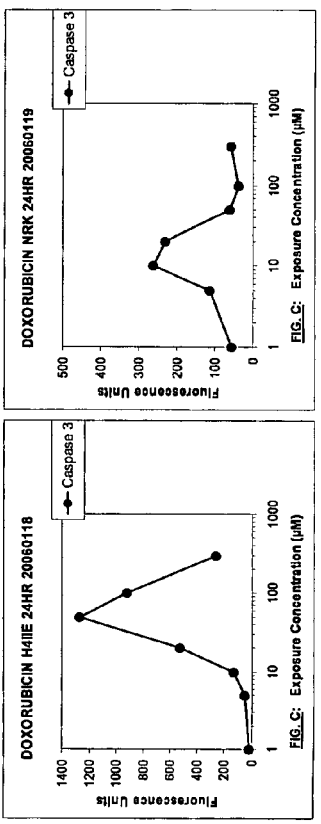
H4IIE

FIGURE 11
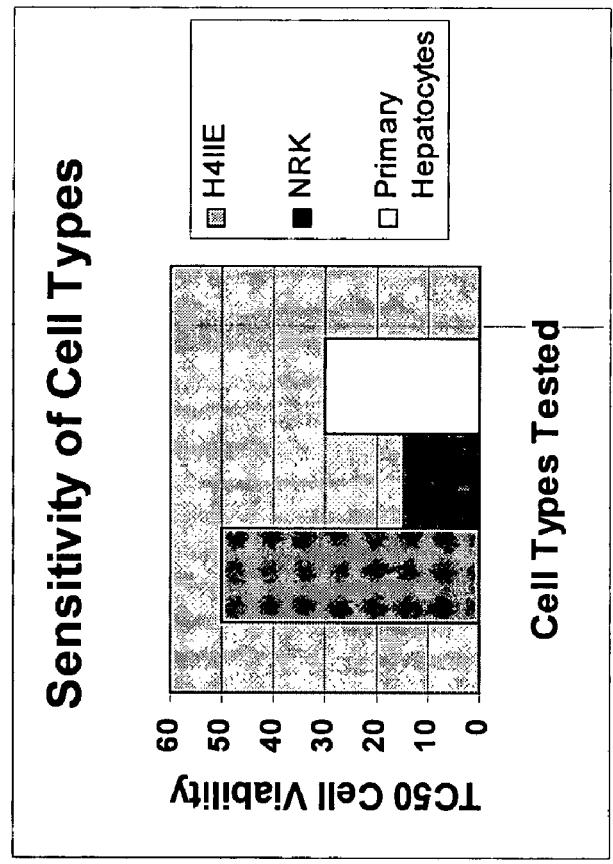
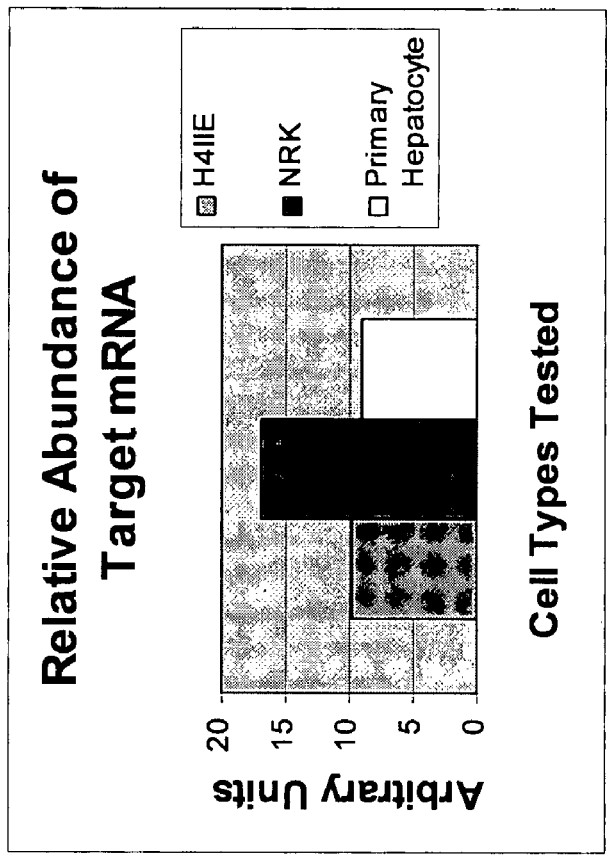

METABOLIC STABILITY ASSAY

CLIENT Compound A RAT CARDIOMYOCYTE (CM) 1HR

FIGURE 17
CLIENT Compound A RAT CARDIOMYOCYTE (CM) 3HR
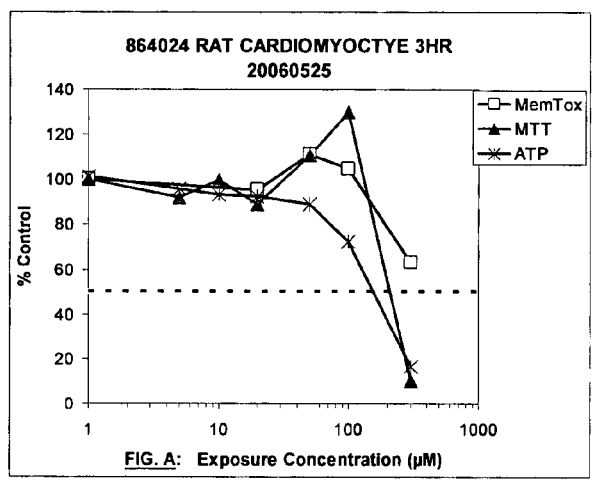
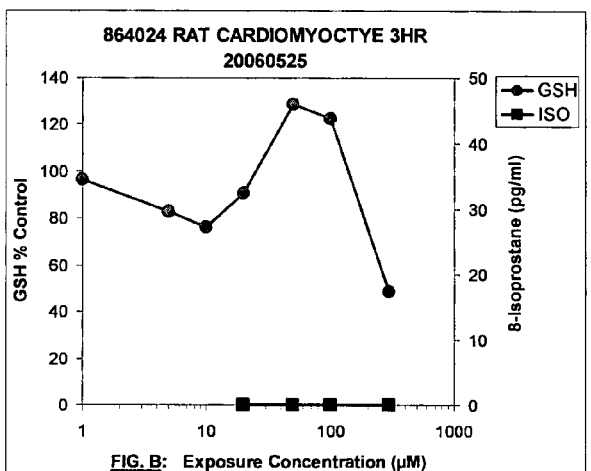
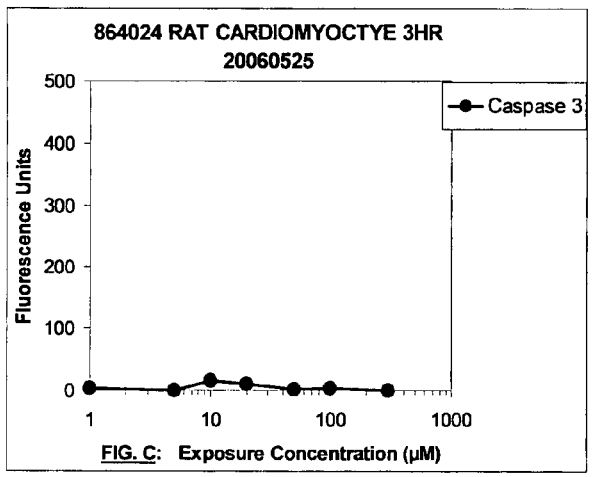
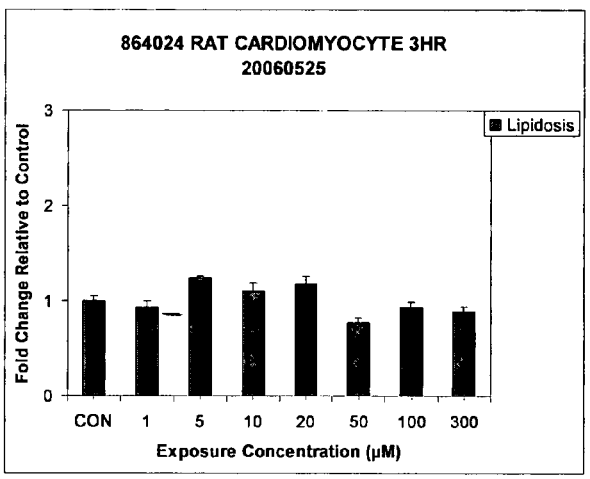

CLIENT Compound A RAT CARDIOMYOCYTE (CM) 6HR

CLIENT Compound A RAT CARDIOMYOCYTE (CM) 24HR

ADRIAMYCIN RAT CARDIOMYOCYTE (CM) 1HR

ADRIAMYCIN RAT CARDIOMYOCYTE (CM) 3HR

ADRIAMYCIN RAT CARDIOMYOCYTE (CM) 6HR

ADRIAMYCIN RAT CARDIOMYOCYTE (CM) 24HR

CLIENT Compound A DCFDA RAT CARDIOMYOCYTE (CM) TIME COURSE

ADRIAMYCIN DCFDA RAT CARDIOMYOCYTE (CM) TIME COURSE

FIGURE 25A: <u>CLIENT Compound A</u> ANP (bDNA) RAT CARDIOMYOCYTE (CM) TIME COURSE
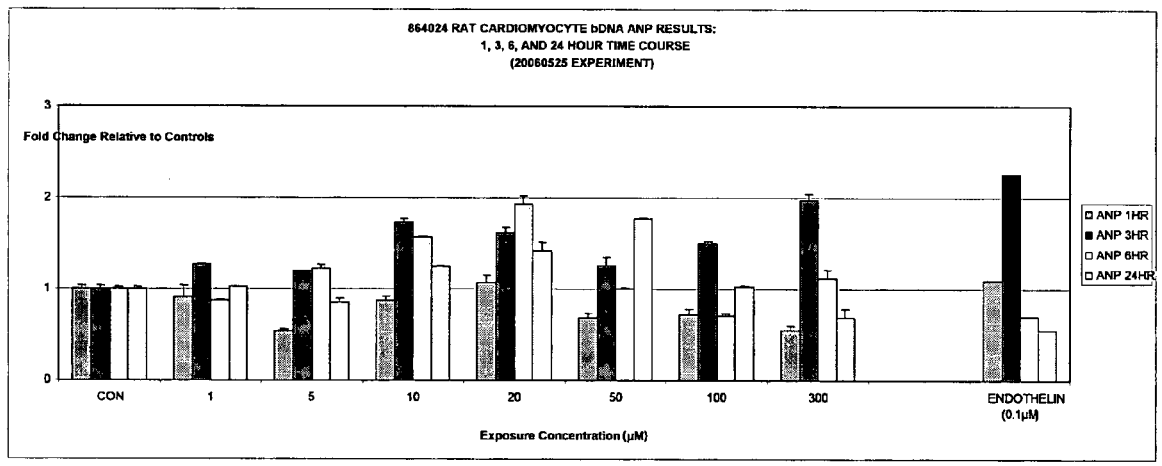
FIGURE 25B: <u>CLIENT Compound A</u> BNP (bDNA) RAT CARDIOMYOCYTE (CM) TIME COURSE
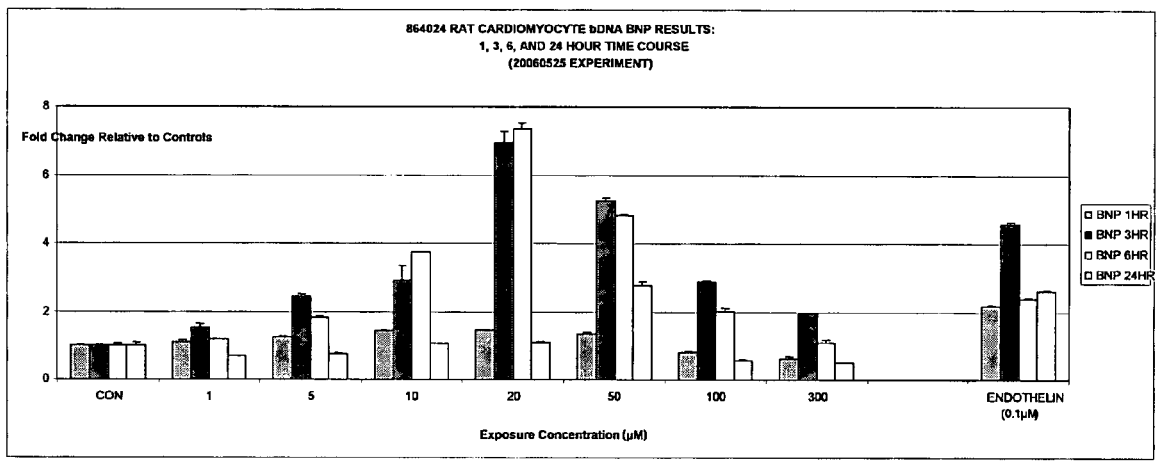
FIGURE 25C: <u>CLIENT Compound A</u> p53 (bDNA) RAT CARDIOMYOCYTE (CM) TIME COURSE
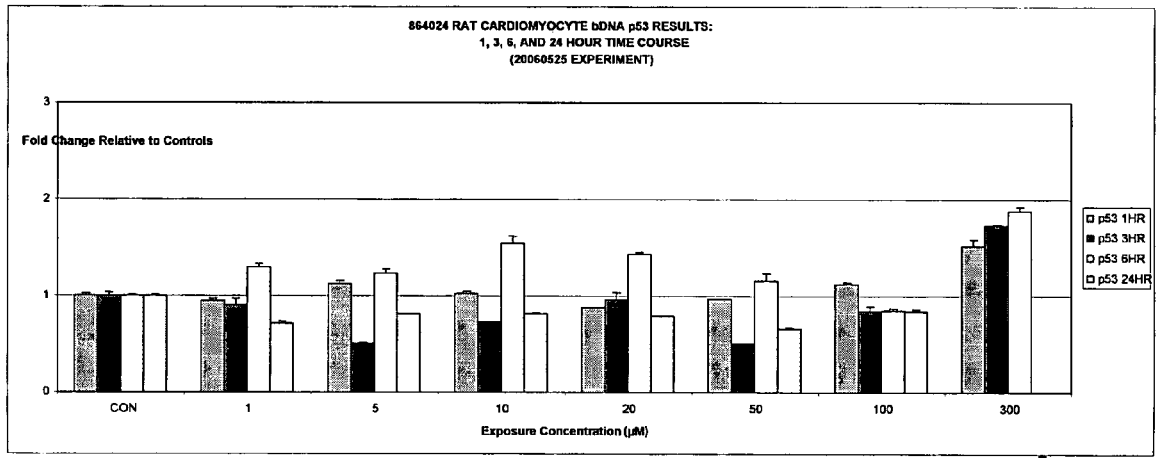

Figure 26A: Client Compound A BAX (bDNA) RAT CARDIOMYOCYTE (CM) TIME COURSE
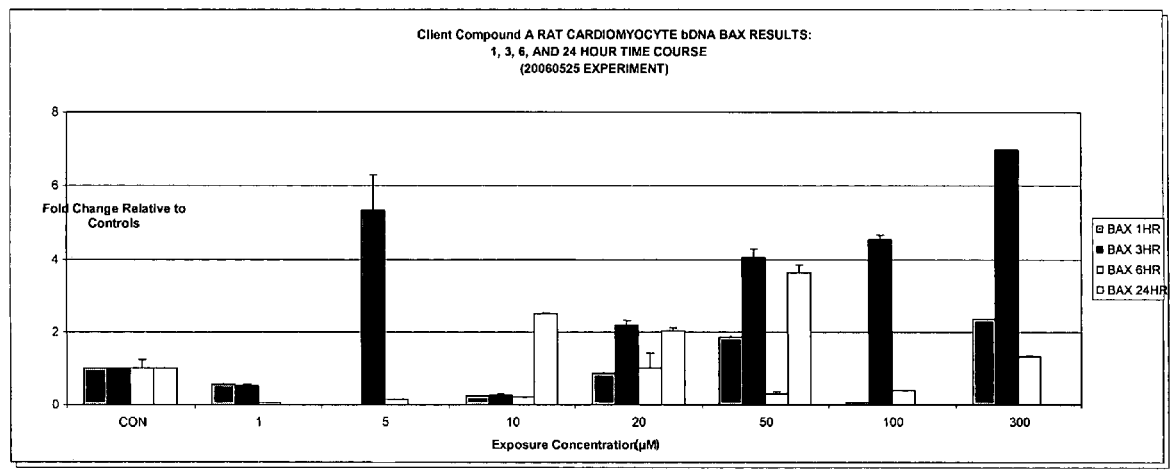
Figure 26B: Client Compound A Bcl2 (bDNA) RAT CARDIOMYOCYTE (CM) TIME COURSE
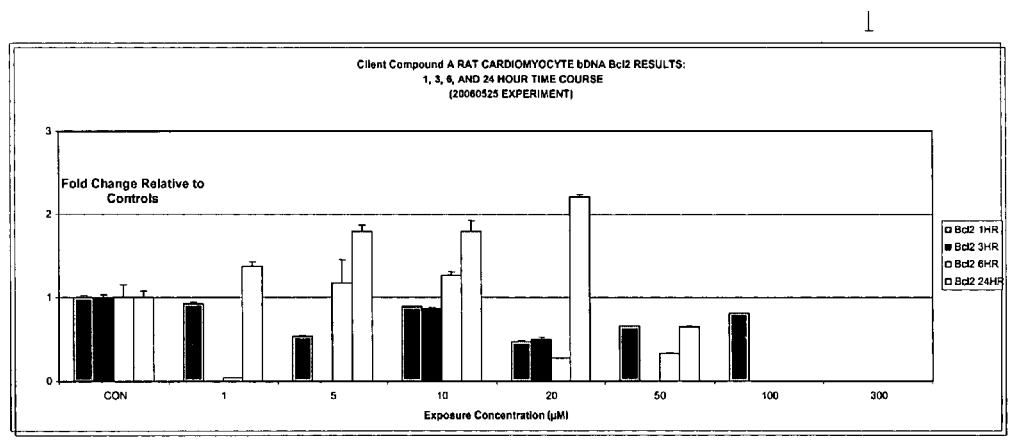

FIGURE 26C: CLIENT Compound A iNOS (bDNA) RAT CARDIOMYOCYTE (CM) TIME COURSE
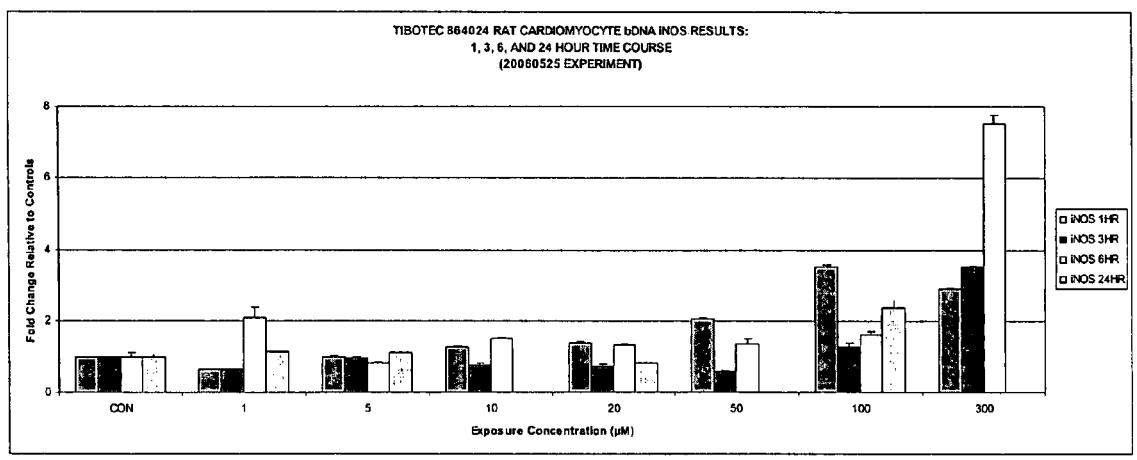

Figure 27A: ADRIAMYCIN ANP (bDNA) RAT CARDIOMYOCYTE (CM) TIME COURSE
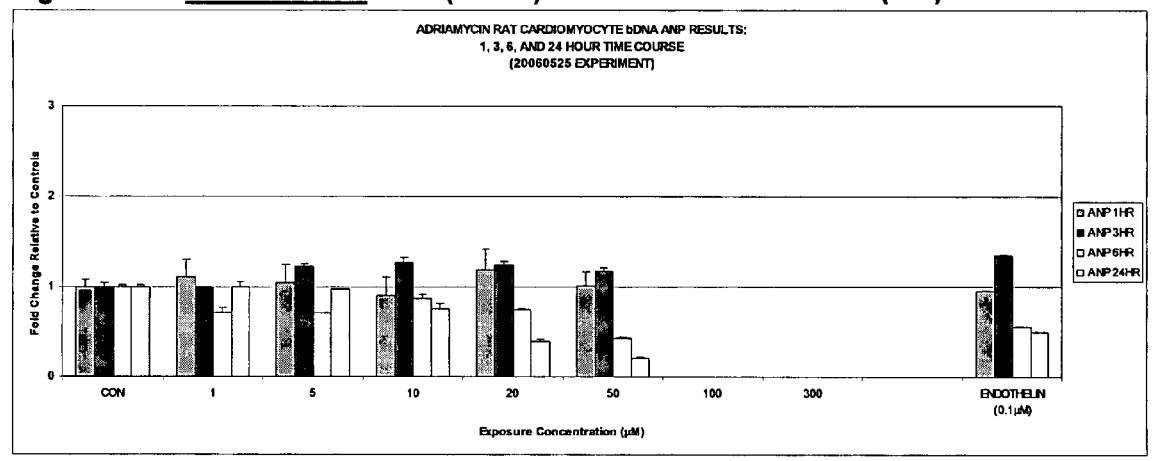
Figure 27B: ADRIAMYCIN BNP (bDNA) RAT CARDIOMYOCYTE (CM) TIME COURSE
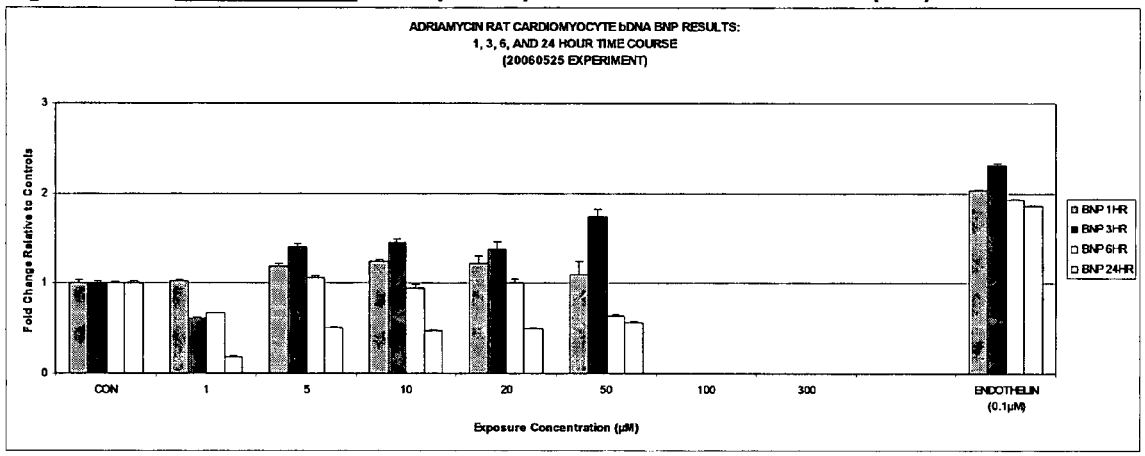
Figure 27C: ADRIAMYCIN iNOS (bDNA) RAT CARDIOMYOCYTE (CM) TIME COURSE
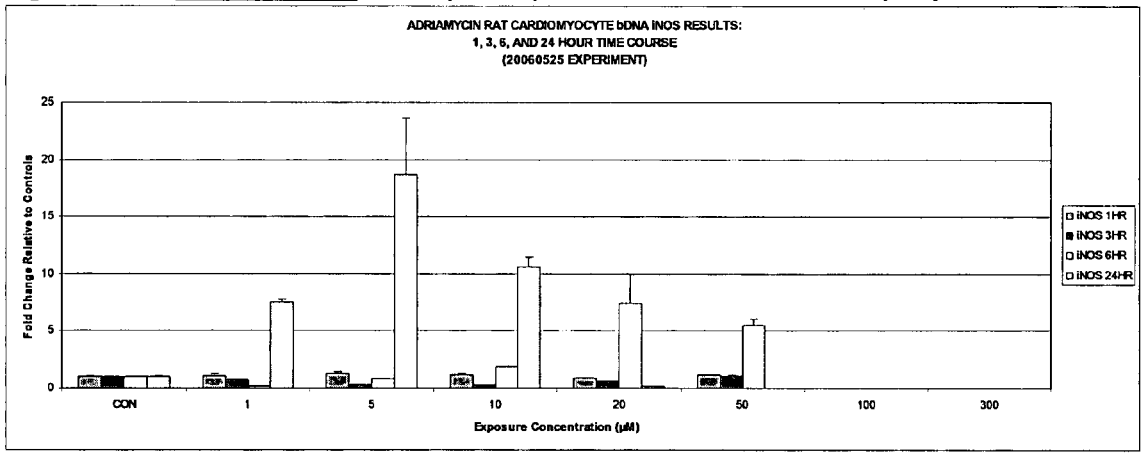

Figure 28A: ADRIAMYCIN BAX (bDNA) RAT CARDIOMYOCYTE (CM) TIME COURSE
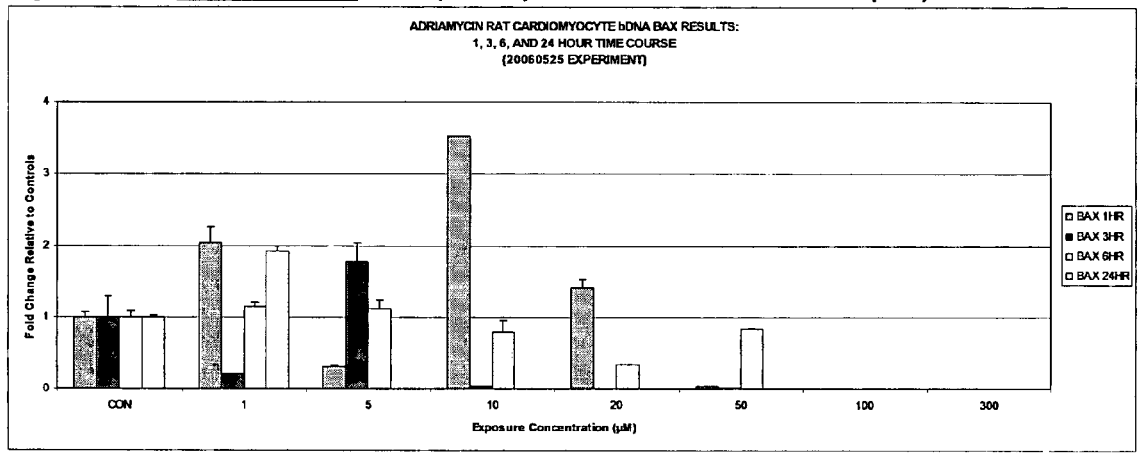
Figure 28B: ADRIAMYCIN Bcl2 (bDNA) RAT CARDIOMYOCYTE (CM) TIME COURSE
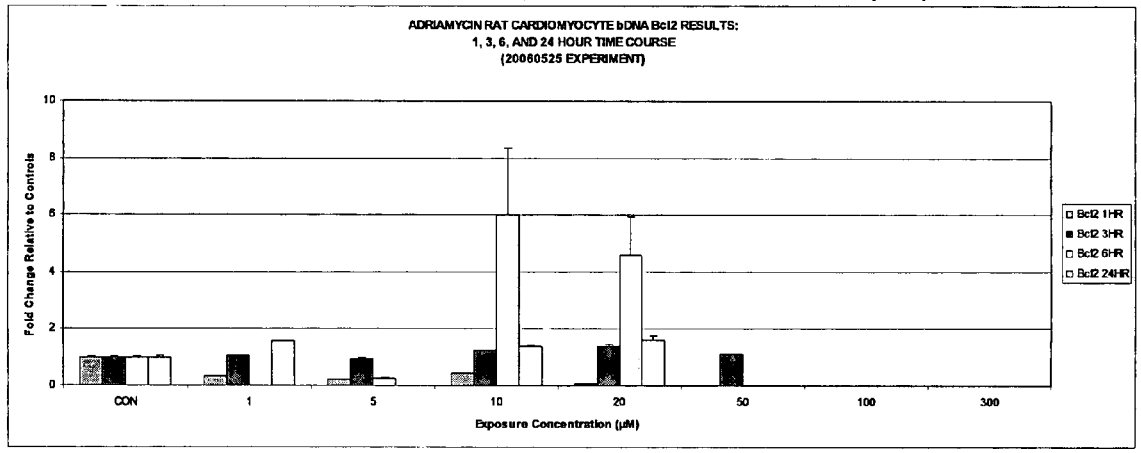
Figure 28C: ADRIAMYCIN p53 (bDNA) RAT CARDIOMYOCYTE (CM) TIME COURSE
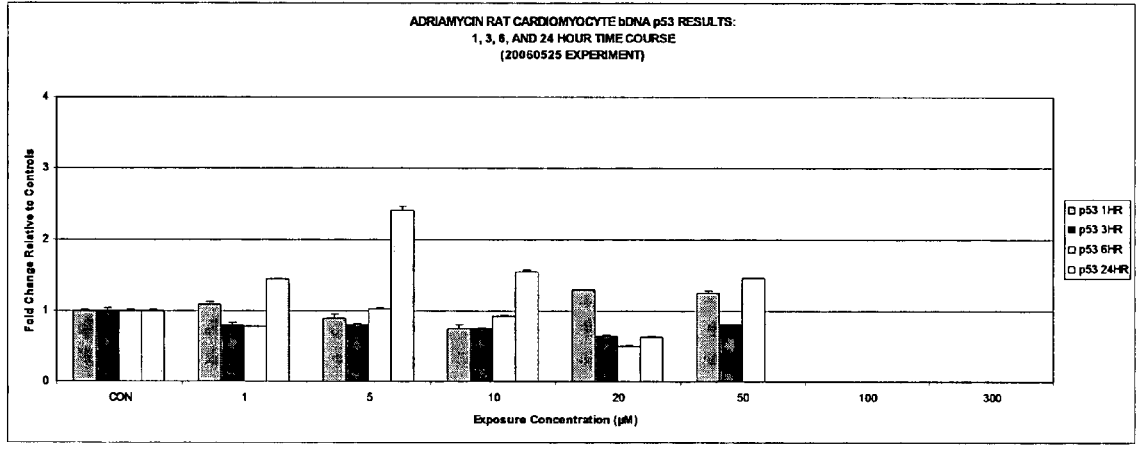

Figure 29: CLIENT Compound A H4IIE 24HR
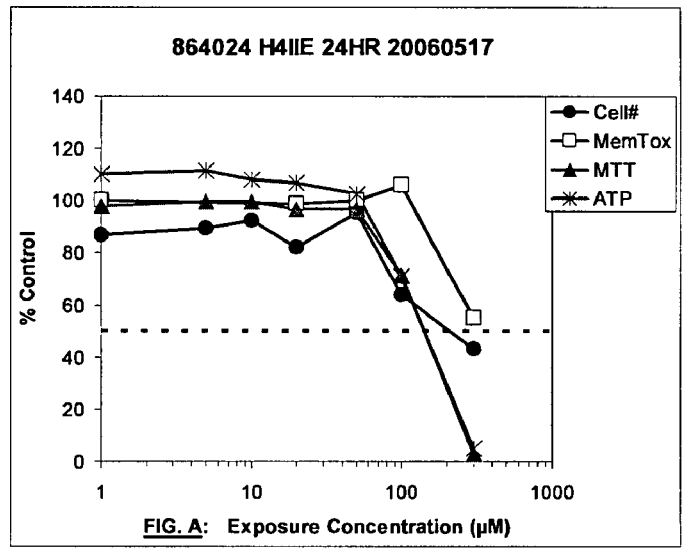
FIG. A: Exposure Concentration (µM)
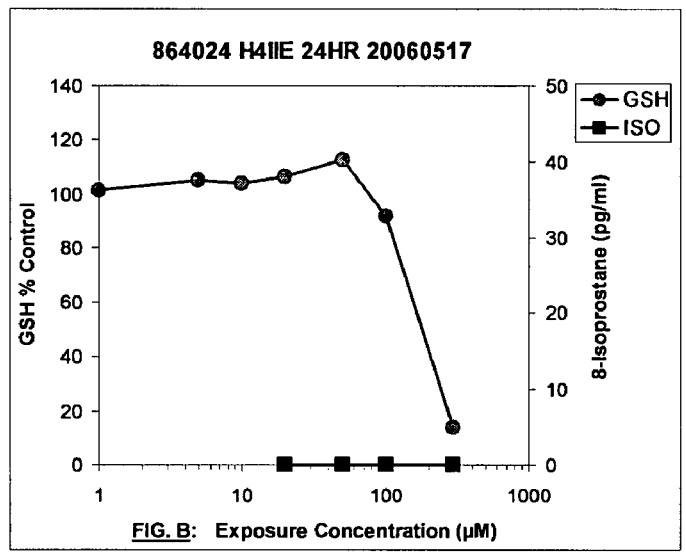
FIG. B: Exposure Concentration (µM)
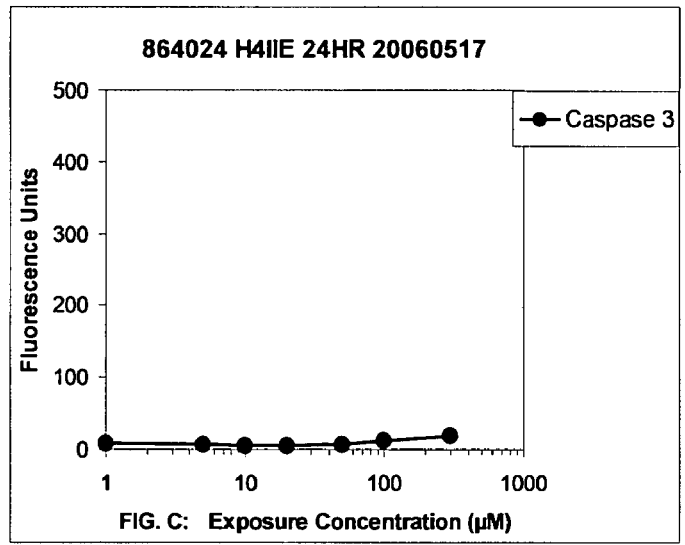
FIG. C: Exposure Concentration (µM)

Figure 30: ADRIAMYCIN H4IIE 24HR
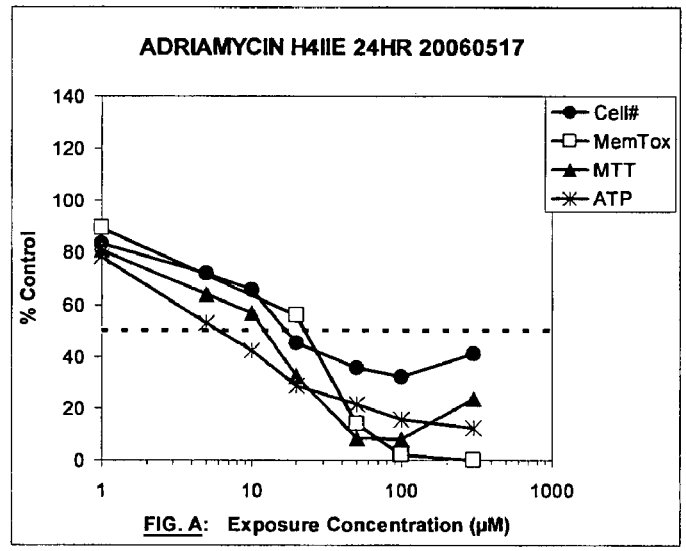
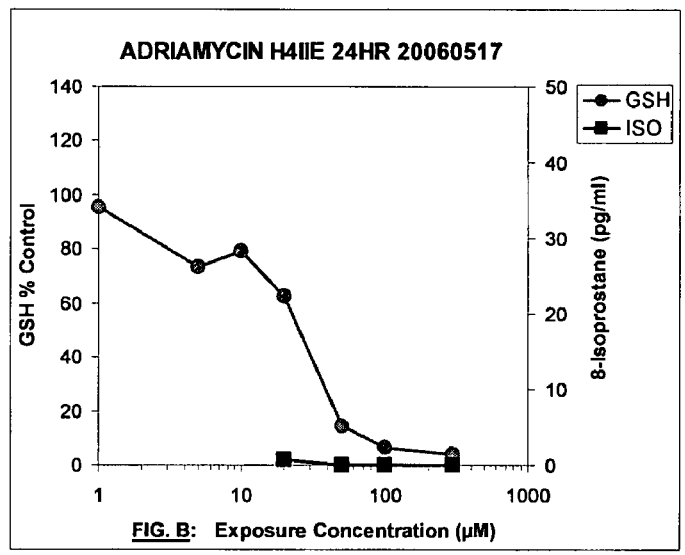
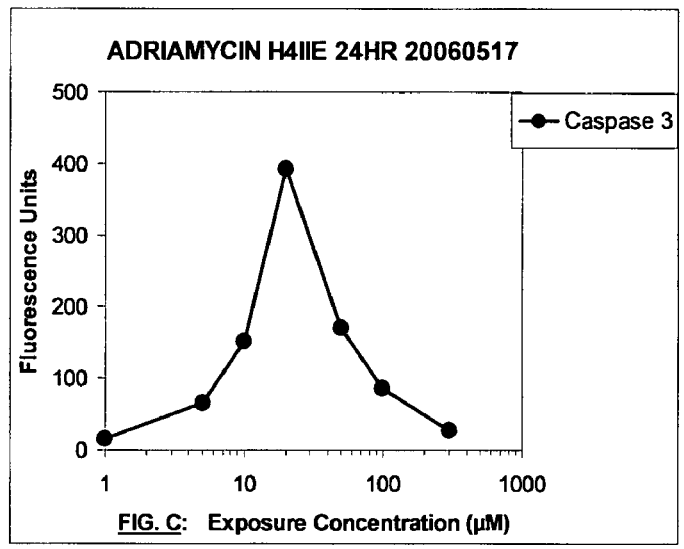

Figure 31: IDARUBICIN RAT CARDIOMYOCYTE (CM) 24HR
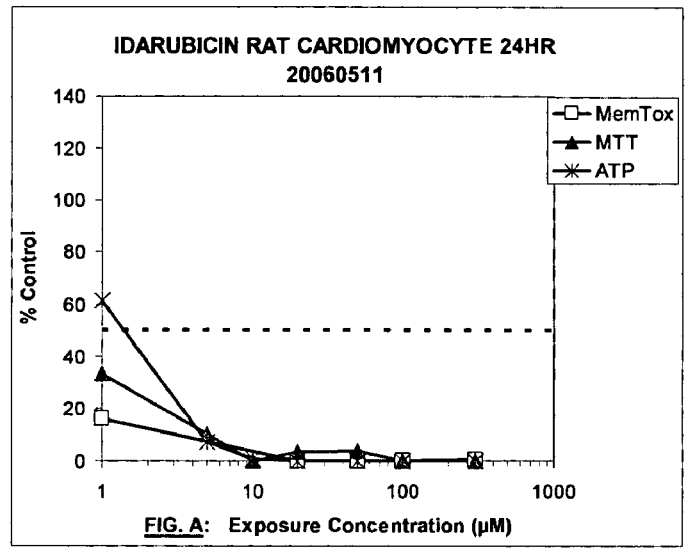
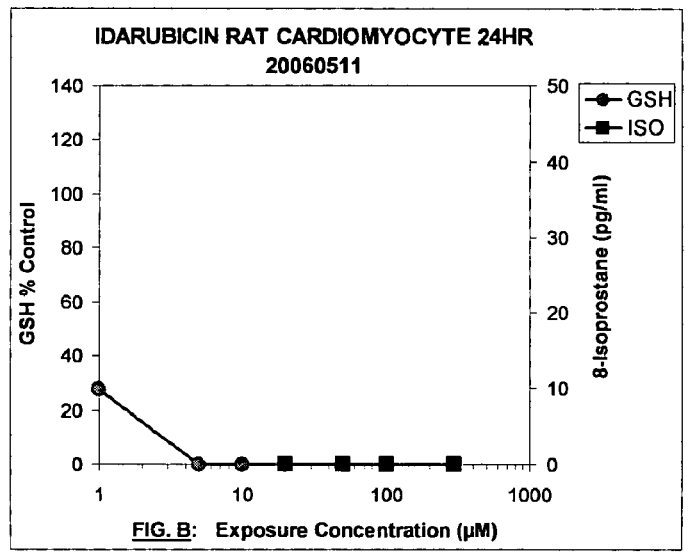
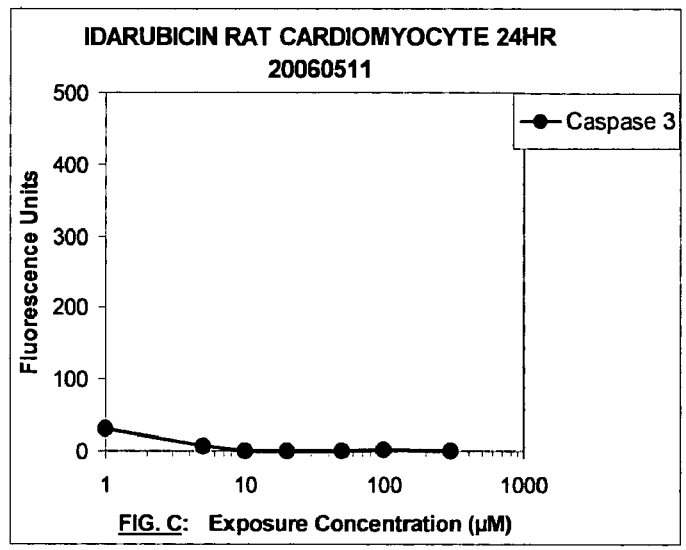

Figure 32: MITOXANTRONE RAT CARDIOMYOCYTE (CM) 24HR
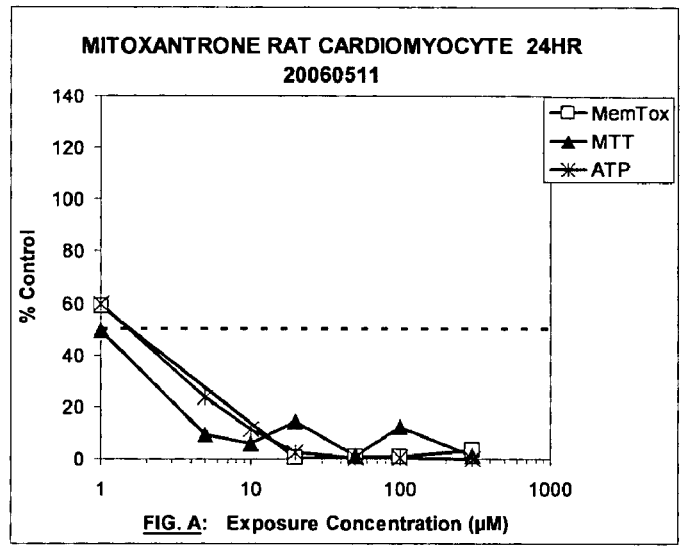
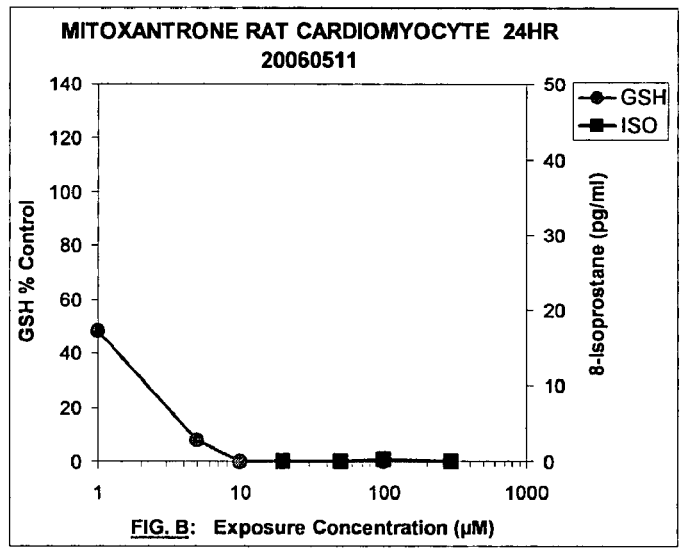
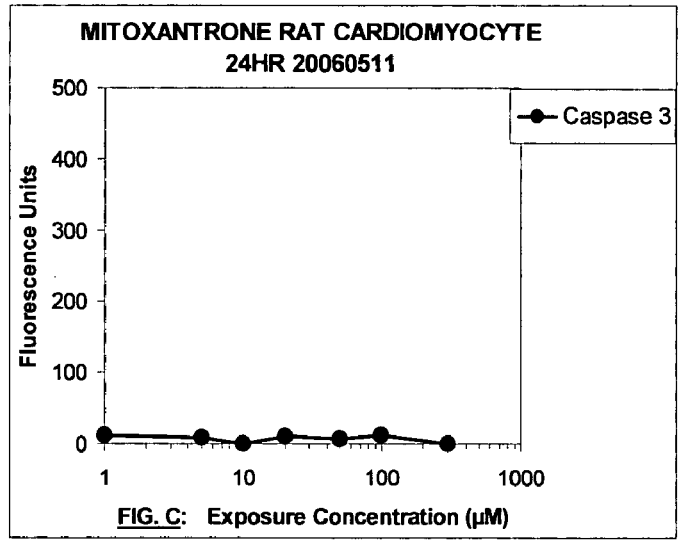

Figure 33: DAUNORUBICIN RAT CARDIOMYOCYTE (CM) 24HR
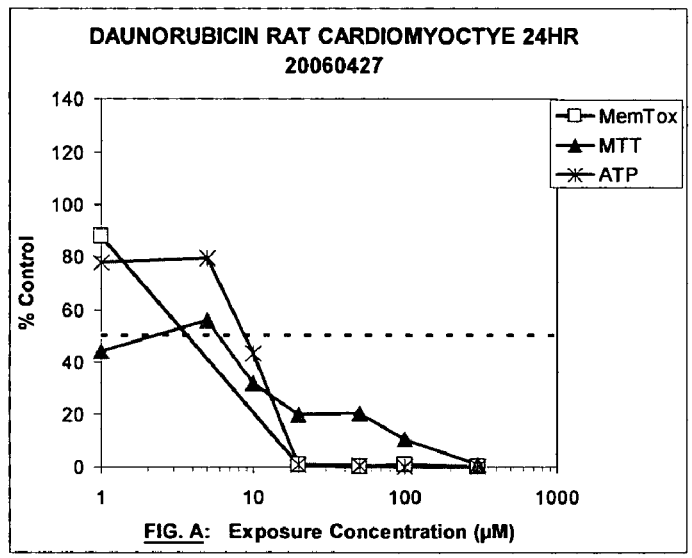
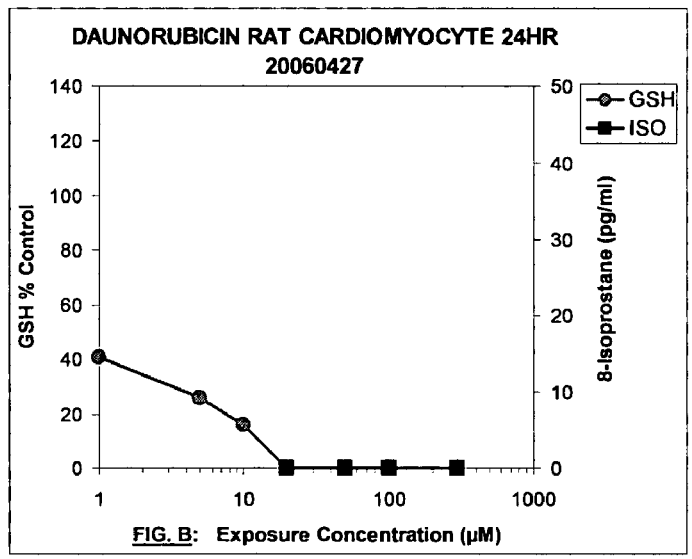
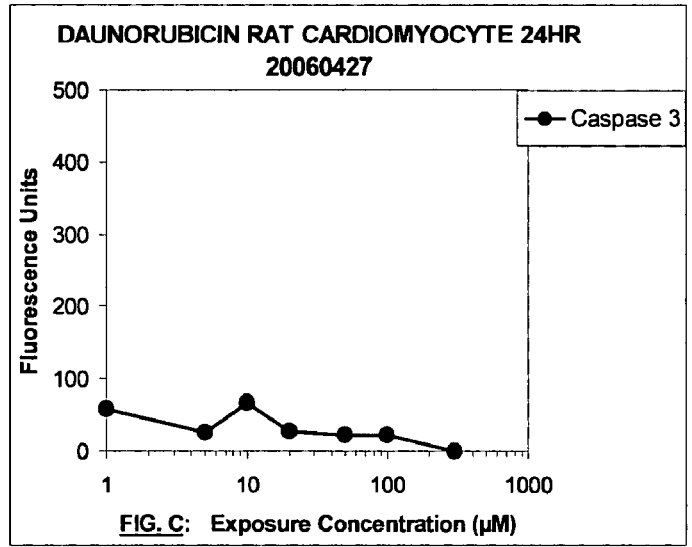

Figure 34: PIRARUBICIN RAT CARDIOMYOCYTE (CM) 24HR
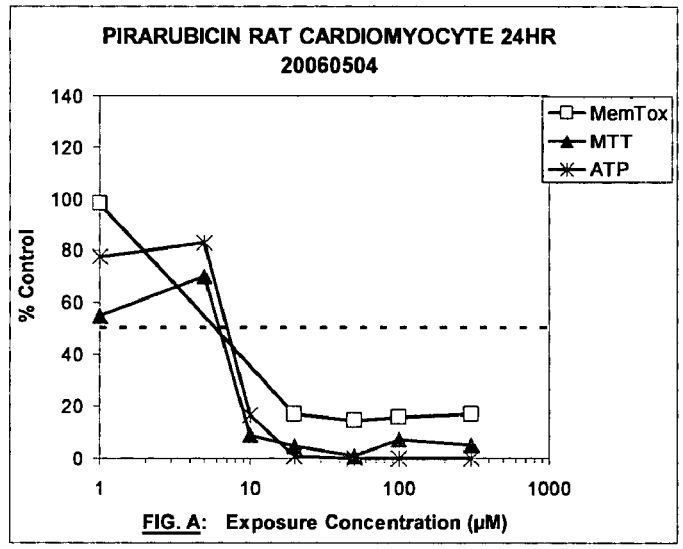
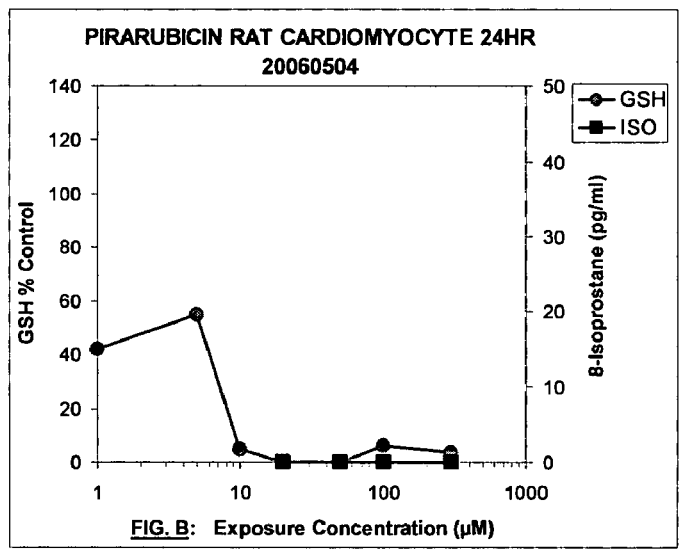
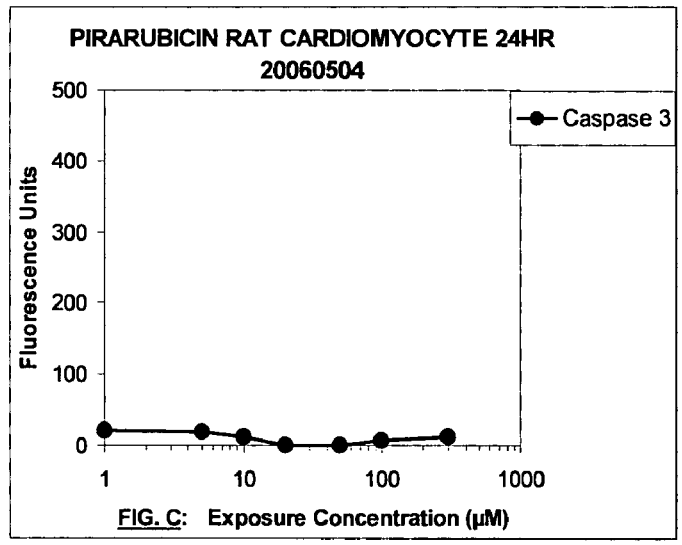

Figure 35: EPIRUBICIN RAT CARDIOMYOCYTE (CM) 24HR
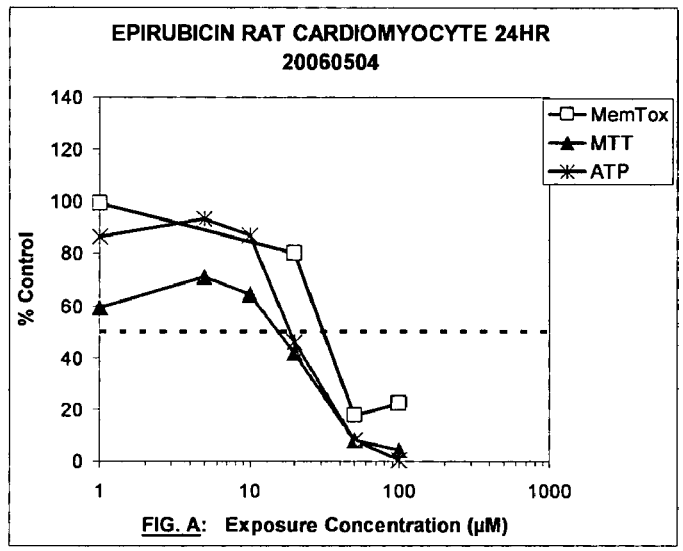
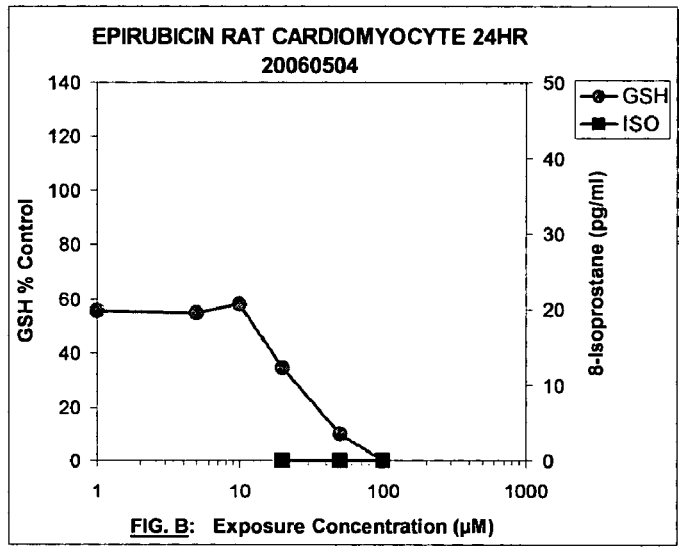
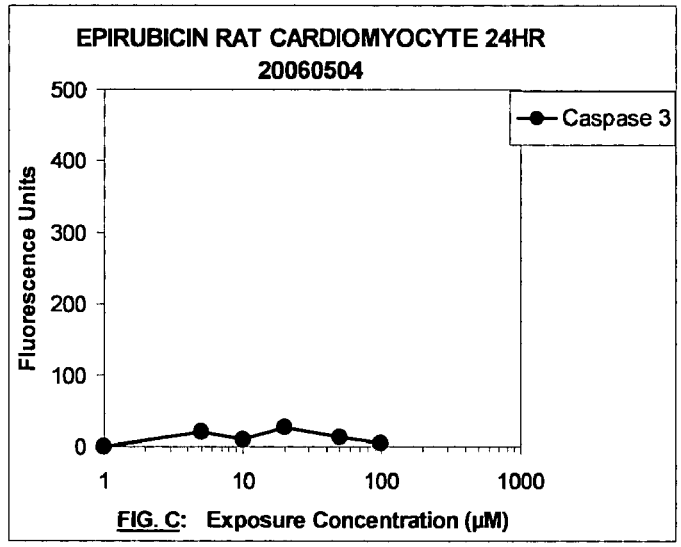

Figure 36: RITONAVIR RAT CARDIOMYOCYTE (CM) 24HR
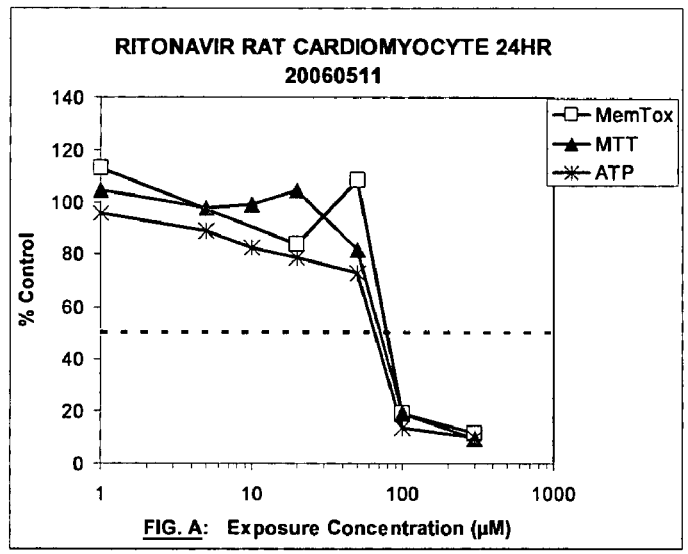
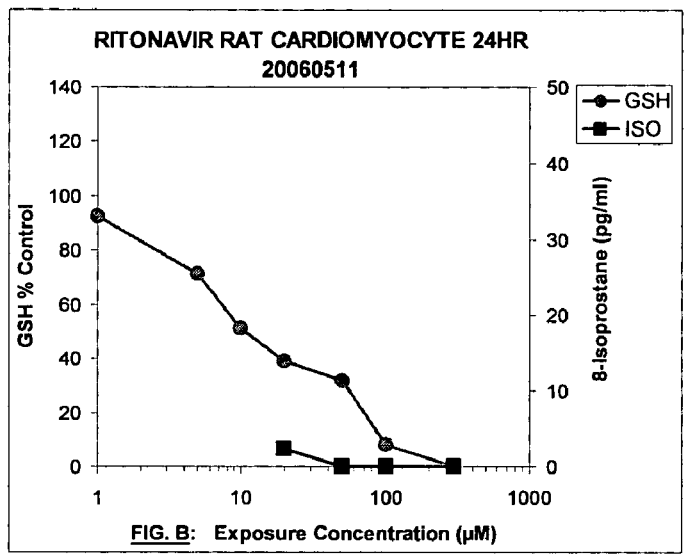
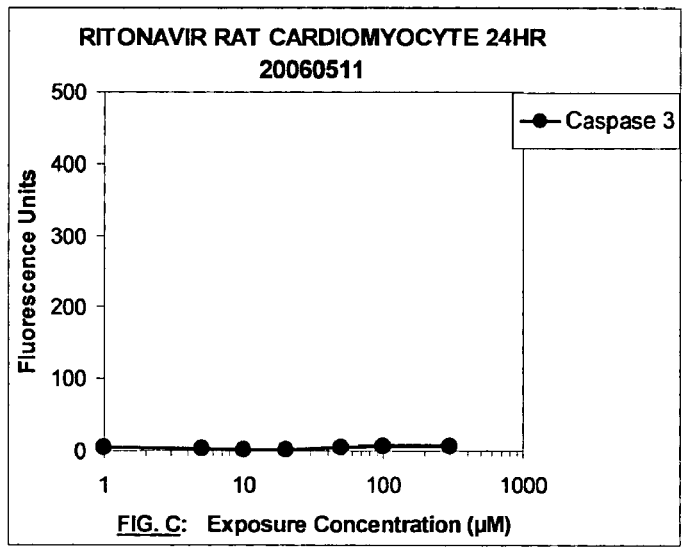

Figure 37: EFAVIRENZ RAT CARDIOMYOCYTE (CM) 24HR
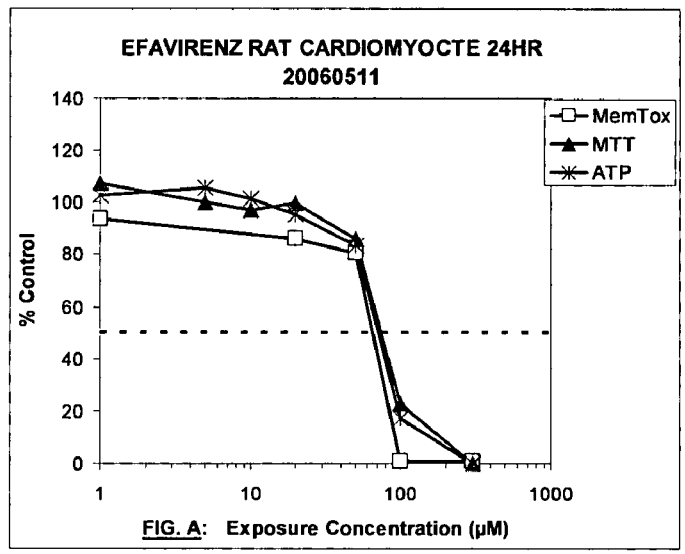
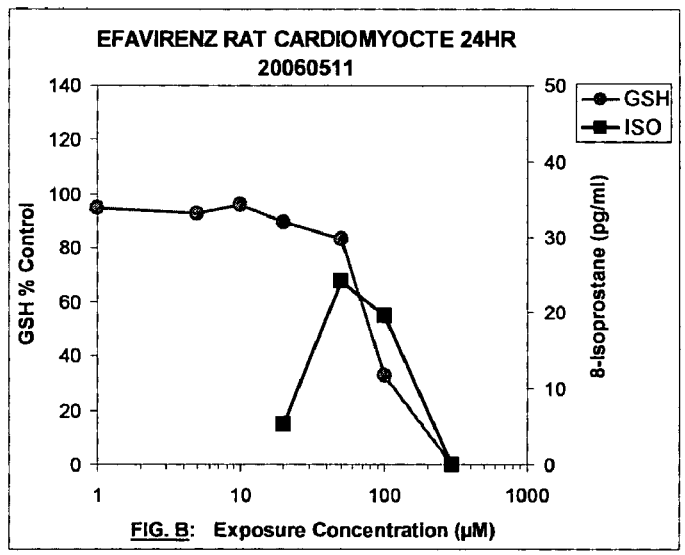
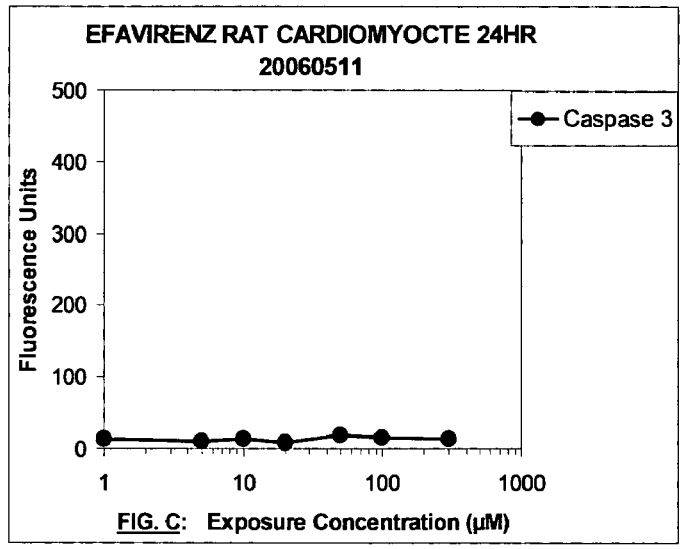

Figure 38: LOPINAVIR RAT CARDIOMYOCYTE (CM) 24HR
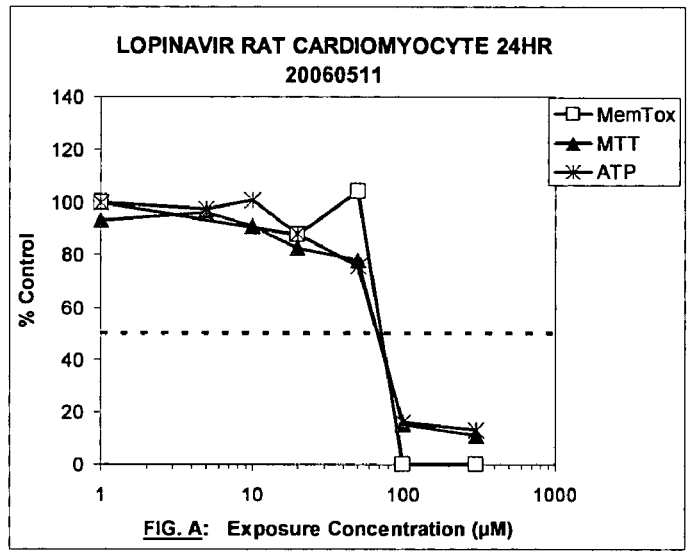
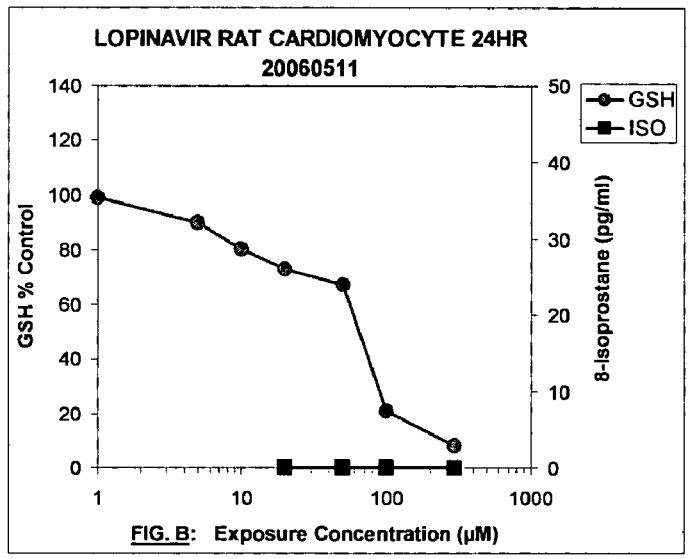
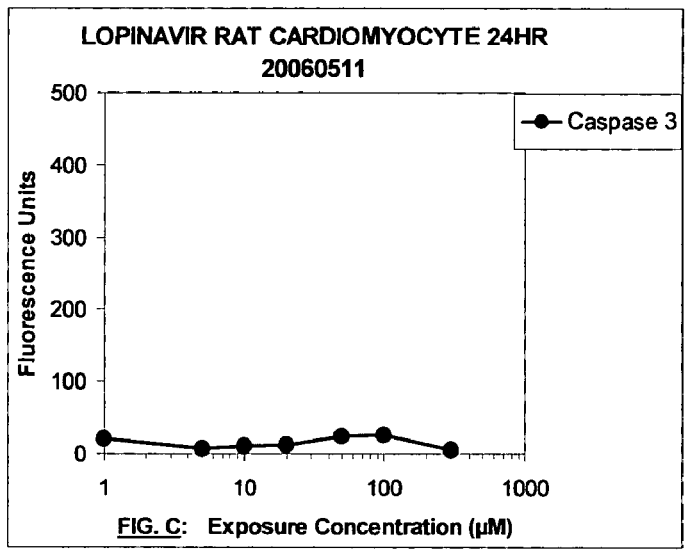

Figure 39: DELAVIRDINE RAT CARDIOMYOCYTE (CM) 24HR
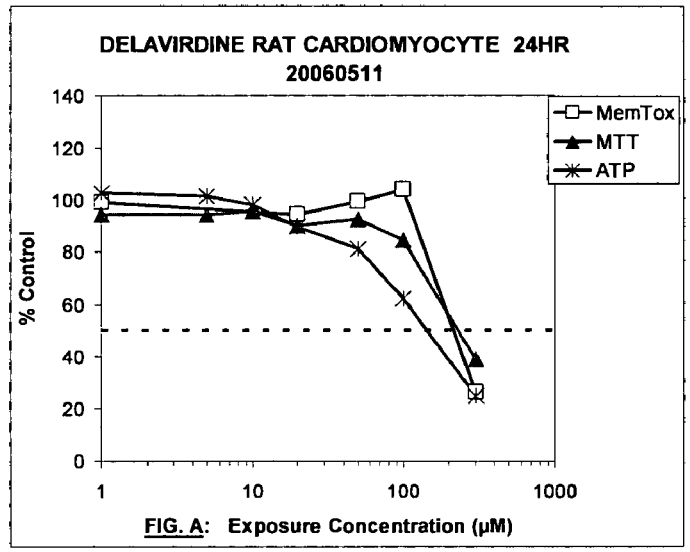
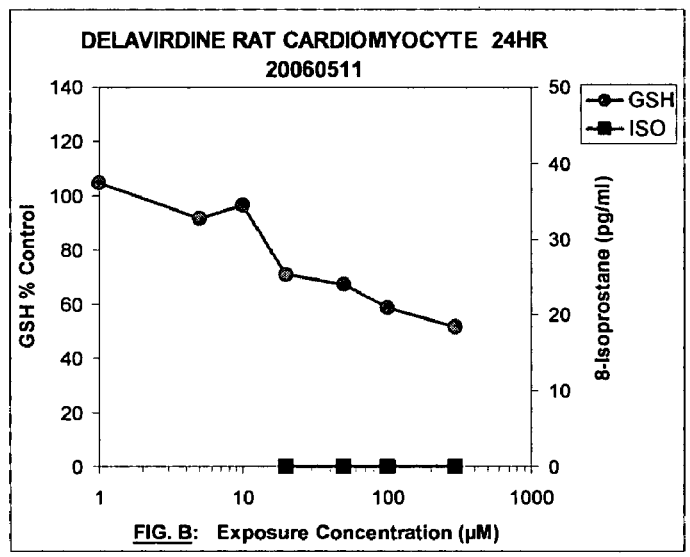
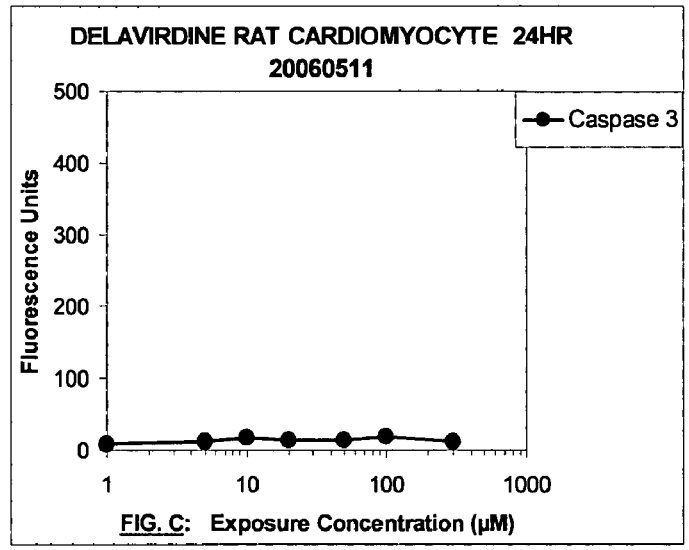

Figure 40: ABACAVIR RAT CARDIOMYOCYTE (CM) 24HR
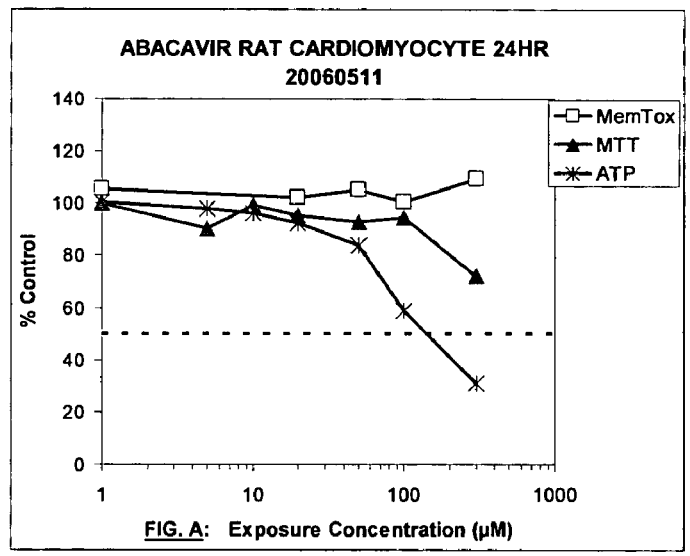
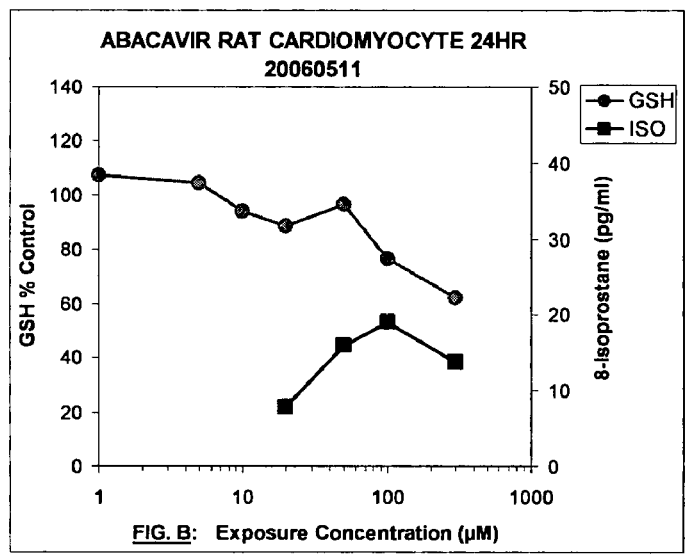
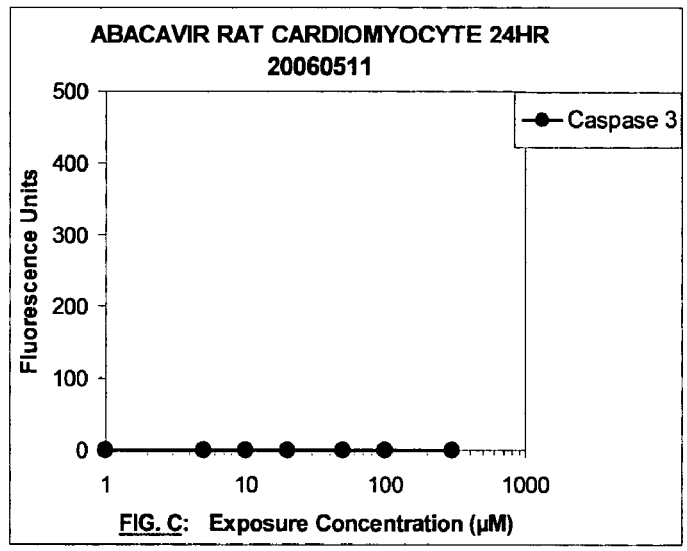

Figure 41: <u>INDINAVIR</u> RAT CARDIOMYOCYTE (CM) 24HR
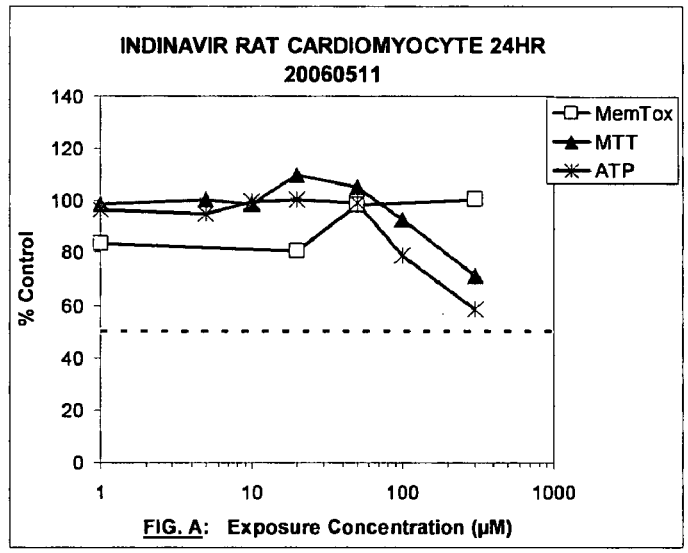
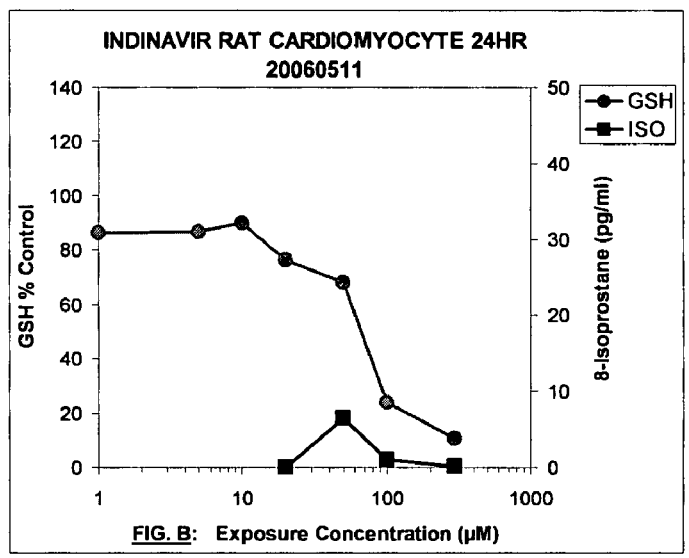
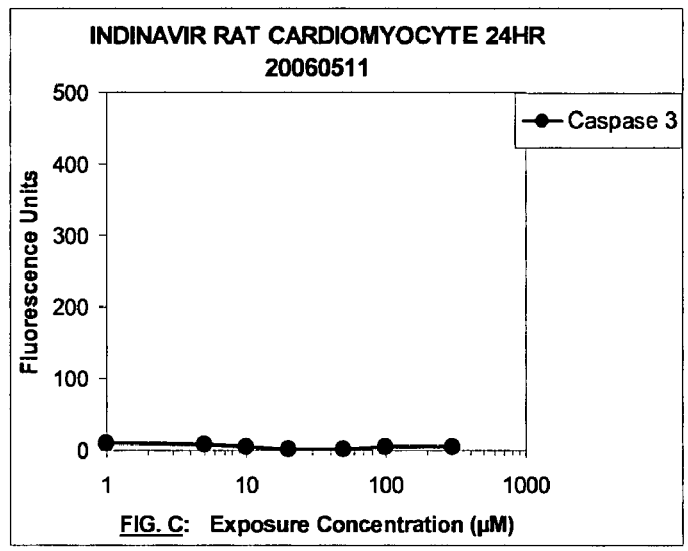

Figure 42: NEVIRAPINE RAT CARDIOMYOCYTE (CM) 24HR
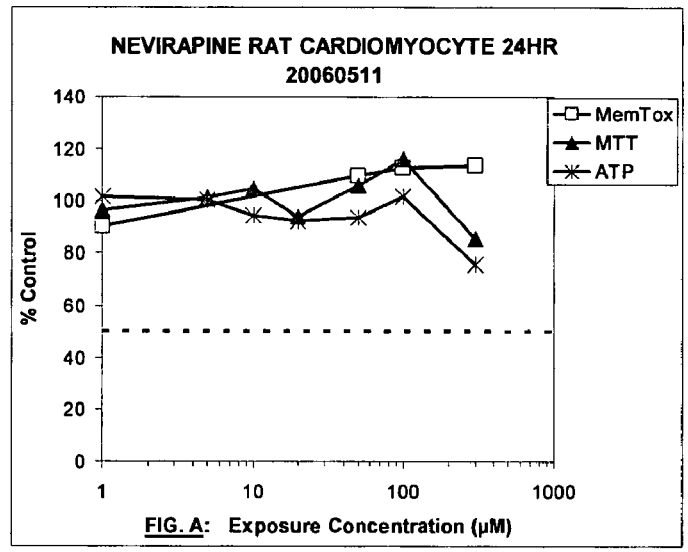
FIG. A: Exposure Concentration (µM)
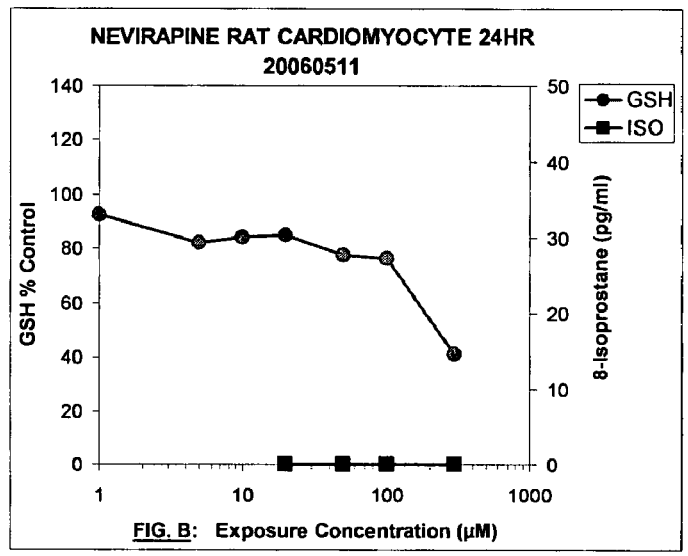
FIG. B: Exposure Concentration (µM)
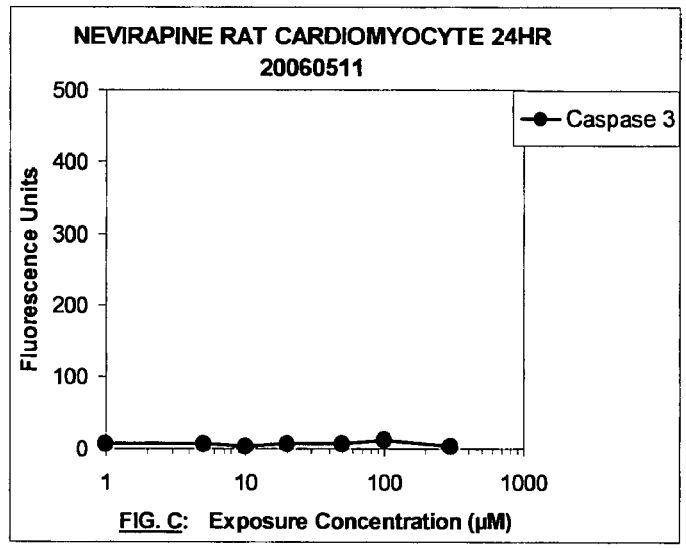
FIG. C: Exposure Concentration (µM)

Figure 43: <u>AZT</u> RAT CARDIOMYOCYTE (CM) 24HR
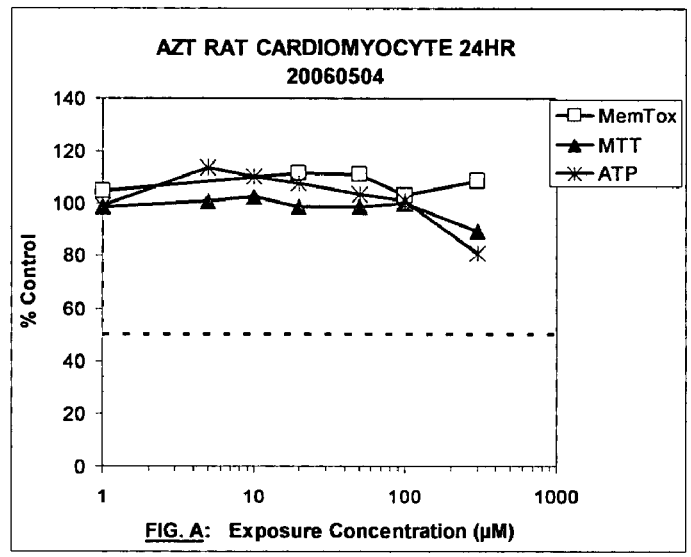
FIG. A: Exposure Concentration (µM)
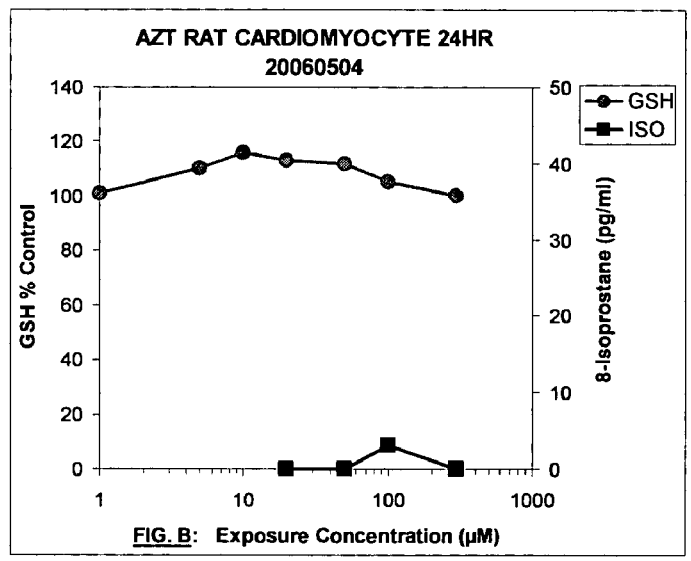
FIG. B: Exposure Concentration (µM)
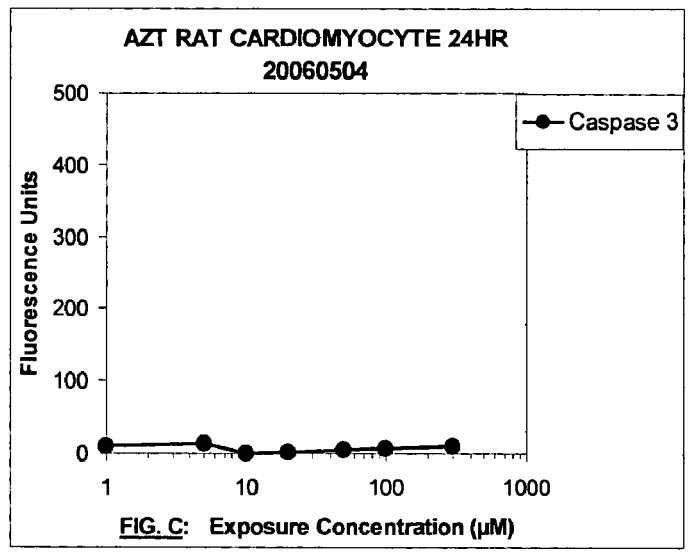
FIG. C: Exposure Concentration (µM)

Figure 44: ROTENONE RAT CARDIOMYOCYTE (CM) 24HR
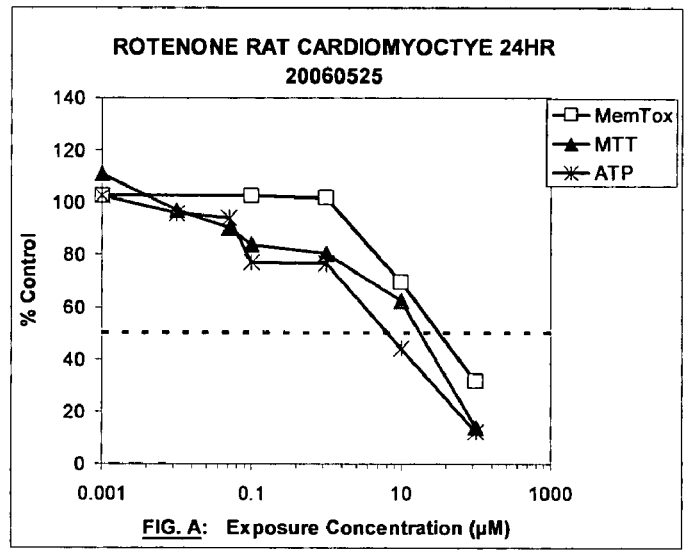
FIG. A: Exposure Concentration (μM)
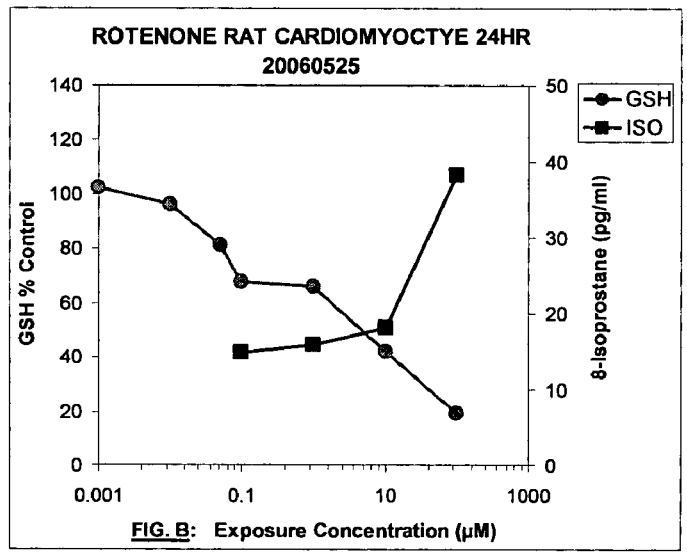
FIG. B: Exposure Concentration (μM)
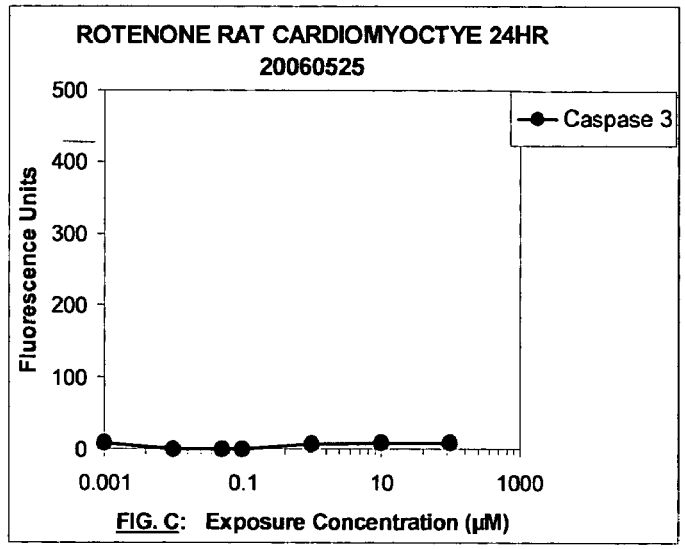
FIG. C: Exposure Concentration (μM)

Figure 45: CAMPTOTHECIN RAT CARDIOMYOCYTE (CM) 24HR
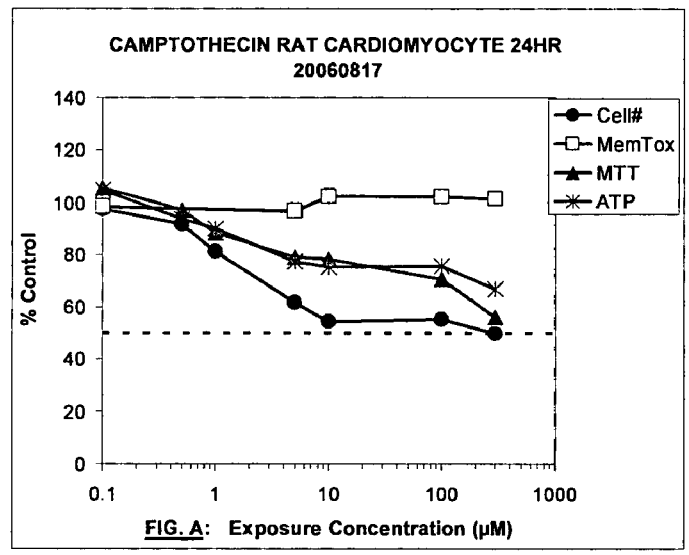
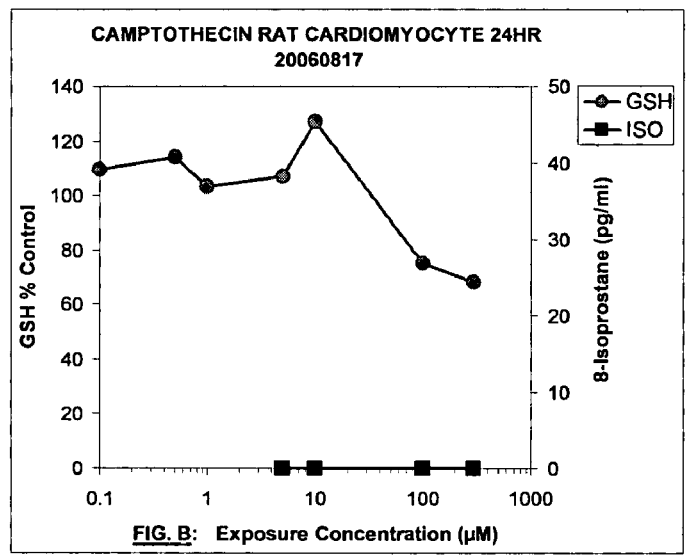
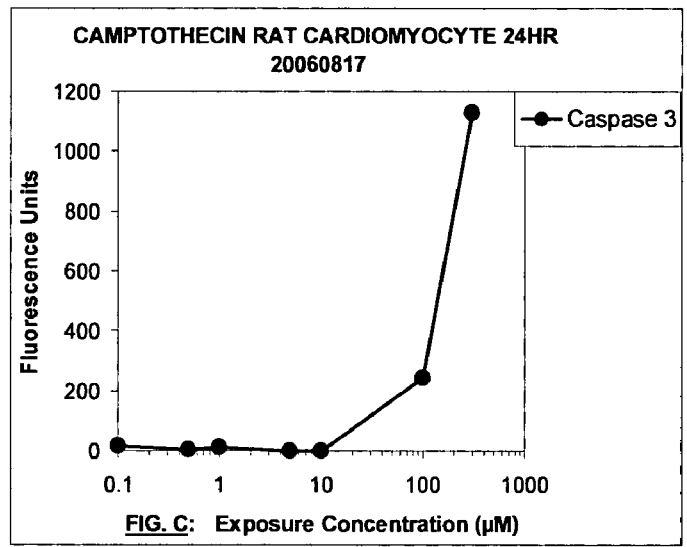

Figure 46: IDARUBICIN H4IIE 24HR
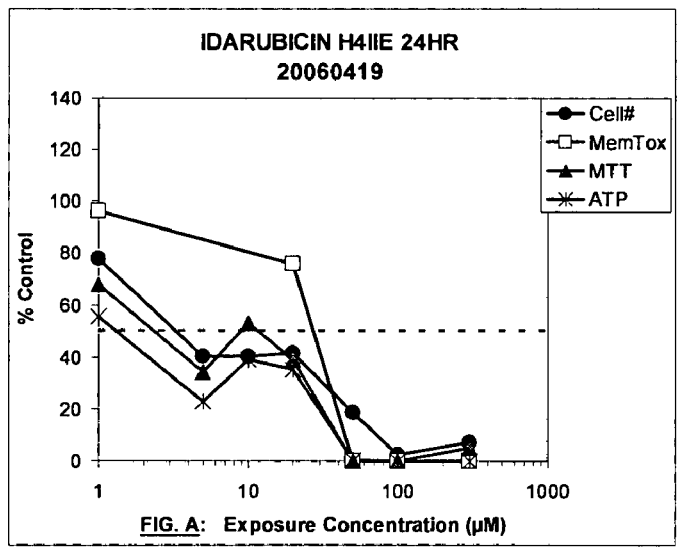
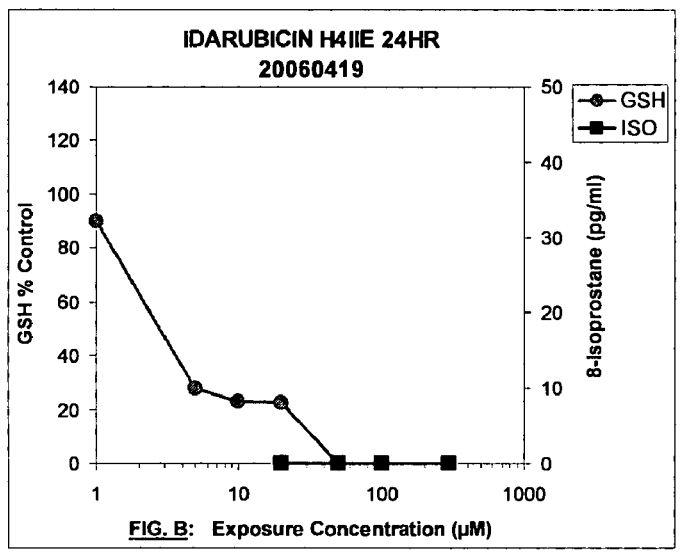
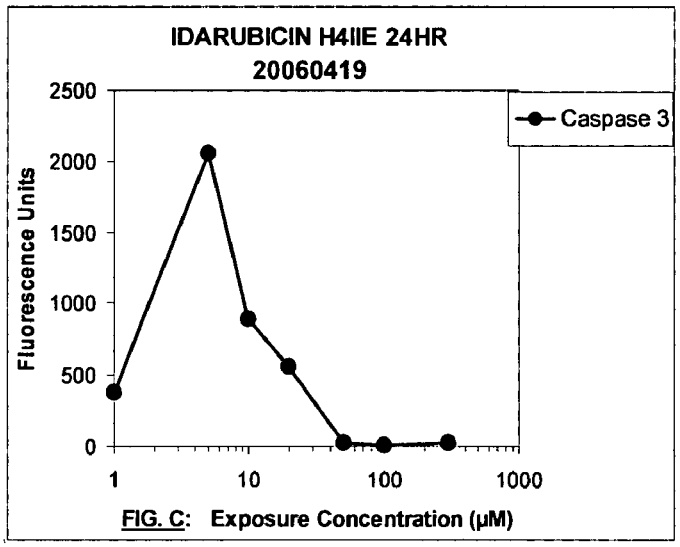

Figure 47: DAUNORUBICIN H4IIE 24HR
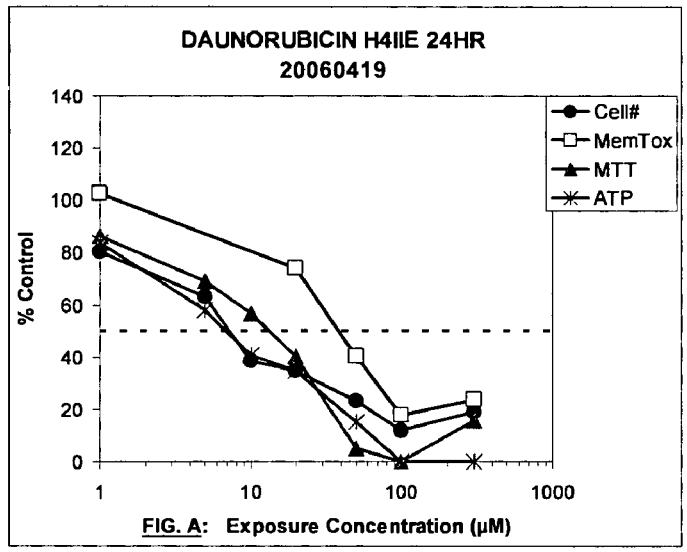
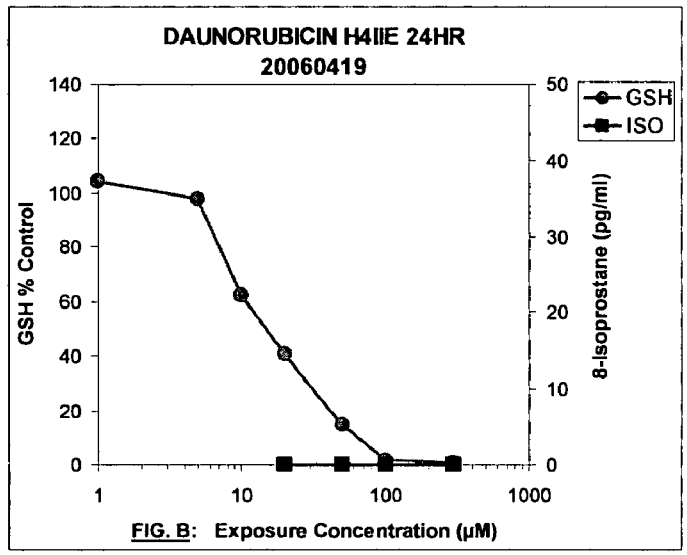
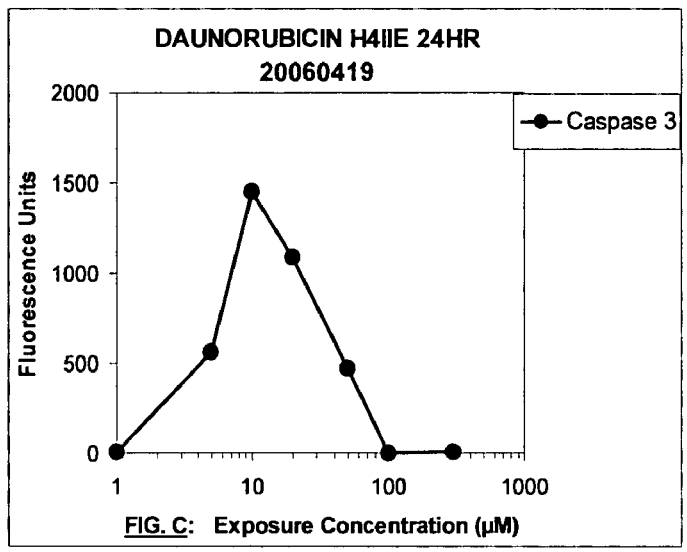

Figure 48: PIRARUBICIN H4IIE 24HR
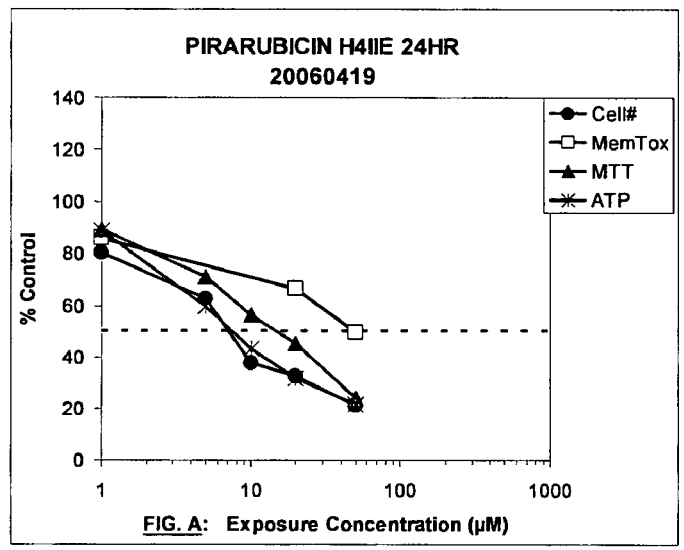
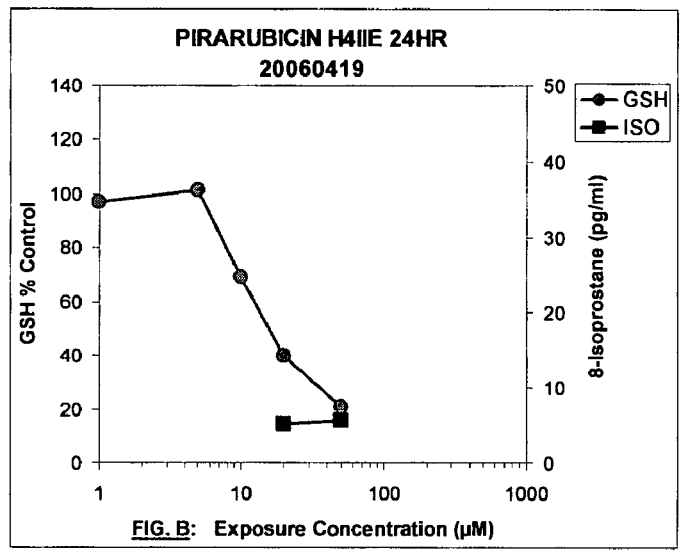
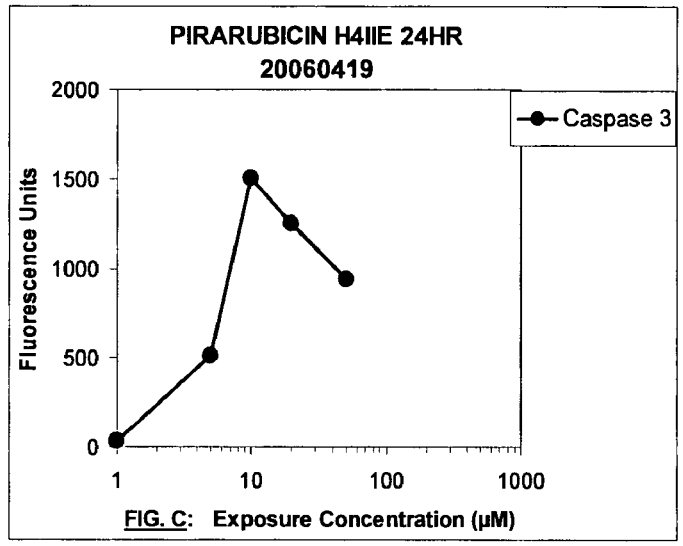

Figure 49: DOXORUBICIN H4IIE 24HR
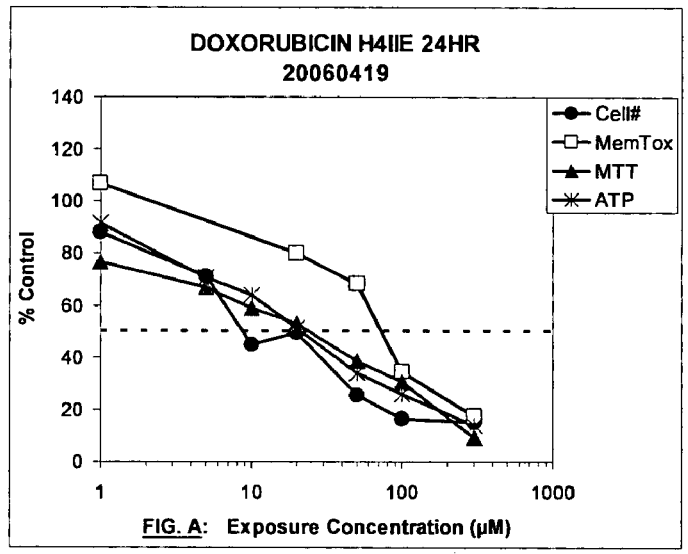
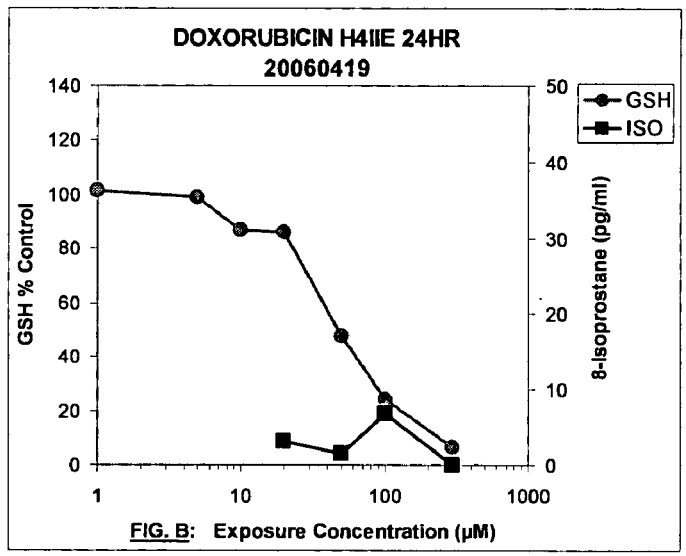
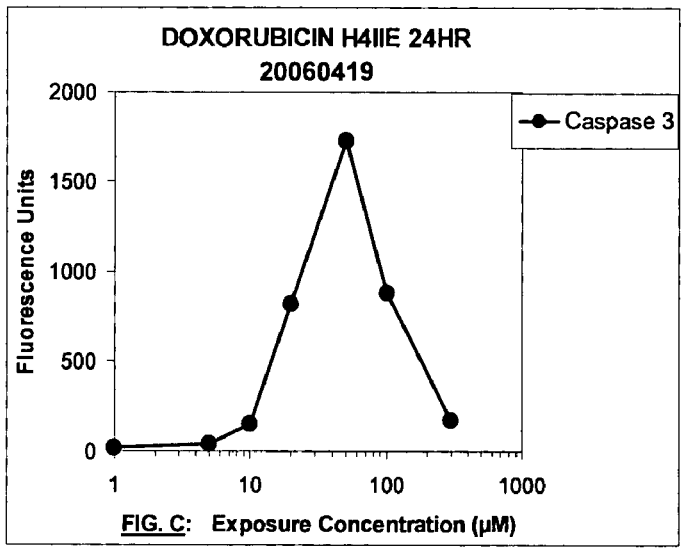

Figure 50: EPIRUBICIN H4IIE 24HR
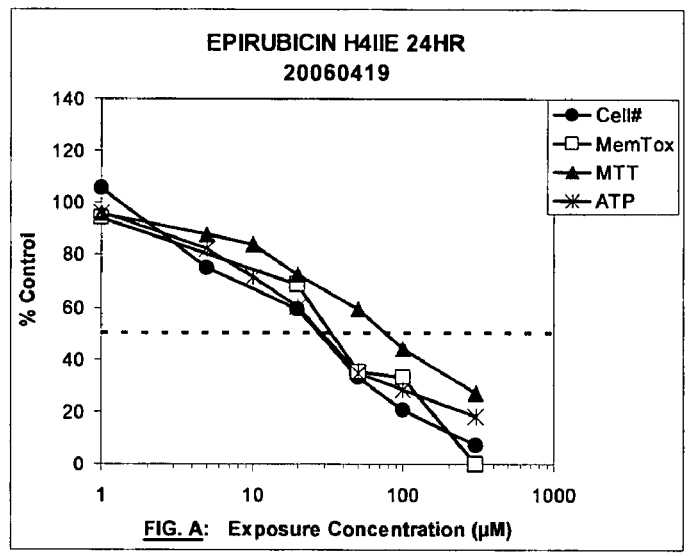
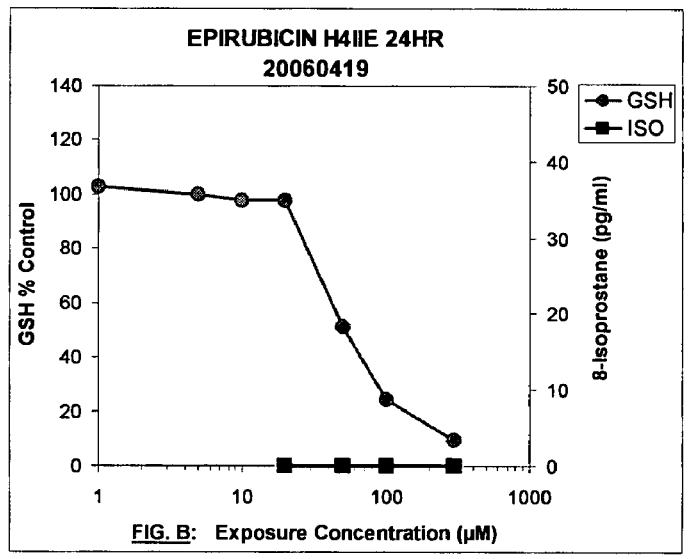
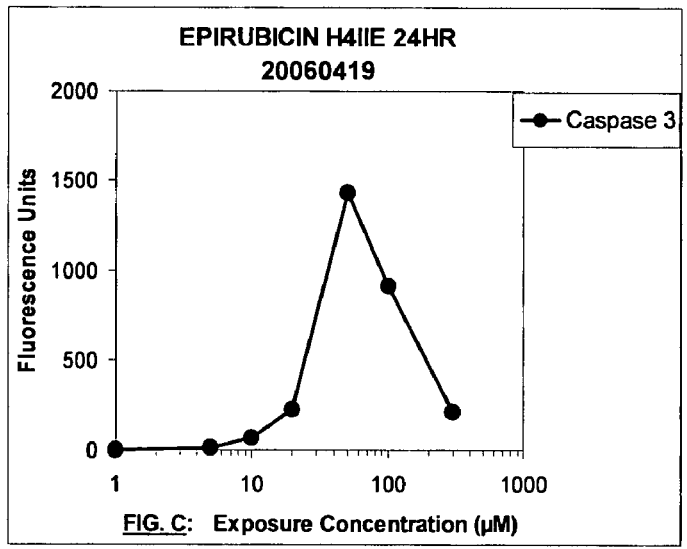

Figure 51: MITOXANTRONE H4IIE 24HR
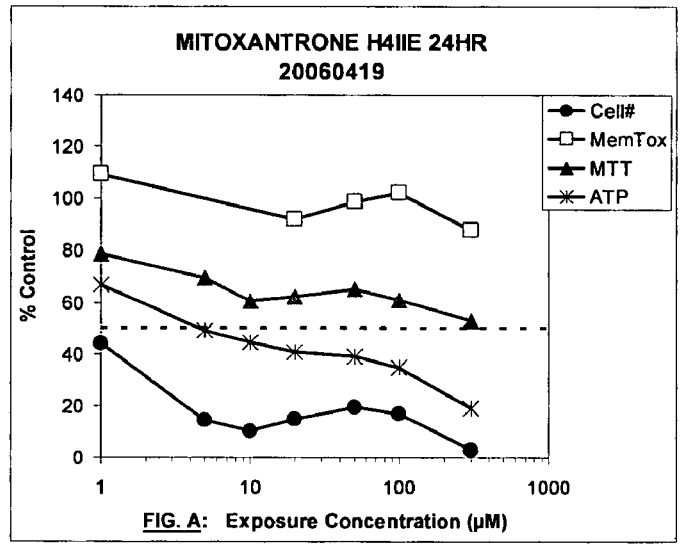
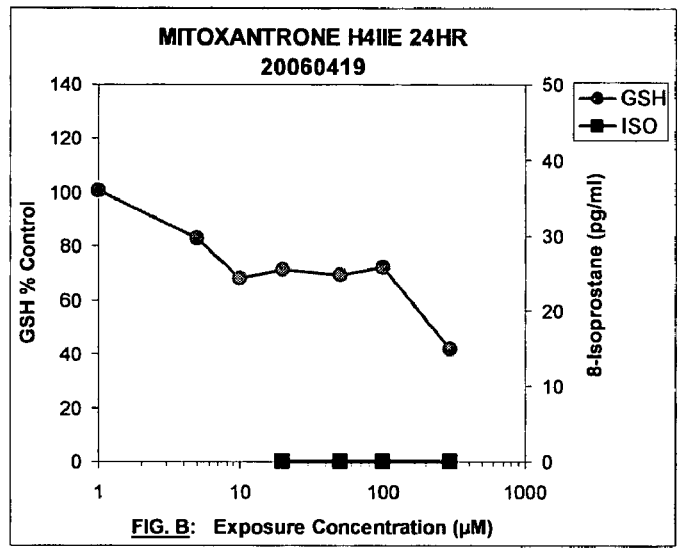
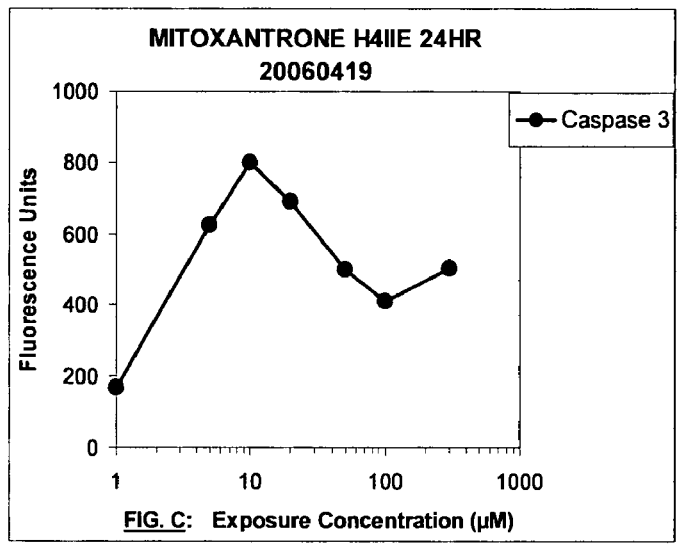

Figure 52: EFAVIRENZ H4IIE 24HR
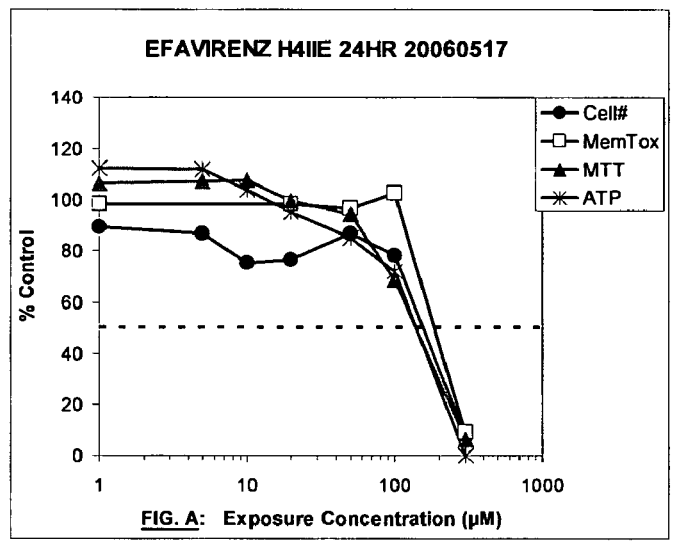
FIG. A: Exposure Concentration (μM)
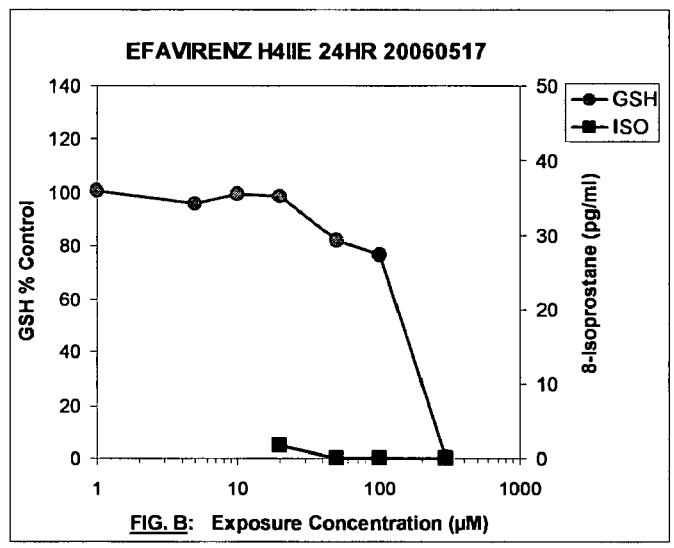
FIG. B: Exposure Concentration (μM)
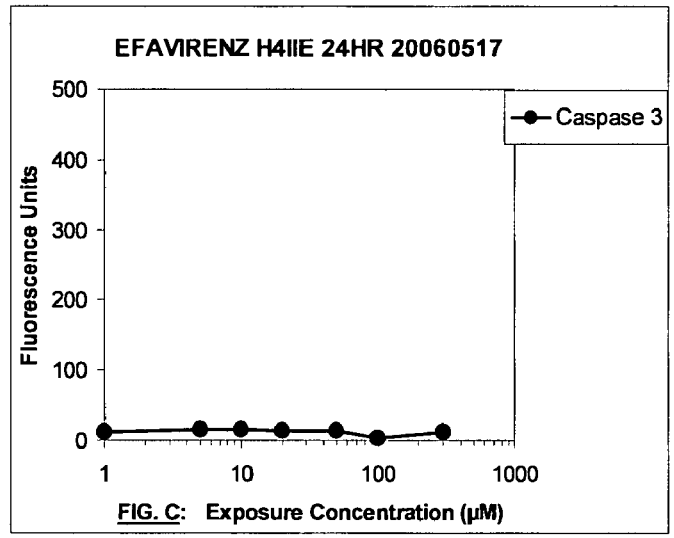
FIG. C: Exposure Concentration (μM)

Figure 53: RITONAVIR H4IIE 24HR
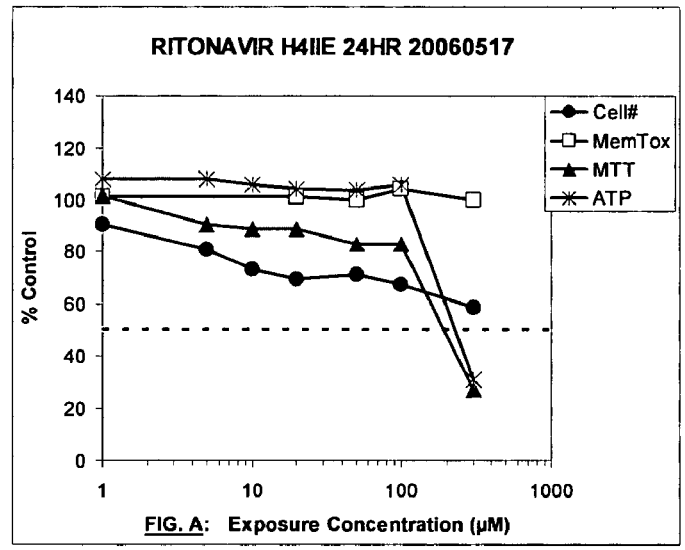
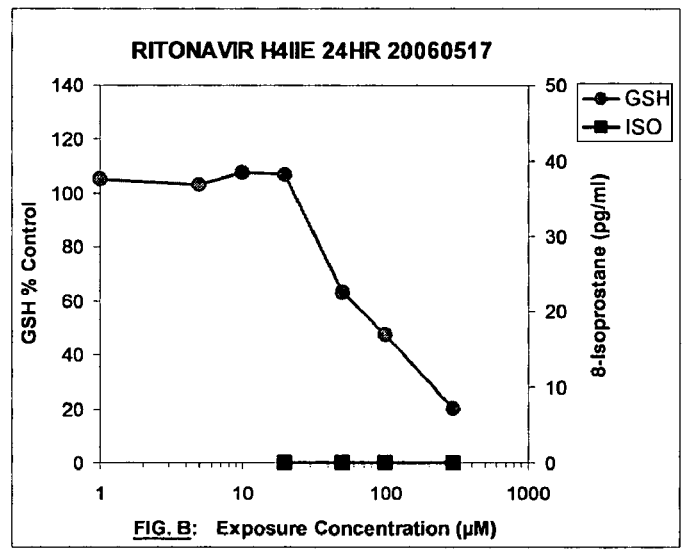
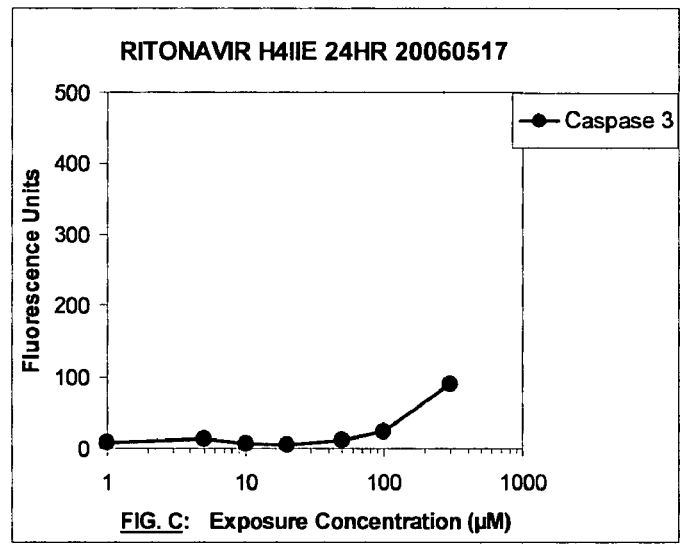

Figure 54: DELAVIRDINE H4IIE 24HR
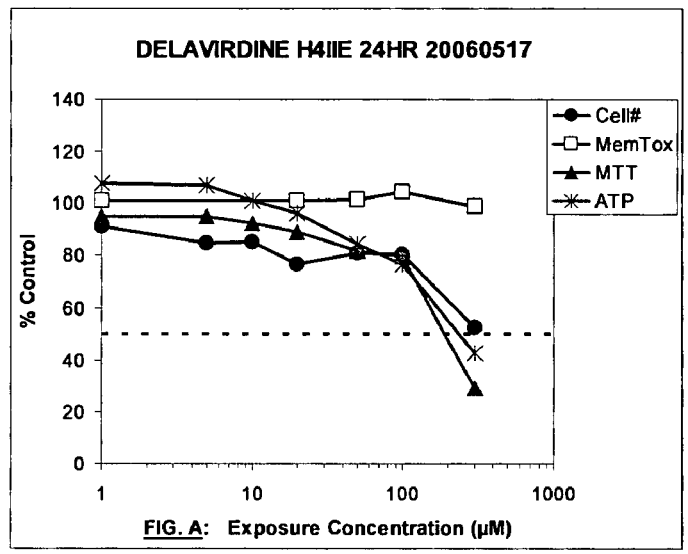
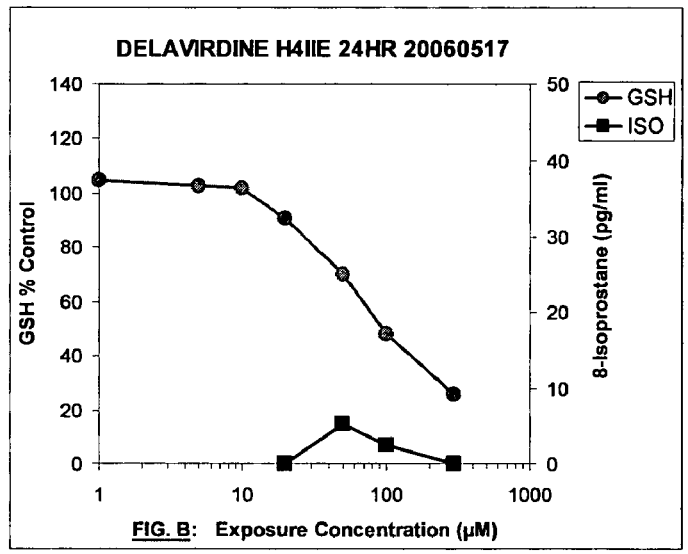
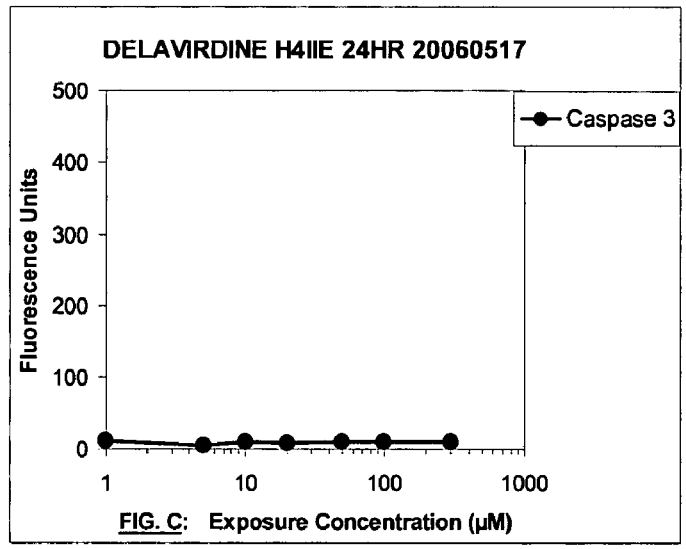

Figure 55: LOPINAVIR H4IIE 24HR
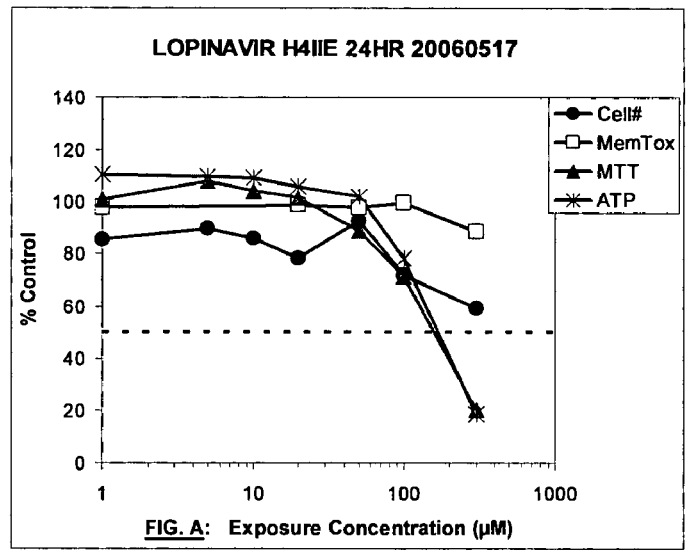
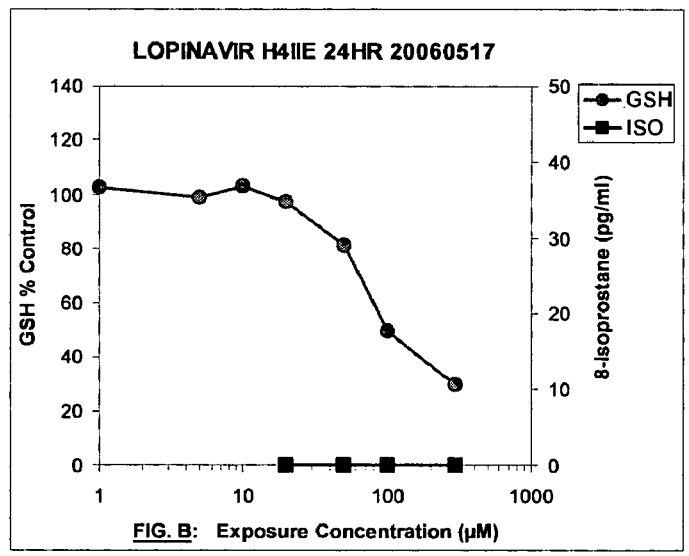
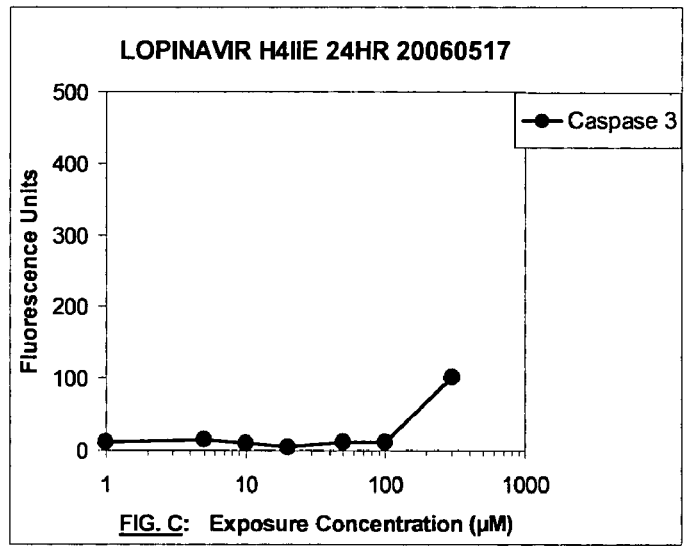

Figure 56: ABACAVIR H4IIE 24HR
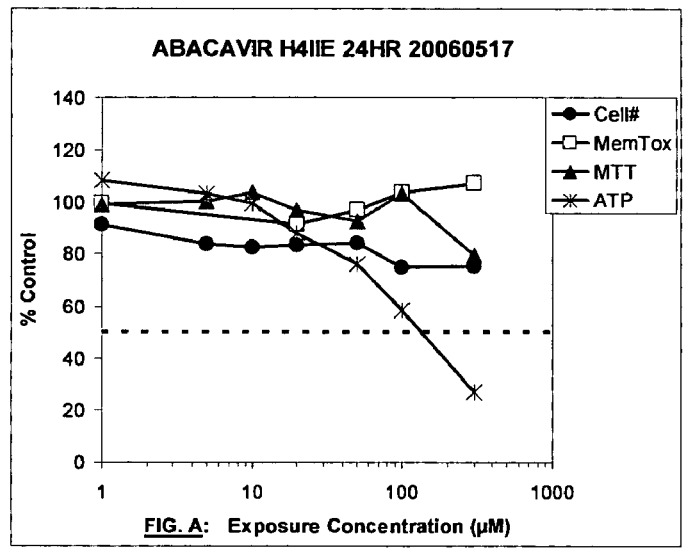
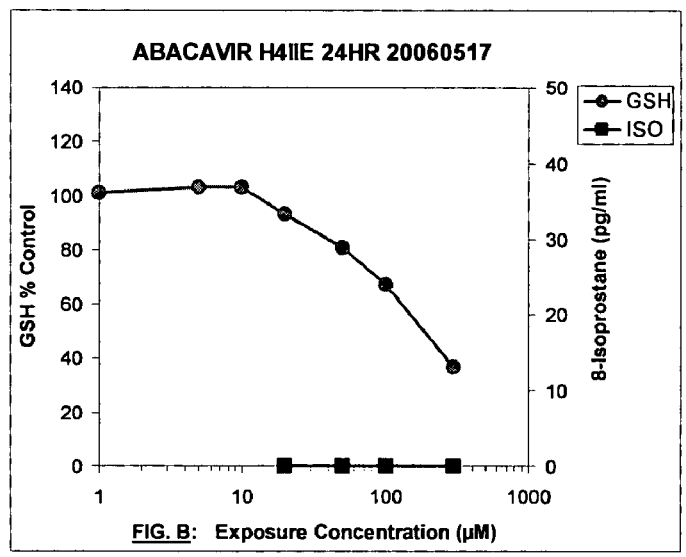
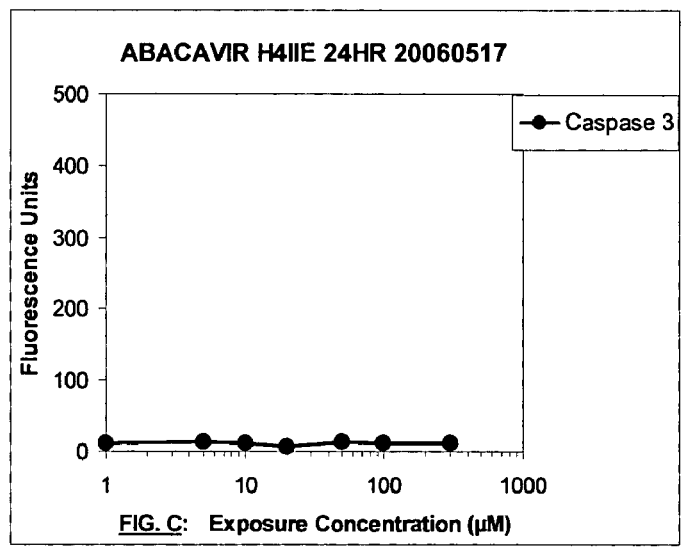

Figure 57: INDINAVIR H4IIE 24HR
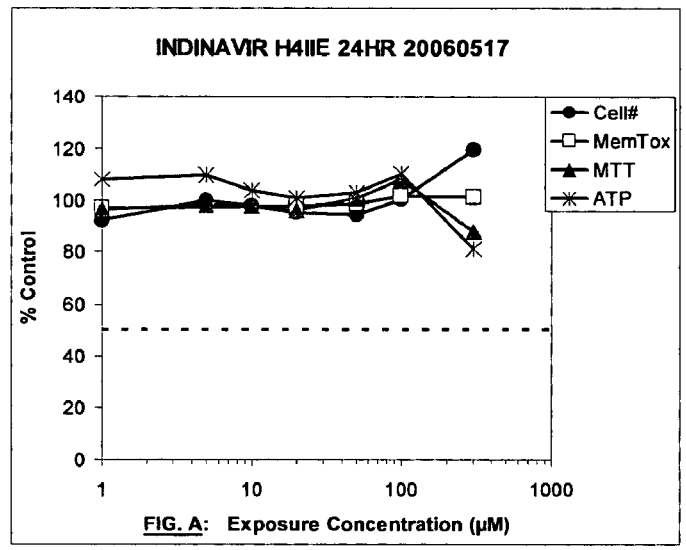
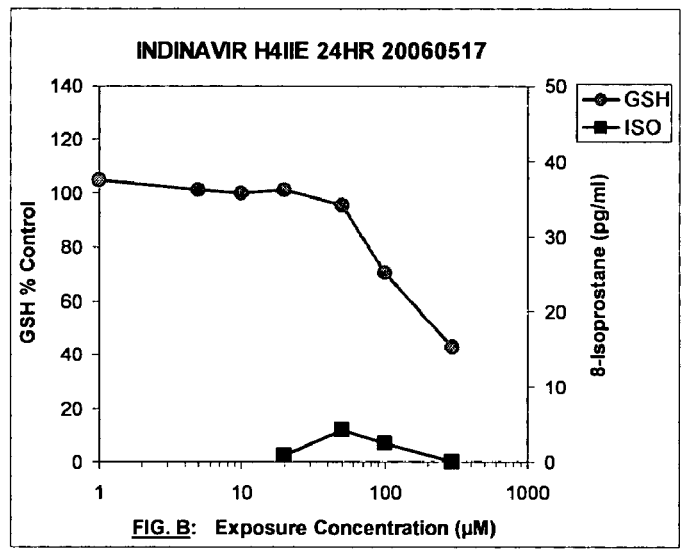
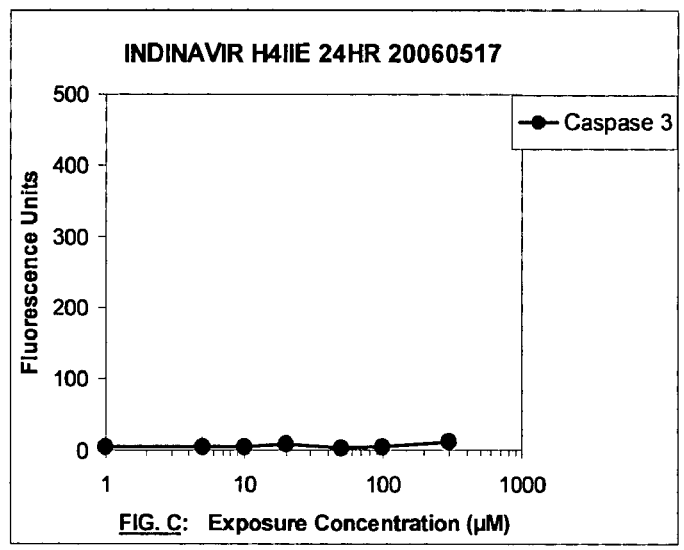

Figure 58: NEVIRAPINE H4IIE 24HR
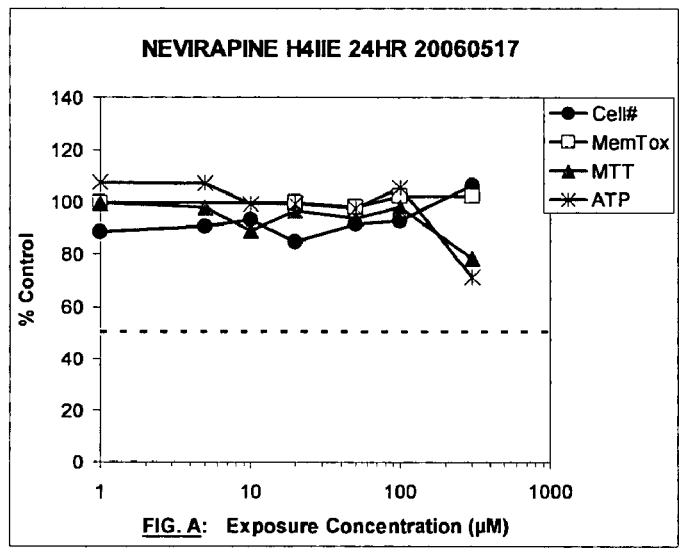
FIG. A: Exposure Concentration (μM)
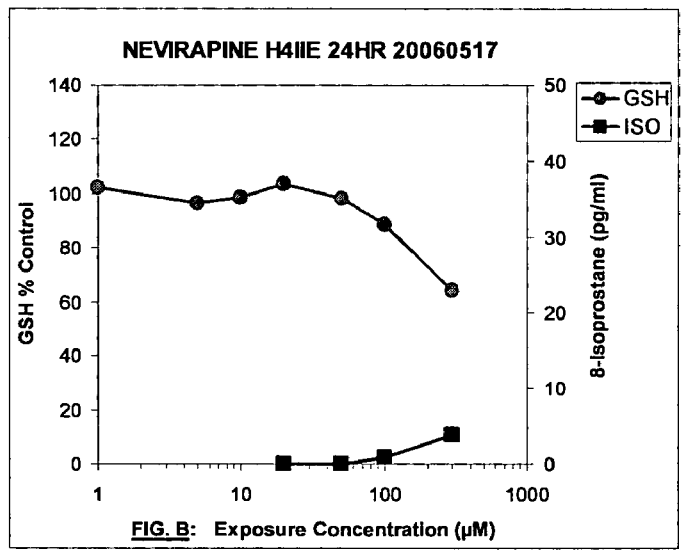
FIG. B: Exposure Concentration (μM)
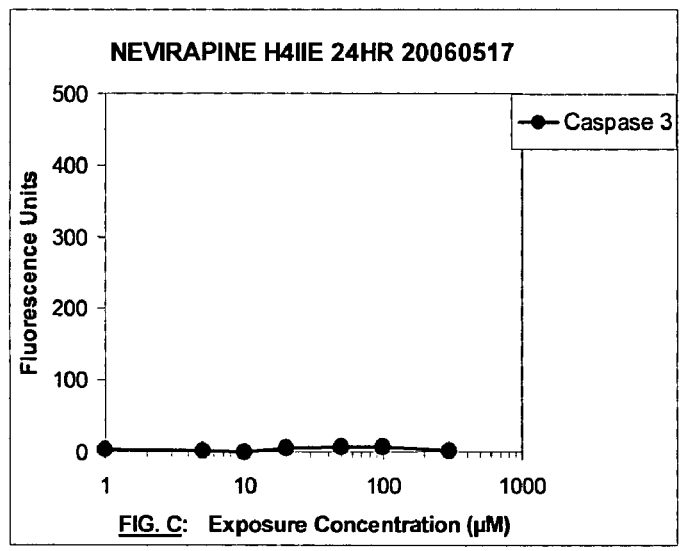
FIG. C: Exposure Concentration (μM)

Figure 59: AZT H4IIE 24HR
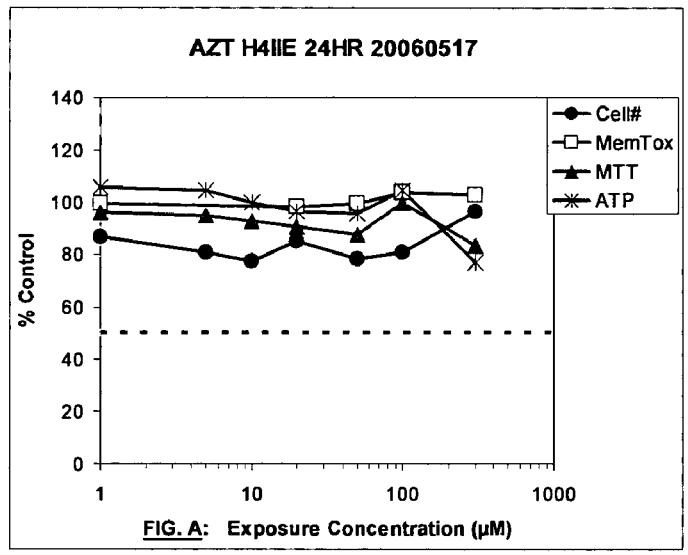
FIG. A: Exposure Concentration (μM)
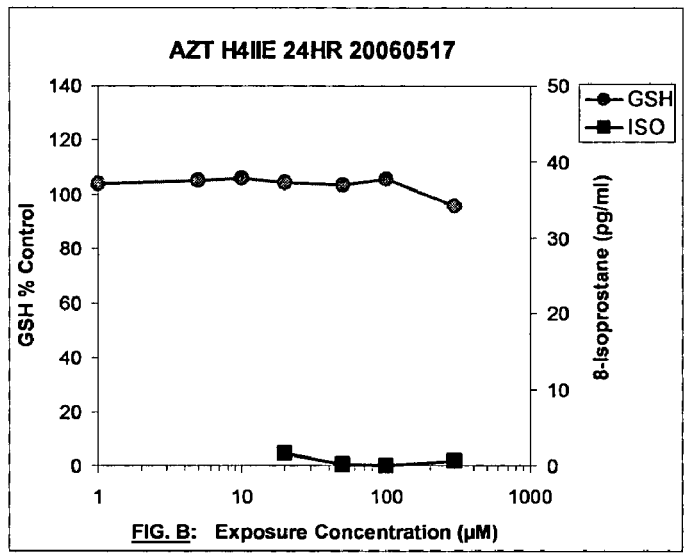
FIG. B: Exposure Concentration (μM)
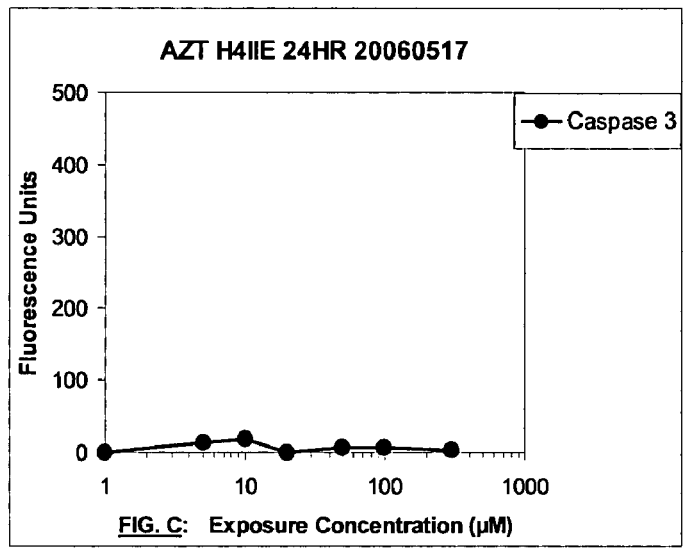
FIG. C: Exposure Concentration (μM)

Figure 60: ROTENONE H4IIE 24HR
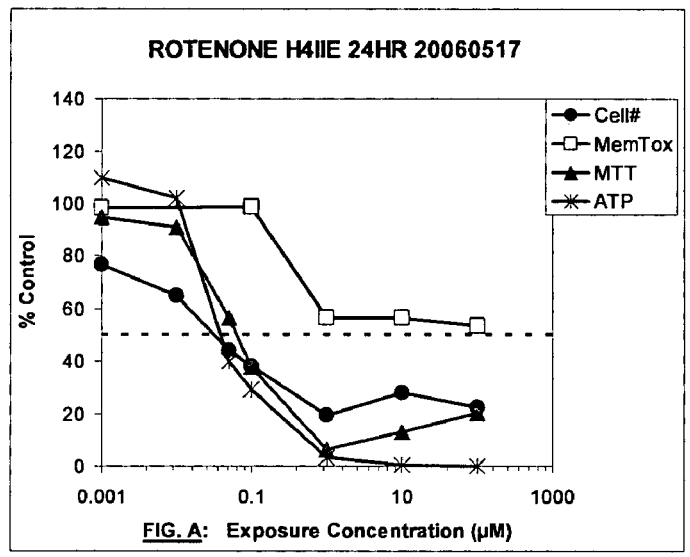
FIG. A: Exposure Concentration (μM)
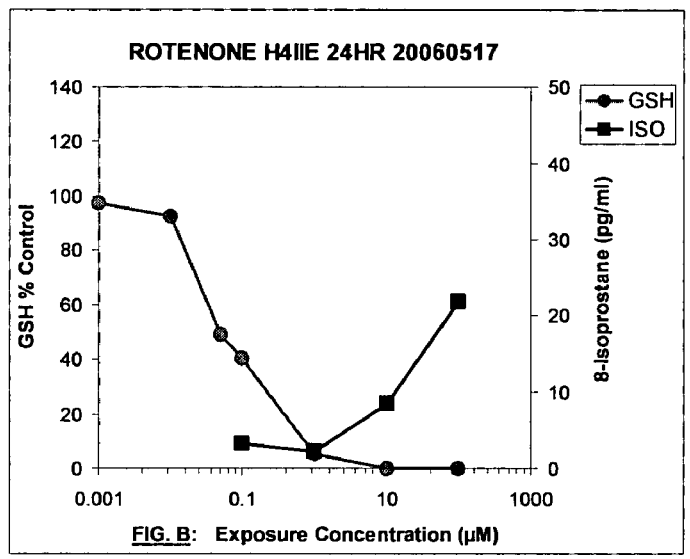
FIG. B: Exposure Concentration (μM)
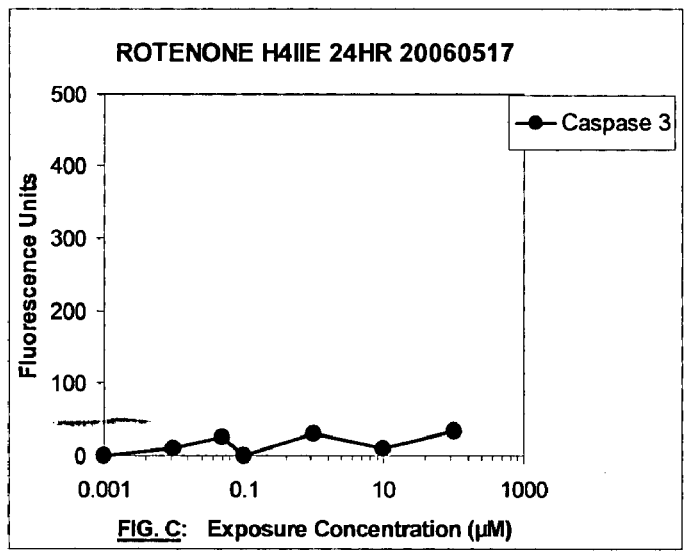
FIG. C: Exposure Concentration (μM)

Figure 61: CAMPTOTHECIN H4IIE 24HR
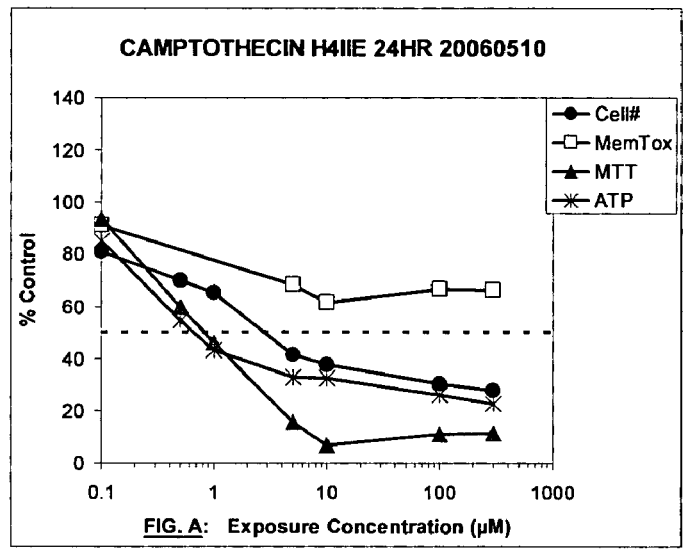
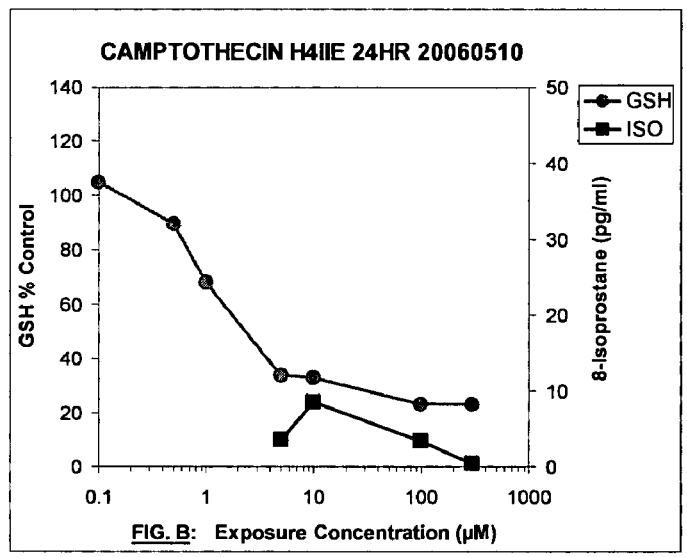
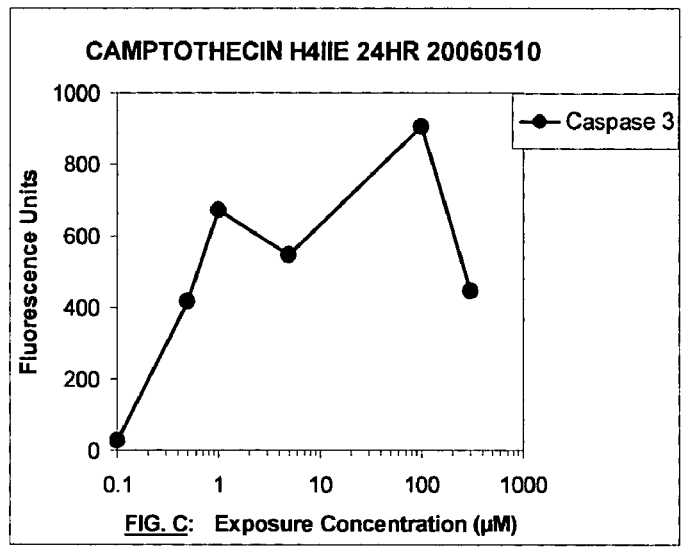

Figure 65: Metabolic Activation in Rat and Dog Microsomes
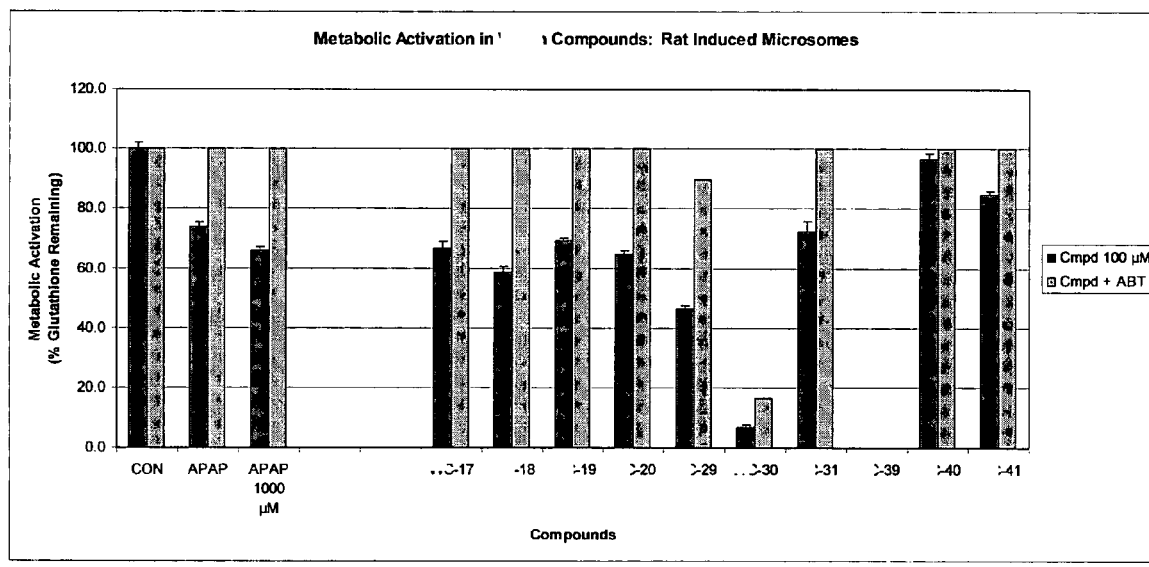
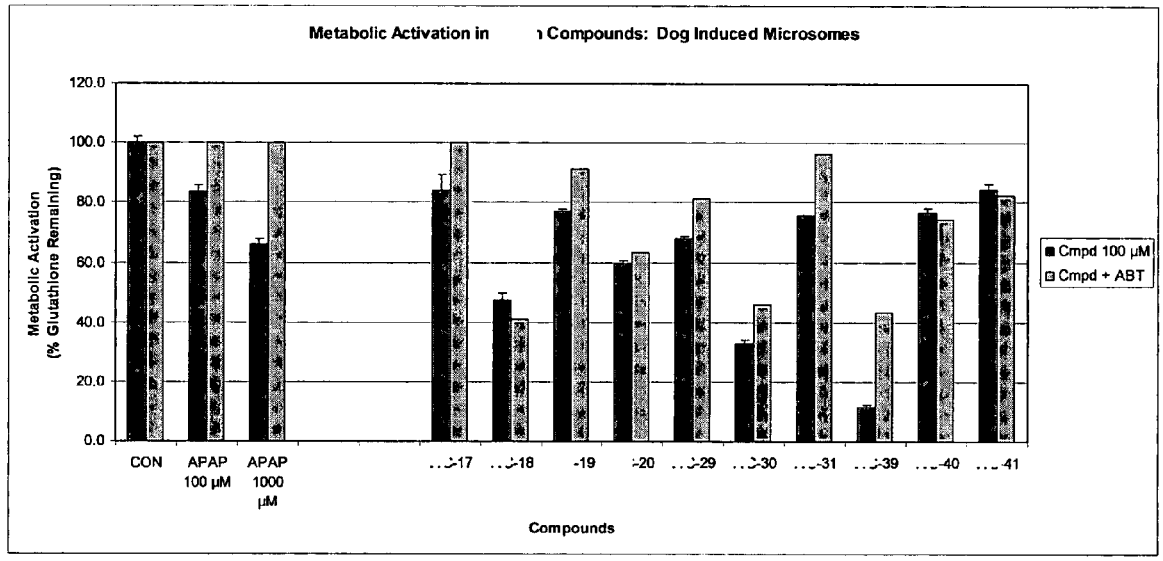

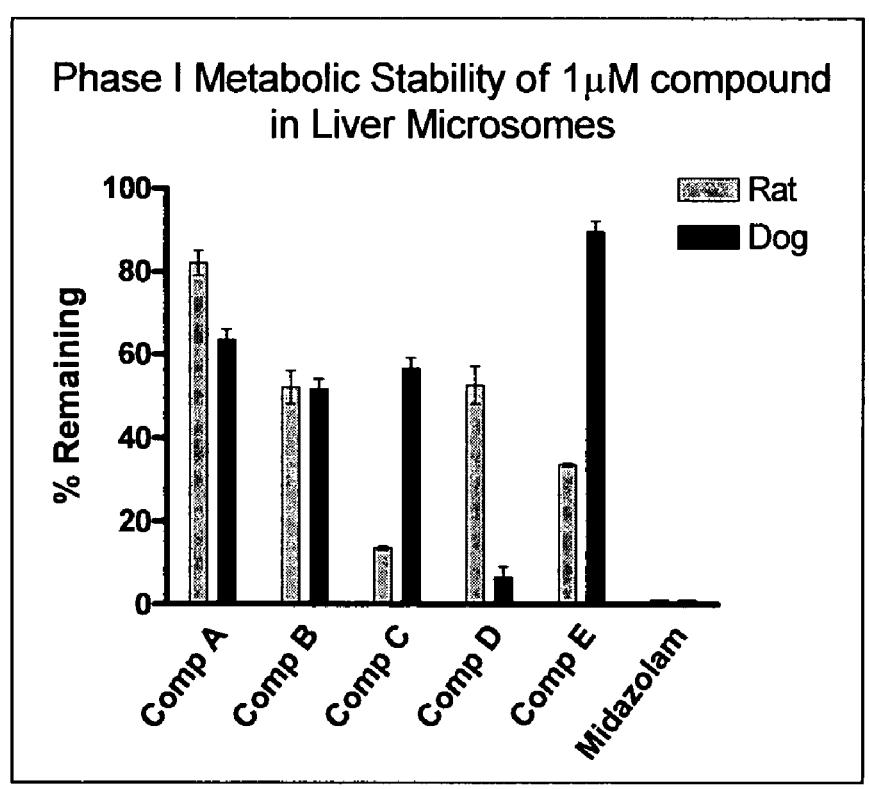
Figure 66: Metabolic Stability in Rat and Dog Microsomes

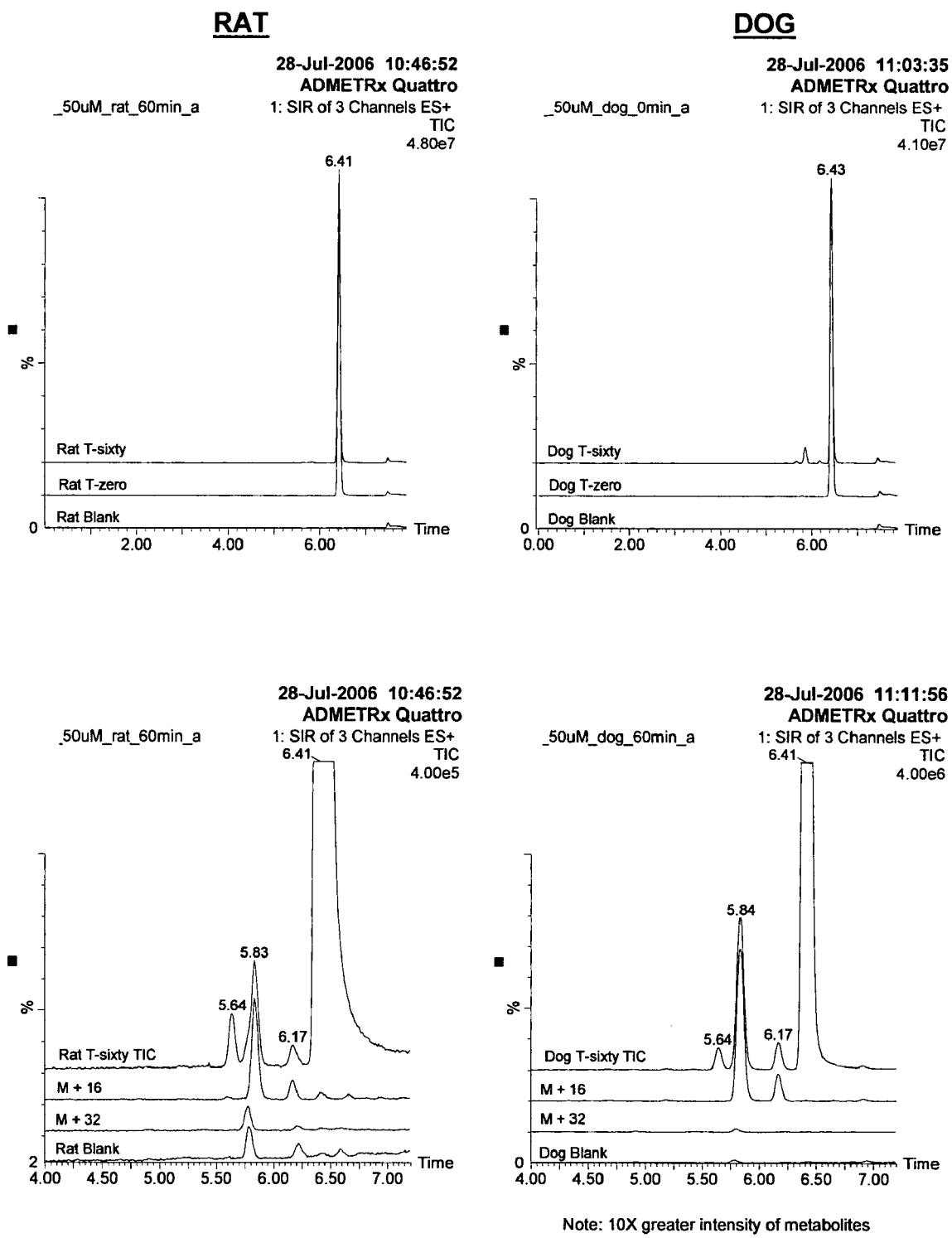
Figure 67: Microsomal Metabolism of COMP A in Rat and Dog
Note: 10X greater intensity of metabolites

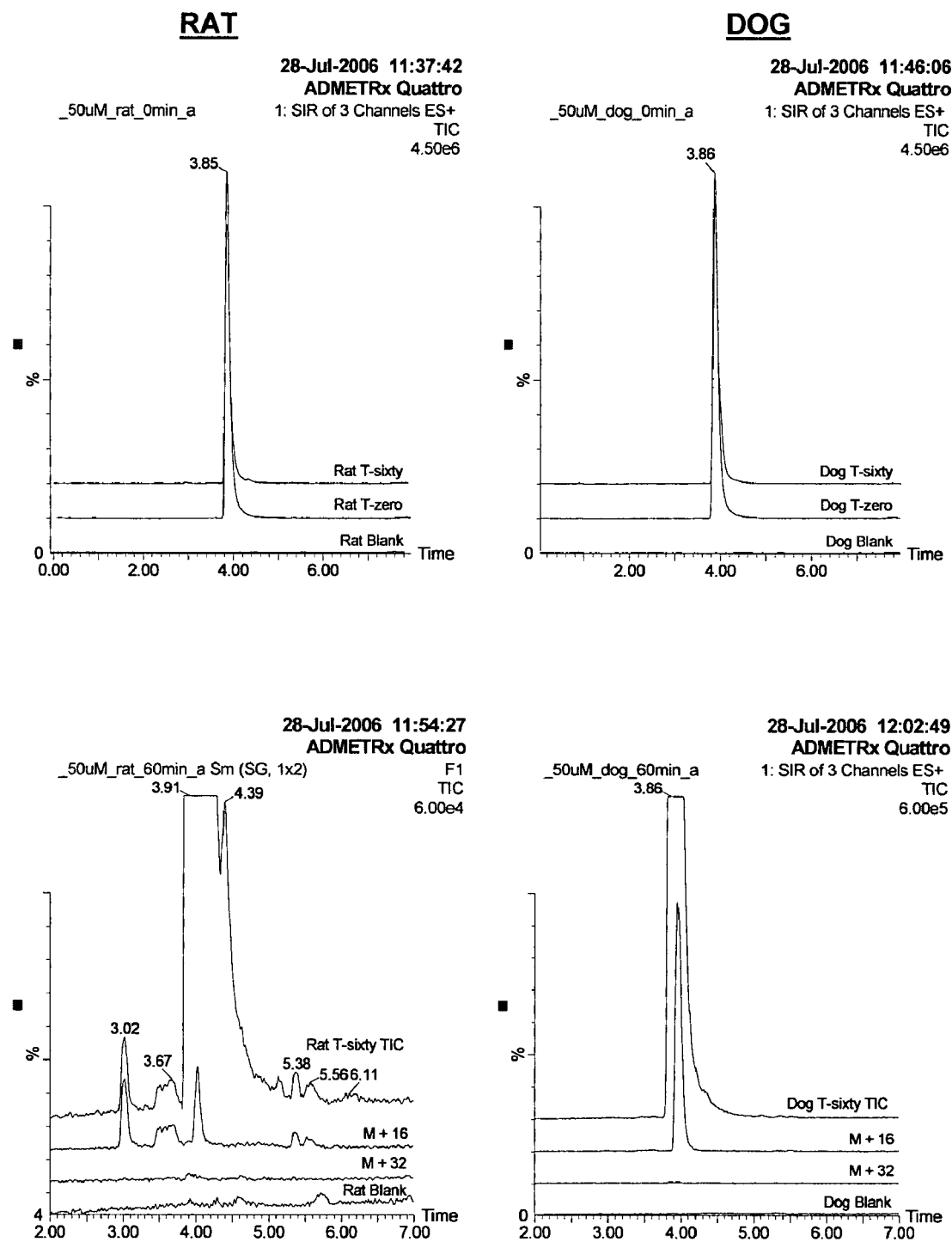
Figure 68: Microsomal Metabolism of COMP B in Rat and Dog

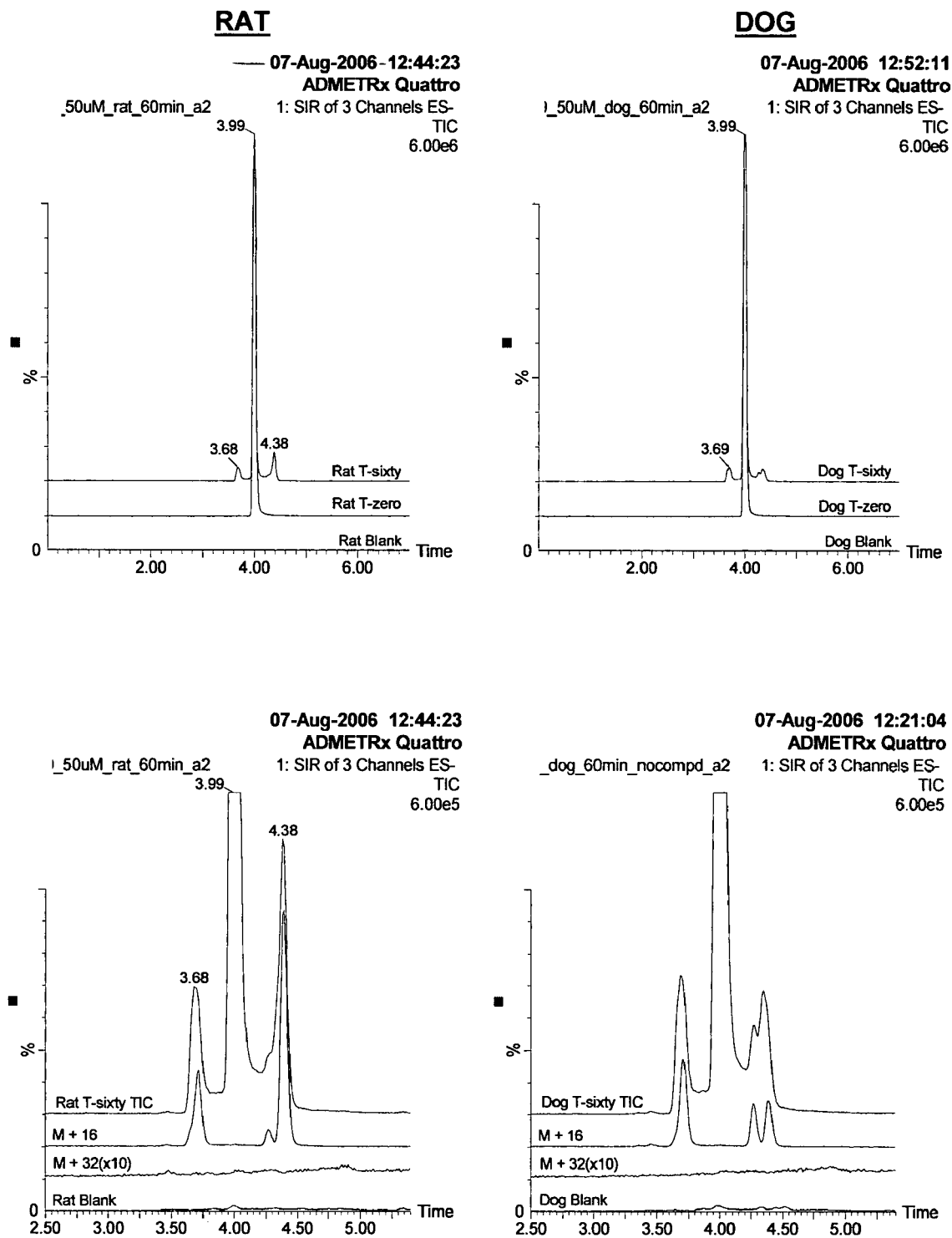
Figure 69: Microsomal Metabolism of COMP C in Rat and Dog

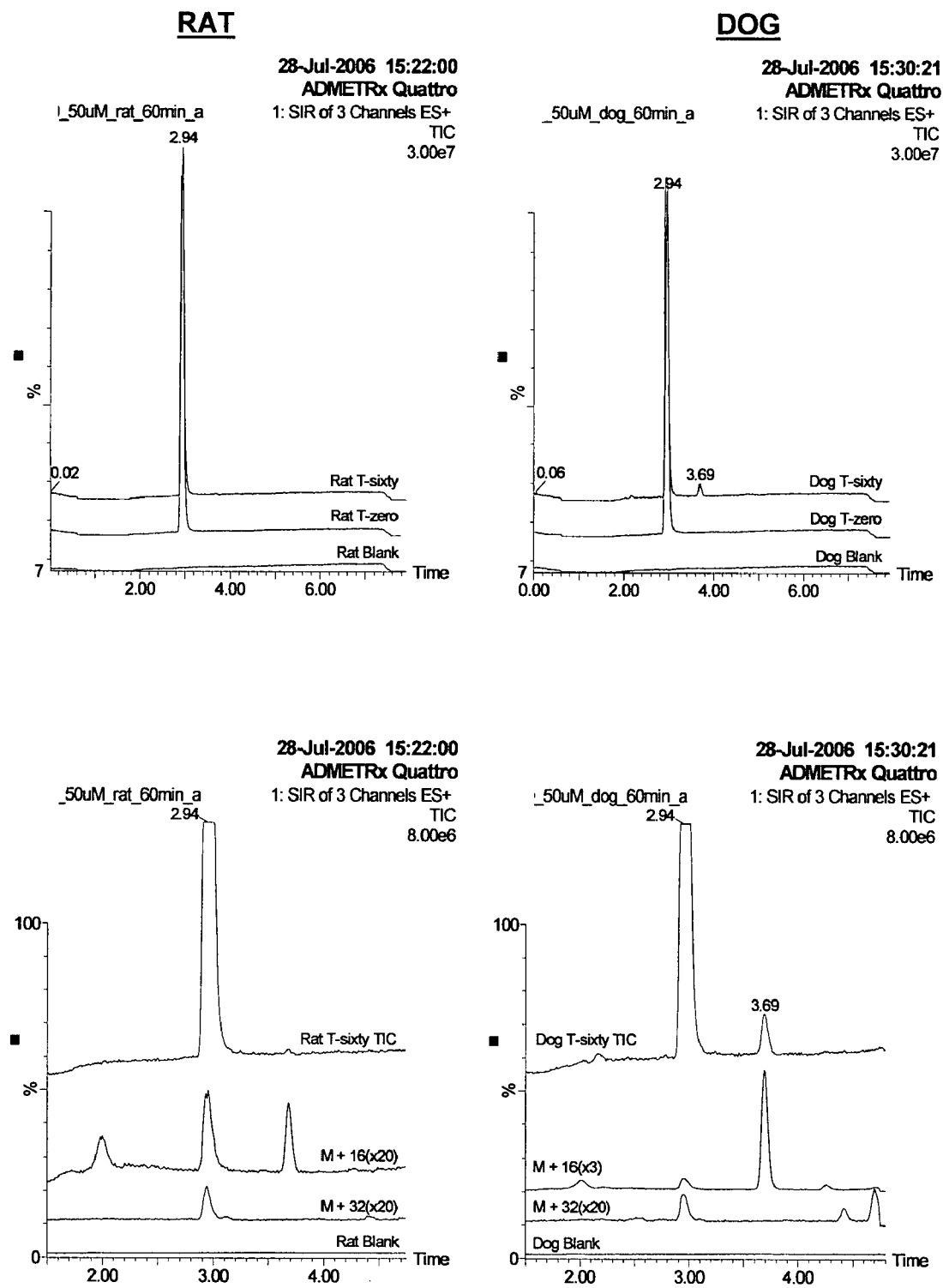
Figure 70: Microsomal Metabolism of COMP D in Rat and Dog

Figure 71: Microsomal Metabolism of COMP E in Rat and Dog
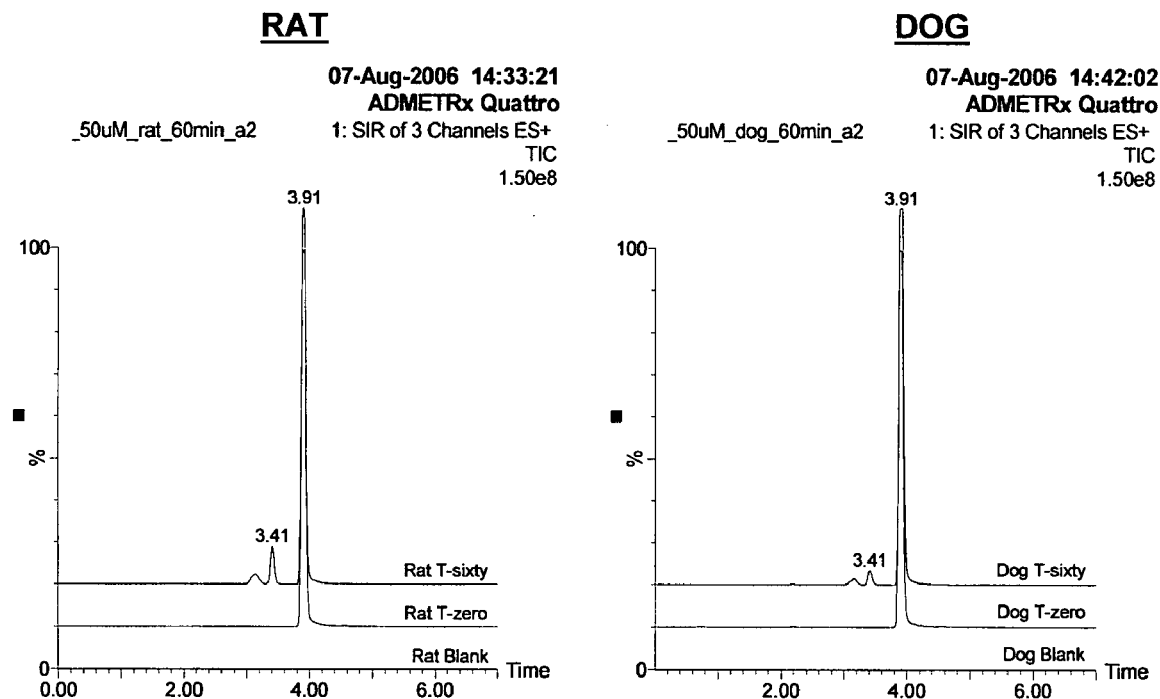
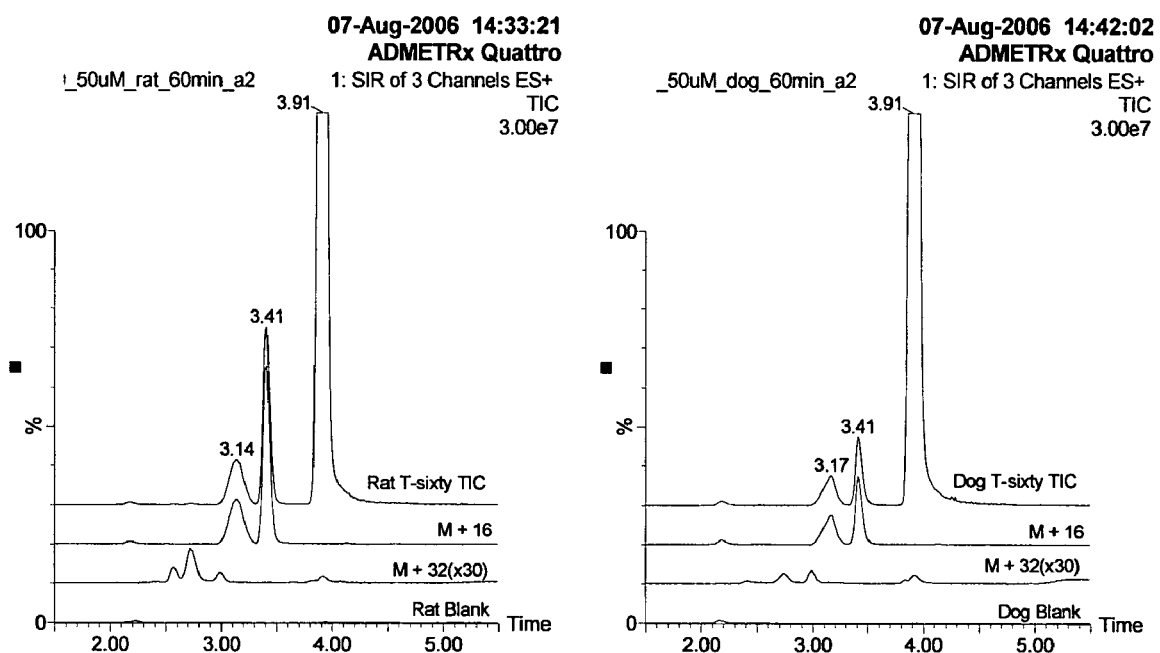

Figure 72:
COMP B Rat Primary Hepatocyte 48Hr (after 24Hr induction w/ 50μM PB+15μM BNF)
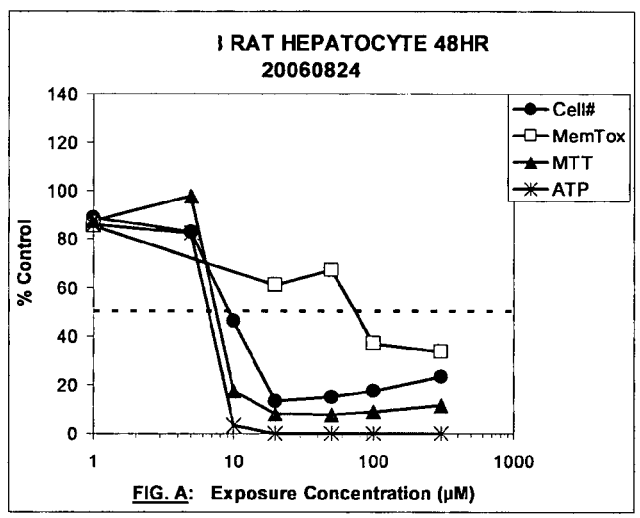
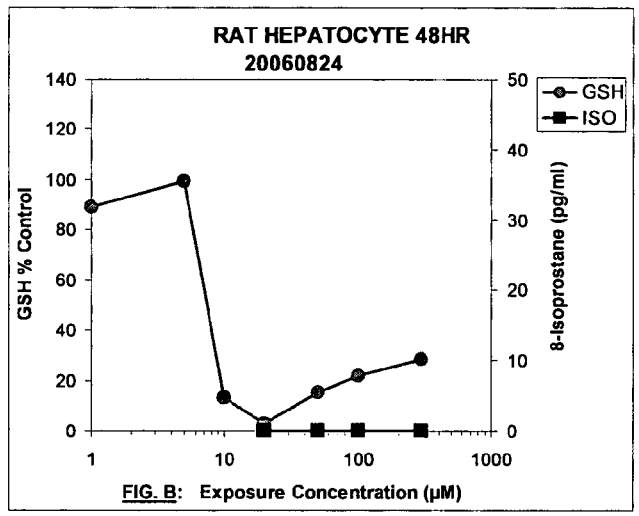
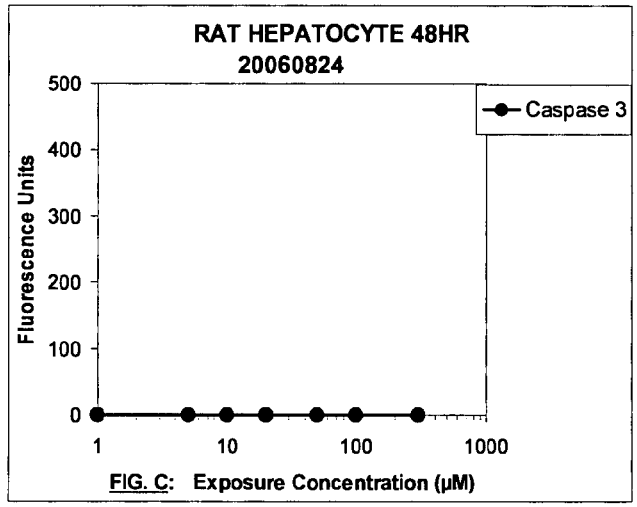

Figure 73: COMP D Rat Primary Hepatocyte 48Hr (after 24Hr induction w/ 50µM PB+15µM BNF)

NOTE: Compound interference in GSH assay at highest exposure concentration; also, potential compound interference at higher exposure concentrations for general tox assays.

Figure 74:
COMP B Dog Primary Hepatocyte 48Hr (after 24Hr induction w/ 50µM PB+15µM BNF)
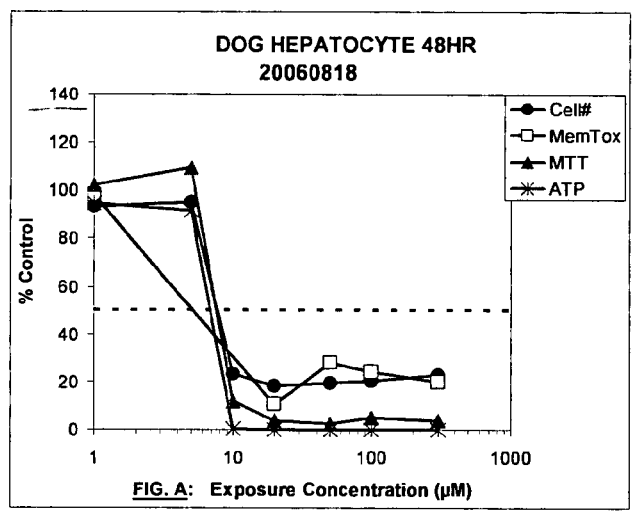
FIG. A: Exposure Concentration (µM)
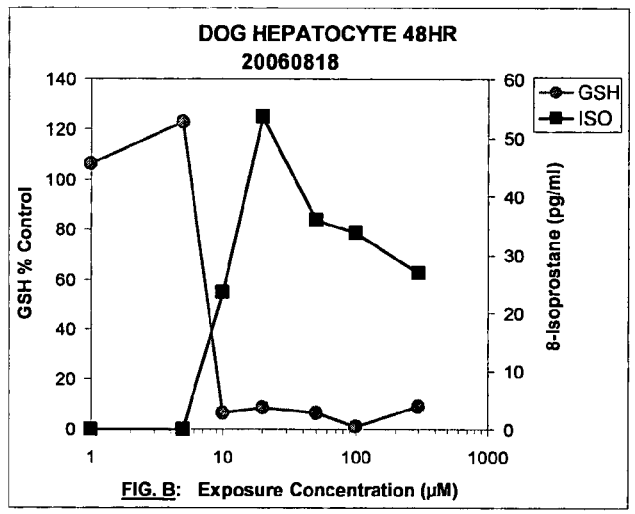
FIG. B: Exposure Concentration (µM)
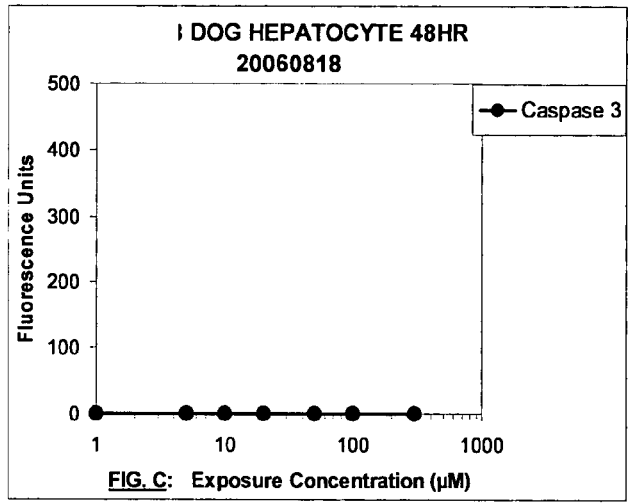
FIG. C: Exposure Concentration (µM)

Figure 75:
COMP D Dog Primary Hepatocyte 48Hr (after 24Hr induction w/ 50μM PB+15μM BNF)
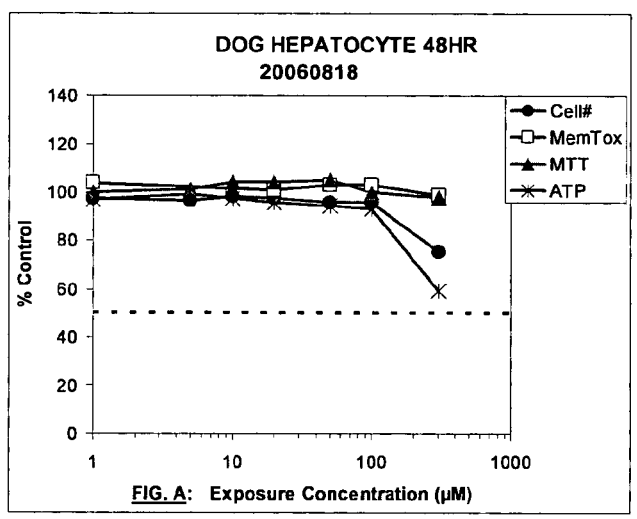
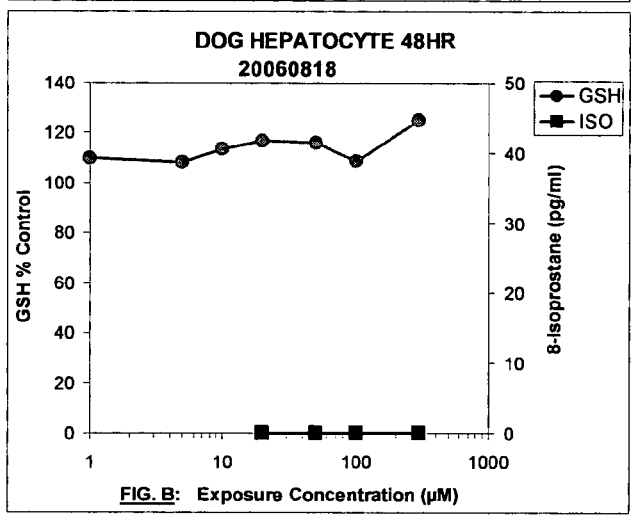
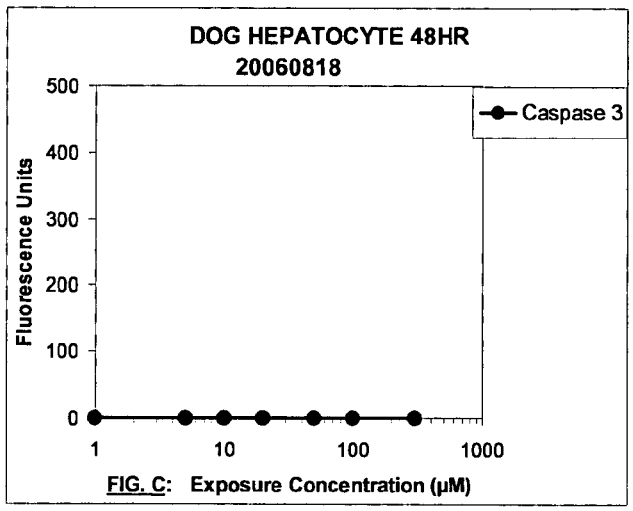

Figure 76A: COMP A 24Hr & 6Hr (Preliminary)
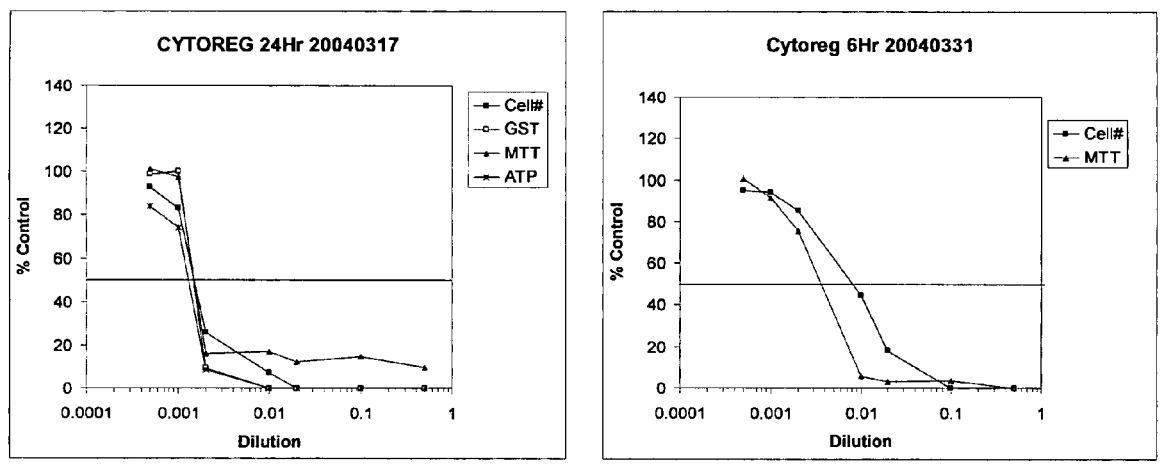
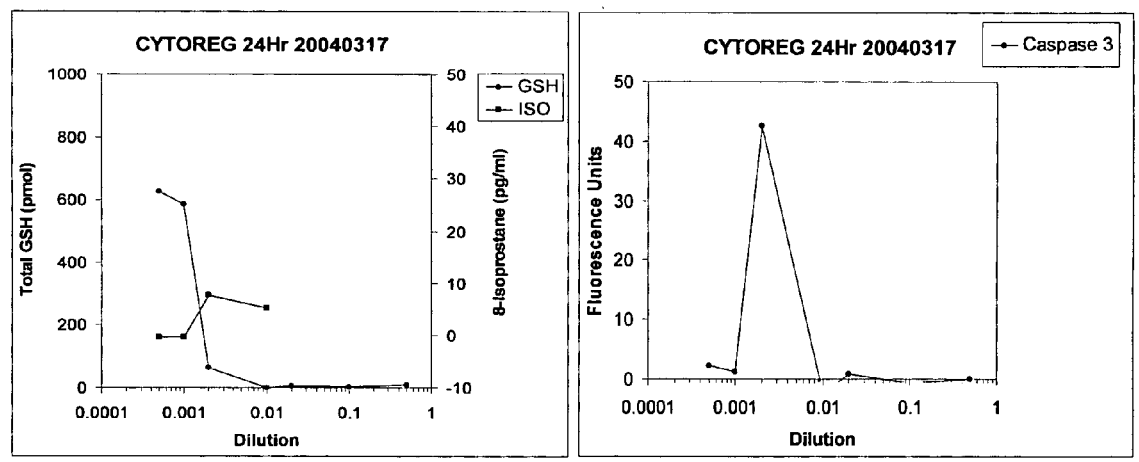

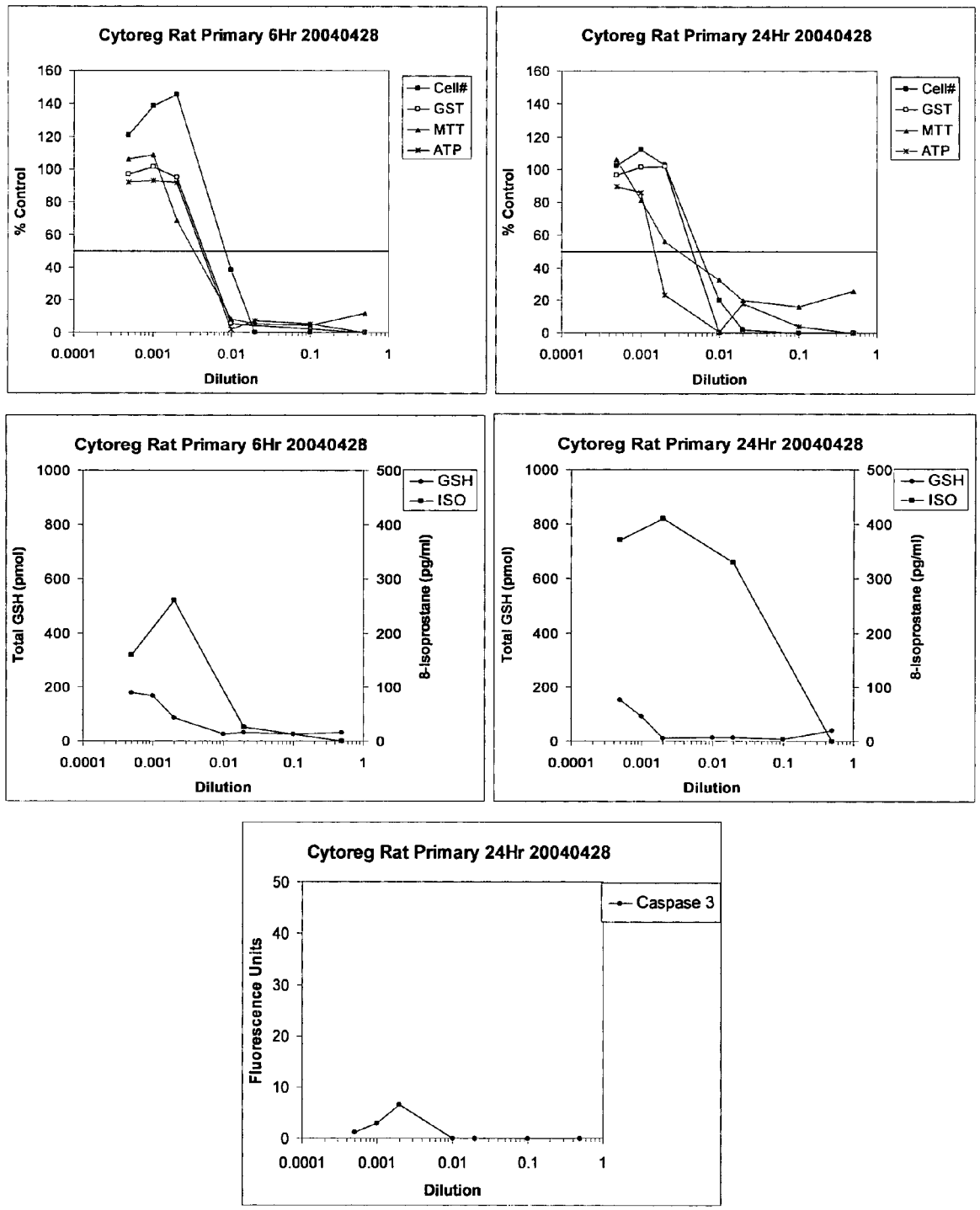
Figure 76B: Comp A in Rat Primary Hepatocytes (6 Hr and 24 Hr)

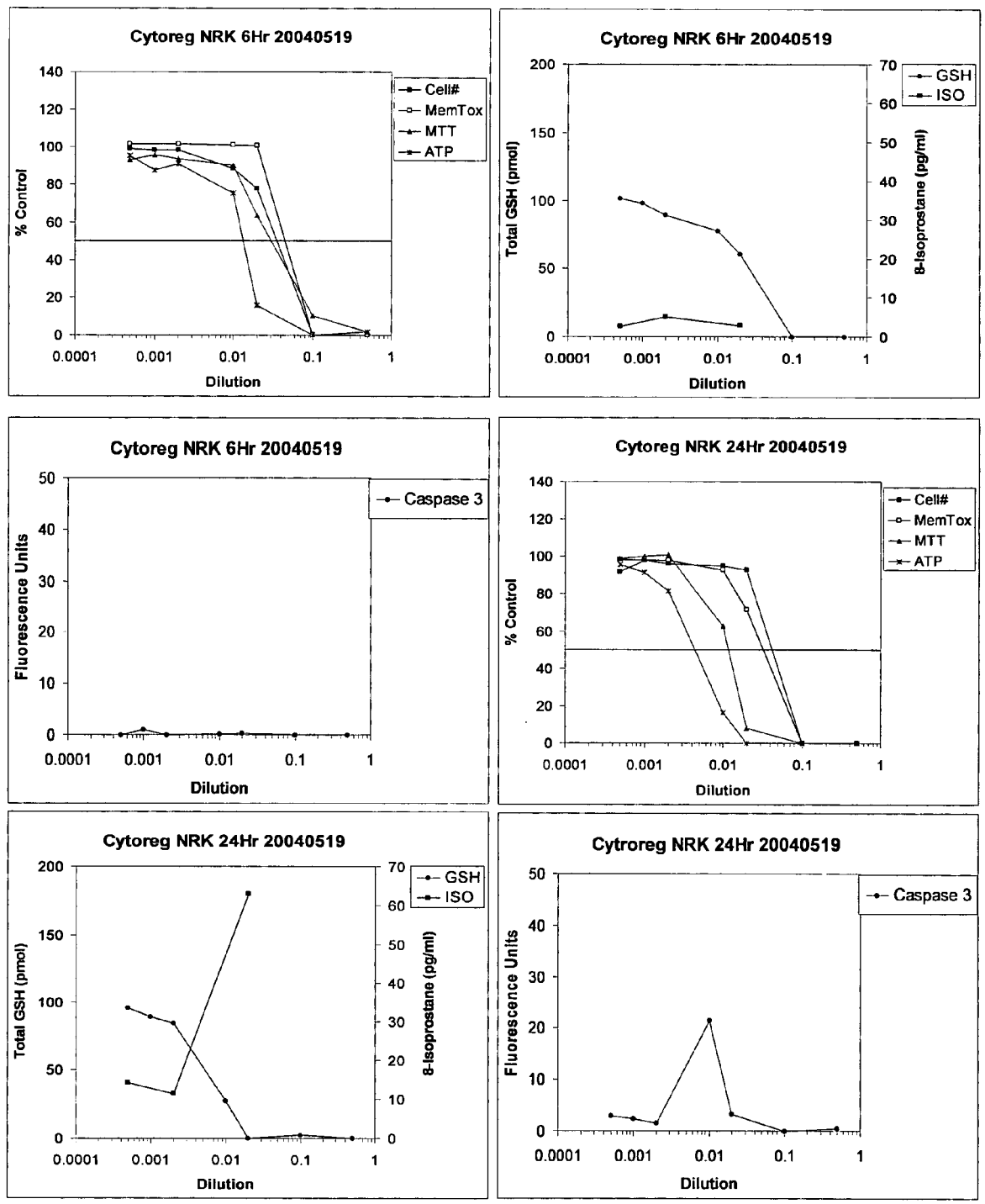

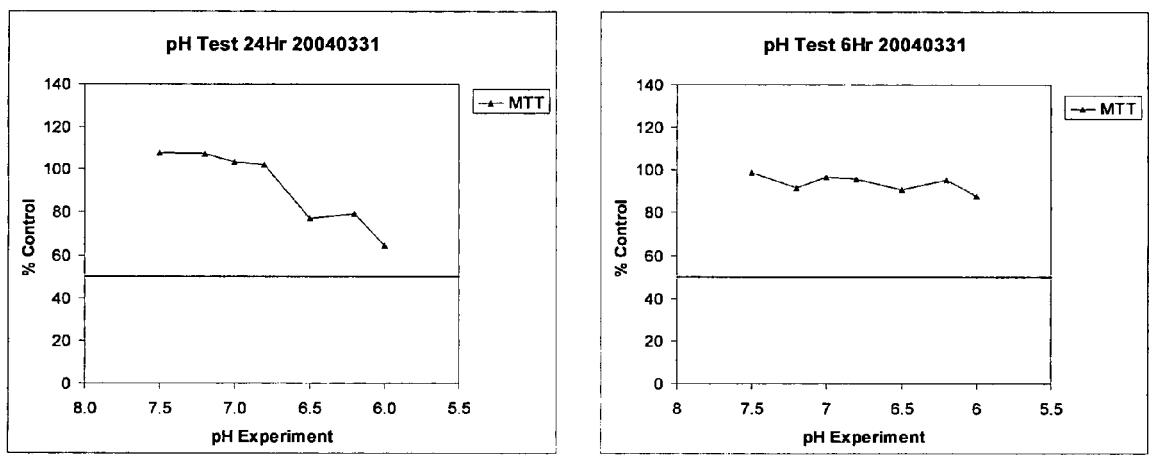
Figure 77A: pH EXPERIMENT 24Hr & 6Hr (Both Preliminary)

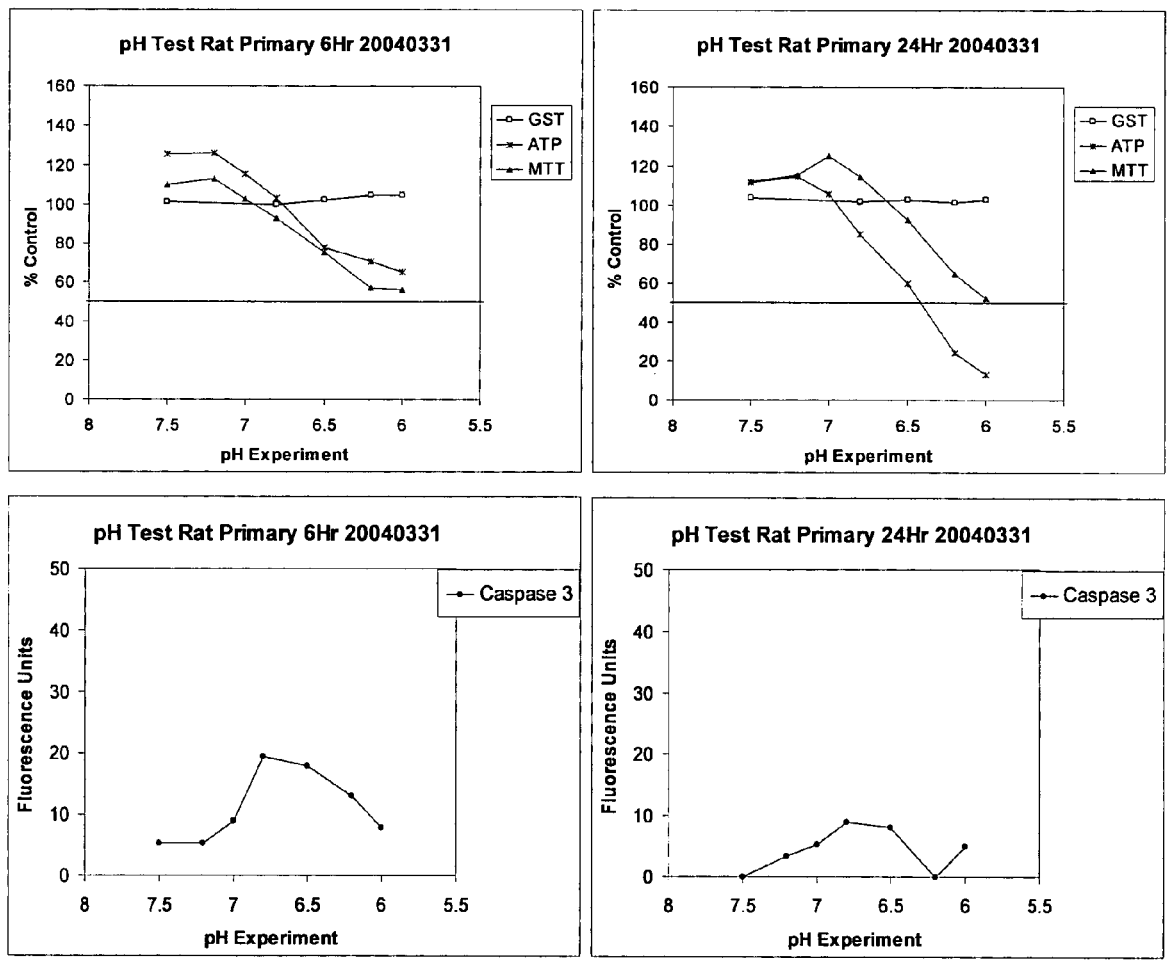
Figure 77B: pH Experiment in Rat Primary Hepatocytes (6 Hr and 24 Hr)

Figure 77C: pH Test NRK 6Hr
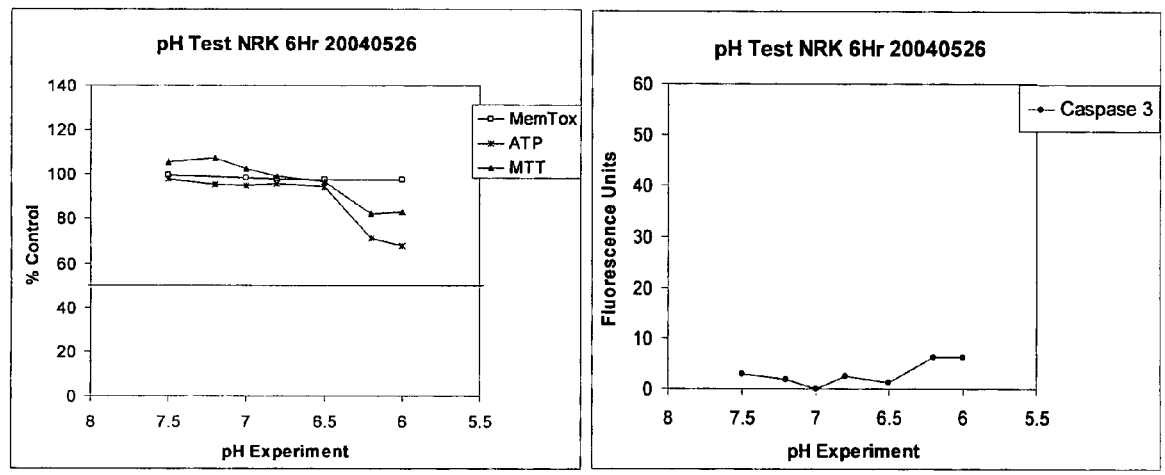
pH Test NRK 24Hr
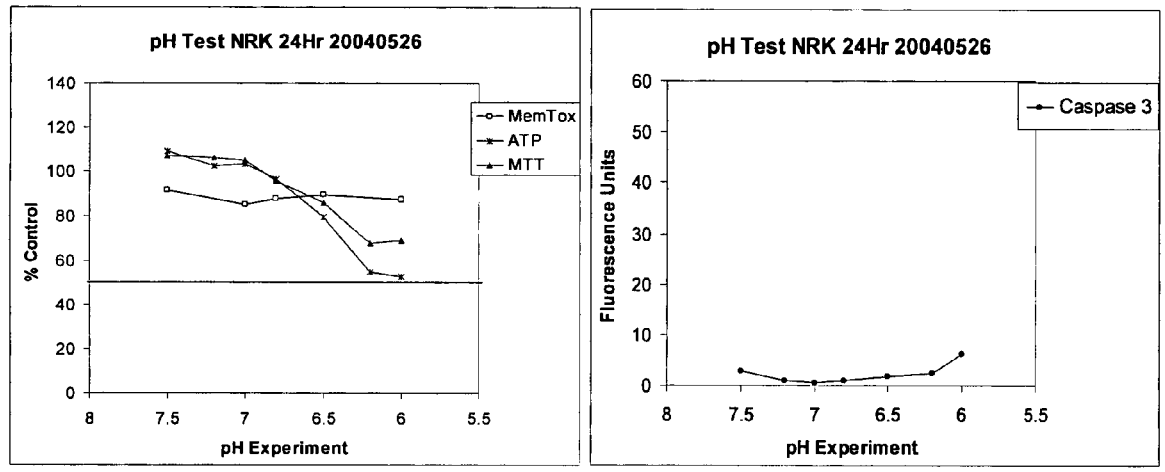

Figure 78: Camptothecin NRK 6Hr
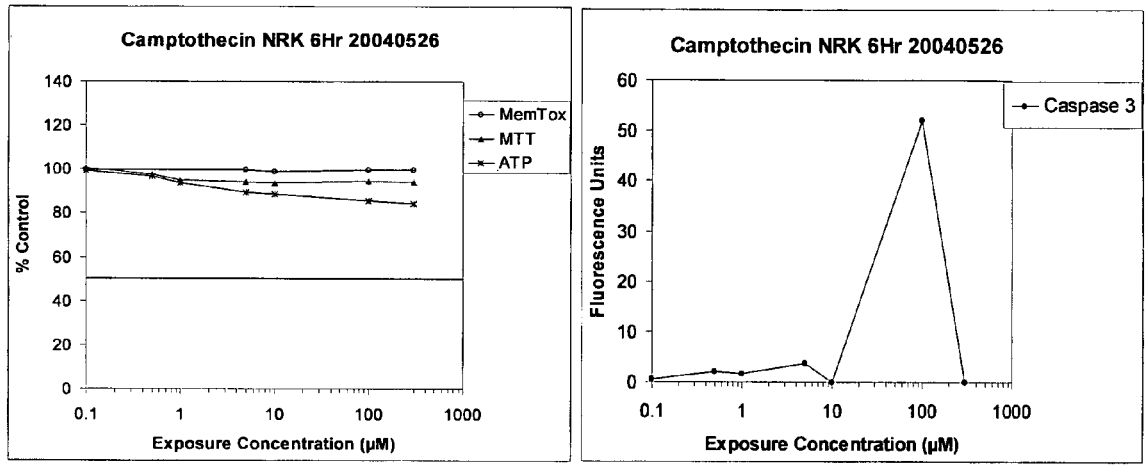
Figure 79: Camptothecin NRK 24Hr
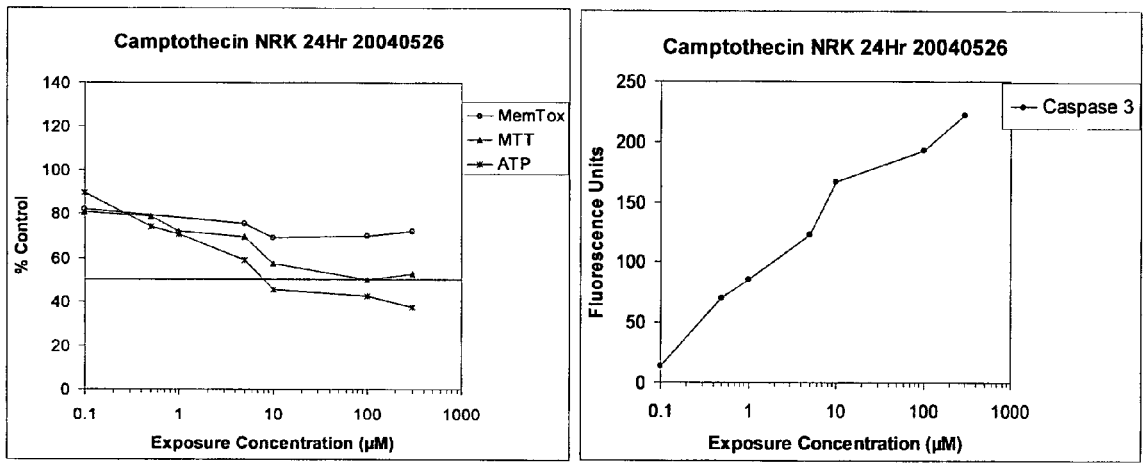
Figure 80: Rotenone NRK 6Hr
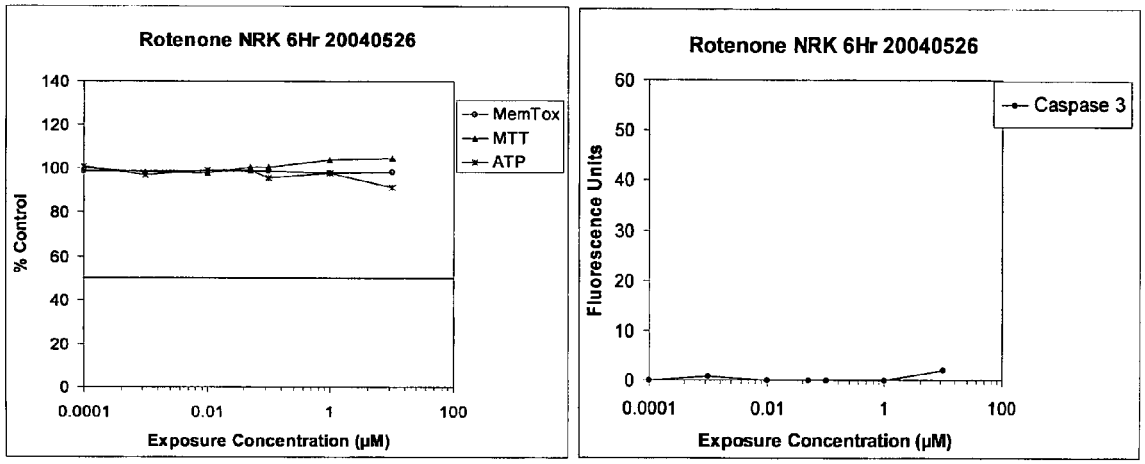

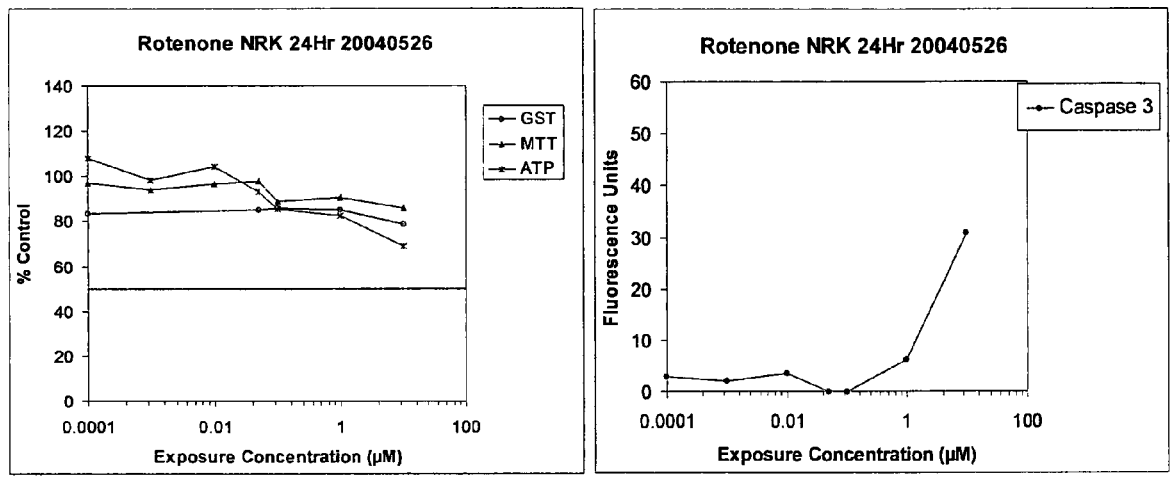
Figure 81: Rotenone NRK 24Hr
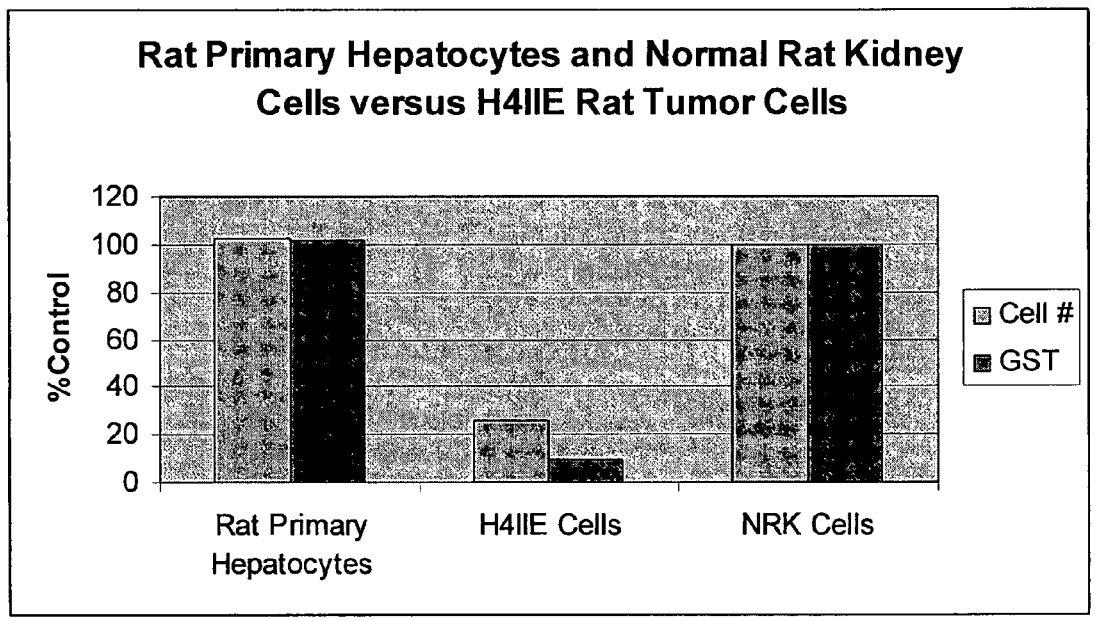
FIGURE 82
NRK = Normal Rat Kidney Cells

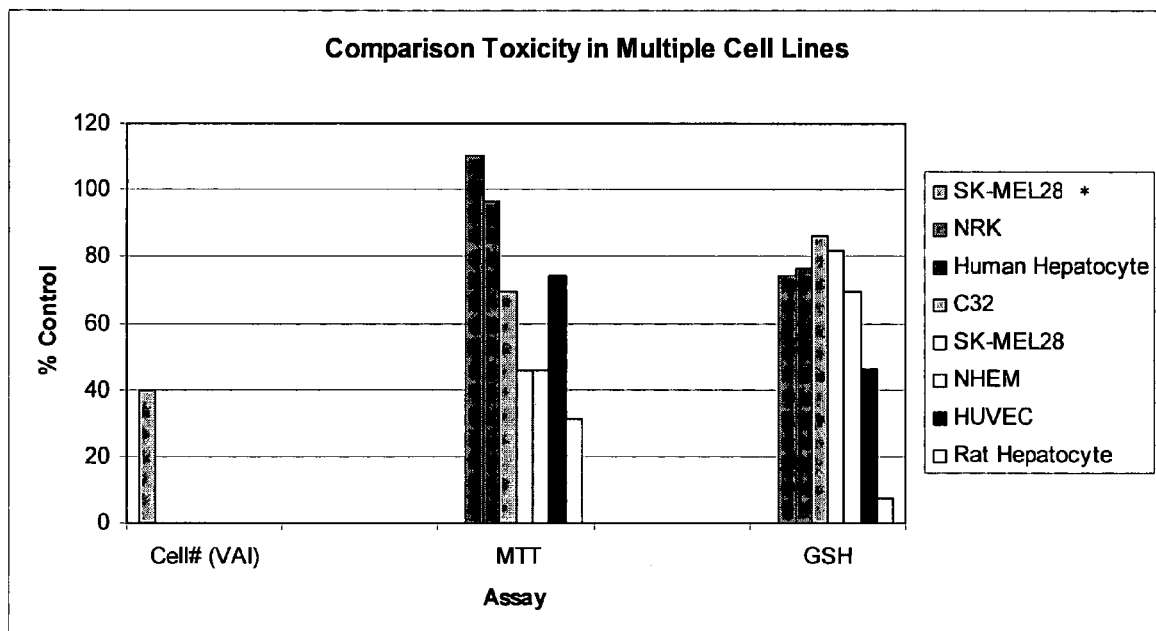
Figure 83: COMP A SK-MEL28 24HR MTT and GSH COMPARISON TOXICITY in MULTIPLE CELL LINES Figure 84: COMP A SK-MEL28 24HR and MTT COMBINED LOW / HIGH EXPOSURES
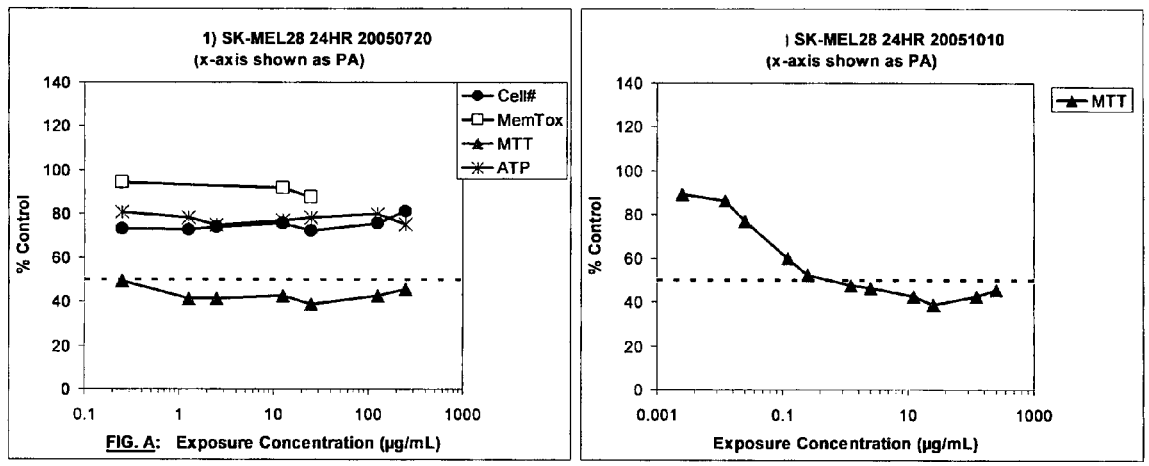
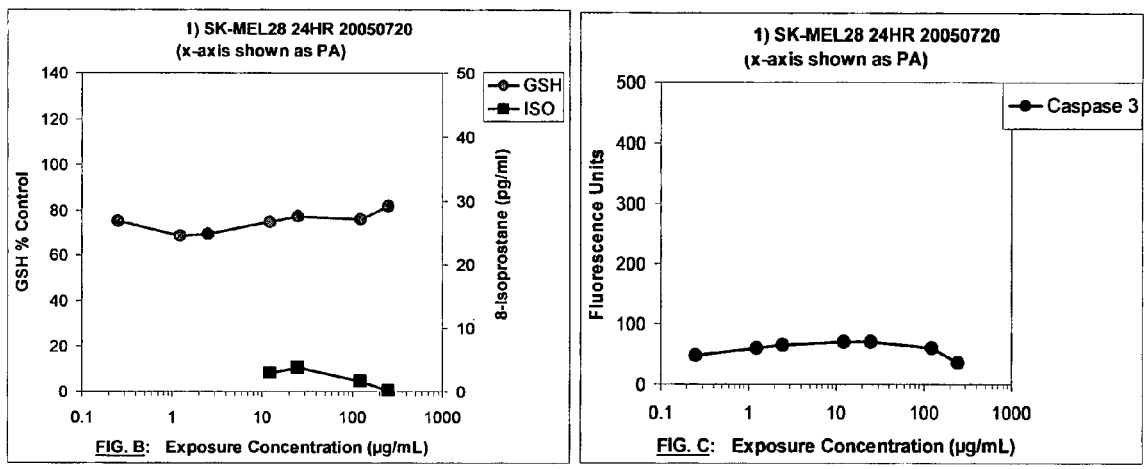

Figure 85: COMP A (Low Dose Exposure) SK-MEL28 24HR and 72HR
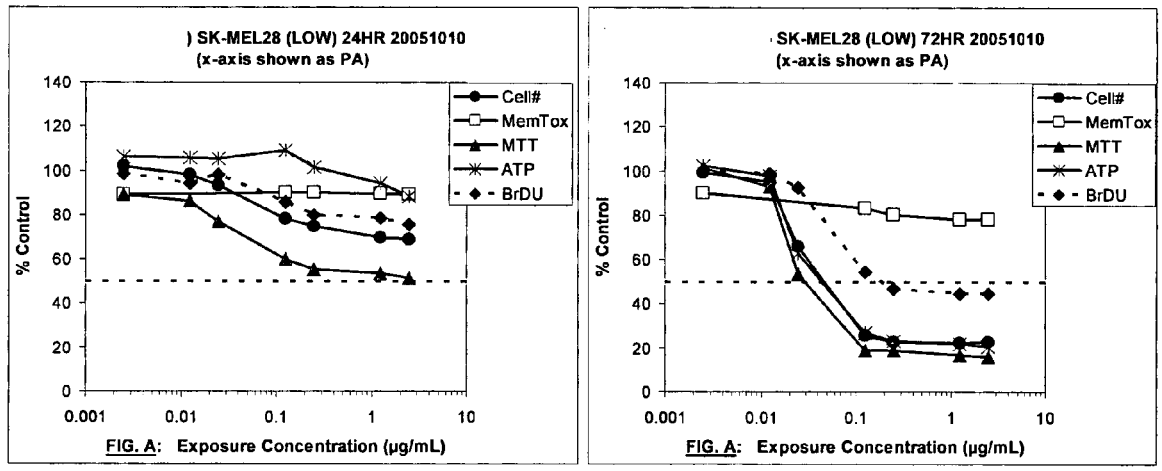
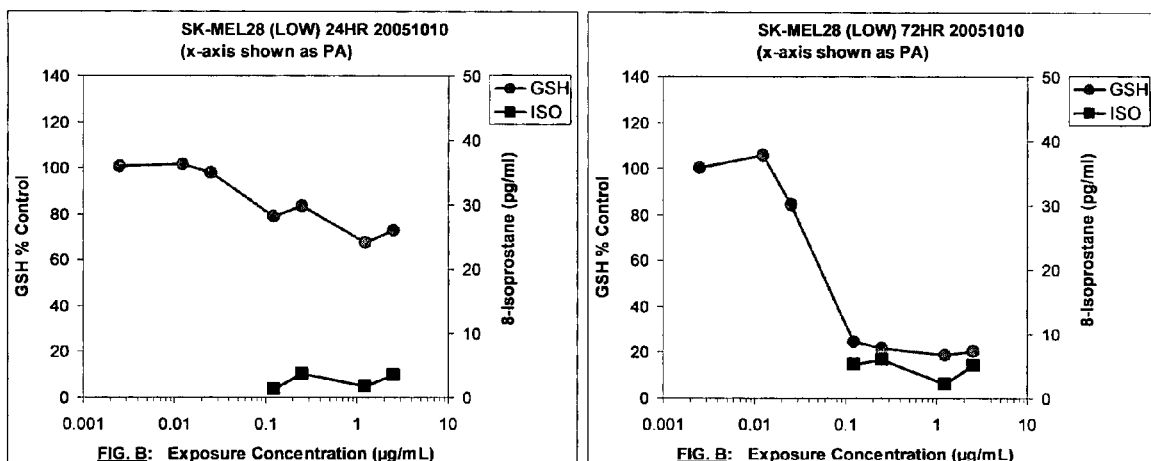
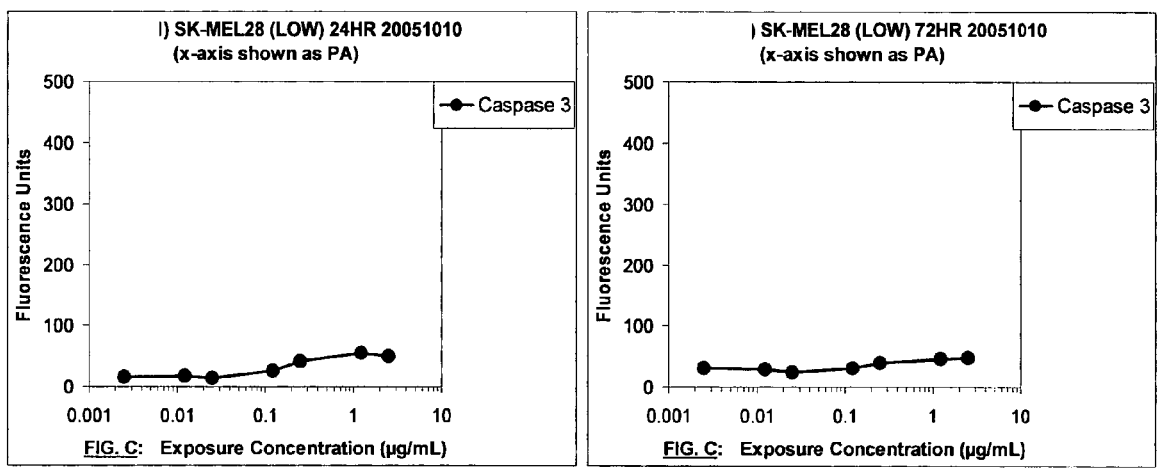

Figure 86: COMP A HUMAN HEPATOCYTE 24HR
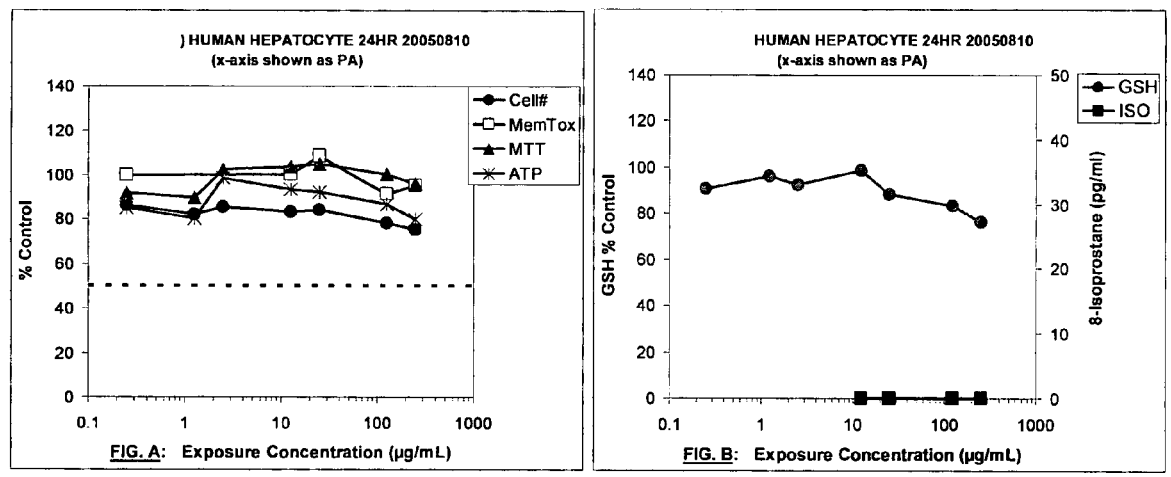
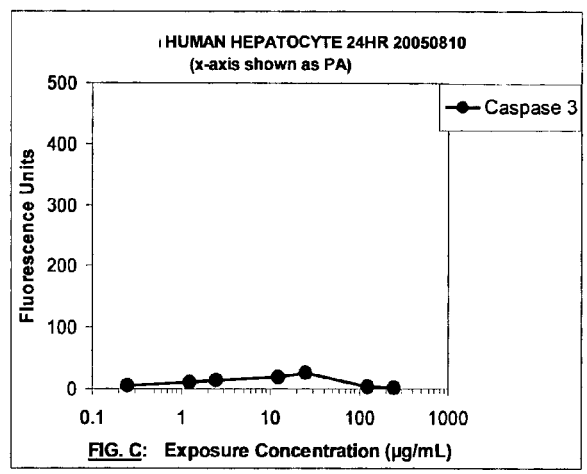

Figure 87: COMP A HUVEC 24HR
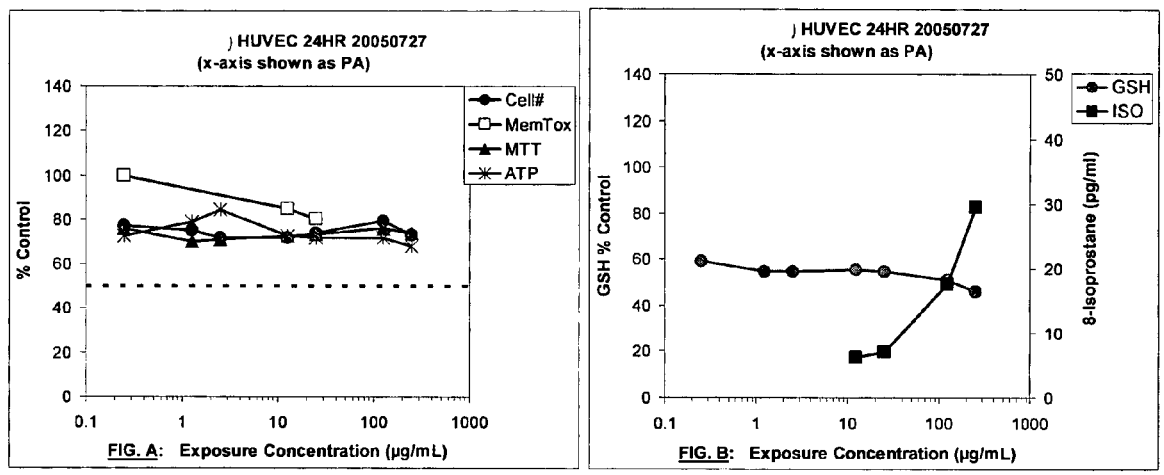
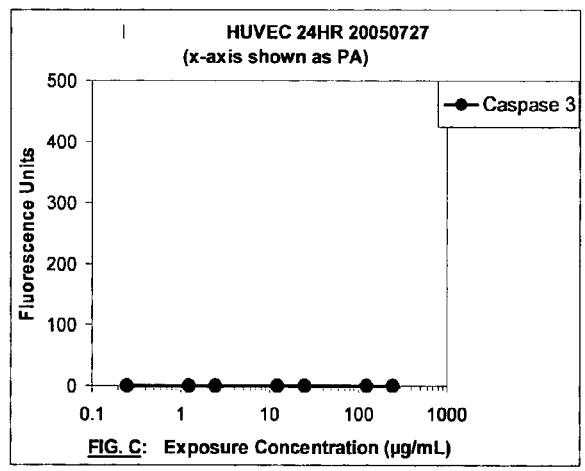

Figure 88: COMP A C32 24HR
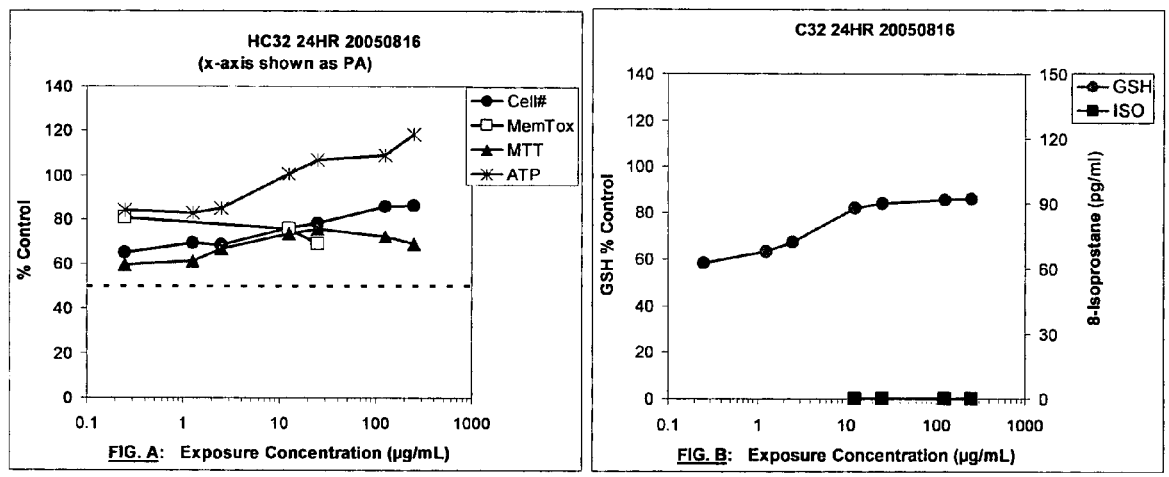
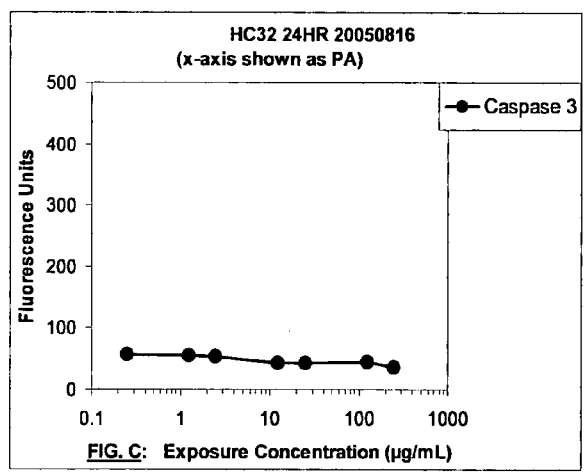

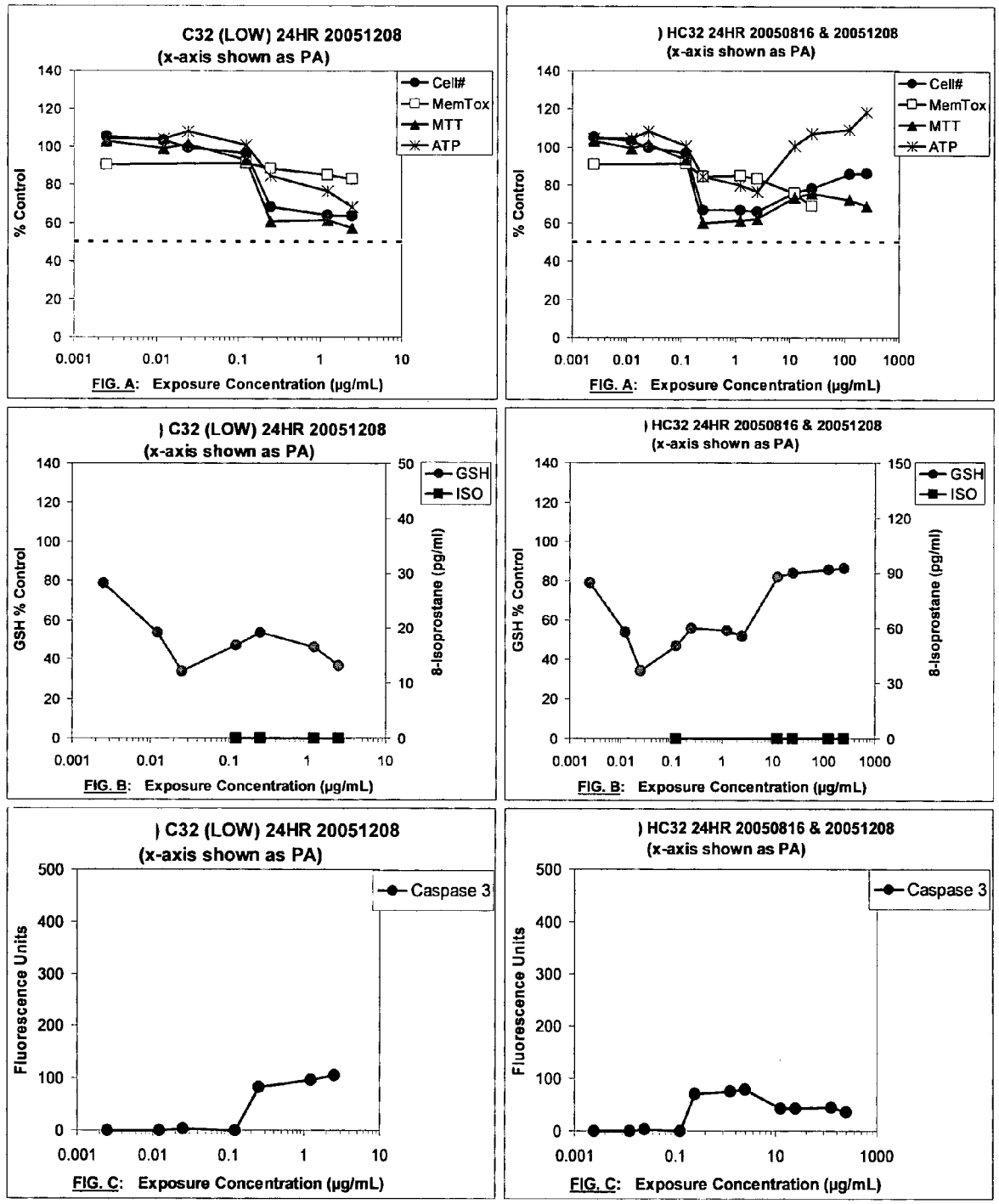
Figure 89: COMP A C32 (LOW) 24HR and COMBINED LOW / HIGH EXPOSURES

Figure 90: COMP A NHEM 24HR
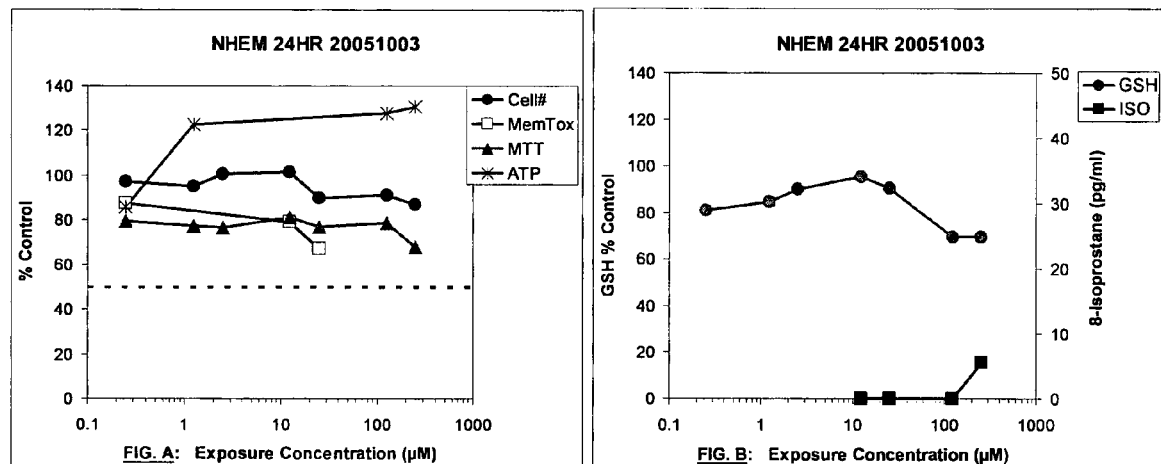
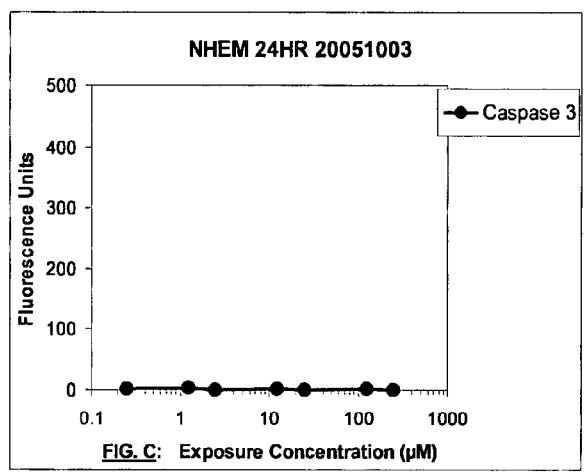

Figure 91: CAMPTOTHECIN SK-MEL28 24HR
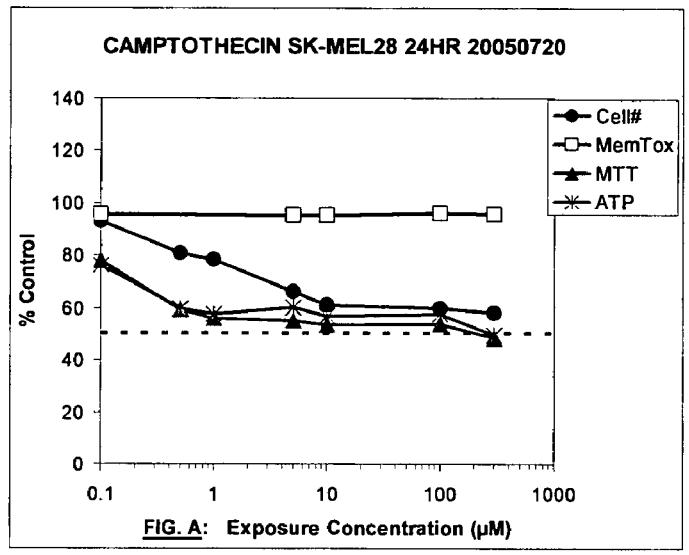
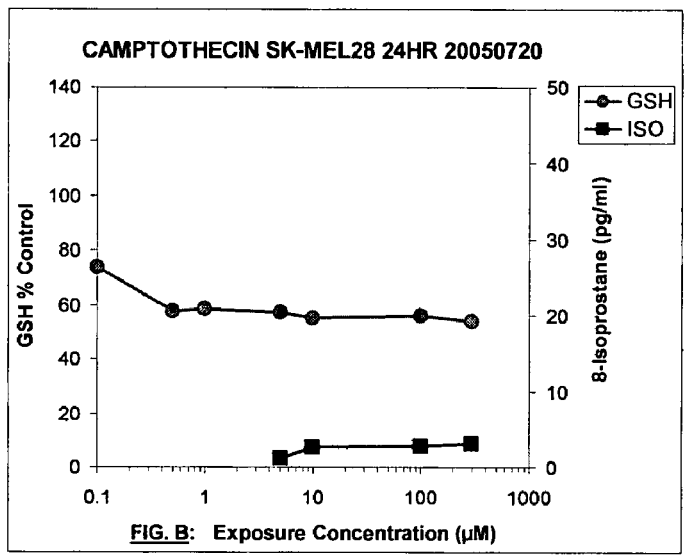
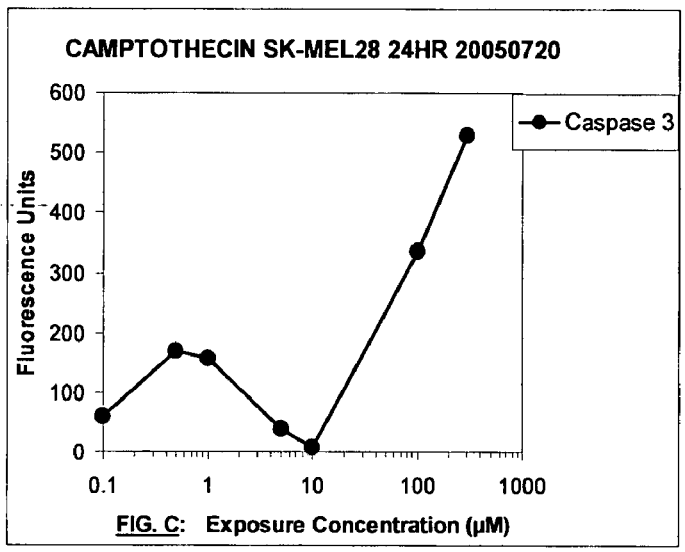

Figure 92: CAMPTOTHECIN #2 SK-MEL28 24HR and 72HR
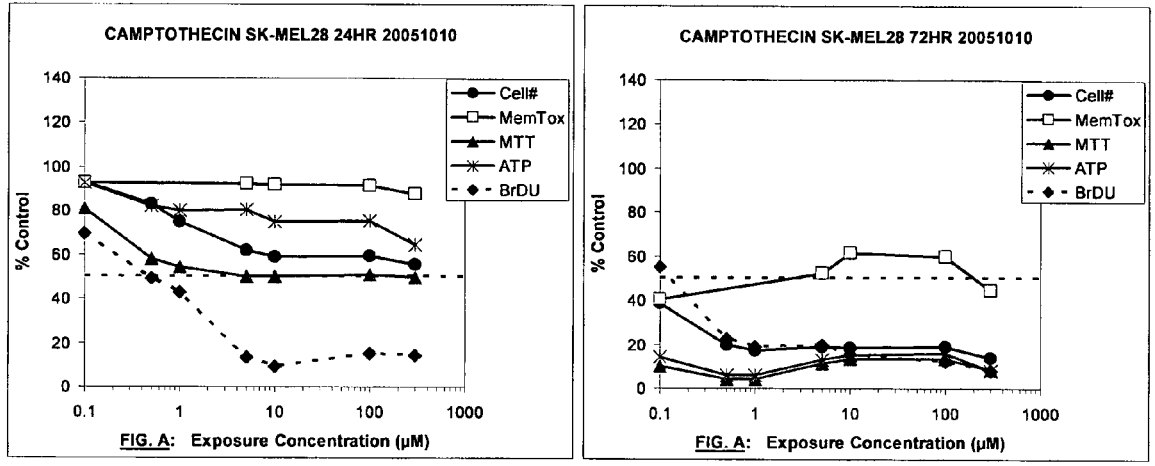
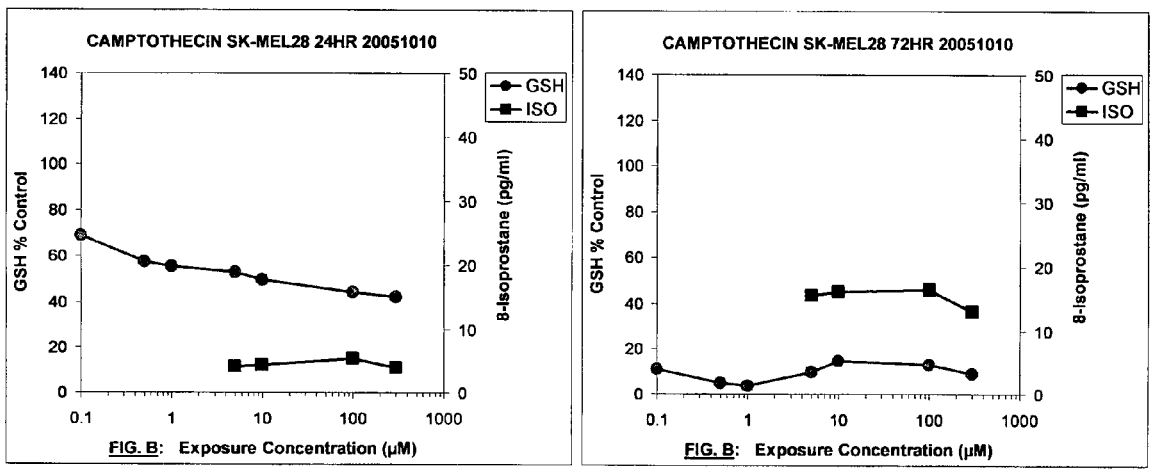
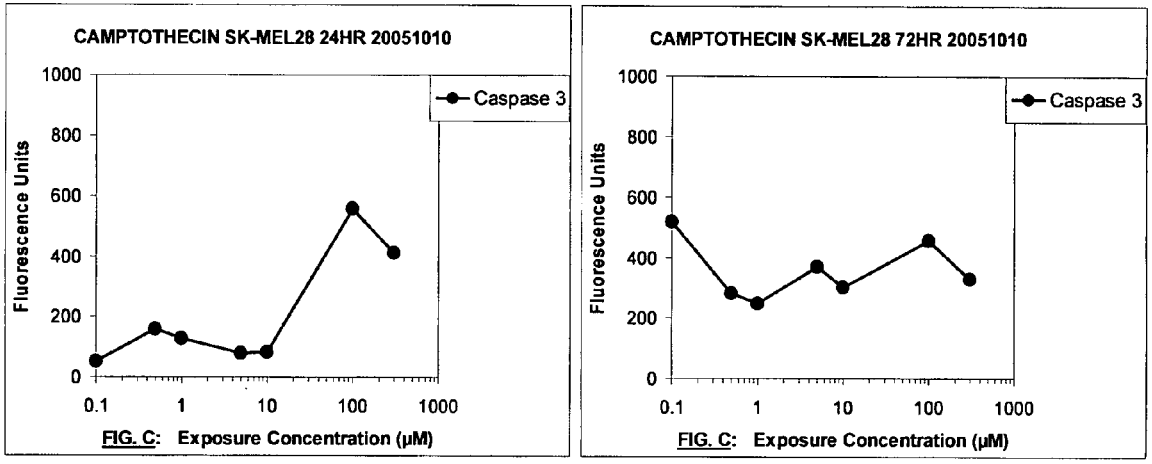

Figure 93: CAMPTOTHECIN HUMAN HEPATOCYTE 24HR
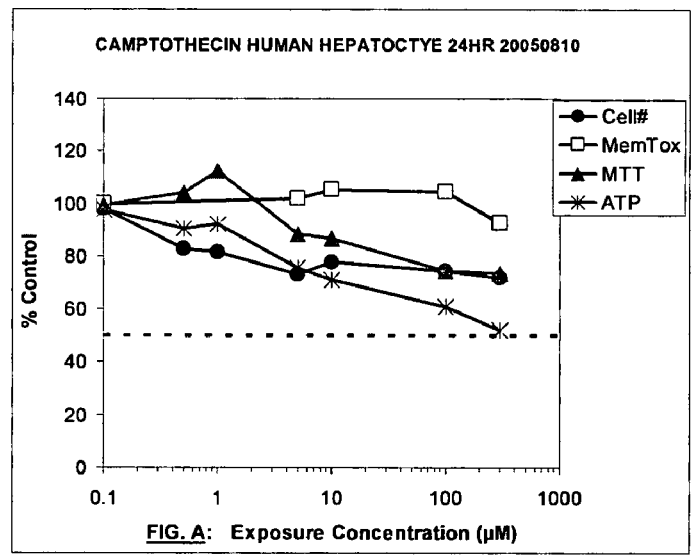
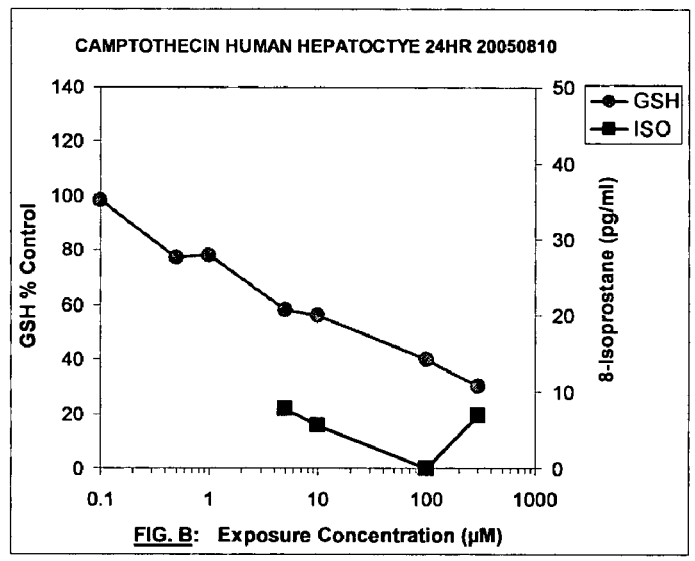
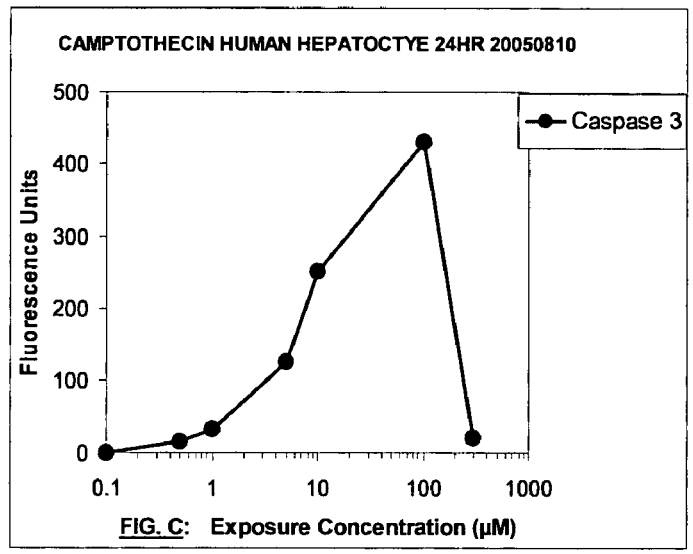

Figure 94: CAMPTOTHECIN HUVEC 24HR
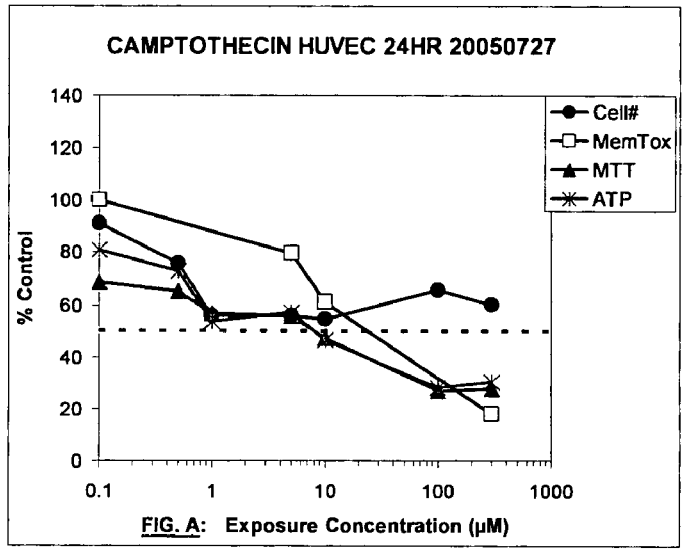
FIG. A: Exposure Concentration (μM)
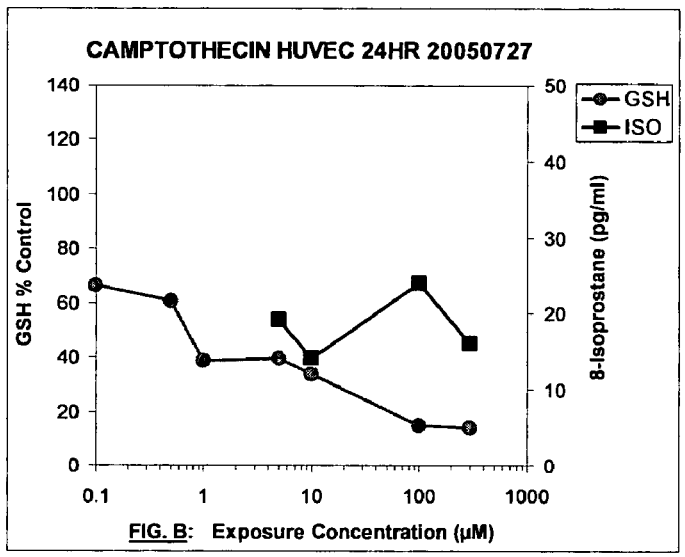
FIG. B: Exposure Concentration (μM)
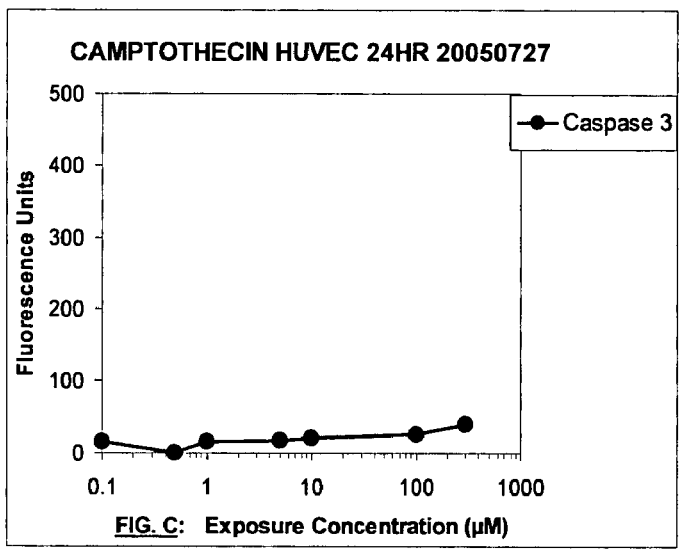
FIG. C: Exposure Concentration (μM)

Figure 95: CAMPTOTHECIN C32 24HR
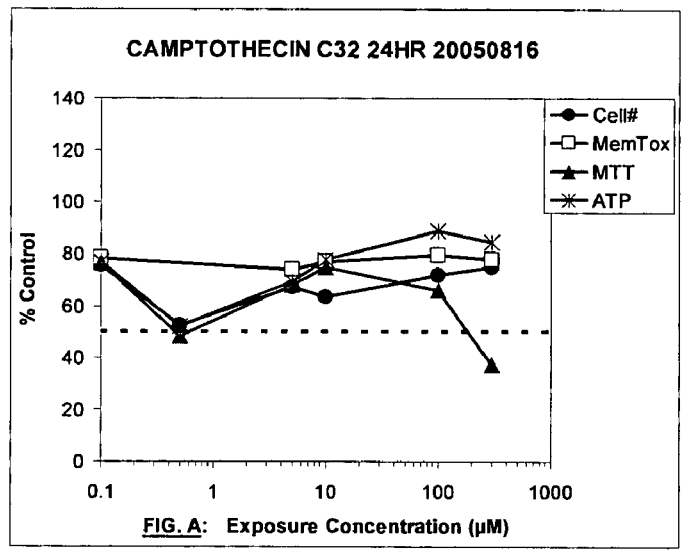
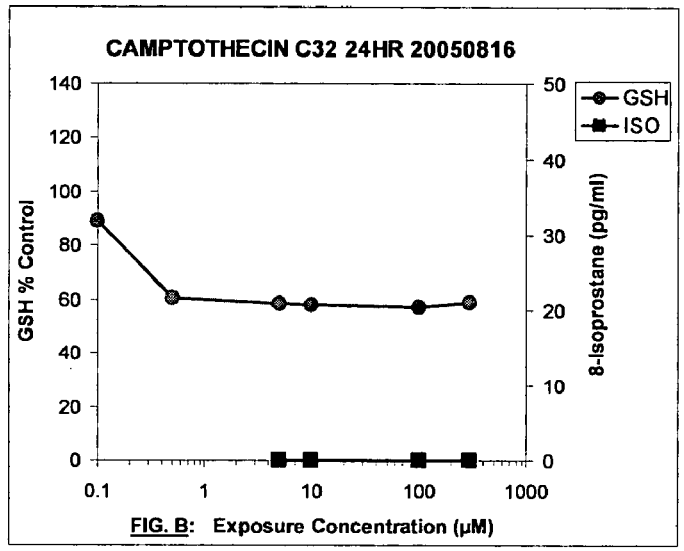
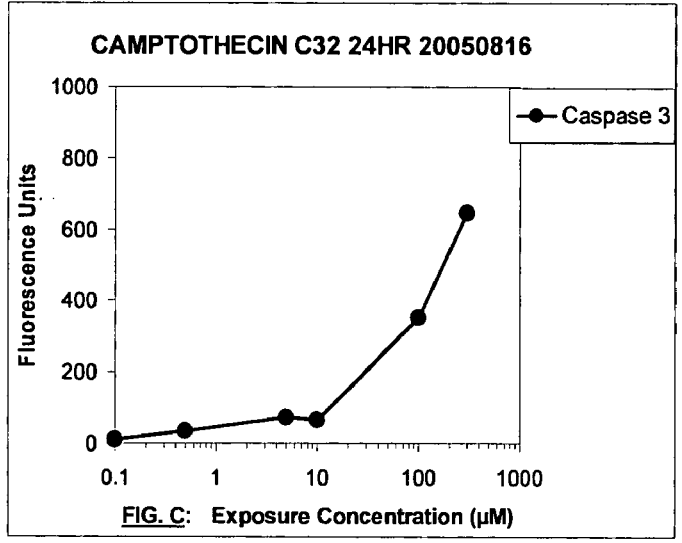

Figure 96: CAMPTOTHECIN NHEM 24HR
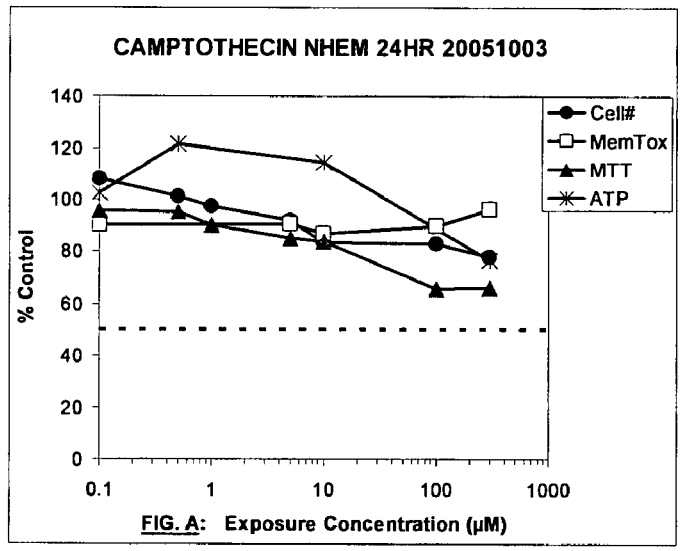
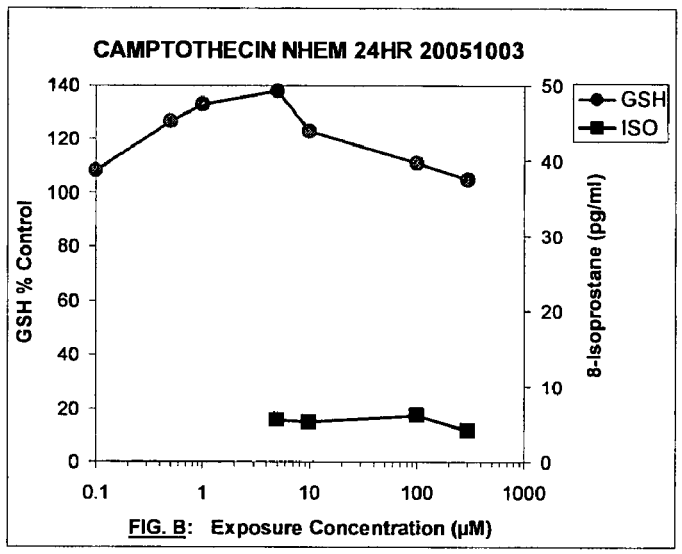
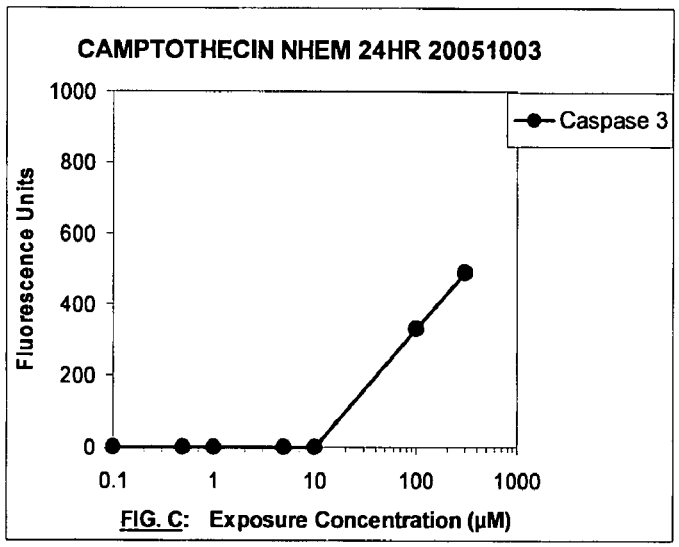

Figure 97: ROTENONE SK-MEL28 24HR
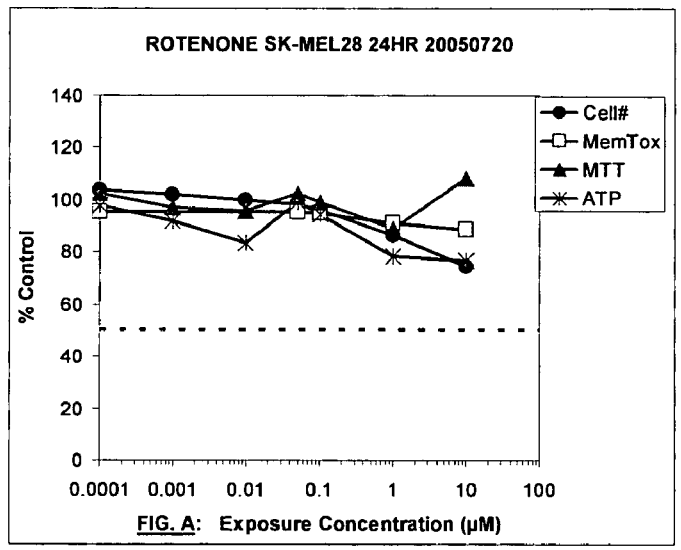
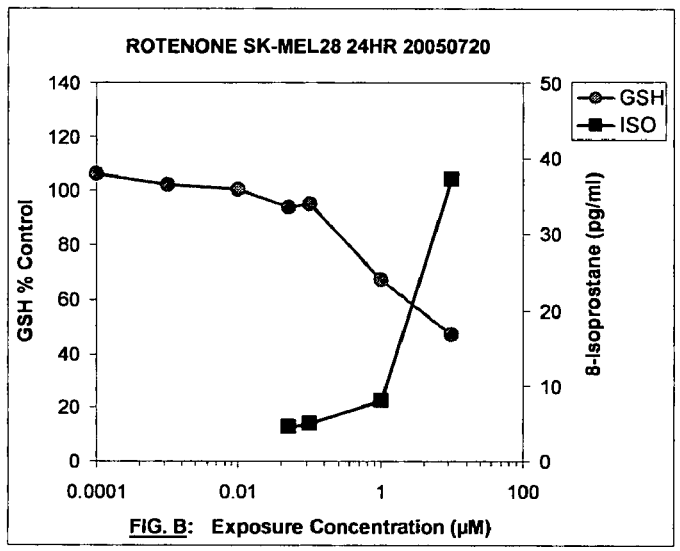
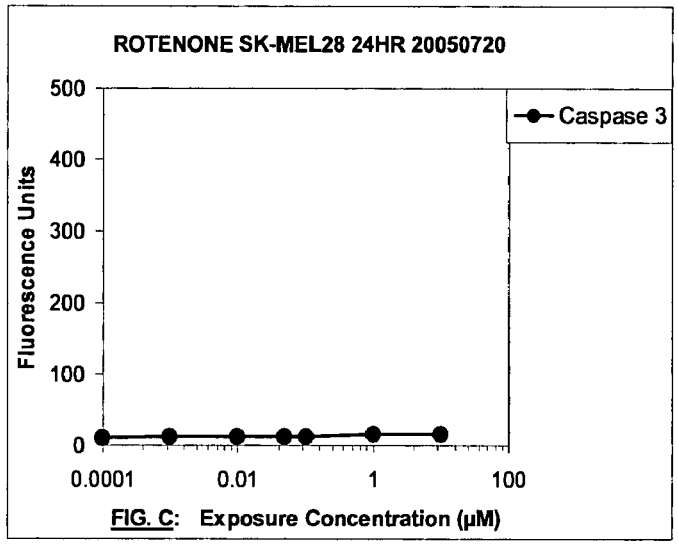

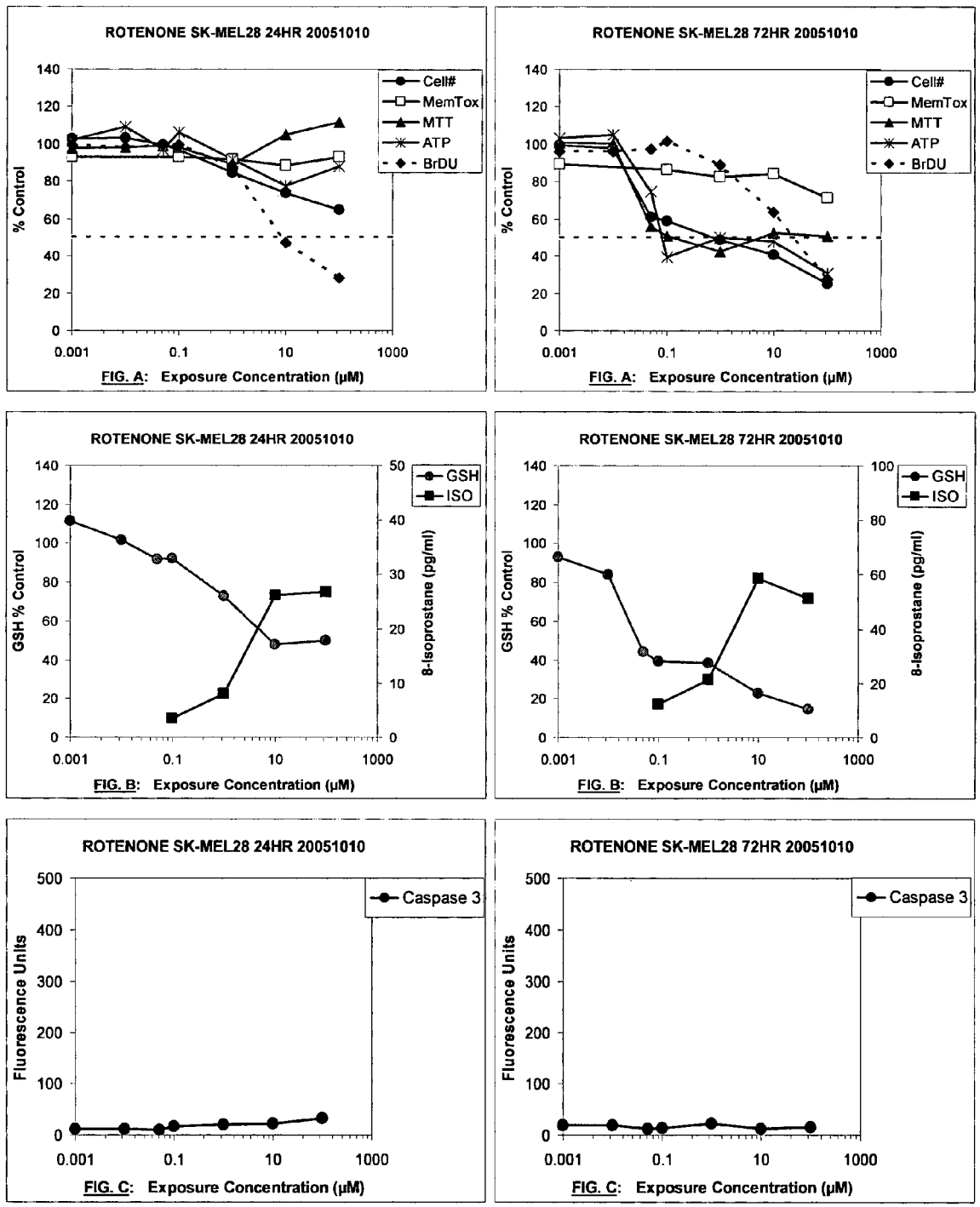
Figure 98: ROTENONE #2 SK-MEL28 24HR and 72HR

Figure 99: ROTENONE HUMAN HEPATOCYTE 24HR
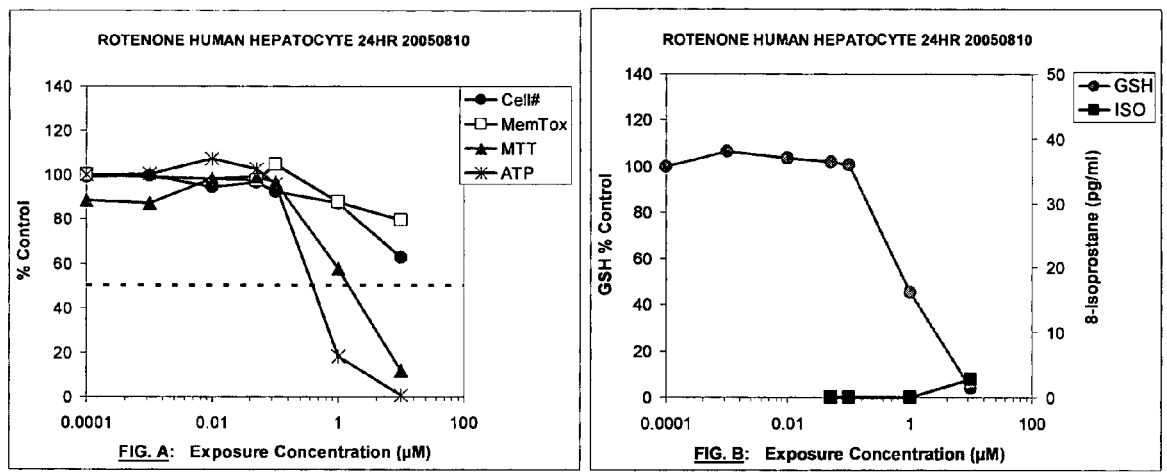
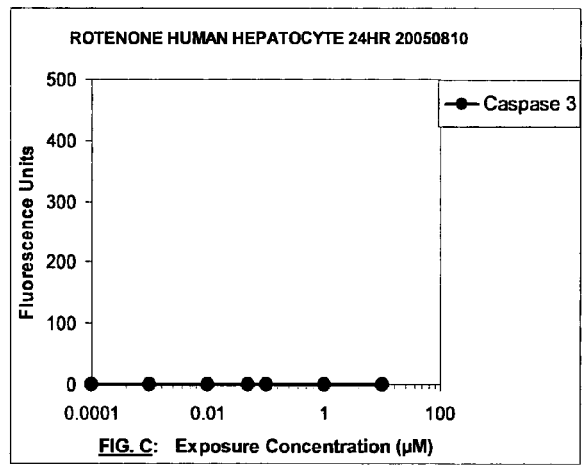

Figure 100: ROTENONE HUVEC 24HR
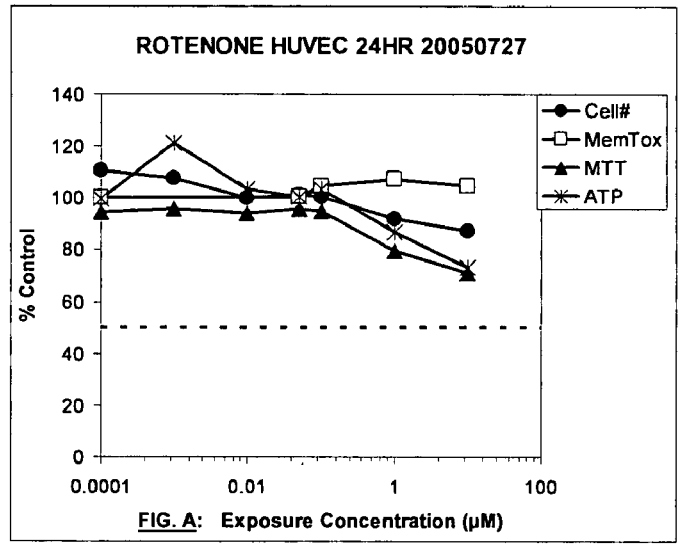
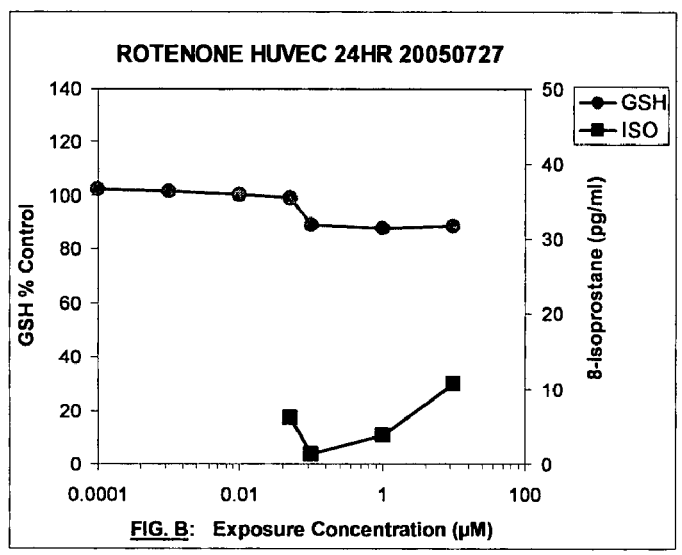
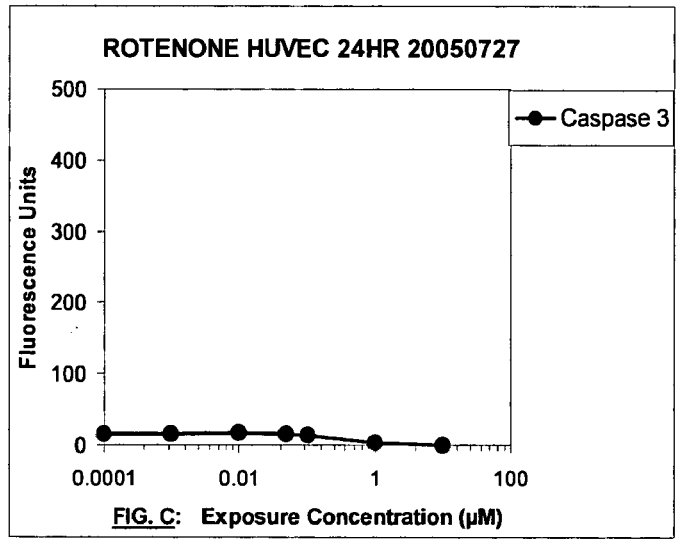

Figure 101: ROTENONE C32 24HR
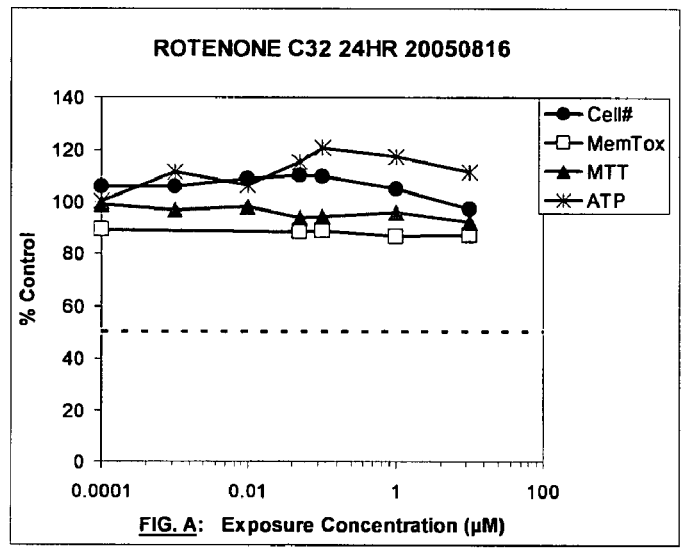
FIG. A: Exposure Concentration (μM)
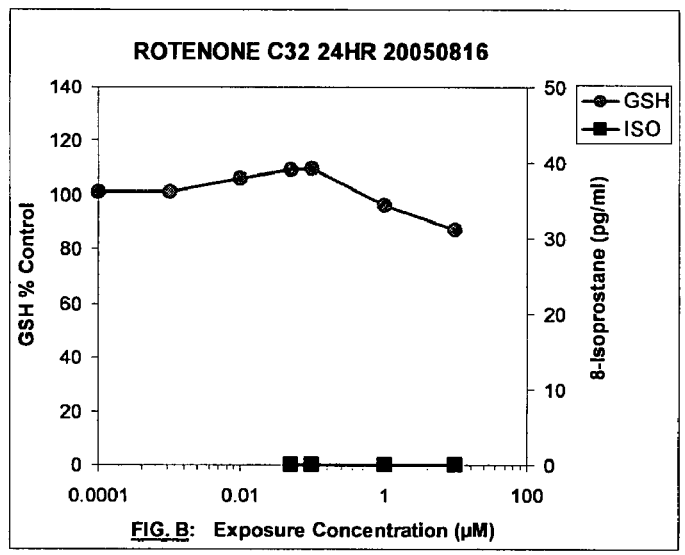
FIG. B: Exposure Concentration (μM)
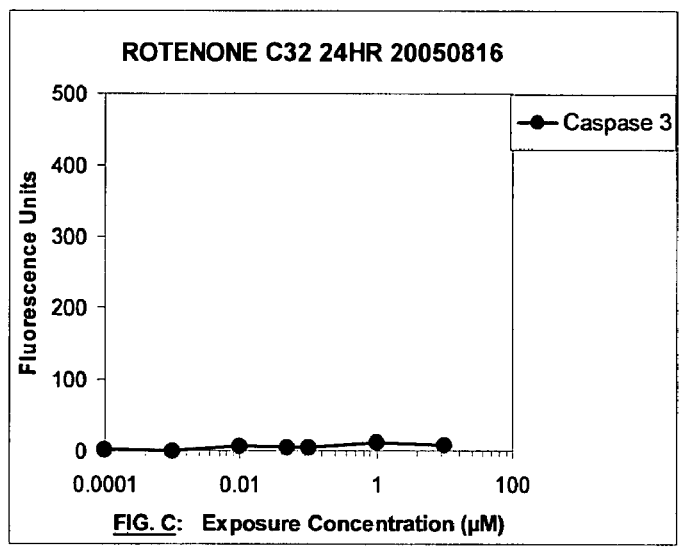
FIG. C: Exposure Concentration (μM)

Figure 102: ROTENONE NHEM 24HR
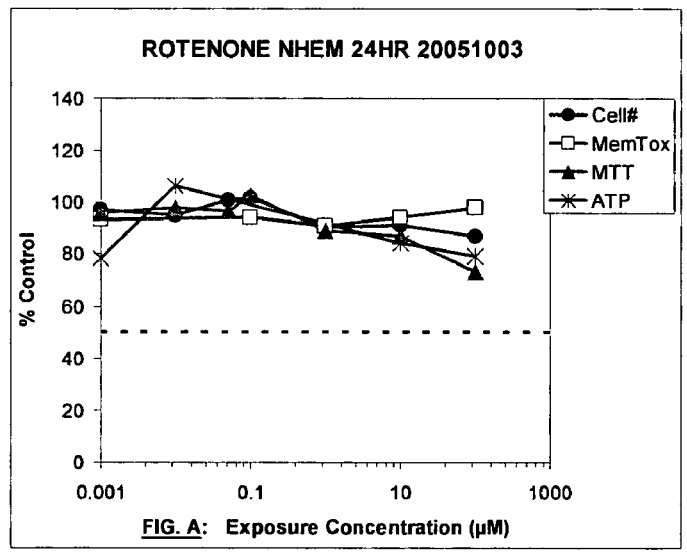
FIG. A: Exposure Concentration (μM)
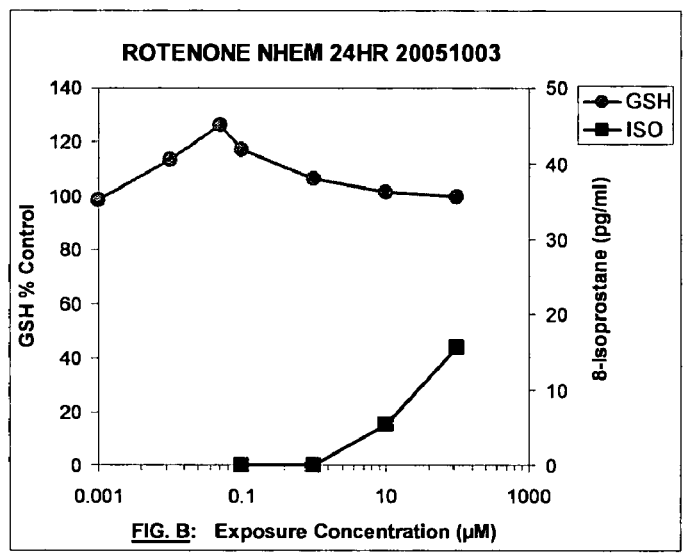
FIG. B: Exposure Concentration (μM)
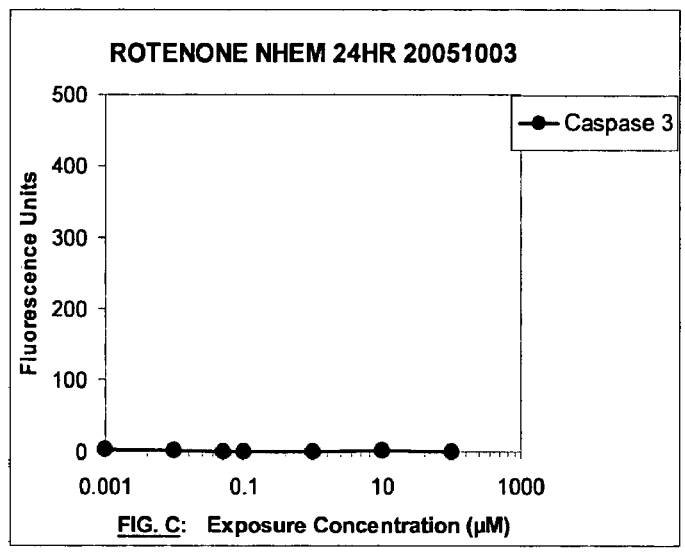
FIG. C: Exposure Concentration (μM)

TOXICITY SCREENING METHODS

CROSS REFERENCE TO RELATED APPLICATIONS

This application claims benefit under 35 U.S.C. 119(e) of U.S. Ser. No. 60/779,660, filed Mar. 6, 2006, and U.S. Ser. No. 60/743,599, filed Mar. 21, 2006. The entire contents of each of the above-referenced patent applications are hereby expressly incorporated herein by reference.

STATEMENT REGARDING FEDERALLY SPONSORED RESEARCH OR DEVELOPMENT

Not Applicable.

FIELD OF THE INVENTION

The present application for patent relates to in vitro methods for predicting in vivo toxicity of chemical compounds, including organ-specific and species-specific toxicity of such chemical compounds and drug-drug interactions, understanding the relative toxicity of drug candidates and identifying mechanisms of toxicity.

BACKGROUND

The process of identifying a new drug candidate is long and tedious with many promising compounds eliminated from development during preclinical toxicity testing in animals. One reason for the high number of drop out compounds during the preclinical phase is the lack of useful toxicity data early in the discovery program. Many pharmaceutical companies have recognized this in the last several years. The time and expense associated with the drug discovery process has lead to a search for efficiencies that can be realized in the process.

To date, evaluation of in vivo toxicity of a given candidate substance as a potential drug has involved the use of animal models. Underlying the animal tests is the assumption that the effects observed in animals are applicable and predictive of effects in humans. In general, when the dosage is based on a per unit of body surface area, toxicology data from animals is applicable to humans. On the other hand, when the dosage is based on animal body weight, humans are typically more susceptible to toxicity than the test animals. Nevertheless, the vast majority of drugs are developed to be given on the basis of body weight.

Additionally, the actual numbers of animals used in drug testing are much lower than the human population likely to be exposed to the drug if the candidate is actually brought to market. For example, a 0.01% incidence of human exposure to a given drug means that approximately 25,000 out of 250 million individuals are exposed to a drug. To detect such a low incidence in animals would require that 30,000 animals be exposed to the drug. This is clearly an impractical number considering the variety of drugs in development at any given time. Consequently, exposure of fewer animals to high doses of candidate substances is desirable to identify hazards to humans exposed to low doses.

Modern drug development proceeds through a series of stages in which a vast library of compounds is gradually narrowed in a series of successive steps. The use of animals in the initial stages of drug development, in which the number of compounds still being considered is relatively large, is an expensive and inefficient method of producing toxicological data for new drugs especially in light of the fact that most chemicals this early in development, ultimately, Will not be considered drug candidates. Thus, a significant need for alternative toxicological screening methods exists. Indeed, various approaches to toxicological screening prior to the animal testing stage have been proposed.

A common approach to solving the toxicology data deficit has been to incorporate in vitro toxicity testing of compounds of interest into the drug discovery process at a time when new compounds are being identified for potency and efficacy against therapeutic targets. Quality toxicity data at this early stage permits pharmaceutical chemists to attempt to "design out" toxicity while maintaining efficacy/potency. It has proved difficult, however, to develop robust in vitro toxicity testing systems that provide data that is consistently and reliably predictive of in vivo toxicity.

Key issues have been deciding on the type and nature of assays to be utilized and the test system to be employed. There are many biochemical and molecular assays that claim to assess toxicity in cells grown in culture. However, when only one or even two assays are used over a limited range of exposure concentrations, the probability of false negative and false positive data is high. Some of the most commonly used assays include, but are not limited to, leakage of intracellular markers as determined by lactate dehydrogenase (LDH), glutathione S-transferase (GST), and potassium, and the reduction of tetrazolium dyes such as MTT, XTT, Alamar Blue, and INT. All have been used as indicators of cell injury. Prior art in vitro toxicity screens typically only involve the use of one or two endpoints. The resulting data provides a yes/no or live/dead answer. This minimalist approach to the toxicity-screening problem has resulted in little progress towards developing a robust screening system capable of providing a useful toxicity profile that has meaning for predicting similar toxicity in animals. Therefore, there remains a need in the art for the development of new screening systems that provide more useful toxicity information, especially toxicity information that can be obtained rapidly and cost-effectively at early stages of the drug discovery process. A need exists for toxicity screening systems that do not require the use of animals but that provide reliable information on relative toxicity, mechanism of toxicity, and that effectively predict in vivo toxicity.

The drug discovery process is often under significant time pressures, and any time lost while waiting for toxicity data can prove expensive. Thus, a need also exists for in vitro toxicity screening methods and systems optimized for providing relevant information relating to in vitro toxicity in a relatively short time frame.

In some drug development efforts, it is desirable to evaluate the toxicity potential for one or more compounds in particular organ systems. Obtaining this information at a late stage in the process can render significant efforts and expense essentially useless. Thus, a need also exists for in vitro toxicity screening methods and systems that provide relevant information relating to in vivo toxicity in particular organ systems and functions, such as information relating to the cardio toxicity potential of a compound.

Some drug discovery efforts implicate toxicity considerations that are of little or no concern in other efforts. For example, most anti-tumor drugs are either cytostatic or cytotoxic. For cytostatic compounds, off-target toxicity is an important consideration considering the desired result of use of the compound. This consideration is even more critical for cytotoxic compounds. Thus, a need also exists for in vitro toxicity screening methods and systems for specific classes of compounds that have unique or special considerations, such as compounds being investigated for anti-tumor activity.

An important component of any new drug evaluation is the potential for a compound to exhibit species specific toxicity. For example, in the animal testing stage of a drug development effort, rodent studies may show no adverse signs, while a study in a non-rodent species may show severe or even lethal toxicity. When this occurs, repeat animal testing may be required, and significant questions regarding the relevancy of the results to human exposure and toxicity can be raised, each of which can introduce significant delay and expense into the drug discovery effort. Thus, a need also exists for in vitro toxicity screening methods and systems that provide relevant information relating to potential species-specific toxicity.

Another concern during the drug development process is the potential for drug-drug interactions in which one drug alters the pharmacokinetics of a co-administered drug. Having relevant information concerning the ability of a compound of interest to be co-administered with other drugs, or not to be administered with other drugs, may aid in making determinations as to which compounds should be advanced in the process and which compounds should be halted. Thus, a need also exists for in vitro toxicity screening methods and systems that provide relevant information relating to the potential for a compound to produce drug-drug interactions in vivo.

It is to such novel toxicity screening systems that the present invention is directed.

BRIEF DESCRIPTION OF THE DRAWINGS

FIG. 3 illustrates concentration response analyses for Celebrex in H4IIE cells and rat cardiomyocytes at 24 hours exposure. Celebrex would have passed as a safe drug in these analyses, and the heart had greater sensitivity than the liver cells at high exposures.

FIG. 9 illustrates concentration response analyses for methotrexate in three rat cell types: H4IIE tumor cells, NRK (normal rat kidney cells), and rat primary hepatocytes.

FIG. 10 illustrates concentration response analyses for Doxorubicin (Adriamycin) in three rat cell types: H4IIE tumor cells, NRK (normal rat kidney cells), and rat primary hepatocytes.

FIG. 11 contains bar graphs that illustrate the differentiation of target versus off-target effects (left panel) and cell sensitivity (right panel) for H4IIE, NRK, and primary hepatocyte cells exposed to an anti-tumor drug.

FIG. 17 illustrates concentration response analyses for Compound A in rat cardiomyocytes following a 3 hour exposure.

FIG. 25 contains bar graphs illustrating bDNA analyses of the cardiac hypertrophy markers ANP (FIG. 25A), BNP (FIG. 25B), and p53 (FIG. 25C) for Compound A in rat cardiomyocytes at 1, 3, 6 and 24 hours.

FIG. 26 contains bar graphs illustrating bDNA analyses of the cardiac hypertrophy markers BAX (FIG. 26A), Bcl2 (FIG. 26B), and iNOS (FIG. 26C) for Compound A in rat cardiomyocytes at 1, 3, 6 and 24 hours.

FIG. 27 contains bar graphs illustrating bDNA analyses of the cardiac hypertrophy markers ANP (FIG. 27A), BNP (FIG. 27B), and iNOS (FIG. 27C) for Adriamycin in rat cardiomyocytes at 1, 3, 6 and 24 hours.

FIG. 28 contains bar graphs illustrating bDNA analyses of the cardiac hypertrophy markers BAX (FIG. 28A), Bcl2 (FIG. 28B), and p53 (FIG. 28C) for Adriamycin in rat cardiomyocytes at 1, 3, 6 and 24 hours.

FIG. 29 illustrates concentration response analyses for Compound A in H4IIE cells following a 24 hour exposure.

FIG. 30 illustrates concentration response analyses for Adriamycin in H4IIE cells following a 24 hour exposure.

FIG. 31 illustrates concentration response analyses for Idarubicin in rat cardiomyocyte cells following a 24 hour exposure.

FIG. 32 illustrates concentration response analyses for Mitoxantrone in rat cardiomyocyte cells following a 24 hour exposure.

FIG. 33 illustrates concentration response analyses for Daunorubicin in rat cardiomyocyte cells following a 24 hour exposure.

FIG. 34 illustrates concentration response analyses for Pirarubicin in rat cardiomyocyte cells following a 24 hour exposure.

FIG. 35 illustrates concentration response analyses for Epirubicin in rat cardiomyocyte cells following a 24 hour exposure.

FIG. 36 illustrates concentration response analyses for Ritonavir in rat cardiomyocyte cells following a 24 hour exposure.

FIG. 37 illustrates concentration response analyses for Efavirenz in rat cardiomyocyte cells following a 24 hour exposure.

FIG. 38 illustrates concentration response analyses for Lopinavir in rat cardiomyocyte cells following a 24 hour exposure.

FIG. 39 illustrates concentration response analyses for Delavirdine in rat cardiomyocyte cells following a 24 hour exposure.

FIG. 40 illustrates concentration response analyses for Abacavir in rat cardiomyocyte cells following a 24 hour exposure.

FIG. 41 illustrates concentration response analyses for Indinavir in rat cardiomyocyte cells following a 24 hour exposure.

FIG. 42 illustrates concentration response analyses for Nevirapine in rat cardiomyocyte cells following a 24 hour exposure.

FIG. 43 illustrates concentration response analyses for AZT in rat cardiomyocyte cells following a 24 hour exposure.

FIG. 44 illustrates concentration response analyses for Rotenone in rat cardiomyocyte cells following a 24 hour exposure.

FIG. 45 illustrates concentration response analyses for Camptothecin in rat cardiomyocyte cells following a 24 hour exposure.

FIG. 46 illustrates concentration response analyses for Idarubicin in H4IIE cells following a 24 hour exposure.

FIG. 47 illustrates concentration response analyses for Daunorubicin in H4IIE cells following a 24 hour exposure.

FIG. 48 illustrates concentration response analyses for Pirarubicin in H4IIE cells following a 24 hour exposure.

FIG. 49 illustrates concentration response analyses for Doxorubicin in H4IIE cells following a 24 hour exposure.

FIG. 50 illustrates concentration response analyses for Epirubicin in H4IIE cells following a 24 hour exposure.

FIG. 51 illustrates concentration response analyses for Mitoxantrone in H4IIE cells following a 24 hour exposure.

FIG. 52 illustrates concentration response analyses for Efavirenz in H4IIE cells following a 24 hour exposure.

FIG. 53 illustrates concentration response analyses for Ritonavir in H4IIE cells following a 24 hour exposure.

FIG. 54 illustrates concentration response analyses for Delavirdine in H4IIE cells following a 24 hour exposure.

FIG. 55 illustrates concentration response analyses for Lopinavir in H4IIE cells following a 24 hour exposure.

FIG. 56 illustrates concentration response analyses for Abacavir in H4IIE cells following a 24 hour exposure.

FIG. 57 illustrates concentration response analyses for Indinavir in H4IIE cells following a 24 hour exposure.

FIG. 58 illustrates concentration response analyses for Nevirapine in H4IIE cells following a 24 hour exposure.

FIG. 59 illustrates concentration response analyses for AZT in H4IIE cells following a 24 hour exposure.

FIG. 60 illustrates concentration response analyses for Rotenone in H4IIE cells following a 24 hour exposure.

FIG. 61 illustrates concentration response analyses for Camptothecin in H4IIE cells following a 24 hour exposure.

FIG. 65 contains bar graphs illustrating metabolic activation of test compounds in rat-induced microsomes (top panel) and dog-induced microsomes (bottom panel).

FIG. 66 contains a bar graph illustrating the metabolic stability of test compounds A-E in rat and dog microsomes.

FIG. 67 contains ion chromatograms illustrating microsomal metabolism of Compound A in rat and dog.

FIG. 68 contains ion chromatograms illustrating microsomal metabolism of Compound B in rat and dog.

FIG. 69 contains ion chromatograms illustrating microsomal metabolism of Compound C in rat and dog.

FIG. 70 contains ion chromatograms illustrating microsomal metabolism of Compound D in rat and dog.

FIG. 71 contains ion chromatograms illustrating microsomal metabolism of Compound E in rat and dog.

FIG. 72 illustrates concentration response analyses of Compound B in rat primary hepatocytes following a 48 hour exposure (after 24 hour induction with 50 μM PB plus 15 μM BNF).

FIG. 74 illustrates concentration response analyses of Compound B in dog primary hepatocytes following a 48 hour exposure (after 24 hour induction with 50 μM PB plus 15 μM BNF).

FIG. 75 illustrates concentration response analyses of Compound D in dog primary hepatocytes following a 48 hour exposure (after 24 hour induction with 50 μM PB plus 15 μM BNF).

FIG. 76 illustrates concentration response analyses of Compound A following 6 and 24 hour exposures in a rat hepatoma cell line H4IIE (FIG. 76A), rat primary hepatocytes (FIG. 76B), and normal rat kidney (NRK) cells (FIG. 76C).

FIG. 77 illustrates pH test analyses of Compound A following 6 and 24 hour exposures in a H4IIE cells (FIG. 77A), rat primary hepatocytes (FIG. 77B), and NRK cells (FIG. 77C).

FIG. 78 illustrates concentration response analyses for Camptothecin in NRK cells following a 6 hour exposure.

FIG. 79 illustrates concentration response analyses for Camptothecin in NRK cells following a 24 hour exposure.

FIG. 80 illustrates concentration response analyses for Rotenone in NRK cells following a 6 hour exposure.

FIG. 81 illustrates concentration response analyses for Rotenone in NRK cells following a 24 hour exposure.

FIG. 82 contains a graph that illustrates cell specificity for an anti-tumor drug screened therein. Rat primary hepatocytes and normal rat kidney (NRK) cells were not sensitive to the anti-tumor drug, whereas H4IIE cells were highly sensitive to the anti-tumor drug.

FIG. 83 contains a bar graph that illustrates a toxicity comparison between multiple cell lines. SK-MEL28 and C32 are human tumor cell lines; SK-MEL28* refers to data provided by the sponsor. NRK, normal rat kidney cells. NHEM, Normal Human Epidermal Melanocyte. HUVEC, human umbilical vein endothelial cells.

FIG. 84 contains concentration response analyses for Compound A in SK-MEL28 tumor cells following a 24 hour exposure, and MTT combined low/high exposures.

FIG. 85 illustrates concentration response analyses for Compound A (low dose exposure) in SK-MEL28 cells following 24 and 72 hour exposures.

FIG. 86 illustrates concentration response analyses for Compound A in human hepatocytes following a 24 hour exposure.

FIG. 87 illustrates concentration response analyses for Compound A in HUVEC (human umbilical vein endothelial cells) following a 24 hour exposure.

FIG. 88 illustrates concentration response analyses for Compound A in C32 tumor cells following a 24 hour exposure.

FIG. 89 illustrates concentration response analyses for Compound A in C32 cells (low exposure) following a 24 hour exposure, and combined low/high exposures.

FIG. 90 illustrates concentration response analyses for Compound A in NHEM cells following a 24 hour exposure.

FIG. 91 illustrates concentration response analyses for Camptothecin in SK-MEL28 cells following a 24 hour exposure.

FIG. 92 illustrates concentration response analyses for Camptothecin in SK-MEL28 cells following 24 and 72 hour exposures.

FIG. 93 illustrates concentration response analyses for Camptothecin in human hepatocytes following a 24 hour exposure.

FIG. 94 illustrates concentration response analyses for Camptothecin in human umbilical vein endothelial cells (HUVEC) following a 24 hour exposure.

FIG. 95 illustrates concentration response analyses for Camptothecin in C32 cells following a 24 hour exposure.

FIG. 96 illustrates concentration response analyses for Camptothecin in NHEM cells following a 24 hour exposure.

FIG. 97 illustrates concentration response analyses for Rotenone in SK-MEL28 cells following a 24 hour exposure.

FIG. 98 illustrates concentration response analyses for Rotenoone in SK-MEL28 cells following 24 and 72 hour exposures.

FIG. 99 illustrates concentration response analyses for Rotenone in human hepatocytes following a 24 hour exposure.

FIG. 100 illustrates concentration response analyses for Rotenone in human umbilical vein endothelial cells (HUVEC) following a 24 hour exposure.

FIG. 101 illustrates concentration response analyses for Rotenone in C32 cells following a 24 hour exposure.

FIG. 102 illustrates concentration response analyses for Rotenone in NHEM cells following a 24 hour exposure.

DETAILED DESCRIPTION OF EXEMPLARY EMBODIMENTS

Figure 1:
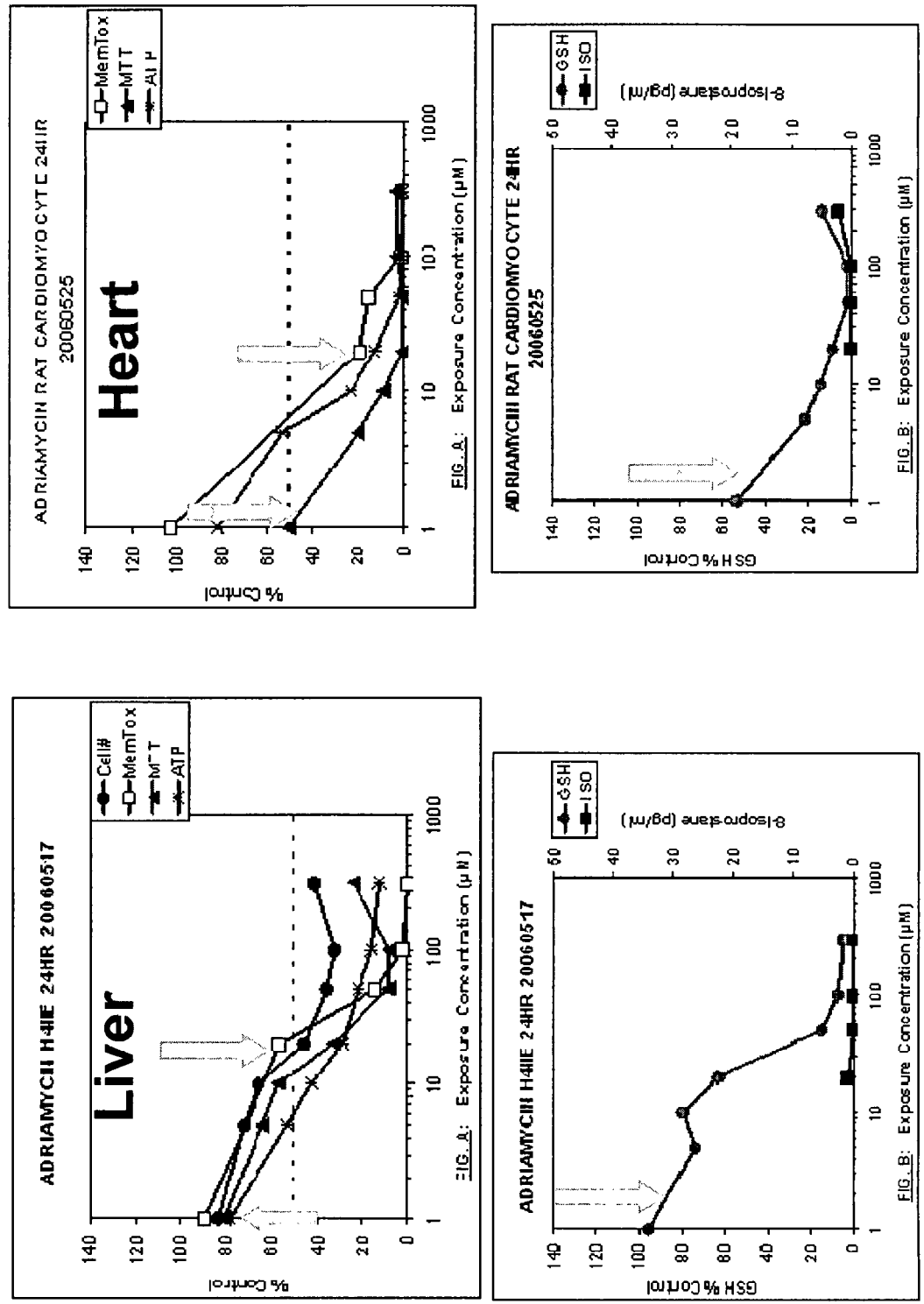
FIG. 1 illustrates concentration response analyses for adriamycin in H4IIE (liver cells) and rat cardiomyocytes at 24 hours exposure. The dual cell model indicates that adriamycin is most toxic to heart.

The following detailed description and appendices describe and illustrate various exemplary embodiments. The description and drawings serve to enable one skilled in the art to make and use the invention, and are not intended to limit the scope of the invention in any manner.

Relevant background information is available in U.S. Pat. No. 6,998,249 issued to McKim and Cockerell on Feb. 14, 2006 and entitled "TOXICITY SCREENING METHOD", the contents of which are expressly incorporated into this disclosure in their entirety.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Presently, it takes between three and five years to bring new potentially therapeutic compounds from the early discovery process to preclinical development (in vivo animal testing). The toxicity data for such compounds is generally not available until the preclinical animal toxicity tests are performed.

Numerous drugs reach this stage of development only to be discarded from further development due to toxic liability. Such failures represent a tremendous loss in company resources. Understandably, a technique that could predict the toxicity of these multitude of compounds that arrive at or near the initial synthesis stage of drug discovery would have an enormous impact on the efficiency with which new drugs are identified by eliminating, early in the drug discovery process, compounds that have an unfavorable toxicity profile. An immediate expected benefit of more powerful, early stage in vitro toxicity testing is the reduction of the number of these three to five year drug discovery cycles that result in failures, and thus reduce the average number of cycles required to develop successful new therapeutics. Related benefits include reduced costs for drug development and more rapid availability of new pharmaceuticals to the medical community. Reduced failure rates may lengthen the portion of a patent's term that valuable compounds enjoy commercial exploitation.

In addition, in the animal testing stage of a drug development effort, one animal species may show no adverse effects upon administration of a drug, whereas a second animal species may exhibit severe or even lethal toxicity. When this occurs, repeat animal testing may be required, and significant questions regarding the relevancy of the results to human exposure and toxicity can be raised. Therefore, the ability to identify these species-specific toxicity differences in vitro would be of great value.

The present invention provides methods for prioritizing new chemical entities within a class for further development, identifying mechanisms of toxicity and organ-specific and species-specific toxicities and for estimating in vivo toxicity early in the drug development and discovery process. As such, these methods can be used to prioritize large numbers of new compounds for further drug development. In addition, the methods greatly increase the probability that an identified agent will be successful in preclinical toxicity testing. The adaptability of these in vitro methods for high-throughput analysis makes them an economical and cost-effective addition to a drug discovery program.

In particular, the present invention provides a cluster analysis in which two or more different biochemical endpoints are evaluated in order to predict the in vivo toxicity concentration of a given compound, prioritize compounds based on relative toxicity, and identify mechanisms of toxicity. In certain embodiments, these assays measure changes in specific biochemical processes, which are essential for normal cellular functions, following a 24-hour exposure to a broad range of concentrations of the compound. In certain other embodiments, these assays may be measured following both a 6-hour exposure and a 24-hour exposure to a broad range of concentrations of the compound.

The toxicity cluster analyses of the present invention allow the determination of appropriate information relating to changes occurring in specific cellular processes. This information in turn is used to obtain a more complete profile of cellular injury and/or cytotoxicity. Further, the analyses described herein may be utilized to identify specific types of toxicity, i.e., toxicity to certain cell types such as but not limited to, cardiac cells; toxicity due to drug-drug interactions; species-specific toxicity, and the like.

I. Cluster Analysis Toxicity Screening

In the present invention, cluster analysis toxicity screening is presented as a method of predicting the in vivo toxicity of a given compound. In particular aspects, these assays will involve culturing cells in culture medium that comprises a plurality of concentrations of the chemical compound; measuring a plurality of cell health indicators of the cell in response to culturing in at least three concentrations of the chemical compound and predicting $TC_{50}$ and a toxic concentration ($C_{tox}$) of the chemical compound from such measurements. The various embodiments involved in conducting such assays are described in further detail below.

Assay Format

In certain embodiments, the CATS technique will be used to prioritize and identify compounds that will be of a potential therapeutic value. The inventors have discovered that analyzing multiple endpoints yields significant information regarding the toxicity of a given compound.

In certain embodiments, the present invention concerns a method for identifying such compounds. It is contemplated that this screening technique will prove useful in the general prioritization and identification of compounds that will serve as lead therapeutic compounds for drug development. The invention will be a useful addition to laboratory analyses directed at identifying new and useful compounds for the intervention of a variety of diseases and disorders including, but not limited to, Alzheimer's disease, other disorders and diseases of the central nervous system, metabolic disorders and diseases, cancers, diabetes, depression, immunodeficiency diseases and disorders, immunological diseases and disorders, autoimmune diseases and disorders, gastrointestinal diseases and disorders, cardiovascular diseases and disorders, inflammatory diseases and disorders, and infectious diseases, such as a microbial, viral or fungal infections.

In specific embodiments, the present invention is directed to a method for determining the in vivo cytotoxicity of a candidate substance by employing a method including generally: a) culturing cells in culture medium that comprises a plurality of concentrations of said chemical compound; b) measuring a first indicator of cell health at four or more concentrations of said chemical compound; c) measuring a second indicator of cell health at four or more concentrations of said chemical compound; d) measuring a third indicator of cell health at four or more concentrations of said chemical compound; and e) predicting a toxic concentration ($C_{tox}$) of said chemical compound from the measurements of steps (b), (c) and (d).

In certain aspects, the method may further involve predicting a $TC_{50}$ of said chemical compound from the measurements of steps (b), (c) and (d). For any particular assay, the $TC_{50}$ represents the concentration of a compound which causes fifty percent of a maximal toxic response in the assay. As described in greater detail below, when CATS is run under certain conditions, $TC_{50}$ can be selected as a predicted $C_{tox}$.

The foregoing method requires preparing cell cultures. Such a cell may be a primary cell in culture or it may be a cell line. The cells may be obtained from any mammalian source that is amenable to primary culture and/or adaptation into cell lines. In lieu of generating cell lines from animals, such cell lines may be obtained from, for example, American Type Culture Collection, (ATCC, Rockville, Md.), or any other Budapest treaty or other biological depository. The cells used in the assays may be from an animal source or may be recombinant cells tailored to express a particular characteristic of, for example, a particular disorder for which the drug development is being considered. In one embodiment, the cells are derived from tissue obtained from humans or other primates, rats, mice, rabbits, sheep, dogs and the like. Techniques employed in mammalian primary cell culture and cell line cultures are well known to those of skill in that art. Indeed, in the case of commercially available cell lines, such cell lines are generally sold accompanied by specific directions of growth, media and conditions that are preferred for that given cell line.

The present invention predicts the cytotoxicity of a given compound by measuring two or more indicators of cell health in a given cell. The cell chosen for such an endeavor will depend on the putative site of in vivo toxicity to be determined. For example, the liver is a particularly prevalent site of in vivo drug toxicity. Thus, the use of liver cells (either primary or cell lines derived from liver cells) in the assays described herein is specifically contemplated. In certain embodiments, the inventors have found that the H4IIE cell line (ATCC #CRL-1548) is an excellent candidate for predicting the cytotoxic effects of compounds on the general health of hepatic cells. In addition, because the H4IIE cell line is a proliferating cell population, the system will be useful in identifying compounds that adversely affect other proliferating cell types such as hematopoietic cells. Such cells can be used to identify chemotherapeutic agents that have extremely low hepatotoxicity but high toxicity to proliferating cells. (See Example 5 of U.S. Pat. No. 6,998,249, issued to McKim et al. on Feb. 14, 2006, the contents of which have been incorporated herein previously).

While the H4IIE cell line is described herein as a particularly contemplated cell line, it should be understood that any mammalian primary hepatic cell or hepatic cell line will be useful in the present invention. In certain embodiments, the cell is a rat hepatic cell line. In addition to H4IIE, other rat cell lines contemplated for use in the present invention include, but are not limited to MH1C1 (ATCC CCL144), clone 9 (ATCC CRL-1439), BRL 3A (ATCC CRL-1442), H4TG (ATCC CRL-1578), H4IIEC3 (ATCC CRL-166), McA-RH7777 (ATCC CRL-1601) McA-RH8994 (ATCC CRL-1602), N1-S1 Fudr (ATCC CRL-1603) and N1-S1 (ATCC CRL-1604).

In other embodiments, the cell is a human liver cell. A human hepatic cell line acceptable for use in the methods described by the present invention is HepG2 (ATCC HB-8065). Additionally, other exemplary human hepatic cell lines that may be useful in the present invention include but are not limited to C3A (ATCC CRL-10741), DMS (ATCC CRL-2064), SNU-398 (ATCC CRL-2233), SNU449 (ATCC CRL-2234), SNU-182 (ATCC CRL-2235), SNU475 (ATCC CRL2236), SNU-387 (ATCC CRL-2237), SNU423 (ATCC CRL-2238), NCI-H630 (ATCC CRL-5833), NCI-H1755 (ATCC CRL-5892), PLC/PRF/5 (ATCC CRL8024), Hep3B (HB-8064) and HTB-52 (ATCC HTB-52).

While the above cells will be useful indicators of hepatic cell toxicity, the present invention may be employed to determine, monitor or otherwise predict cytotoxicity in a variety of tissue types. It should be understood that the in vivo sites of cellular toxicity that those of skill in the art will want to monitor will include the in vivo sites of action of the particular test compound as well as sites remote from the site of action of the test compound. Therefore, cell lines that may be used in assays will include cell lines derived from other common sites of in vivo cytotoxicity such as the kidney, heart and pancreas. While these tissues, along with the liver, may be the primary tissues that one would select to monitor cytotoxicity, it should be understood that the assays of the present invention may be employed to predict the cytotoxic effects of a test compound on cells derived from brain, nerve, skin, lung, spleen, endometrial, stomach and breast tissue, as well as stem cells and hematopoietic cells. Use of hematopoietic cells or "stem" cells or cell lines derived therefrom in cytotoxicity assays is particularly contemplated.

For example, one embodiment of the present invention is directed to a method of determining a level of cardiac toxicity of a chemical compound. For such analyses, primary cardiac cells would be utilized. In particular, freshly isolated cardiomyocytes from 7-day old rats may be utilized in accordance with the present invention.

In another embodiment, the present invention may include performing such methods with more than one cell type. For example, to analyze the toxicity of an anti-tumor compound, it would be beneficial to examine the effects of the compound on different cell types, i.e., cancer-derived proliferating cells, proliferating cells derived from normal tissue, and non-proliferating cells derived from normal tissue. The use of these different cell types allows for the differentiation between target versus off target effects of the anti-tumor compound.

Alternatively, the same cell type from two or more different mammalian species may be utilized in accordance with the present invention. The use of cells from different species allows for the identification of potential species specific toxicity of a compound.

In particular embodiments, the cells are seeded in multi-well (e.g. 96-well) plates and allowed to reach log phase growth. In H4IIE cells, this growth period is approximately 48 hours. Preferred media and cell culture conditions for this cell-line are detailed in the Examples.

Once the cell cultures are thus established, various concentrations of the compound being tested are added to the media and the cells are allowed to grow exposed to the various concentrations for 24 hours. While the 24 hour exposure period is described, it should be noted that this is merely an exemplary time of exposure and testing the specific compounds for longer or shorter periods of time is contemplated to be within the scope of the invention. As such it is contemplated that the cells may be exposed for 6, 12, 24, 36, 48 or more hours. Increased culture times may sometimes reveal additional cytotoxicity information, at the cost of slowing down the screening process.

Furthermore, the cells may be exposed to the test compound at any given phase in the growth cycle. For example, in some embodiments, it may be desirable to contact the cells with the compound at the same time as a new cell culture is initiated. Alternatively, it may be desirable to add the compound when the cells have reached confluent growth or arc in log growth phase. Determining the particular growth phase cells are in is achieved through methods well known to those of skill in the art.

The varying concentrations of the given test compound are selected with the goal of including some concentrations at which no toxic effect is observed and also at least two or more higher concentrations at which a toxic effect is observed. A further consideration is to run the assays at concentrations of a compound that can be achieved in vivo. For example, assaying several concentrations within the range from 0 micromolar to about 300 micromolar is commonly useful to achieve these goals. It will be possible or even desirable to conduct certain of these assays at concentrations higher than 300 micromolar, such as, for example, 350 micromolar, 400 micromolar, 450 micromolar, 500 micromolar, 600 micromolar, 700 micromolar, 800 micromolar, 900 micromolar, or even at millimolar concentrations. The estimated therapeutically effective concentration of a compound provides initial guidance as to upper ranges of concentrations to test. Additionally, as explained in greater detail below, CATS analysis may further include assaying a range of concentrations that includes at least two concentrations at which cytotoxicity is observable in an assay. It has been found that assaying a range of concentrations as high as 300 micromolar often satisfies this criterion.

In an exemplary set of assays, the test compound concentration range under which the CATS is conducted comprises dosing solutions which yield final growth media concentration of 0.05 micromolar, 0.1 micromolar, 1.0 micromolar, 5.0 micromolar, 10.0 micromolar, 20.0 micromolar, 50.0 micromolar, 100 micromolar, and 300 micromolar of the compound in culture media. As mentioned, these are exemplary ranges, and it is envisioned that any given assay will be run in at least two different concentrations, and the concentration dosing may comprise, for example, 4, 5, 6, 7, 8, 9,10, 11, 12, 13, 14, 15 or more concentrations of the compound being tested. Such concentrations may yield, for example, a media concentration of 0.05 micromolar, 0.1 micromolar, 0.5 micromolar, 1.0 micromolar, 2.0 micromolar, 3.0 micromolar, 4.0 micromolar, 5.0 micromolar, 10.0 micromolar, 15.0 micromolar, 20.0 micromolar, 25.0 micromolar, 30.0 micromolar, 35.0 micromolar, 40.0 micromolar, 45.0 micromolar, 50.0 micromolar, 55.0 micromolar, 60.0 micromolar, 65.0 micromolar, 70.0 micromolar, 75.0 micromolar, 80.0 micromolar, 85.0 micromolar, 90.0 micromolar, 95.0 micromolar, 80.0 micromolar, 110.0 micromolar, 120.0 micromolar, 130.0 micromolar, 140.0 micromolar, 150.0 micromolar, 160.0 micromolar, 170.0 micromolar, 180.0 micromolar, 190.0 micromolar, 200.0 micromolar, 210.0 micromolar, 220.0 micromolar, 230.0 micromolar, 240.0 micromolar, 250.0 micromolar, 260.0 micromolar, 270.0 micromolar, 280.0 micromolar, 290.0 micromolar, and 300 micromolar in culture media. It will be apparent that a cost-benefit balancing exists in which the testing of more concentrations over the desired range provides additional information, but at additional cost, due to the increased number of cell cultures, assay reagents, and time required. In one embodiment, ten different concentrations over the range of 0 micromolar to 300 micromolar are screened.

Typically, the various assays described in the present specification may employ cells seeded in 96 well plates or 384 cell plates. The cells are then exposed to the test compounds over a concentration range, for example, 0-300 micromolar. The cells are incubated in these concentrations for a given period of, for example, 6 and/or 24 hours. Subsequent to the incubation, the assays of the cluster are performed for each test compound. In one embodiment, all the assays are performed at the same time such that a complete set of data are generated under similar conditions of culture, time and handling. However, it may be that the assays are performed in batches within a few days of each other.

In specific embodiments, the indicators of cell health and viability include but are not limited to, indicators of cellular replication, mitochondrial function, energy balance, membrane integrity and cell mortality. In other embodiments, the indicators of cell health and viability further include indicators of oxidative stress, metabolic activation, metabolic stability, enzyme induction, enzyme inhibition, and interaction with cell membrane transporters.

The compounds to be tested may include fragments or parts of naturally-occurring compounds or may be derived from previously known compounds through a rational drug design scheme. It is proposed that compounds isolated from natural sources, such as animals, bacteria, fungi, plant sources, including leaves and bark, and marine samples may be assayed as candidates for the presence of potentially useful pharmaceutical compounds. Alternatively, pharmaceutical compounds to be screened for toxicity could also be synthesized (i.e., man-made compounds).

The types of compounds being monitored may be antiviral compounds, antibiotics, anti-inflammatory compounds, antidepressants, analgesics, antihistamines, diuretic, antihypertensive compounds, antiarrythmia drugs, chemotherapeutic compounds for the treatment of cancer, antimicrobial compounds, among others.

Regardless of the source or type of the compound to be tested for cytotoxicity, it may be necessary to monitor the biological activity of the compounds to provide an indication of the therapeutic efficacy of a particular compound or group of compounds. Of course, such assays will depend on the particular therapeutic indication being tested. Exemplary indications include efficacy against Alzheimer's disease, cancer, diabetes, depression, immunodeficiency, autoimmune disease, gastrointestinal disorder, cardiovascular disease, inflammatory disease and the like.

Cluster Analyses Assays

The use of multiple assays to develop a toxicity profile for new drugs proves to be a very powerful tool for accurately assessing the effects of a compound in a living system.

Selective assays used in the clusters of the present invention provide key information pertaining to the toxicity profile of a given compound. The assays may be performed such that information regarding the various parameters is obtained at the same time during the drug development phase of drug discovery as opposed to performing the assays at different times during the drug development scheme. In one embodiment, the assays are performed in a batch all at the same time. In other aspects, it may be useful to perform the assays on cell cultures all generated at the same time from an initial cell line.

Modules may be designed in which a cluster of assays address a specific concern. Thus, in order to monitor the effect of a specific compound on the general health of a cell, monitoring membrane integrity, mitogenesis, mitochondrial function and energy balance will be particularly useful. The specific assay employed for any of these endpoints is not considered to be limiting. Thus, any assay that provides an indication of membrane integrity may be combined with any assay that is predictive of mitogenesis (cell replication) along with any assay that is an indicator of mitochondrial function and energy balance.

In addition to a module for determining the general cell health, other modules of interest would include those that are directed to determining for example, oxidative stress, cell cycle parameters, acute inflammatory response, apoptosis, endocrine responses and interaction with cell membrane transporters such as Pgp.

In a module that determines oxidative stress, production of reactive oxygen species (ROS), reactive nitrogen species (RNS), or lipid peroxidation may be monitored. Exemplary assays to be employed in the cluster may involve monitoring endpoints that include but are not limited to glutathione/glutathione disulfide (GSH/GSSG), dichlorofluoroscindiacetate (DCFDA), lipid peroxidation, 8-isoprostane, 8-oxy guanine (8-oxy G) DNA adducts, thiobarbituric acid (TBARS), and malondialdehyde (MDA).

Modules designed to monitor cell cycle may include determining the effect on the presence or level of any given cell cycle indicator including but not limited to p53, p21, TGFβ, CDK1, PCNA, telomerase, nitric oxide, and inducible nitric oxide synthase (iNOS). Again any particular assay may be employed to determine the level or amount of any given cell cycle indicator.

Modules to monitor apoptosis may include any assays described herein or otherwise known in the art. One example of such an assay is a caspase-3 assay; however, the present invention is to be understood to not be limited to the use of such assay, and any apoptosis assay may be substituted therefor in accordance with the present invention.

In a module designed to determine interactions with cell membrane transporter, an exemplary assay to be employed in the cluster may involve measuring a chemical compound's interaction with P-glycoprotein (Pgp). Pgp is a well characterized human ABC-transporter of the MDR/TAP subfamily. It is extensively distributed and expressed in normal cells such as those lining the intestine, liver cells, renal proximal tubular cells, and capillary endothelial cells comprising the blood brain barrier. Pgp is an ATP-dependent efflux pump with broad substrate specificity that likely evolved as a defense mechanism against harmful substances. Pgp transports various substrates across the cell membrane, thus allowing for the regulation of the distribution and bioavailability of drugs.

As stated above the specific assay to monitor any of the given parameters is not considered crucial so long as that assay is considered by those of skill in the art to provide an appropriate indication of the particular biochemical or molecular biological endpoint to be determined, such as information about mitochondrial function, energy balance, membrane integrity, cell replication, and the like. The following sections provide exemplary assays that may be used in the context of the present invention. This is not intended to be an exhaustive treatise on the description of these assays but rather is to be a guidance as to the type of assays that are available to those of skill in the art.

Compounds that produce direct effects on the cells typically alter mitochondrial function, by either up- or down regulating oxidative respiration. This means that cellular energy in the form of ATP may be altered. Mitochondrial function can be used as an indicator of cytotoxicity and cell proliferation. Healthy mitochondria catalyze the reduction of 3-(4,5-dimethylthiazol-2-yl)-2,5-diphenyltetrazolium bromide (MTT) to a blue or purple formazan compound. The relatively insoluble formazan blue is extracted into isopropanol and the absorbance of the extract measured. A high absorbance value indicates viable cells and functional mitochondria. Conversely, a decrease in the intensity of color suggests either a loss of cells, or direct toxic effects on the mitochondria. The MTT assay is well known to those of skill in the art and has been described in for example, the MTT mitochondrial dye assay is described in Mosmann, J Immunol. Methods 65, 55-63, 1983 and in Denizot et al., J Immunol. Methods. 89, 271-277, 1986. A similar assay that monitors XTT mitochondrial dye is described by Roehm et al., J. Immunol. Methods, 142, 257-265, 1991. In addition, those of skill in the art also may determine mitochondrial function by performing for example an Alamar Blue assay [Goegan et al., Toxicol. In vitro 9, 257-266. 1995], a Rhodamine 123 assay, or a cytochrome C oxidase assay.

ATP provides the primary energy source for many cellular processes and is required to sustain cell and tissue viability. Intracellular levels of ATP decrease rapidly during necrosis or apoptosis. Therefore, changes in the cellular concentration of ATP can be used as a general indicator of cell health. When normalized on a per cell basis, ATP can provide information on the energy status of the cell and may provide a marker to assess early changes in glycolytic or mitochondrial function. Assays that allow a determination of ADP/ATP energy balance are well known in the art (Kangas et al., Med Biol, 62, 338-343, 1984).

Measurements of α-GST leakage from cultured cells into the media can be used to assess membrane integrity. This assay is specific for the alpha form of GST that exists at high concentrations in the cytosol of hepatocytes. An ELISA kit purchased from Biotrin Inc. was used to measure GST. GST leakage assays, have been described in the literature, for example, Redick et al., J Biol. Chem. 257, 15200-15203. Oberley et al., Toxicol. Appl. Pharmacol. 131, 94-107, 1995; Feinfeld, J Clin Chem Clin Biochem. 24, 529-532, 1986.

Other assays for determining membrane integrity include, but are not limited to, assays that determine lactate dehydrogenase activity, aspartyl aminotransferase, alanine aminotransferase, isocitrate dehydrogenase, sorbitol dehydrogenase, glutamate dehydrogenase, ornithine carbamyl transferase, γ-glutamyl transferase, and alkaline phosphatase.

The ability of cells to divide requires coordinated signaling between a vast array of intracellular receptors. Cell replication or "mitogenesis" requires the cells to be functioning at optimum. A change in the ability to replicate is therefore an indication of stress or abnormal function. An exemplary assay that will allow the determination of cell replication is the CYQUANT® assay system from Invitrogen, Molecular Probes (Carlsbad, Calif.). Additional assays that may be used to provide an indication of mitogenesis may include, but are not limited to, monitoring $^3$H-thymidine incorporation and a BrdU incorporation assay. In addition, mitogenesis may be monitored by determining the function, presence or absence of a component that controls cell cycle. Exemplary components will be well known to those of skill in the art and include, but are not limited to, p53, p21, TGF-β, CDK1, PCNA and the like.

Certain of the assays performed as part of the CATS analysis will involve measuring components of the media whereas others will involve measuring cell number or parameters from the cells or cell lysates. The CATS analysis advantageously involves selecting some assays that can use media and others that can use cells from a single well.

Predicting In vivo Toxicity of a Compound from In vitro Analyses

Once all data for a given cluster of assays are received, the data are analyzed to obtain a detailed profile of the compound's toxicity. For example, most conveniently, the data are collated over a dose response range on a single graph. In such an embodiment, the measurement evaluated for each parameter (i.e., each indicator of cell health) at any given concentration is plotted as a percentage of a control measurement obtained in the absence of the compound. However, it should be noted that the data need not be plotted on a single graph, so long as all the parameters are analyzed collectively to yield detailed information of the effects of the concentration of the compound on the different parameters to yield an overall toxicity profile. As set forth below, this overall toxicity profile will facilitate a determination of a plasma concentration $C_{tox}$ that is predicted to be toxic in vivo. $C_{tox}$ represents an estimate of the sustained plasma concentration in vivo that would result in toxicity, such as hepatotoxicity or hematopoietic toxicity.

A fundamental premise in the field of toxicology is that all compounds are poisons, and that it is the dose of the compound that determines a beneficial/therapeutic effect versus a toxic effect. Dose is affected by time of exposure, dosing regimens, pharmacokinetic parameters such as absorption, metabolism and elimination, by difference between species being treated, and by route of administration. All these factors influence the plasma concentration of a drug and its duration of exposure. Thus, in principle, in vitro screens need only account for metabolism and time of exposure. In theory, an increased exposure time should shift the dose response curve to the left (e.g., $TC_{50}$ is lower or the compound appears more toxic over longer exposure times). These factors all have been considered in the selection of $C_{tox}$ in the CATS assay.

For example, in vitro time course experiments utilizing H4IIE cells were conducted to evaluate the change in the dose-response curves for chloramphenical and ketoconazole over a 72 hour exposure period. The data indicated that the largest shift in $TC_{50}$ values occurred between 24 and 48 hours and that extended exposures (72 hours) had little or no effect on the toxicity profile. From these data it was determined that the NOEL of the 24-hour exposure correlated well with in vivo toxicity and provided acceptable estimates of the plasma concentration in vivo that would result in toxicity. When compared to in vivo animal studies, the 24-hour $TC_{50}$ concentration for the most sensitive toxicity exceeded the concentration at which toxicity occurred. However, the NOEL of the 24 hour period also correlated with the 72-hour $TC_{50}$ concentration for the more sensitive assays, and thus the 72-hour $TC_{50}$ concentration also provided acceptable estimates of the plasma concentration in vivo that would result in toxicity.

Studies such as these indicate that a preferred concentration for setting $C_{tox}$ is the highest concentration at which there is no observed effect on any of the indicators being measured in the cluster analysis, especially a 24-hour cluster analysis. The $TC_{50}$ concentration in the most sensitive of toxicity assays in a 72 hour cluster analysis has been observed to correlate with the 24 hour NOEL/$C_{tox}$, and thus represents another datapoint in the CATS analysis that works as an estimate of the sustained plasma concentration in vivo that would result in toxicity. It will be apparent that 24 hour assays are more time-effective, and consequently, the 24 hour NOEL/$C_{tox}$ represents a preferred data point to select as $C_{tox}$ in a CATS assay. It will also be apparent that, with further time studies, it may be possible to select an equally suitable $C_{tox}$ at other CATS assay time points (e.g., between 24 and 72 hours, or less than 24 hours).

In certain embodiments, the predicting comprises performing concentration response analyses of measurements from at least three separate assays that are employed in the cluster analysis. For example, in the cell health cluster, such predicting will involve monitoring the concentration response effect of the compound on a first health indicator which monitors cellular replication, a second cell health indicator which monitors mitochondrial function, and a third cell health indicator which monitors membrane integrity. Of course, it is understood that fourth, fifth, sixth or more cell health indicators also may be employed. From these concentration response analyses, the highest concentration of the chemical compound at which a measurable toxic effect of the chemical compound is not observable, i.e. NOEL, is determined and the $C_{tox}$ is identified as the concentration that correlates to the NOEL. In choosing the concentrations of the compound for analysis, one of skill in the art should devise a dose response regimen which is selected to provide an indication of cell health at concentrations of at least two concentration values higher than the $C_{tox}$ concentration.

In the specific embodiments, the results of the analyses are depicted on a single graph on which the values are presented relative to control. The term "relative to control" means that the measurements in the presence of a given concentration of the compound are compared to a similar assay performed in the absence of the compound. The measurement in the absence of the compound is presented as the 100% measurement. The effect of the compound is thus determined as a raw figure which is then adjusted relative to that measurement that is determined in the absence of the compound.

In certain instances, there may be enough biological activity information generated for a compound or series of compounds from efficacy/activity experiments to predict a plasma concentration in humans that will be required to see a therapeutic effect. Even where such a prediction is premature, there may at least be some activity data indicating concentration of a compound or series of compounds needed to achieve a biological effect that correlates with a desired therapeutic activity. In such instances, it becomes possible to use the in vitro data from CATS analysis to estimate a therapeutic index (TI). TI for a drug is calculated by dividing the toxic concentration (conventionally a $TC_{50}$ value) by the beneficial therapeutic concentration. Thus, the larger the TI number, the safer the drug. For example, for a compound which has a $TC_{50}$ value greater than 100 micromolar, an estimated $C_{tox}$ value of 50 micromolar and an estimated therapeutic concentration of 0.2 micromolar, a TI of 500 is obtained. If the estimated $C_{tox}$ is used as the toxic concentration, then a TI of 250 is obtained. This would represent a safe drug at least in terms of liver toxicity. A TI that is at least 10 is preferred, and a TI of 100 is particularly preferred. Of course, values higher than 100 will be indicative of the drug being especially safe and would be most preferred.

Thus, in one embodiment of the invention useful for prioritizing candidate therapeutic agents, one performs an in vitro activity assay to determine concentrations of chemical compounds required to achieve an activity ($C_{ther}$), wherein the activity correlates with a desired therapeutic effect in vivo; predicts cytotoxicity of the compounds according to CATS assay procedures described herein; determines the ratio of $C_{tox}$:$C_{ther}$ for each compound to provide an Estimated Therapeutic Index (ETI) for each compound; and prioritizes the compounds as candidate therapeutic agents from the ETIs, wherein a higher ETI correlates with a higher priority for further development. The use of an estimated $TC_{50}$ from the CATS assays also would be suitable for generating ETIs and prioritizing compounds, especially where one is working with a family of structurally related compounds, and the $TC_{50}$ is from the same particular assay in the CATS battery of assays. (A primary piece of data often used to compare relative toxicity of compounds is the concentration of drug that produces a half maximal effect in any given assay. This value is referred to as the toxic concentration that produces a 50% response or $TC_{50}$).

II. Use of Toxicity Cluster Assays to Identify Potential Non-Toxic New Therapeutics In certain embodiments, the assays of the present invention may be used as part of a drug discovery program to identify a putative therapeutic compound with limited toxicity. Drug discovery begins with the identification of a range of candidate substances that show promise in a targeted therapeutic area. This first step can result in several hundred "hits". The discovery team is then faced with the question of which compounds to run in subsequent screens. CATS analysis at this stage allows teams to prioritize the compounds based on estimated toxicity or estimated relative toxicity values. The top compounds are put through a range of additional screens for efficacy and specificity. The idea is to identify the core structure or template that shows the most promise for future drug development efforts. Once the template is selected, additional chemistry and structure activity analyses are performed to increase the potency of the compound. This process yields the lead compounds. A CATS screen at this stage of the process may be performed to provide toxicity data on these potential lead compounds. The top lead compounds are selected to enter preclinical animal testing. At the animal testing stage, 30% of all drug candidates fail due to unanticipated toxicity. Incorporation of CATS screening early in the discovery process should greatly reduce the number of compounds that fail during this late stage.

The CATS technique described in the present invention may be employed at any stage in the drug discovery program but is especially valuable early in the discovery process. The information obtained from the cluster analysis provides the chemists with the appropriate information to design out toxicity, while maximizing potency and efficacy in the new templates. In addition, data obtained from the toxicity cluster analysis can identify subcellular targets of the compounds that generate the toxicity. Using these methods, the putative therapeutic compounds can be ranked or prioritized based on their relative toxicities and relative toxicity compared to known drugs in the same therapeutic and chemical class. For example, the antifungal ketoconazole could be used as a reference compound for new antifungals of the azole class.

High throughput assays for screening numerous compounds for toxicity are specifically contemplated. In certain embodiments, the high throughput screens may be automated. In high throughput screening assays, groups of compounds are exposed to a biological target. These groups may be assembled from collections of compounds previously individually prepared and since stored in a compound bank, the assembly being random or guided by the use of similarity programs from which similar structures are formed.

In addition, there has also been a rapid growth in the deliberate preparation and use of libraries and/or arrays of compounds. Each library contains a large number of compounds which are screened against a biological target such as an enzyme or a receptor. When a biological hit is found, the compound responsible for the hit is identified. Such a compound, or lead, generally exhibits relatively weak activity in the screen but forms the basis for the conduct of a more traditional medicinal chemistry program to enhance activity. The libraries may be prepared using the rapidly developing techniques of combinatorial chemistry or by parallel synthesis (DeWitt el al, Proc Natl Acad Sci, 90, 6909, 1993; Jung et al, Angew Chem Int Ed Engl, 31:367-83, 1992; Pavia etal., Bioorg Med Chem Lett, 3:387-96, 1993).

Alternatively, the compounds to be screened may be from a library based upon a common template or core structure [see for instance Eliman and Bunin, J Amer Chem Soc, 114: 10997, 1992 (benzodiazepine template), WO 95/32184 (oxazolone and aminidine template), WO 95/30642 (dihydrobenzopyran template) and WO 95/35278 (pyrrolidine template)]. The template will have a number of functional sites, for instance three, each of which can be reacted, in a step-wise fashion, with a number of different reagents, for instance five, to introduce 5×5×5 different combinations of substituents, giving a library containing 125 components. The library will normally contain all or substantially all possible permutations of the substituents. The template may be a 'biased' template, for instance incorporating a known pharmacophore such as a benzodiazepine ring or an 'unbiased' template, the choice of which is influenced more by chemical than biological considerations.

Thus, the present invention may be used to identify lead compounds for drug discovery. In addition to the library screening discussed above, such lead compounds may be generated by random cross screening of single synthetic compounds made individually in the laboratory or by screening extracts obtained from natural product sources such as microbial metabolites, marine sponges and plants.

In another alternative, the compounds may be generated through rational drug design based on the structure of known biologically active compounds and/or their sites of biological action. This has now been complemented by the powerful techniques of computer-assisted drug design. The goal of rational drug design is to produce structural analogs of biologically active molecules of interest. Such technologies will yield potentially thousands of compounds for a particular indication that may be screened for cytotoxicity using the present invention.

III. Kits

In certain aspects of the present invention, all the necessary components for conducting the CATS assays may be packaged into a kit. Specifically, the present invention provides a kit for use in a cytotoxicity assay, the kit comprising a packaged set of reagents for conducting two or more cell health assays selected from the group consisting of a cycle evaluation assay, mitochondrial function assay, energy balance assay, cell death assay, oxidative stress assay, metabolic activation assay, and metabolic stability assay; wherein said two or more cytotoxicity assays are distinct from each other. In addition to the reagents, the kit may also include instructions packaged with the reagents for performing one or more variations of the CATS assay of the invention using the reagents. The instructions may be fixed in any tangible medium, such as printed paper, or a computer-readable magnetic or optical medium, or instructions to reference a remote computer data source such as a worldwide web page accessible via the internet.

While the above embodiments contemplate kits in which there is one assay performed from each of the classes of cycle evaluation, mitochondrial function, energy balance and cell death assays it is contemplated that the kits and the methods may involve conducting more than one of any type of the assay. As such in addition to the kits comprising the reagents for a first, second, third, fourth and fifth assay, it is contemplated that the kits also may comprise the reagents for conducting a second assay from each of the classes. Therefore, it is contemplated that the kits also may comprise the reagents for conducting a plurality of distinct cell cycle evaluation assays; the reagents for conducting a plurality of distinct mitochondrial function assays; the reagents for conducting a plurality of distinct energy balance assays and the reagents for conducting a plurality of distinct cell death assays.

The present invention also contemplates kits constructed for use in any of the specific toxicity screening assays described herein, including but not limited to, organ-specific screens such as cardiac specific screen, anti-tumor screen, drug-drug interaction screen, species-specific screen, multicell screen, and the like. Such kits would be constructed as described herein above but would contain the reagents necessary for the assays specific to such screens, as described in detail herein. For example but not by way of limitation, a kit for a cardiac specific screen will include a packaged set of reagents for conducting the two or more cell health assays as described in detail herein above, as well as a packaged set of reagents for conducting at least one cardiac-specific cell health assay selected from the group consisting of assays of cardiac hypertrophy, QT interval prolongation, and cardiac cell physiology. A kit for an anti-tumor screen in accordance with the present invention may include the packaged set of reagents for conducting the two or more cell health assays as described in detail herein above, as well as a packaged set of reagents for conducting an assay of the expression level of one or more target molecules. A kit for a species-selector screen in accordance with the present invention may include a packaged set of reagents for conducting one or more assays related to metabolic activation, metabolic stability and/or metabolic profiling, and may further include the packaged set of reagents for conducting the two or more cell health assays as described herein above. A kit for a drug-drug interaction screen in accordance with the present invention may include a packaged set of reagents for conducting one or more assays related to cytochrome P450 enzyme induction, cytochrome P450 inhibition and/or metabolic activation, and may further include the packaged set of reagents for conducting the two or more cell health assays as described herein above.

Introduction to In vitro Toxicity Screening

There are several key cellular events that can be used to assess compound toxicity. These include, but are not limited to, loss of membrane integrity, mitogenesis, and altered mitochondrial function. Most drug evaluations focus on a single endpoint such as cell viability (live versus dead cells). This approach can lead to false negative or false positive results. The screening approach described in the present invention combines the results of several biochemical assays to obtain toxicity profiles for each test compound. Test compounds were evaluated for cytotoxicity in Tier 1 (general cell health) screening assays. Each assay was chosen because it monitors an important cellular process that can provide information on toxicity and on the potential mechanisms of toxicity.

Leakage of intracellular proteins, such as lactate dehydrogenase (LDH), into the outer milieu can provide information on cell death through disruption of the cell membrane. The release of α-glutathione S-transferase (α-GST) was used to monitor membrane integrity or cell death in this study. In blood, α-GST is a specific liver protein that provides information on cell death that is more reliable than the release of lactate dehydrogenase (LDH) (Vickers, 1994; Redi, 1995). The primary reasons for this are as follows: LDH is present in red blood cells and therefore medium that contains more than 10% serum will have high levels of background LDH activity that could mask small changes in release from the test cells. The assay is based on enzyme activity, which means that compounds that directly inhibit LDH activity would result in false negative data. In comparison, α-GST is found only in hepatocytes and kidney proximal tubule cells, not in serum. Thus, background levels are extremely low. The α-GST assay is an ELISA that measures protein mass, not activity, and therefore is less likely to be influenced by the test compounds. The presence of α-GST in blood samples collected during in vivo studies indicates toxicity specific to the liver.

Information on cell number relative to controls is important in order to determine whether or not a compound is acutely toxic or simply slowing, or inhibiting cell replication. Cell number was determined in vitro, using a modified propidium iodide assay or comparable assay such as the CyQUANT® GR-fluorescence assay (Wilson et. al., 1999).

Compounds that alter mitochondrial function or cellular energy balance will ultimately produce cell death. Therefore it is important to monitor the effects of the test compounds on mitochondrial function and energy balance. The reduction of tetrazolium dyes such as 3-[4,5-dimethylthiazol-2-yl]-2,5-diphenyltetrazolium bromide (MTT) (Mosmann, 1983; Huveneers-Oorsprong, et al., 1997) and Alamar blue (A B) (Goegan et al., 1995) to chromaphores detectable by spectrophotometric or fluorometric analysis have been used extensively as indicators of cell viability. Early reports suggested that reduction of these dyes occurred solely in the respiratory chain of mitochondria (Slater et al., 1963). More recent studies provide strong evidence that other mitochondrial and cytosolic pathways utilizing NADH or NADPH as electron donors are also involved (Berridge and Tan, 1993; Andrews et al., 1997). Thus, while MTT and AB remain excellent general indicators of cell health, they may not be predictive of mitochondrial function in the absence of supporting data such as ATP or mitochondrial membrane permeability.

When MTT data are combined with information about cell number and membrane integrity it is possible to develop a more complete toxicological profile. Evaluating a compound in a "panel" of assays with diverse biochemical endpoints builds redundancy into the screening process and reduces false positive or negative results. In addition, multi-endpoint analysis provides information on relative toxicity between test or reference compounds as well as insight into potential mechanisms of toxicity. This information should provide early indications of potential adverse effects of new chemicals early in the discovery process. This information can then be used to design new compounds with improved therapeutic indices.

In order to provide the most meaningful and up-to-date toxicity data, current assays may be deleted and or new assays added to the screening methods of the present invention. The most complete toxicity profile will be obtained by evaluating test compounds in at least 4-5 different assays; however, it is possible that some evaluations will be done with fewer endpoints. In these instances evaluation of data should be done with caution and interpretations should not go beyond making relative comparisons to other compounds.

Cardiac Toxicity Screening

Adverse events in the heart are of three general types: (1) QT prolongation of ion channel effects, (2) hypertrophy, and (3) cytotoxicity. The processes involved in the mechanical contraction and relaxation of the heart muscle are complex and are controlled by ion movement. The electrophysiology of the beating heart includes atrial depolarization (P-wave), ventricular depolarization (QRS), and ventricular repolarization (T). Several drugs have been shown to increase the QT interval through interference with potassium ($K^+$) movement. This can lead to Torsade de Pointe, ventricular fibrillation and sudden death. Because of the serious nature of these events, regulatory authorities have issued requirements for evaluation of new chemical entities for potential QT prolongation prior to regulatory submission.

Therefore, the present invention provides a method of determining a level of cardiac specific cytotoxicity by monitoring compound effects on mitochondrial function, cell membrane integrity, oxidative stress, cell mortality, oxidative stress, heart cell viability, heart cell morphology, and cardiac cell physiology/beat rate.

In such a method of determining a level of cardiac toxicity of a chemical compound, cardiomyocytes are typically isolated and established as primary cultures. Test compounds are added over several exposure concentrations, and the following analyses may be performed: mitochondrial function (such as but not limited to, an ATP assay), cell membrane integrity (such as but not limited to, a GST leakage assay or Troponin I release assay), cell mortality, and oxidative stress assays and other cell health function assays as described herein. Such assays are performed as described herein previously. In addition, further analyses performed in accordance with this particular method of the present invention include the following: cardiac hypertrophy assays, QT interval prolongation assays, and cardiac cell physiology assays, as described in further detail herein below. Once such assays are performed, a level of cardiac toxicity for the chemical compound is determined as described in U.S. Pat. No. 6,998,249 (previously incorporated herein by reference), and/or as described herein previously.

Cardiac hypertrophy refers to an increase in the size of the heart or in a select area of the tissue. Hypertrophy occurs due to an increase in the size of cells, while the number of cells stays the same. In general, cardiac hypertrophy allows the heart to maintain or increase cardiac output as a compensatory response to stress. However, a prolonged state of hypertrophy can lead to a reduction in ejection-fraction and heart failure. It is therefore important to evaluate new chemical entities for potential cardiac toxicity.

In response to hypertrophy there is seen an increased expression of numerous cardiac genes, and thus methods of measuring cardiac hypertrophy involve detecting the levels of such cardiac hypertrophy markers. Such methods may measure the levels of mRNA expression or protein expression by well known methods in the art. Examples of cardiac hypertrophy markers include, but are not limited to, atrial natriuretic peptide (ANP), brain natriuretic peptide (BNP), skeletal α-actin, C-fos and C-jun, and the like.

The term "QT interval" as used herein will be understood to refer to a measure of the time between the start of the Q wave and the end of the T wave in the heart's electrical cycle. The QT interval is thus dependent on the heart rate (the faster the heart rate, the shorter the QT interval). If abnormally prolonged or shortened, there is a risk of developing ventricular arrhythmias.

QT interval prolongation may be measured utilizing assays that measure the disruption of ion channels. One example of such type of assay is a hERG channel assay.

The hERG channel assay is described herein as associated with an indication of QT interval prolongation, and such assay is also a primary indicator of $K^+$-channel blockage. HERG. (which stands for "Human Ether-a-go-go Related Gene") encodes a potassium ion channel responsible for the repolarizing $I_{Kr}$ current in the cardiac action potential. This channel is sensitive to drug binding, which can result in decreased channel function and the so-called acquired long QT syndrome. Although there exist other potential targets for adverse cardiac effects, the vast majority of drugs associated with acquired QT prolongation are known to interact with the HERG potassium channel. One of the main reasons for this phenomenon is the larger inner vestibule of the HERG channel, thus providing more space for many different drug classes to bind and block this potassium channel. Therefore, as mentioned above, regulatory authorities have issued requirements for evaluation of new chemical entities for potential QT prolongation prior to regulatory submission.

It is to be understood that the present invention is not limited to the particular hERG inhibition assay described herein. Other methods of measuring QT-prolongation known in the art also fall within the scope of the present invention.

Methods of measuring cardiac cell physiology may be monitored by any methods described herein or known in the art. In particular, cardiac cell physiology may be measured by determining the percentage of beating cells or the beat rate per 30 second intervals.

In a further embodiment, a method of determining cardiac specific toxicity is provided. In such method, freshly isolated liver cells are also provided and subjected to the same assays and analyses as the cardiomyoctes. This will allow for an identification of target organ specificity for chemical compounds that are specifically toxic to cardiac cells. In the method, the analyses from the cardiomyocytes and the liver cells are compared, and it is determined that the chemical compound is more toxic to cardiac cells than non-cardiac cells if the $C_{tox}$ for the cardiac cells is less than the $C_{tox}$ for the non-cardiac cells.

FIG. 1 illustrates an evaluation of the drug adriamycin in the dual cell Cardiotox model of the present invention. By comparing concentration response analyses of membrane permeability (MemTox), MTT, GSH and ATP assays, it can be seen that adriamycin is much more toxic to heart than to liver (see arrows). It is clear that cell viability as determined by membrane integrity is significantly lower in heart cells than at the same exposure concentration in liver cells. Markers of early toxicity such as MTT and GSH are also more sensitive in heart cells than in liver. Exposure concentrations, serum protein, and time are constant in both cell types. These date indicate that the heart would be more sensitive to adriamycin toxicity than liver.

Figure 2:
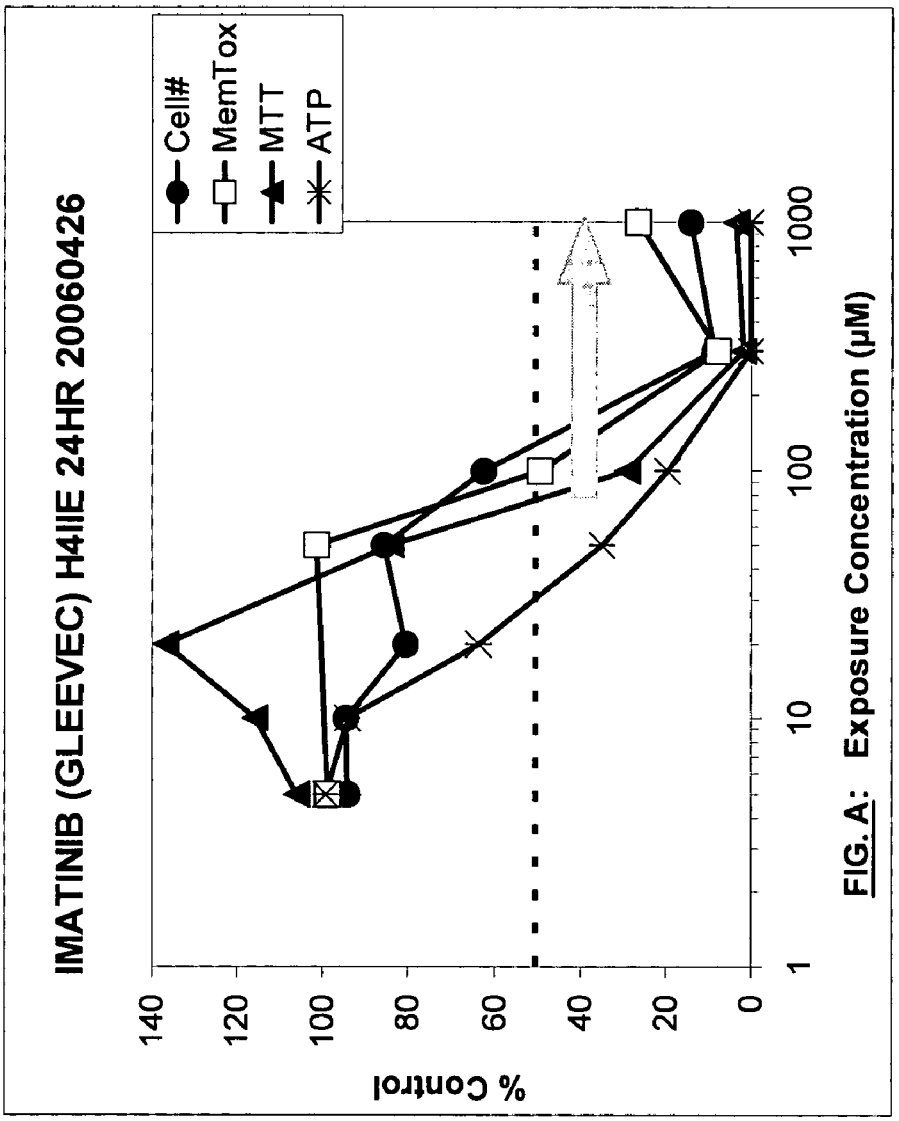
FIG. 2 illustrates concentration response analyses for Imatinib (Gleevec) in H4IIE cells at 24 hours exposure. This liver cell line reveals mitochondria as the most sensitive target for this drug.

In FIG. 2, concentration response analyses for Imatinib (Gleevec) in liver cells are shown. Imatinib is a tyrosine kinase inhibitor used in the treatment of chronic myelogenous leukemia, and such drug has previously been associated with cardiac toxicity, which was hypothesized to occur by mitochondrial damage. Analyses of Imatinib in the H4IIE liver cell line reveals that mitochondria is indeed the most sensitive target. In heart cells, the drug is three to four-fold more potent. By comparing multiple drugs that target tyrosine kinase, a comparative data set can be used to add even more predictive information.

Figure 4:
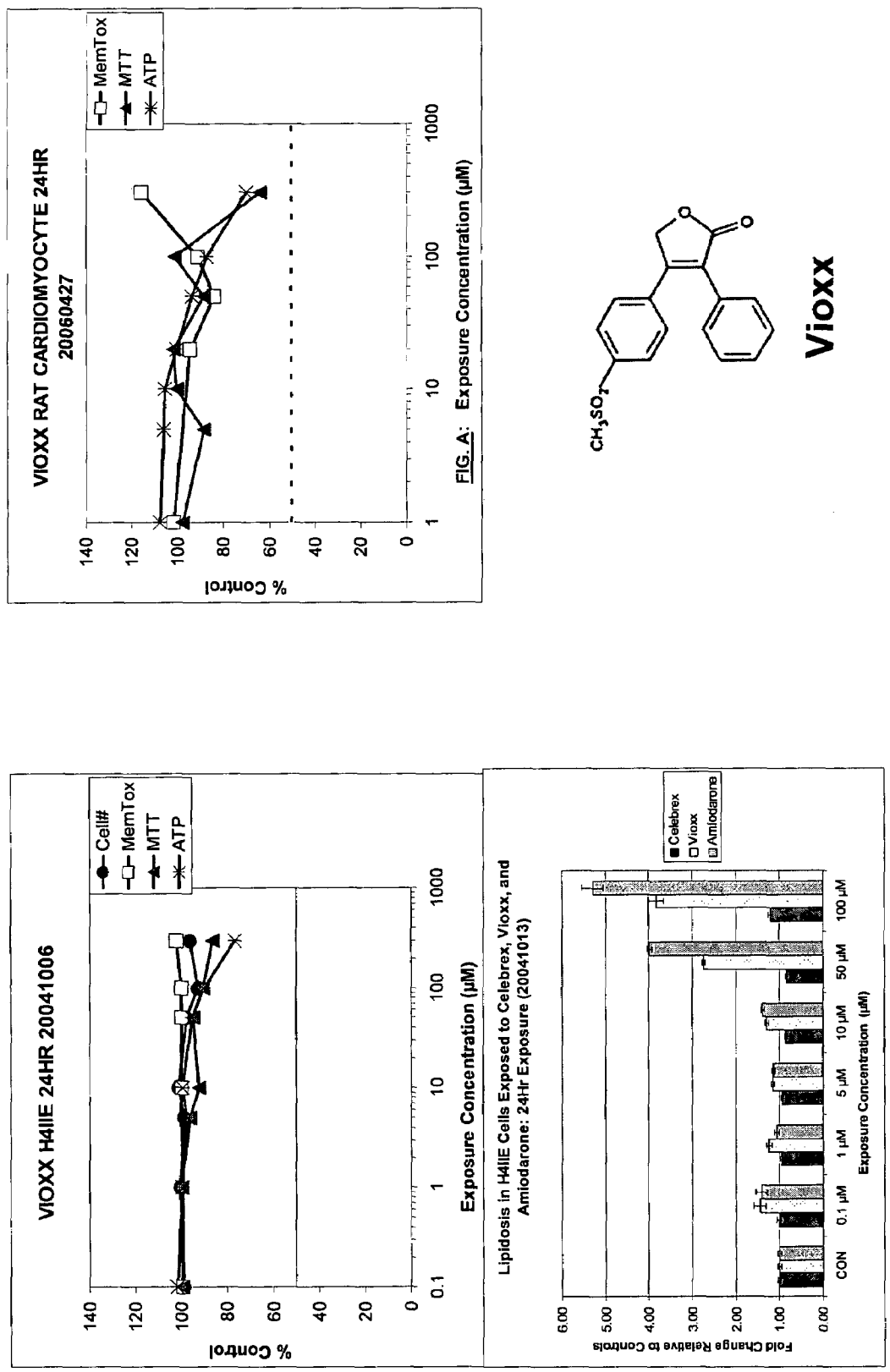
FIG. 4 illustrates concentration response analyses for Vioxx in H4IIE cells and rat cardiomyocytes at 24 hours exposure. Celebrex and Vioxx produce difference biochemical profiles, suggesting that their effects are not related to their target.
Figure 5:
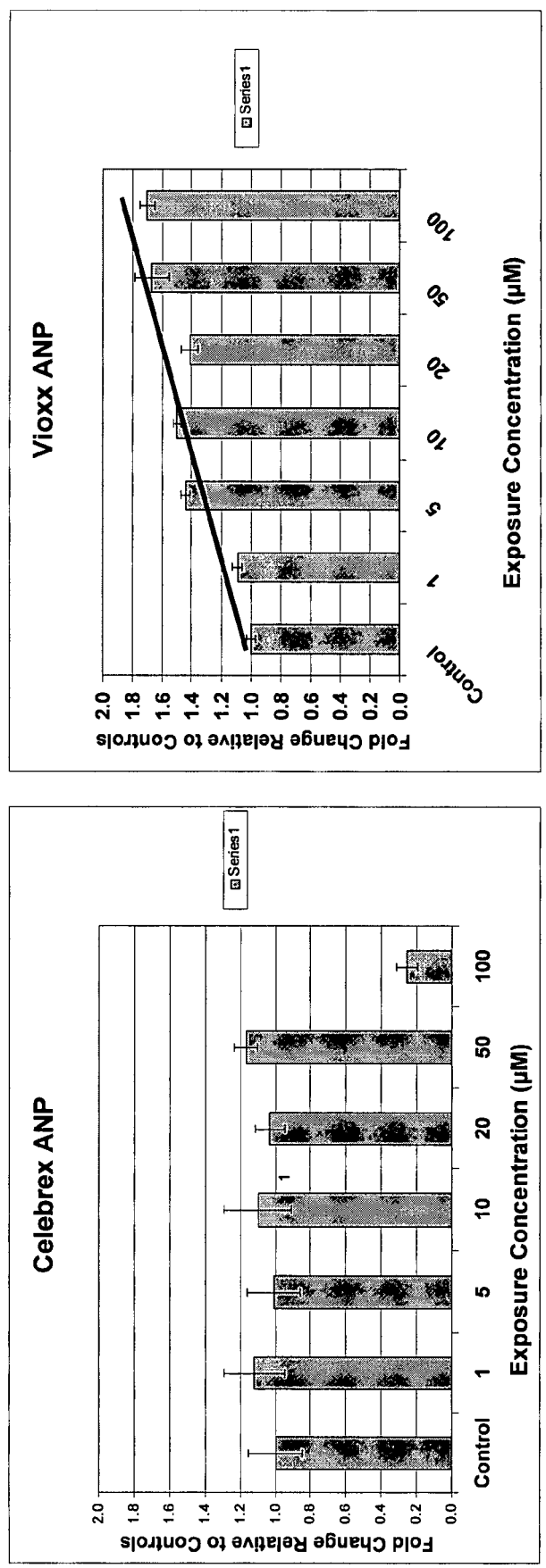
FIG. 5 illustrates analyses of the cardiac hypertrophy marker ANP in rat cardiomyocytes exposed to Celebrex or Vioxx. Induction of ANP was measured and normalized with GAPDH with bDNA technology.

FIGS. 3-5 are directed to a CardioTox screen of the drugs Celebrex (FIGS. 3 and 5) and Vioxx (FIGS. 4-5). Both drugs inhibit COX-2, and Vioxx was voluntarily removed from the market following the discovery of an increased incidence of cardiac toxicity. Both Celebrex and Vioxx would be considered safe based on the in vitro toxicity screen, which utilized measurements of membrane permeability (MemTox), MTT, and ATP. However, Vioxx increased fat accumulation and oxidative stress and was more effective at inducing the hypertrophy marker ANP (FIG. 5). Differences in the toxicity profiles suggest that these effects are not related to the target.

The CardioTox screening panel is designed to provide information on the effects of new drug candidates on QT prolongation and can provide information on the test compound's propensity to produce cardiac toxicity relative to liver toxicity. The cluster of endpoints evaluated exemplifies the systems biology approach to in vitro screening and is the first model that accurately assigns risk for organ specific toxicity differentiating heart from liver adverse effects.

While the above-referenced screen has been described with reference to determining a level of cardiac toxicity, it is to be understood that the present invention is not limited to methods of determining cardiac toxicity, but rather that the methods of the present invention may be utilized to determine organ-specific toxicity for any desired organ. Based on the methods described herein above and below with reference to screening of multiple cell types, one of ordinary skill in the art will easily be able to adapt the methods described herein with reference to cardiac toxicity for use with determining levels of organ-specific toxicity in other tissues and organs, and therefore such methods also fall within the scope of the present invention.

Anti-Tumor Screen

The present invention provides methods for determining a level of toxicity for an anti-tumor drug. Most anti-tumor drugs are designed to either be cytostatic (i.e., suppress cell growth and multiplication) or cytotoxic (cause cell death). If a drug is cytostatic, it is important to understand the "off-target toxicity" of the anti-tumor drug. If a drug is designed to be cytotoxic, then the evaluation of off-target toxicity becomes even more difficult. In both cases, it is important to be able to differentiate toxicity due to intended pharmacology and toxicity related to chemistry.

The primary mechanism of action of a cytostatic anti-tumor drug focuses on targets that are specific to tumor cells. In contrast, cytotoxic anti-tumor drugs target general processes, by directly interacting with DNA or disrupting cell division processes. Tumor cells are more sensitive than normal cells due to their higher rate of division, but for these drugs a considerable amount of non-specific toxicity occurs. Some of the many side effects of cytotoxic drugs include, but are not limited to, hematoxicity, nephrotoxicity, hepatotoxicity, and neurotoxicity, and such side effects are common.

In the Anti-tumor screen of the present invention, at least three different cell types are utilized: (1) tumor derived cells, (2) proliferating cells from normal tissue, and (3) non-proliferating cells from normal tissue. The evaluation of anti-tumor agents in multiple cell types provides information on mechanism-based toxicity versus efficacy. In addition, it may be desirable to include more than three cell types. For example but not by way of limitation, it may be desirable to include more than one type of tumor cell, to determine a drug's efficacy/potency against multiple types of tumors. In addition, it may be desirable to include a specific cell type from more than one species (i.e., hepatocytes from rat and human) to identify species differences in potency/efficacy and/or toxicity of the anti-tumor agent.

The anti-tumor agent can be evaluated in a toxicity screen of key biochemical functions (as described in detail herein above), with emphasis placed on cell proliferation assays as well as biochemical function and cell viability. Comparisons can then be made to quantitative markers in the concentration response curves constructed with the toxicity data. For example, comparisons of $TC_{50}$, $TC_{20}$ and $TC_{90}$ values can prove very useful in the anti-tumor screen of the present invention.

The methods of the present invention provide the ability to separate target from off-target toxicity, which is essential when evaluating an anti-tumor agent. This is performed by determining the relative abundance of the intended target in each of the at least three cell types. The toxicity response calculated in the previous paragraph can then be normalized to the target in each cell.

The advantages of the Anti-tumor screen of the present invention are four-fold: (1) the use of at least three cell types (tumor cell, normal proliferating cell and normal non-proliferating cell); (2) the ability to identify target versus off-target effects; (3) the ability to examine the potency/efficacy and toxicity of the anti-tumor agent in multiple species; and (4) the ability to examine the potency/efficacy and toxicity of the anti-tumor agent in multiple types of tumors.

Figure 6:
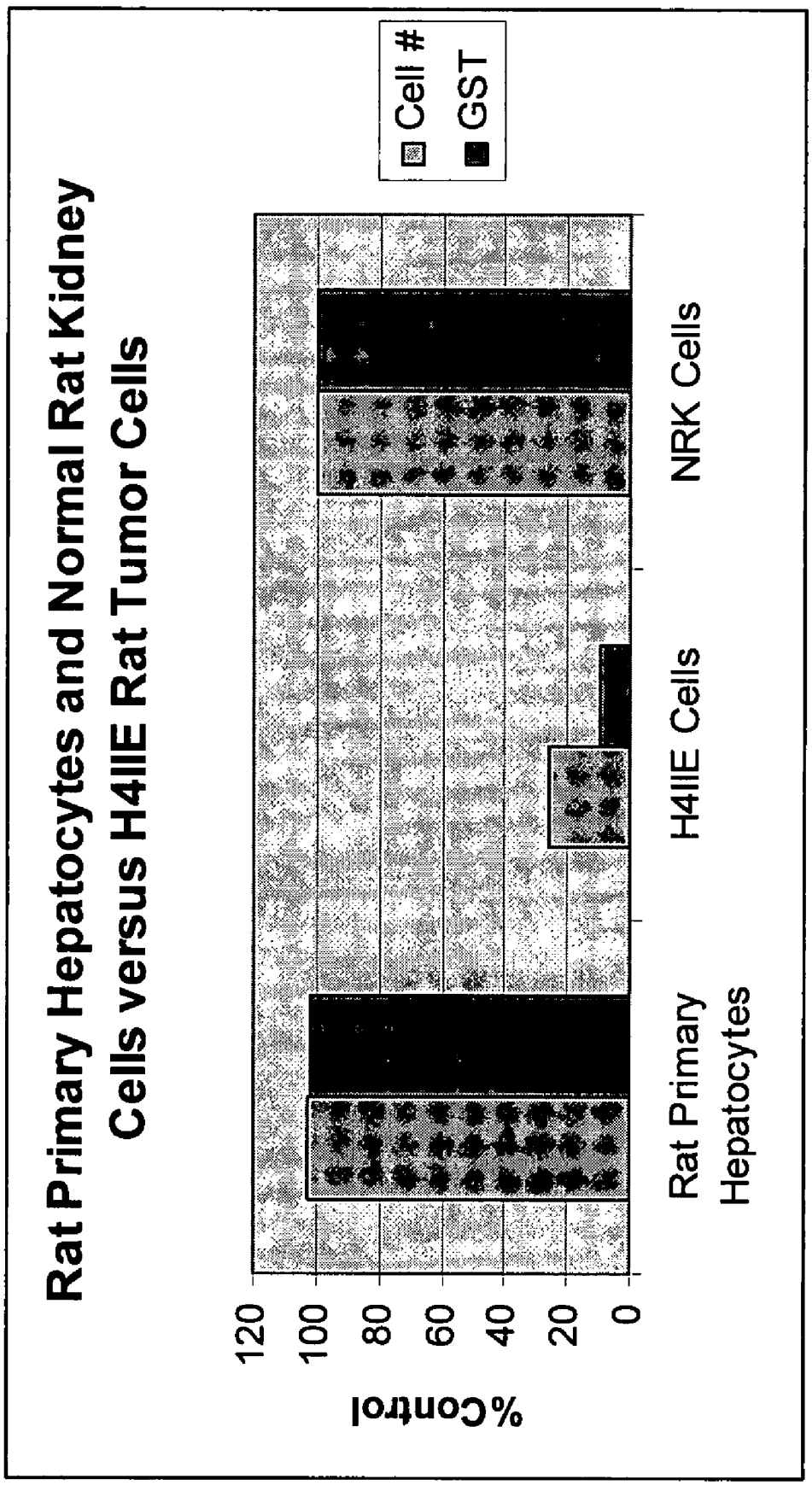
FIG. 6 contains a graph that illustrates cell specificity for an anti-tumor drug screened therein. Rat primary hepatocytes and normal rat kidney (NRK) cells were not sensitive to the anti-tumor drug, whereas H411E cells were highly sensitive to the anti-tumor drug.

In the Anti-Tumor screen illustrated in FIG. 6, cell number and GST assays are shown that demonstrate that the anti-tumor drug is highly tumor cell specific. These results clearly demonstrate that the anti-tumor drug is specifically toxic to the H4IIE tumor cell line, but is not toxic to the rat primary hepatocytes or the normal rat kidney (NRK) cells.

Figure 7:
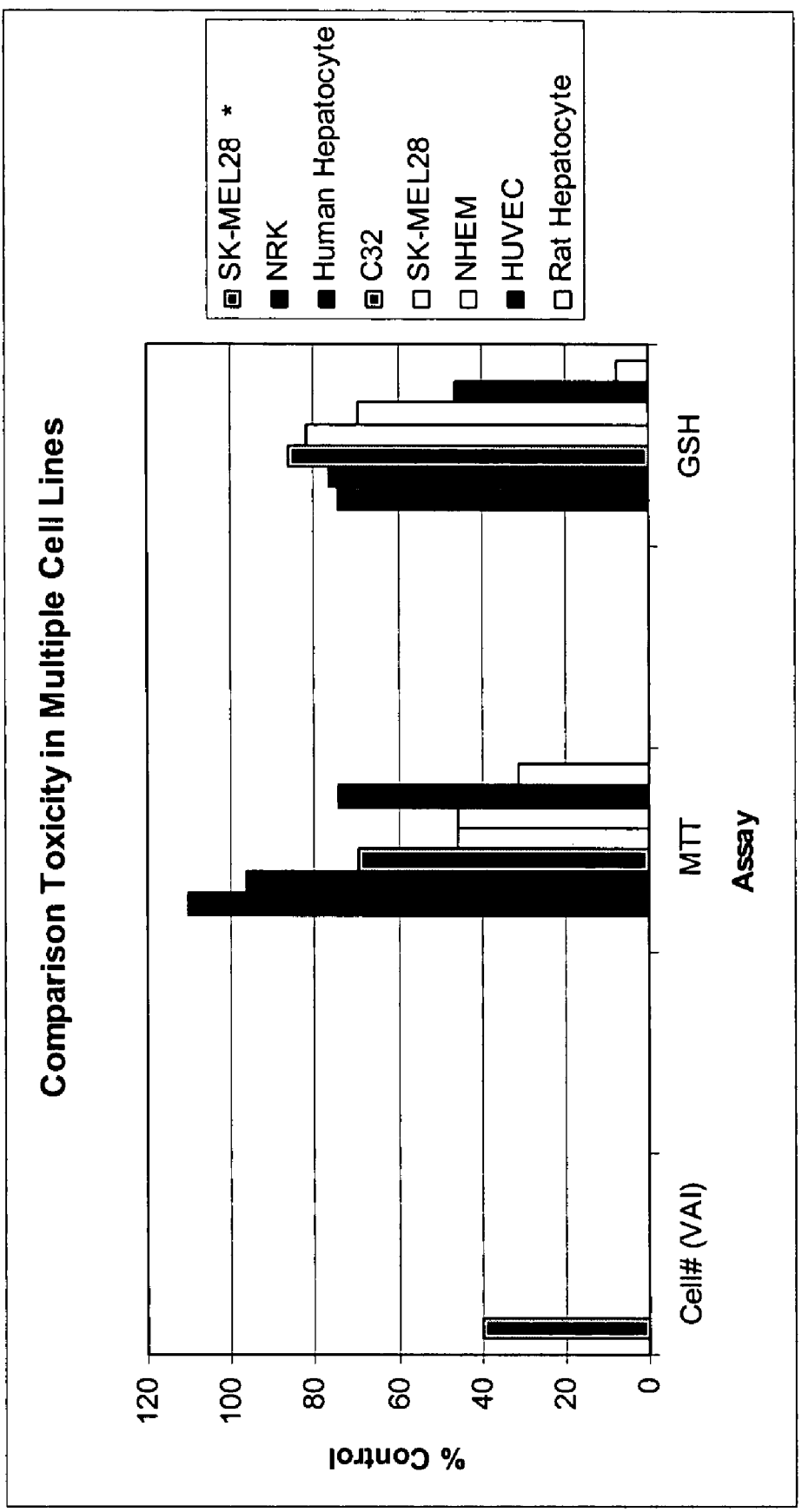
FIG. 7 contains a graph that illustrates a toxicity comparison between multiple cell types. Information regarding drug specificity and species sensitivity can be determined from this type of comparison. SK-MEL28 and C32 are human tumor cell lines; SK-MEL28* refers to data provided by the sponsor. NRK, normal rat kidney cells. HUVEC, human umbilical vein endothelial cells.

FIG. 7 illustrates the advantages of using multiple cell types in the anti-tumor screen of the present invention. This figure illustrates the ability to examine multiple tumor cell types in a single screen (i.e., SK-MEL28, C32). Note that the two tumor cell types were affected more than the non-tumor cells. This figure also illustrates that ability to identify species-specific differences in toxicity. For example, rat hepatocytes were very sensitive to the drug, whereas the drug was much less toxic to human hepatocytes. This demonstrates that a rat would not be the best in vivo model to evaluate the safety of this drug, as the results would over estimate toxicity.

Figure 8:
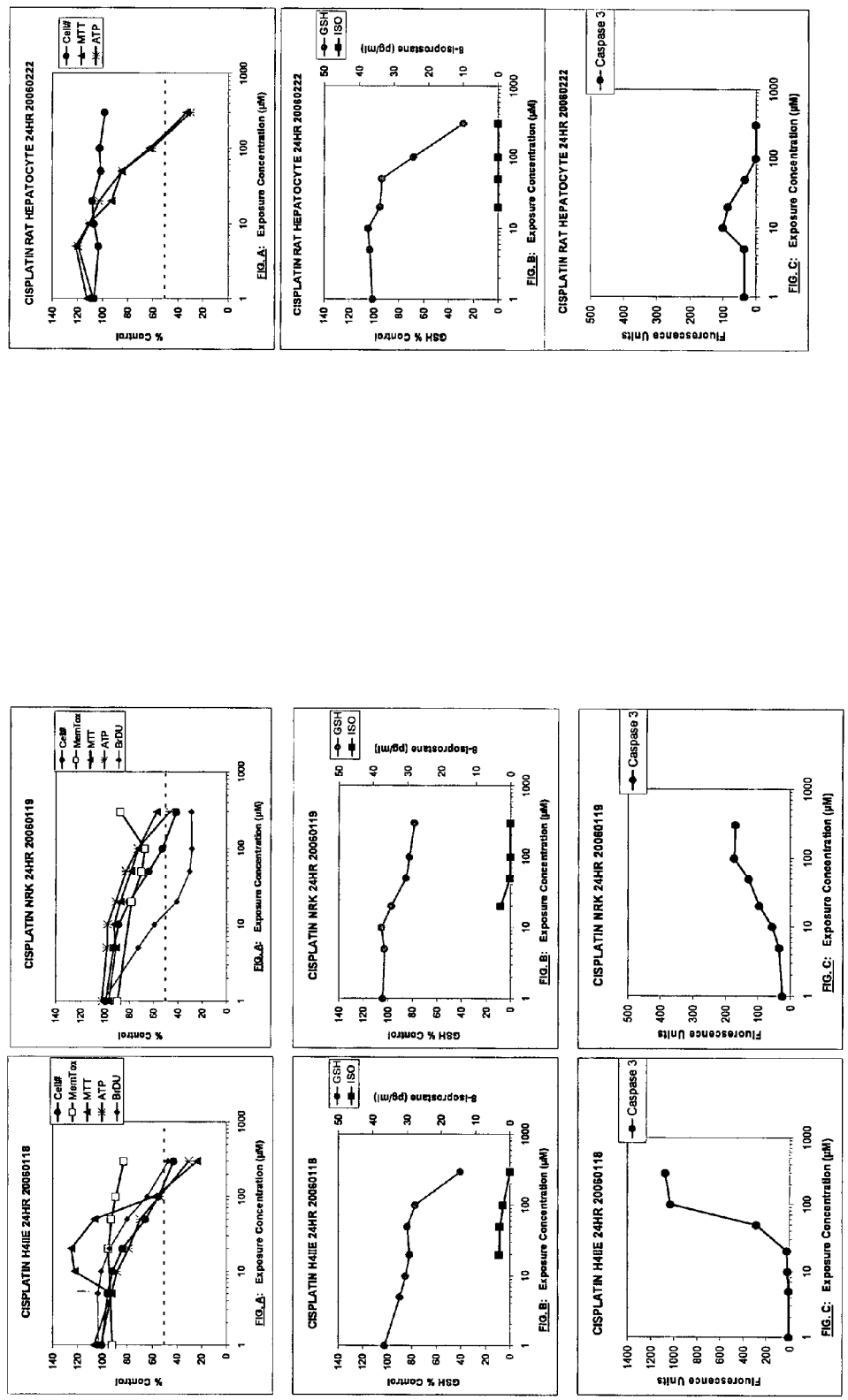
FIG. 8 illustrates concentration response analyses for Cisplatin in three rat cell types: H4IIE tumor cells, NRK (normal rat kidney cells), and rat primary hepatocytes.

FIG. 8 illustrates an anti-tumor screen of the drug Cisplatin in H4IIE tumor cells, rat primary hepatocytes, and NRK (normal rat kidney) cells. Cisplatin is a DNA alkylating agent that exhibits renal toxicity. It is hypothesized to act through mitochondrial toxicity as well as apoptosis. The analyses shown in FIG. 8 illustrates that the liver tumor cell line (H4IIE) is the most sensitive model. All markers except viability (open squares) are reduced, and apoptosis (bottom graph) showed the greatest increase relative to the other cell systems. The NRK cells were most sensitive to cell proliferation, with a moderate increase in apoptosis. The primary hepatocytes model showed mitochondrial effects at higher exposure concentrations with minor changes in apoptosis. Therefore, the anti-tumor screen of the present invention confirms the anti-tumor activity of Cisplatin, and shows that a cytotoxic drug has its greatest potency against tumor cells and cells undergoing replication.

FIG. 9 illustrates an anti-tumor screen of the drug Methotrexate in H4IIE, rat primary hepatocytes, and NRK cells. Methotrexate inhibits folate synthesis, and its toxicity is hypothesized to occur through mitochondrial damage. The analyses shown in FIG. 9 illustrate that the tumor cell line is most sensitive to mitochondrial damage, as determined by the concentration dependent changes in ATP, MTT, and cell number. The mitochondrial damage caused a release of cytochrome c which in turn activated apoptotic pathways. The normal dividing cells (NRK) and the normal non-dividing cells (primary hepatocytes) were considerably less sensitive to these effects.

FIG. 10 illustrates another anti-tumor screen of the present invention, utilizing the drug Doxorubicin. Also known as Adriamycin, Doxorubicin is a topoisomerase inhibitor that exhibits a general toxicity, including cardiac toxicity (see FIG. 1 above), myelotoxicity, and hepatic and renal toxicity. Doxorubicin's toxicity is hypothesized to occur through mitochondrial damage and oxidative stress. FIG. 10 illustrates that this cytostatic drug is toxic to all of the cells tested, and this is consistent with its reported toxicity. When the data from the anti-tumor model are combined with data obtained from the cardiotox model described above, it is clear that this cytotoxic drug is toxic to many tissue types, with the greatest degree of potency observed in heart cells.

FIG. 11 illustrates the ability of the present invention to perform "target profiling" and differentiate target versus off-target effects and cell sensitivity of anti-tumor agents. Different cell lines and primary cells can have considerably different levels of the intended target of the anti-tumor drug. If toxicity assays are performed in multiple cell types without understanding the relative abundance of the target protein, cells with a higher level of target may appear more sensitive to toxicity when in fact the drug is acting as it was designed to do. Thus, to understand toxicity not related to the intended target, the toxicity of the test compound as measured by the $TC_{10}$, $TC_{50}$, or $TC_{90}$ is normalized to the amount of target present. FIG. 11 shows that the amount of target in the H4IIE and primary hepatocytes is similar. In contrast, the NRK cells possess significantly more of the target mRNA. By normalizing the $TC_{50}$ values for viability to the expression of target, it is clear that the H4IIE cells are less sensitive to toxicity than the primary hepatocytes. This is not to say that the H4IIE cells are not responsive (note they are at 50% viability); they simply are more resistant to cell death than the primary hepatocytes. The difference in acute toxicity between the H4IIE and primary hepatocytes can be attributed to off-target toxicity. The NRK cells were most sensitive to the drug, but the toxicity observed could not be differentiated from the intended effect of the drug in the presence of its target. The additional information provided by the target profiling experiment indicates that the target is ubiquitous in nature, and as such drugs designed to interact with this target would be expected to have toxicity in multiple cell types.

Species-Specific Screen

An important component of any new drug evaluation is the potential for species specific toxicity. Rodent studies may show no adverse signs, while a non-rodent species may have severe or even lethal toxicity. When this situation occurs, investigators must begin to ask questions regarding the underlying mechanism, the differences between species, and which species is most relevant to human exposure and potential toxicity. On occasion, the animal tests must be repeated. Answering these questions is costly and time consuming for the company and can delay the delivery of a potentially good drug to market. The ability to screen new drug candidates for potential species-specific toxicity can help scientists select the best and most appropriate second species for animal safety evaluations. More importantly, this information can form the basis of mechanism-based species differences which in turn can provide the most relevant data for human safety assessment communication to the FDA.

The Species-Specific screen of the present invention focuses on metabolic profiles and how they may affect toxicity profiles. The process involves a sequential evaluation of various processes and can be done with any combination of desired animal systems, such as but not limited to, rat, dog, monkey, rabbit and human systems.

In the first step, the metabolic stability of a chemical compound is determined in each species. This analysis determines the rate of metabolism in hepatic microsomes from the species being evaluated.

Figure 12:
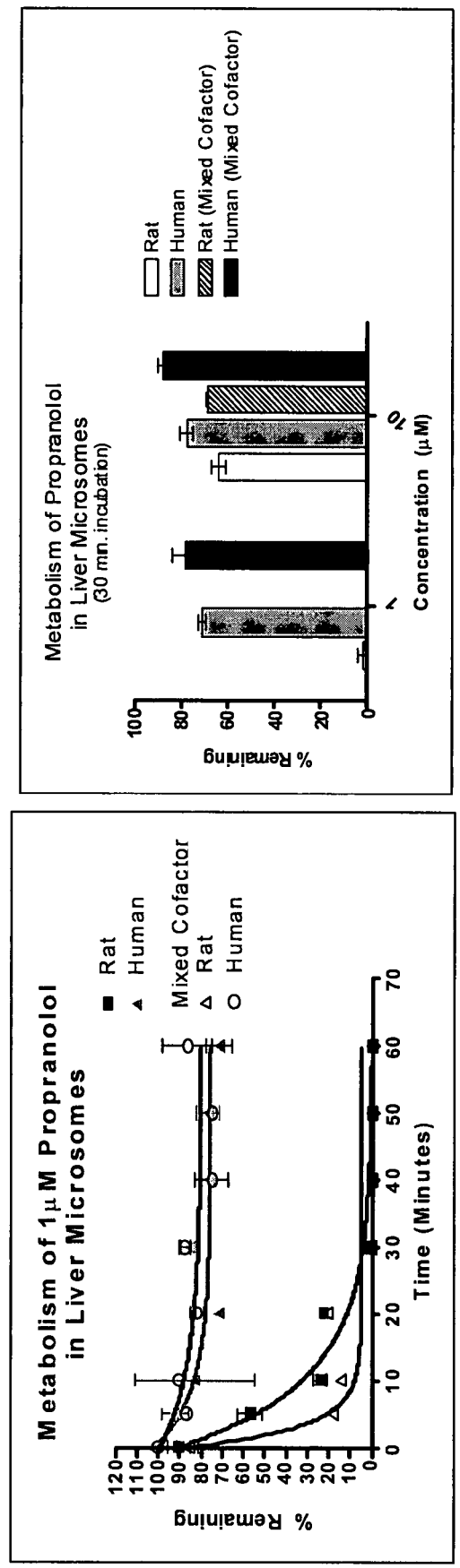
FIG. 12 illustrates a metabolic stability assay of propranolol in rat and human liver microsomes.

FIG. 12 illustrates a metabolic stability assay performed in accordance with the present invention. The metabolism of Propanolol is examined in liver microsomes of rat and human. It is clear that the compound is metabolized to a much greater degree in rat than in human microsomes. The graph on the left depicts rates of metabolism by examining loss of parent over time, while the graph on the right provides basic information on metabolic stability expressed as the amount of parent remaining at the end of the reaction period. The reactions include a single co-factor (NADPH) for phase I metabolism and a second co-factor for glucuronidation or Phase II metabolism if it is required.

In the second step, the metabolic activation or the formation of reactive intermediates is determined in each species. This analysis determines the species specific formation of electrophiles. The system utilizes hepatic microsomes from the species being evaluated. In a novel assay of metabolic activation that is also encompassed within the scope of the present invention, a known amount of reduced glutathione (GSH) is added with the chemical compound, and the disappearance of free GSH is monitored using a labeled probe. The GSH pool decreases in direct proportion to a cytochrome P450-mediated increase in electrophilic intermediates. In a second step of the assay, an inhibitor of cytochrome P450 (such as but not limited to, ABT) is added to the assay, and the decrease in the GSH pool is not observed, thereby confirming that the decrease is due to the cytochrome P450-mediated increase of electrophilic intermediates.

Figure 13:
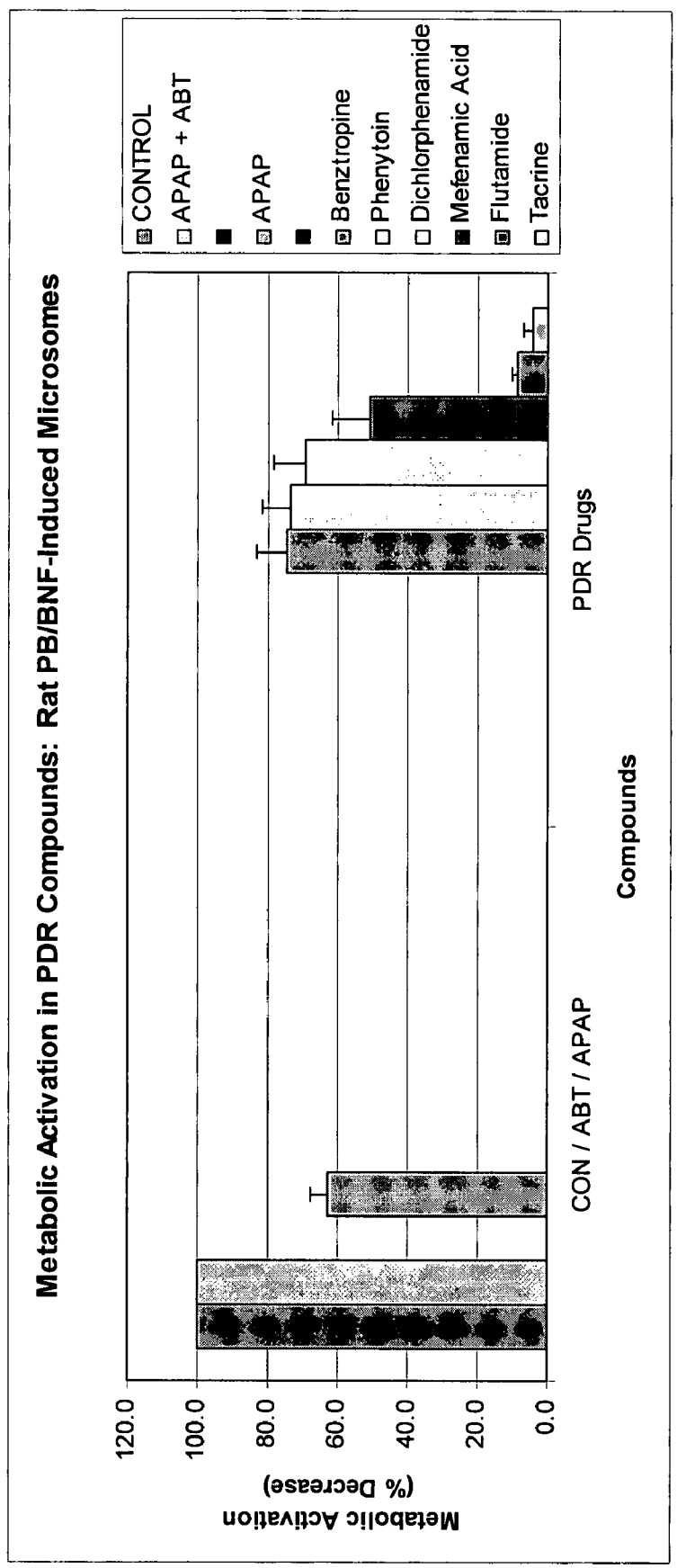
FIG. 13 contains a bar graph illustrating the evaluation of drugs with structural alerts for metabolic activation. APAP, acetaminophen; ABT, 1-Aminobenzotriazole, a cytochrome-P450 inhibitor.

FIG. 13 illustrates the evaluation of drugs with structural alerts for metabolic activation. Acetaminophen (APAP) is included as a control drug that is known to produce reactive intermediates upon metabolism (bars on far left). Note that in the presence of ABT, the loss of GSH is not seen. The drugs on the far right of the graph are all known to undergo metabolic activation. Liver microsomes from Phenobarbital/BNF induced rats were used in the upper graph. As expected, all of the compounds produced a reduction in GSH, but tacrine and flutamide had the most pronounced effects. The formation of reactive intermediates was greater in the induced rat microsomes than in normal human microsomes (bottom graph). These data illustrate the importance of evaluating species specific metabolism and also the ability of the assay to identify drugs that undergo metabolic activation.

In the third step, a qualitative evaluation of the metabolic profiles produced in microsomes from each species is performed. Profiles from each species are compared, and peaks present in one but not the other are flagged.

Figure 14:
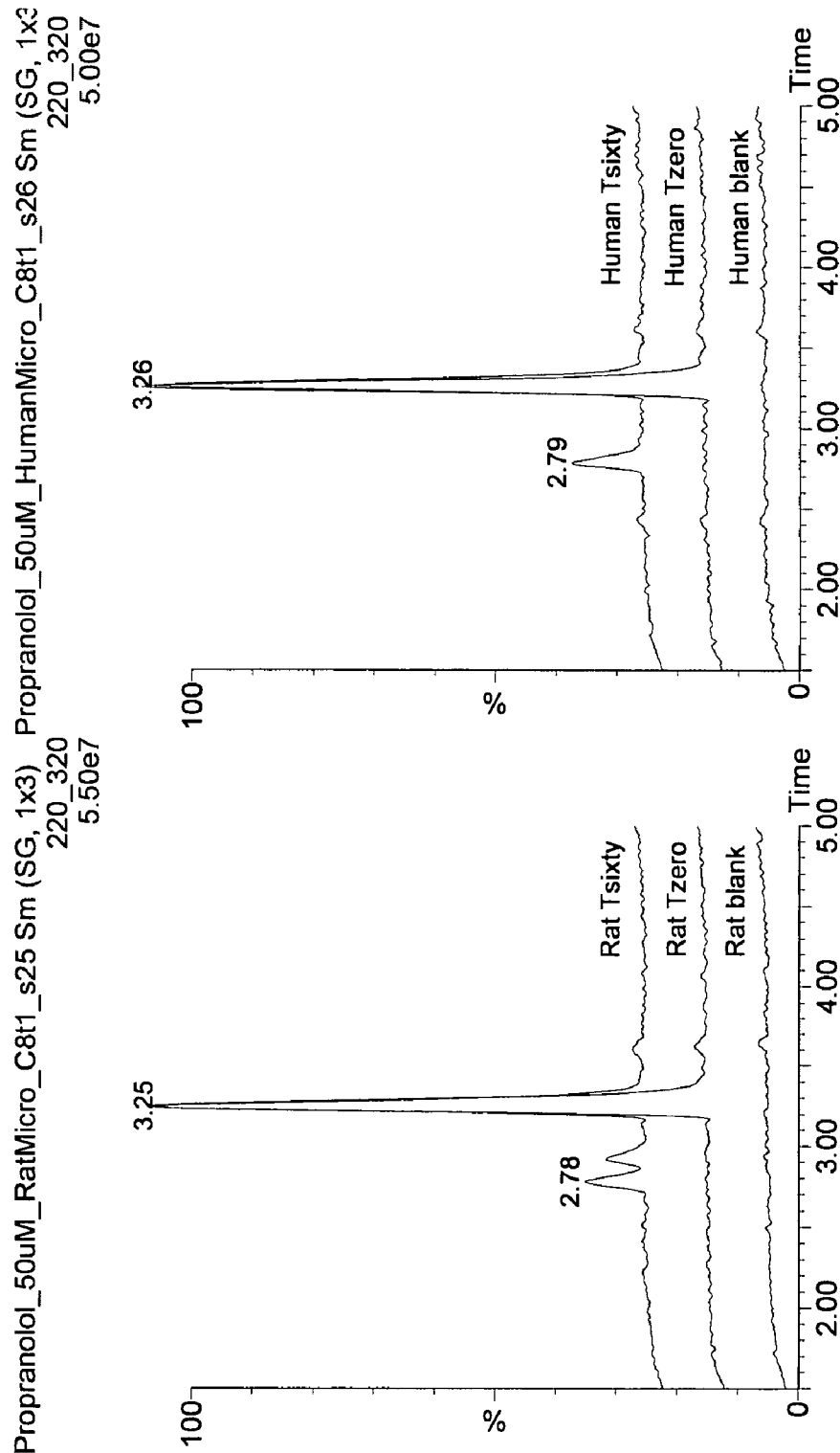
FIG. 14 contains total ion chomatograms illustrating a comparison of propranolol metabolic profiles in rat and human hepatic microsomes.
Figure 15:
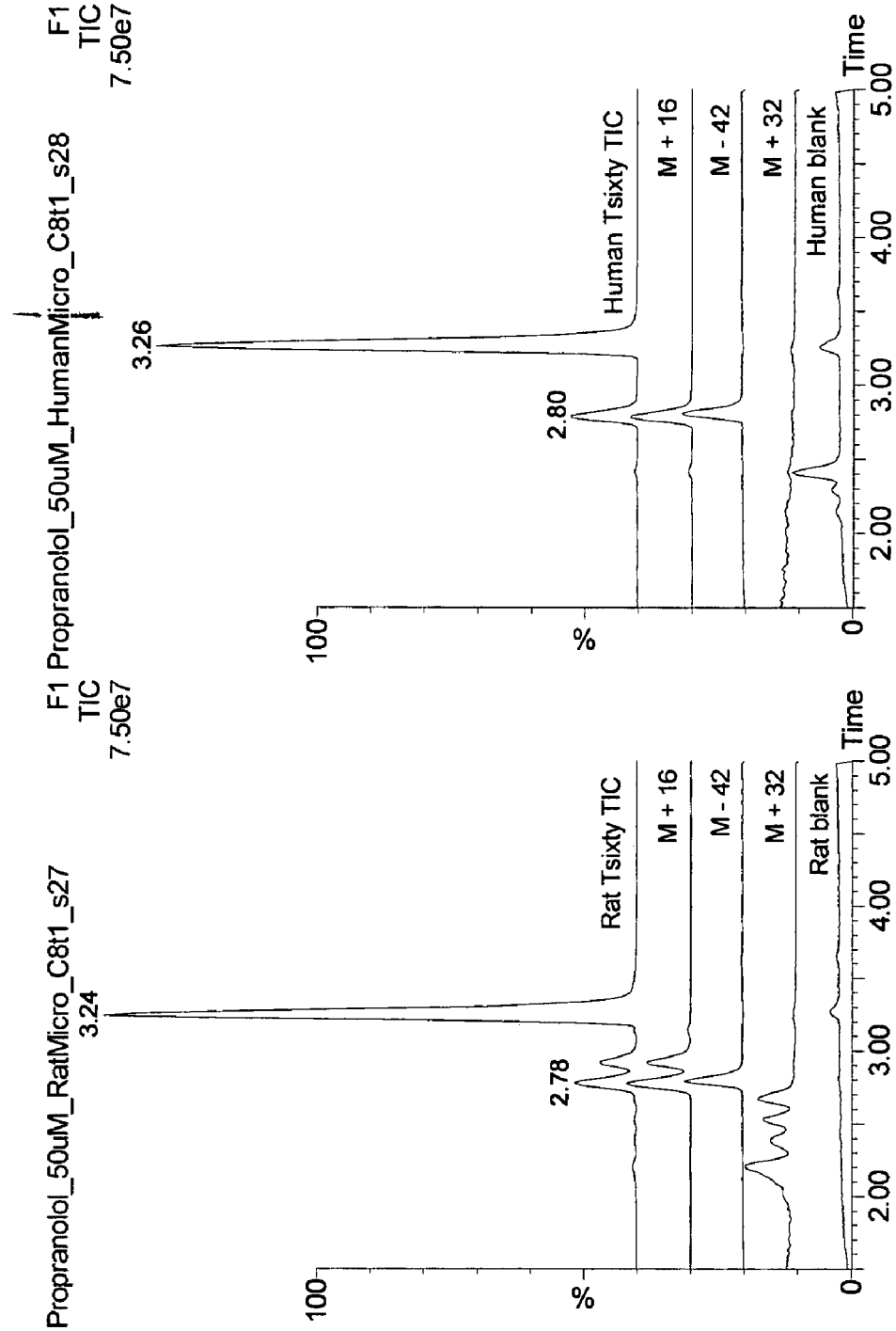
FIG. 15 contains selective ion chromatograms illustrating the different metabolic profiles in rat and human microsomes.

FIGS. 14 and 15 illustrate the analyses of metabolic profiles for rat and human hepatic microsomes in the presence of propanolol by LC/MS in ion selective mode. When human and rat Tsixty profiles are compared in FIG. 14, it is evident that a peak exists between 2.78 and 3.25 in rat that is not present in human. Likewise, in FIG. 15, there are peaks present in the rat Tsixty TIC, M+16 and M+32 that are not present in the human Tsixty TIC, M+16 and M+32. These data indicate the presence of a metabolite in rat that is not present in human.

In the fourth step, the test compound is evaluated in primary hepatocytes from each species against a panel of two or more biochemical markers for cell health. This toxicity is performed as described in detail herein above. Shifts in the toxicity profiles can then be related to changes in metabolism. Taken together and in series, these assays provide a comprehensive picture of potential species specific toxicity linked to metabolism.

IV. Examples

Examples are provided hereinbelow. However, the present invention is to be understood to not be limited in its application to the specific experimentation, results and laboratory procedures. Rather, the Examples are simply provided as one of various embodiments and is meant to be exemplary, not exhaustive.

Example 1

In Vitro Toxicity Screening of Compound A in Rat Cardiomyocytes and Rat Hepatoma (H4IIE) Cells: 1, 3, 6, and 24 Hour Exposures One test compound (Compound A) was received as dry powder and evaluated for potential cytotoxicity in a battery of in vitro assays. The compound was tested using both rat cardiomyocytes (CM) from rat neonates and a rat hepatoma (H4IIE) cell line. The cells were seeded into 96-well plates and cultured in medium containing 20% bovine serum. Following an equilibration period of 48 hr, the cells were treated with the test compound at concentrations of 0, 1, 5, 10, 20, 50, 100, and 300 µM for a maximum of 24 hr (overnight) at 37° C. in 5% $CO_2$. Camptothecin and rotenone were included as positive control compounds. The cell supernatant or the cells themselves were harvested for biochemical analysis. General cytotoxicity was evaluated by monitoring membrane integrity, mitochondrial function, cell proliferation, oxidative stress, and apoptosis. In addition, interaction with P-glycoprotein (PgP) on H4IIE cells and solubility of the test compound were also assessed. The means of each exposure group (n=3-7) were calculated for each assay performed. Intra assay variation well-to-well was typically less than 10% with plate to plate variation typically less than 20%.

The responses obtained in the assays were not normalized to cell number or membrane leakage (MemTox). Thus, for correct interpretation of results, all data must be visually normalized within the graphs in order to ascertain whether the change was directly due to the test compound or the result of difference in cell numbers. Cell number and cell viability are key parameters for correct interpretation of results.

The results are summarized in Tables 1-4 and in FIGS. 16-61. Table 1 compares the test compound $TC_{50}$ values for each assay endpoint. Test compounds are rank-ordered from most to least toxic based on their $TC_{50}$ values and overall shape of the response curves. The $C_{tox}$ value (H4IIE), or estimated sustained blood concentration where toxicity would first be expected to occur in a rat 14-day repeated dose study, is also included in this table. Negative and positive controls are included with every run. Assay response is continually monitored to assure reliable results. Camptothecin and rotenone were included as positive controls for all endpoints (FIGS. 44 and 60 for rotenone and FIGS. 45 and 61 for camptothecin), while DMSO at 0.5% in culture medium was included as a negative control. Table 2 summarizes oxidative stress and apoptosis data, Table 3 summarizes the solubility data, and Table 4 provides information on interaction with PgP.

The $C_{tox}$ (H4IIE) value was developed using 24 hr in vitro toxicity data and was validated by retrospectively evaluating compounds across different classes of drugs in 14-day rat studies in which compounds were administered on a daily basis and pharmacokinetic data was available. These evaluations showed that the $C_{tox}$ value was an accurate prediction of in vivo toxicity. Thus, $C_{tox}$ values are only determined for the 24 hr in vitro results. The 6 hr toxicity analyses are typically not performed but are beneficial for interpretation of results when compound toxicity is high (e.g., Ctox≦20 µM).

The present example was designed to evaluate the relative toxicity of a Hep-C protease inhibitor identified as Compound A compared to two classes (anthracyclines and antiretroviral) of drugs currently on the market that have been associated with cardiac or liver toxicity.

Freshly isolated primary culture of rat neonate cardiomyocytes and a rat hepatoma cell line were used. The endpoints measured in this study were chosen because they represent pivotal points in pathways controlling cell health. The two cell models were selected to provide an estimate of potential cardiac versus systemic toxicity. By comparing the effects observed with Compound A to those observed for several anti-tumor and anti-viral drugs an added perspective regarding the predicted in vivo toxicity of the test compound can be achieved.

Adriamycin was selected as a reference compound because it is a well known anthracycline member causing cardiac toxicity (Horenstein et al, 2000). The cardiac toxicity observed following anthracycline treatment has been linked to the production of reactive oxygen species resulting in depletion of reduced glutathione (GSH), and an increase in membrane lipid peroxidation resulting in damage to cellular macromolecules including mitochondria. The heart appears to be more sensitive to these effects because it has relatively poor antioxidant defense mechanisms relative to other organs such as liver.

The second group of drugs used as reference compounds comprise a wide range of anti-viral drugs including protease inhibitors (PI) such as ritonavir, lopinavir, and indinavir (Esposito et al, 2006; Oldfield and Plosker, 2006; Von Hentig et al, 2006) (FIGS. 36 and 53; 38 and 55; and 41 and 57, respectively) non-nucleoside reverse transcriptase inhibitors (NNRTIs) which include efavirenz, delavirdine, and nevirapine (Perez-Elias et al, 2005) (FIGS. 37 and 52, 39 and 54 and 42 and 58, respectively), and nucleoside reverse transcriptase inhibitors (NRTIs) which include abacavir and AZT (Sriram et al, 2006) (FIGS. 40 and 56 and 43 and 59, respectively). Drugs that resemble nucleosides cause a reduction in mitochondria density which leads to cytotoxicity. One of the mechanisms underlying this effect is inhibition of mitochondrial DNA polymerase gamma which in turn prevents mitochondrial replication resulting in a reduced number of mitochondria in tissue. Typically this is a delayed effect that requires at least one doubling time in order to be detected in vitro (Martin et al, 1994; Lewis and Dalakas, 1995).

The present study had four primary objectives: (1) to evaluate a protease inhibitor drug for Hep-C treatment in cell based models designed to predict in vivo toxicity; (2) to determine if the heart could be a more sensitive target organ of toxicity; (3) compare the test drug's effects to those obtained for several approved anti-tumor and anti-viral drugs currently on the market; and (4) to identify potential mechanism(s) of toxicity.

Figure 16:
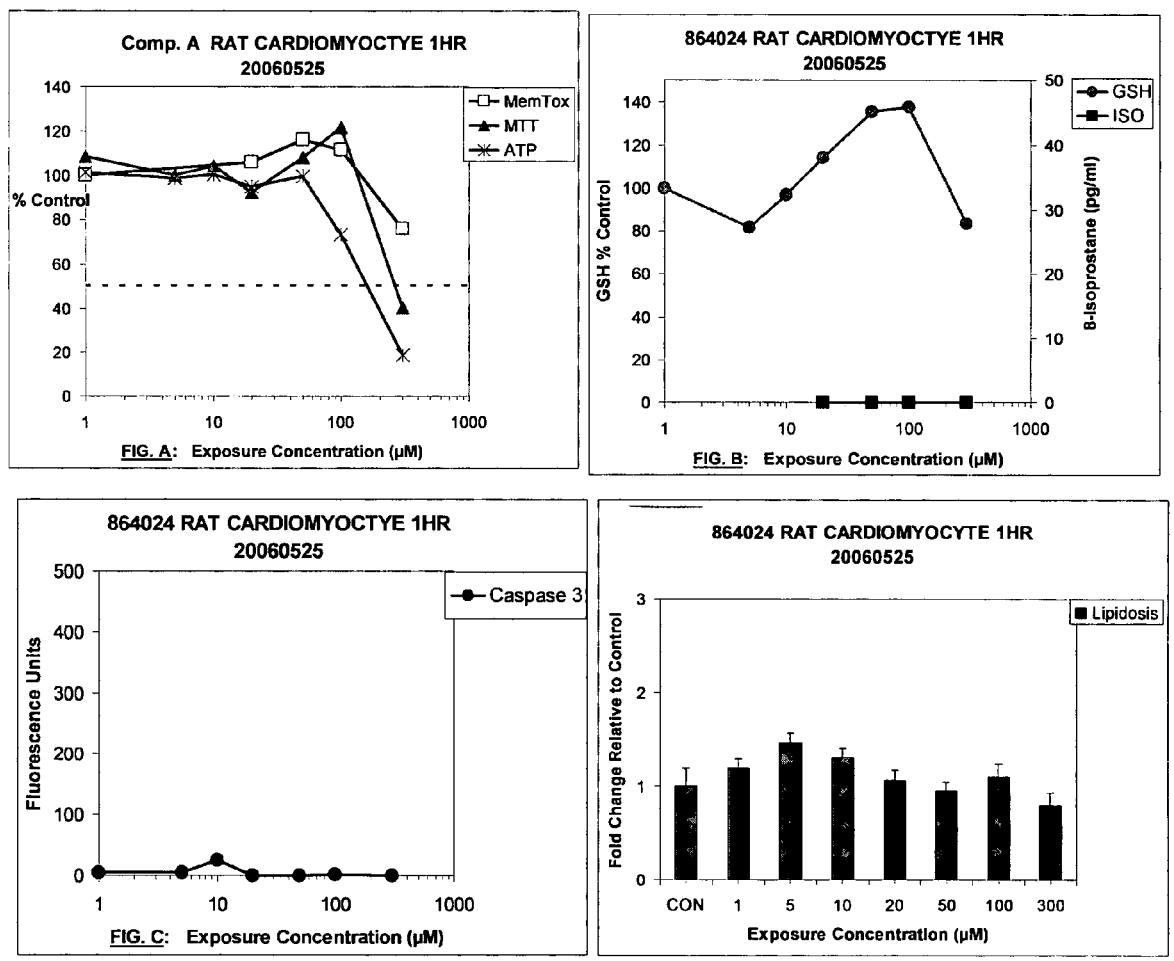
FIG. 16 illustrates concentration response analyses for a Hep-C protease inhibitor, labeled as Compound A, in rat cardiomyocytes following a 1 hour exposure.
Figure 18:
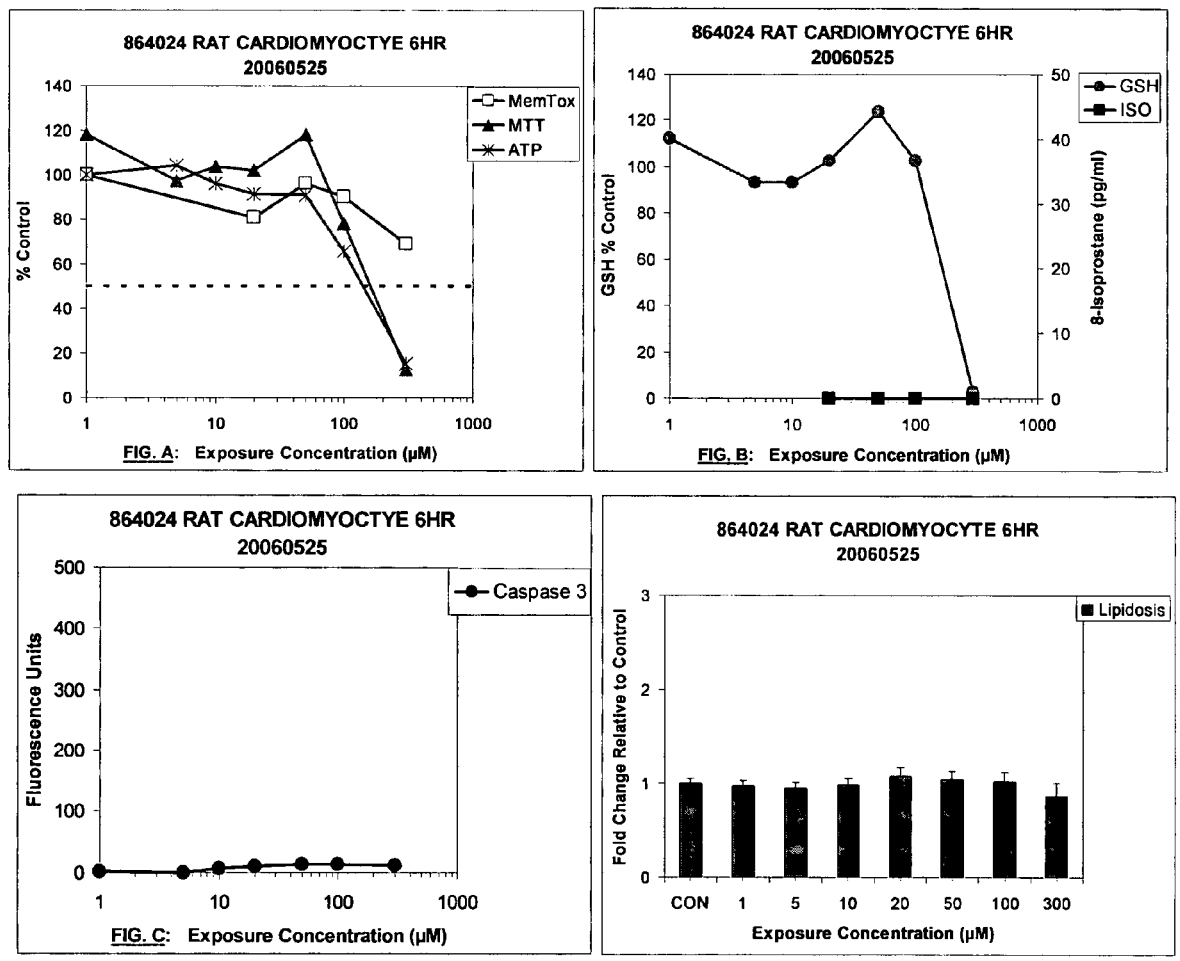
FIG. 18 illustrates concentration response analyses for Compound A in rat cardiomyocytes following a 6 hour exposure.
Figure 21:
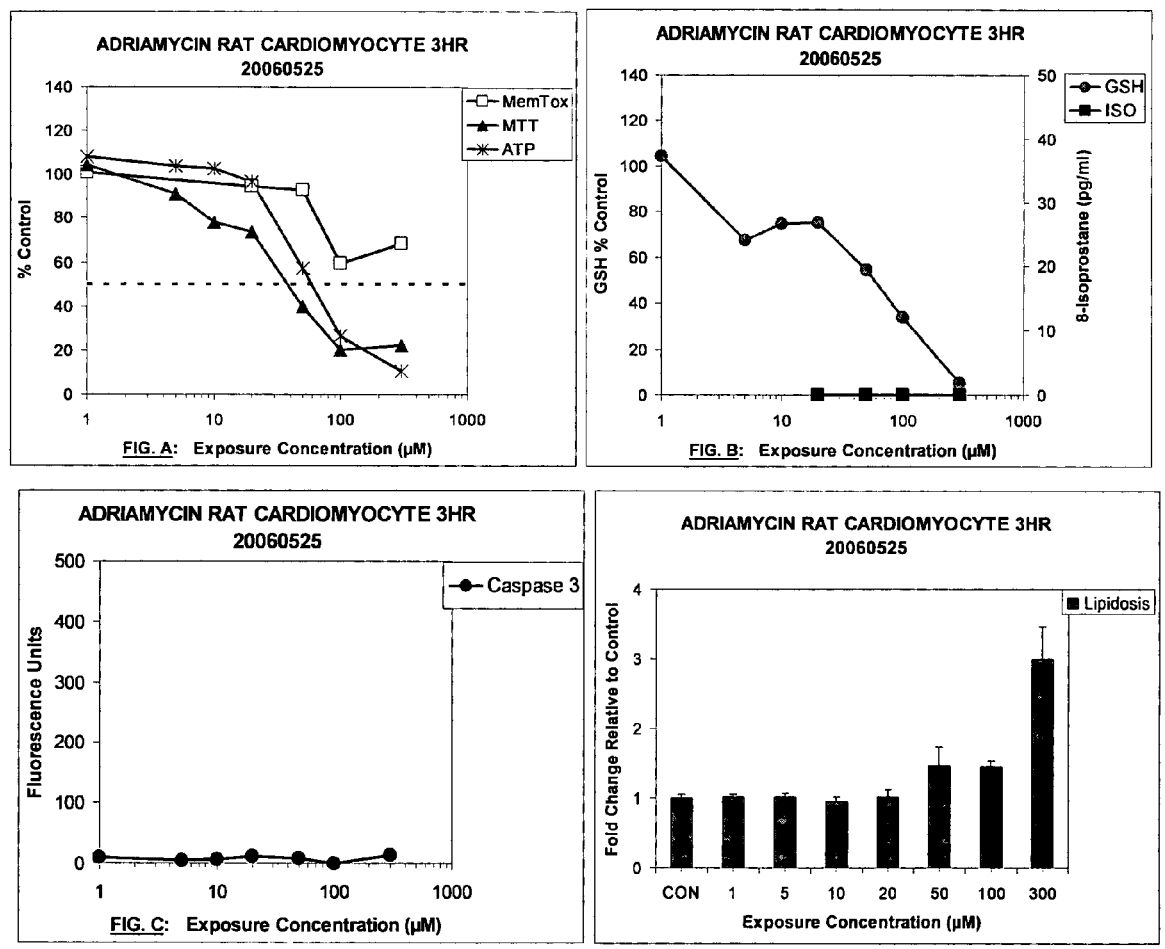
FIG. 21 illustrates concentration response analyses for Adriamycin in rat cardiomyocytes following a 3 hour exposure.
Figure 22:
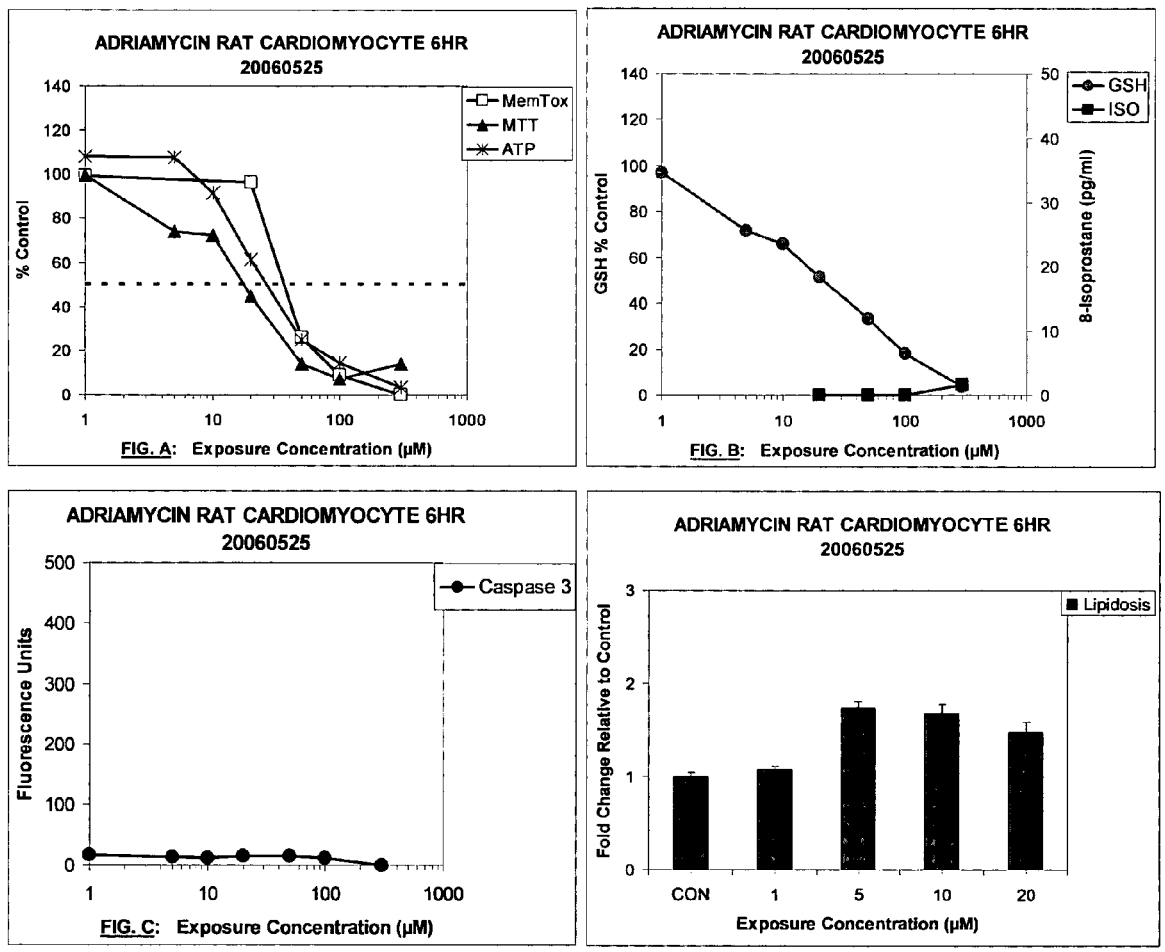
FIG. 22 illustrates concentration response analyses for Adriamycin in rat cardiomyocytes following a 6 hour exposure.
Figure 23:
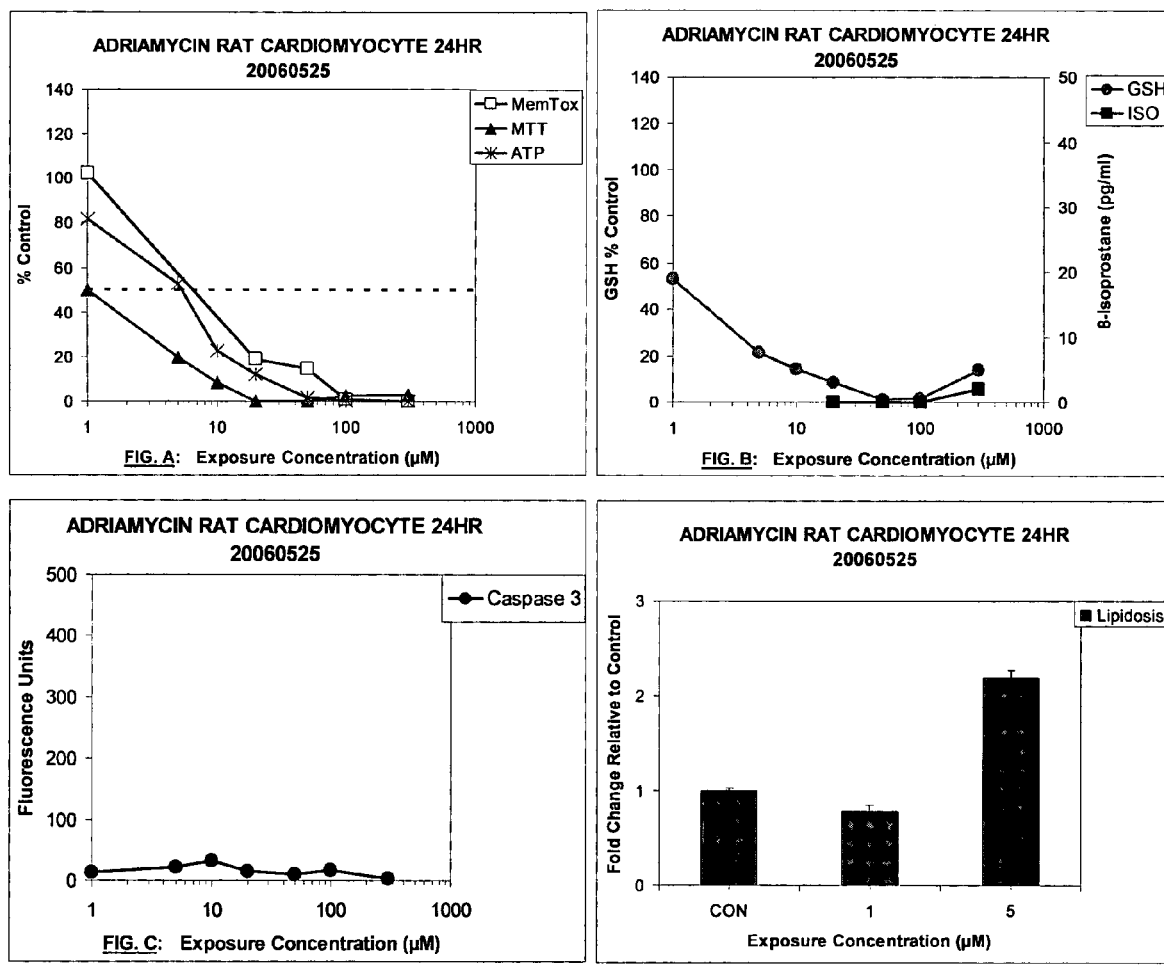
FIG. 23 illustrates concentration response analyses for Adriamycin in rat cardiomyocytes following a 24 hour exposure.
Figure 24A:
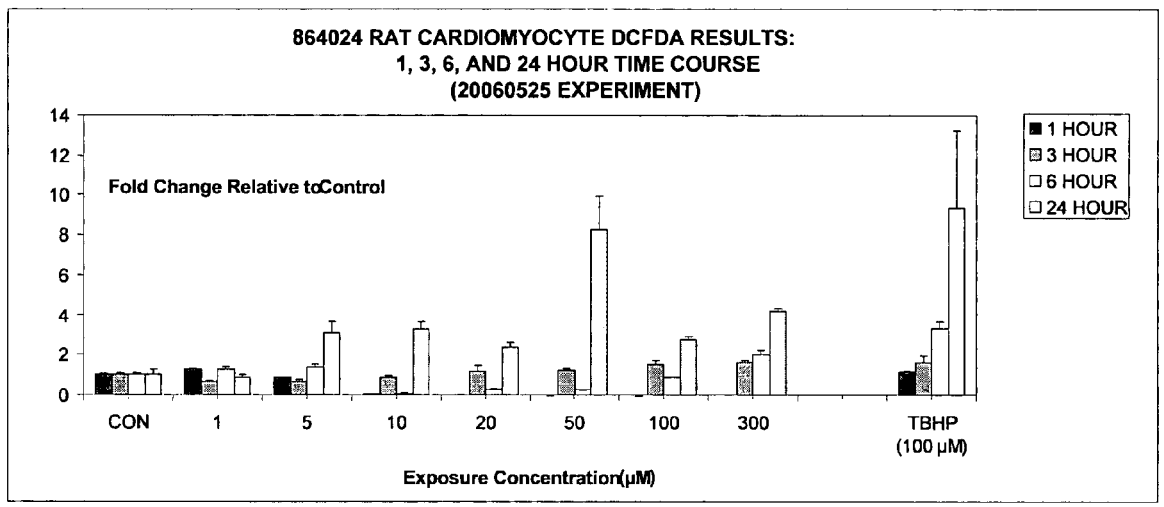
FIG. 24 contains bar graphs that illustrate the results of a dichlorofluoroscindiacetate (DCFDA) analyses for Compound A (FIG. 24A) and Adriamycin (FIG. 24B) at 1, 3, 6 and 24 hours.
Figure 24B:
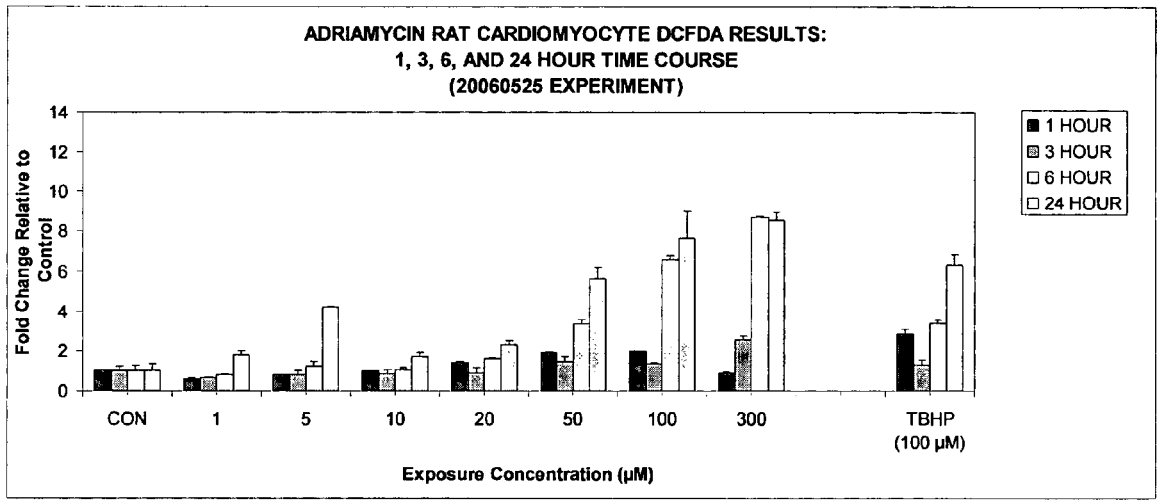

Table 1 summarizes the acute toxicity biochemical effects in cardiomyocytes at 1, 3, 6, and 24 hr. Table 2 summarizes the chronic toxicity markers (glutathione (GSH) and membrane lipid peroxidation) over the same time points. Adriamycin in cardiomyocytes produced significant changes in mitochondrial function as measured by ATP and MTT at 3 and 6 hr and these effects preceded cell death (Table 1; FIGS. 21 and 22). After a 3 hr exposure to adriamycin the most sensitive subcellular targets in the cardiomyocytes were mitochondria and reduction in reduced glutathione (GSH). More than 90% of the cellular GSH had been depleted after 3 hr (Table 2). Cell death occurred by 6 hr of exposure with nearly all cells dead after 24 hr (Table 1 and Table 2; FIGS. 21, 22, and 23). Compared to adriamycin, the test compound Compound A was approximately 64-fold less potent in the MTT assay, 16-fold less potent in the ATP assay and more than 40-fold less effective at inducing cell death (Table 1 summary of rat cardiomyocyte data). This trend was also true when Compound A was compared to the other reference anthracyclines (idarubicin, mitoxantrone, daunorubicin, pirarubicin, and epirubicin) (Table 1 summary of $TC_{50}$ values in rat cardiomyocytes and FIGS. 31-35 and 46-51). Although the mitochondrial markers were most sensitive following exposure to Compound A, the test compound's potency was much lower compared to the anthracyclines. In addition, the test compound (Compound A) did not deplete GSH levels until the highest exposure concentrations were reached (FIGS. 16-18). There was a compensatory increase in GSH levels observed in the mid-exposure ranges that was observed at all time points tested. This increase in GSH was most likely due to induction of GSH-synthetase activity which has been demonstrated for other drugs and chemicals. The induction of GSH-synthetase activity suggests some stress on the cell and indicates a protective or adaptive response by the cell. The results further indicate a mechanism of effect for Compound A different from the anthracyclines. Compound Compound A did not cause cell death under the conditions tested, making it considerably less toxic in the heart than anthracyclines (Table 1). When compared to other PIs, Compound A was less toxic than ritonavir, and lopinavir and slightly more toxic than indinavir (Table 1; FIGS. 19, 36, 38 and 41). All of the PIs reduced GSH levels prior to cell death in the cardiomyocytes and the most toxic PI, ritonavir caused the most pronounced loss of GSH (FIG. 36).

The ability of the test compound Compound A and adriamycin to induce atrial natriuretic peptide (ANP) and B-type natriuretic peptide (BNP) gene expression as markers of cardiac hypertrophy was measured. Hypertrophy of the heart ventricular myocytes is regulated by a complex series of intracellular signaling processes involving angiotensin receptors and a series of down stream gene expression changes (Li et al. 2006). Endothelin-1 (ET-1) induces hypertrophy of cardiomyocytes in vivo and in vitro. The mechanism of ET-1-induced hypertrophy consists in the activation of phospholipase C, protein kinase C, extra cellular signal regulated kinase (ERK) and upregulation of cfos and cjun. The expression of ANP and BNP are upregulated in response to ET-1 (Li et al. 2006).

Expression of ANP and BNP mRNA levels was determined by bDNA analysis of mRNA. ET-1 at 0.1 µM was included as a positive control. Adriamycin had no effect on the expression of either peptide (FIGS. 27A and 27B). The test compound Compound A increased expression of ANP and BNP in a dose and time dependent manner (FIGS. 25A and 25B). In terms of time of exposure, 3 and 6 hr were optimal. BNP mRNA was increased 7-fold over controls following exposure to 20 µM Compound A (FIG. 25B), while ANP was increased approximately 2-fold (FIG. 25A). The positive control ET-1 at an exposure concentration of 0.1 µM increased ANP expression approximately 2-fold after 3 hr (FIG. 25A) and BNP approximately 4.5-fold after 3 hr (FIG. 25B).

Nitric oxide was also evaluated since it has been implicated in many pathways related to oxidative stress, apoptosis, and cardiac hypertrophy. More specifically, adriamycin induced mitochondrial toxicity is reduced in the presence of increased iNOS. Thus, a compensatory response to mitochondrial toxicity may be an increase in iNOS (Chaiswing et al., 2005). In this example, rat cardiomyocytes exposed to adriamycin induced iNOS expression more than 15-fold (FIG. 27C). There was no detectable increase in iNOS gene expression after exposure to the test compound Compound A (FIG. 26C) in cardiomyocytes.

In the hepatoma cell model, the test compound showed similar trends in its toxicity profile; however, the liver cell model was considerably less sensitive to these effects. Serum concentrations were the same in both cell models so differences in cell type sensitivity cannot be attributed to the presence of different protein concentrations. The heart model is providing biochemical information unique to heart that may provide insight into the risk of cardiac related toxicity in vivo.

Figure 19:
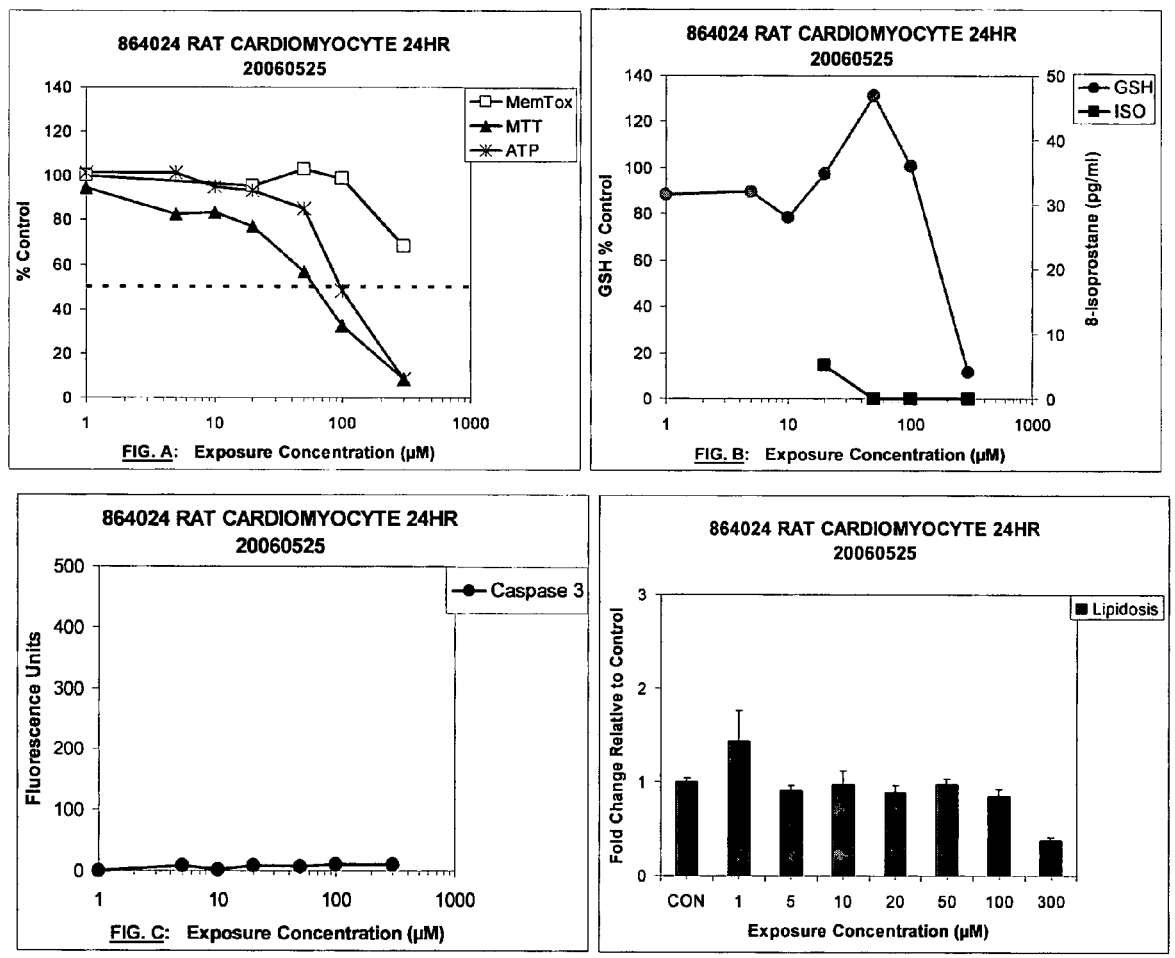
FIG. 19 illustrates concentration response analyses for Compound A in rat cardiomyocytes following a 24 hour exposure.
Figure 20:
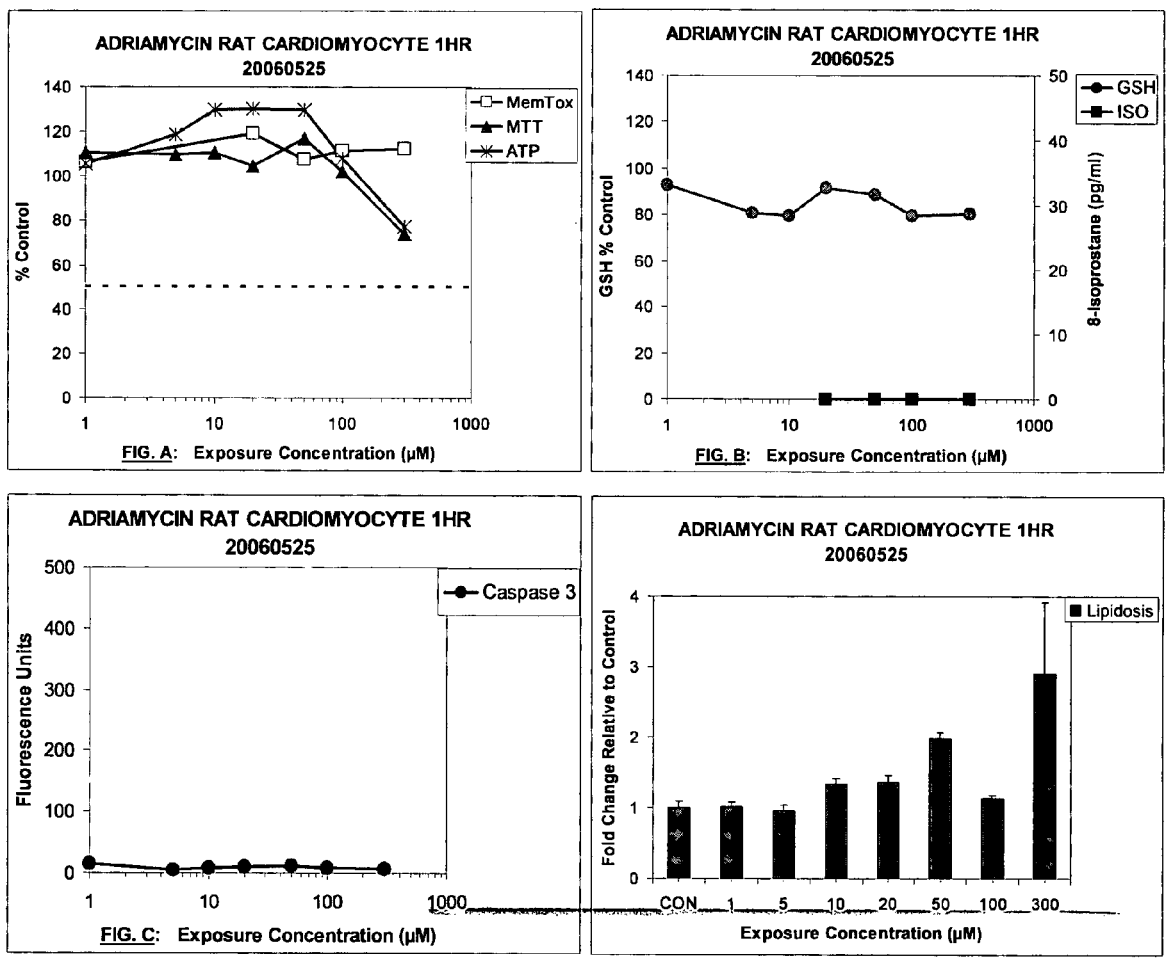
FIG. 20 illustrates concentration response analyses for Adriamycin in rat cardiomyocytes following a 1 hour exposure.

Adriamycin was approximately 5-fold less toxic in liver cells than in the cardiomyocytes. This is based on the relative differences in $TC_{50}$ values for membrane integrity of 33 µM in liver versus 7 µM in myocytes. Effects on mitochondrial markers such as MTT and ATP showed that the former was affected approximately 13-fold less in liver cells compared to myocytes (Table 1 H4IIE data), while the later was affected to a similar magnitude (Table 1 summary of H4IIE data). When cell death was used as the marker, adriamycin was about 2.5-fold more potent in the heart cells than in liver cells (Table 1; FIGS. 23 and 30). Adriamycin produced a significant increase in caspase 3 activity in the liver cell line, a committed step in apoptosis. This change was not observed in the cardiomyocytes (FIGS. 19 and 30). The absence of caspase 3 activity in the cardiomyocytes may have been due in part to the protective effect of Bcl2, which was induced 6-fold after 6 hr at 10 µM and is known to inhibit apoptosis (FIG. 28B). It should be noted that this increase in Bcl2 occurred prior to cell death (FIG. 22). Bcl2 is often induced in response to BAX a protein that promotes apoptosis. A 3-fold increase in BAX was observed after 1 hr and at an exposure concentration of 10 µM (FIG. 28A). The peak exposure concentration that produced Bcl2 expression was lower than the concentration that produced the greatest increase in caspase 3 activity in the liver cell line.

The production of reactive oxygen species (ROS) can be measured using 2'-7'dichloro-dihydrofluorescein diacetate (DCFDA). Fluorescence signal is directly proportional to production of ROS (Fabiani et al., 2005; Mracek et al., 2006; Gonzalez et al., 2006). The test compound Compound A produced a small increase (approximately 2-fold) in DCFDA fluorescence at exposure concentrations of 5 and 10 µM, but this increased to more than 6-fold after a 24 hr exposure to 50 µM. If these data are compared to those depicted in FIG. 29 for toxicity in the liver cell model, the increase in ROS occurs at an exposure concentration just below the first concentration to produce impaired mitochondrial function. This result suggests that the increase in ROS occurred either just prior to perturbation of mitochondrial function or concomitantly. Adriamycin produced only small changes in ROS related fluorescence at exposures where cytotoxicity was minimal. This is apparent by comparing FIG. 24B to FIG. 30. The 4-fold increase at 5 µM occurs as mitochondrial damage is beginning.

Several antiviral drugs are substrates for P-glycoprotein transporter (PgP). Interaction of the test compound as well as the reference compounds with PgP was assessed and the data shown in Table 4 (summary of PgP binding H4IIE cells). The test compound also had PgP interactions of approximately the same magnitude as the other antiviral compounds.

In summary, utilization of a two cell model showed distinct differences in cell sensitivity. The toxicity observed for reference compounds and the underlying mechanisms was consistent with those reported in the literature. Thus, the two model approach provided insight into potential issues related to cardiac toxicity that would not have been identified in the liver cell model. The test compound Compound A was less toxic to hepatoma cells than to cardiomyocytes. The mitochondria and reduction in reduced GSH seem to represent the most sensitive targets in both cell models. However, for a similar test compound concentration, effects on mitochondrial function markers in the liver cell model were 2-to-3 fold lower than those observed in the heart model, based on a comparison of $TC_{50}$ values (Table 1). The Compound A compound induced ANP and BNP expression indicating some potential to cause cardiac hypertrophy.

Materials and Methods

Experimental Protocol: The test compound was provided and stored at 4° C. until needed. Dosing solutions were prepared in complete culture medium. The rat hepatoma (H4IIE) cell line was used as the test system. Cells were seeded into 96-well plates and allowed to equilibrate for approximately 48 hr. Following the equilibration period the cells were exposed to the test compound at concentrations of 0, 1, 5, 10, 20, 50, 100, and 300 µM. Solubility was determined by Nephalometry techniques immediately after dosing and prior to harvesting the cells at 6 or 24 hr. Following the exposure period, the cells or their supernatant (culture medium) were analyzed for changes in cell proliferation, membrane leakage, mitochondrial function, oxidative stress, and apoptosis. The resultant exposure concentration response curves were graphed and analyzed for determining the concentration that produced a half maximal response or $TC_{50}$.

Test and Control Articles: The test compounds were received dry or as a liquid and were used to prepare 20 mM stock solutions in DMSO. This stock was diluted in DMSO to prepare 0.2 mM stock solutions. Both the 20 mM and 0.2 mM stocks were used to prepare dosing solutions of 0, 1, 5, 10, 20, 50, 100, and 300 µM in culture medium. The final concentration of DMSO in the 0-100 µM solutions was 0.5% and at the 300 µM solution DMSO was 1.5%. The final dosing solutions in medium were prepared on the day prior to dosing. The solutions were wrapped in foil or shielded from light and stored at 4° C. until needed.

The details of the preparation and dilutions can be found in the laboratory. All experiments used dimethylsulfoxide (DMSO) as the test article solvent and the negative (solvent) control.

Negative controls of medium plus DMSO (0.5%) were included with and without cells. A positive control for complete cell death received 1 mM digitonin in medium on the day of dosing.

Reagents and Solutions: All chemicals used were reagent grade or better.

Test System: H4IIE Cell Line: Rat cardiomyocytes from rat neonates and rat hepatoma derived H4IIE cells were used as the test systems. The culture medium used for these cells was Eagles Minimum Essential Medium with 10% bovine serum and 10% calf serum. Certified bovine serum and calf serum were from In vitrogen.

Description of Experimental Setup and Biochemical Assays: Flat bottom 96-well plates were seeded with 10,000 cells/well 48 hr prior to dosing. On the morning of the third day after seeding, the test compounds in medium were added to the plates (DMSO=0.5%). The 300 µM treatment had a final DMSO concentration of 1.5%.

During method development experiments, it was determined that the 48 hr cell growth period allows cells to move into a stable growth phase prior to treatment. In addition, the effect of DMSO on cell proliferation, MTT, and α-GST was evaluated at DMSO concentrations ranging from 0.05 to 4%. These studies showed no effects on any of the endpoints tested at concentrations below 2%. Finally, the ability of DMSO to enhance cell uptake and hence toxicity of a compound was also evaluated. No significant differences in toxicity were detected when a broad range of ketoconazole and amphotericin concentrations were tested at final DMSO concentrations of 0%, 0.5% and 1.5%.

All of the assays described below may not have been used to evaluate the compounds submitted. Table 1 provides information on the assays used in this example.

Cell Proliferation: Cell proliferation in each well was measured with propidium iodide (PI). This specific nucleic acid binding dye fluoresces when intercalated within the nucleic acids. The 15 nm shift enhances PI fluorescence approximately 20 times while the excitation maxima are shifted 30-40 nm. During method development experiments, it was determined that Triton-X-100 was the best solution to permeabilize the H4IIE cells thereby allowing the PI access to intracellular RNA and DNA. Fluorescence was measured using a Packard Fusion plate reader or equivalent reader at 540 nm excitation and 610 nm emission.

Bromodexoyurine (BrDU) Incorporation: This assay was used to monitor cumulative changes in DNA replication. The assay uses the thymidine analog BrdU to measure S-phase of cell replication and is considered to be the Gold Standard for cell proliferation. BrDU (10 µM) was included in the test compound dosing solution to allow BrDU incorporation during cell replication. BrDU was included for the duration of the exposure, 24 hr. After completion of exposure period, the cells were fixed and labeled with mouse monoclonal anti-BrDU (FITC). Fluorescence was measured using a Packard Fusion or equivalent plate reader at 485 nm excitation and 530 nm emission.

Membrane Leakage (α-Glutathione S-transferase and/or Adenylate Kinase): The presence of Adenylate Kinase (AK) or α-Glutathione S-transferase (α-GST), both enzyme leakage markers, was measured in the culture medium using an activity assay for Adenylate Kinase and/or an ELISA assay for α-GST. At the end of the exposure period, the medium covering the cells in each well was removed and placed into new 96-well plates with appropriate labeling. These plates containing culture medium were either analyzed immediately or stored at –80° C. until needed for analysis. Luminescence (AK) values were measured with a Packard Fusion or equivalent plate reader, and absorbance (α-GST) values were measured with a Packard SpectraCount™ or equivalent reader at 450 nm and reference absorbance at 650 nm.

Tetrazolium Dye Reduction: 3-[4,5-dimethylthiazol-2-yl] 2,5 diphenyltetrazolium bromide (MTT): After the medium was removed from a plate for α-GST analysis, the cells remaining in each well were evaluated for their ability to reduce soluble-MTT (yellow) to formazan-MTT (purple). An MTT stock solution was prepared in complete medium just prior to use and warmed to 37° C. in a water bath. Once the medium was removed from all wells, MTT solution was added to each well and the plate was allowed to incubate at 37° C. for 3-4 hr. Internal method development experiments have demonstrated that color development is linear over this time.

After the 3-4 hr incubation, all medium was removed and the purple formazan product was extracted using anhydrous isopropanol. Sample absorbance was read at 570 nm and reference absorbance at 650 nm with a Packard Fusion or equivalent plate reader.

Intracellular ATP Levels: Cellular Adenosine triphosphate (ATP) was determined with an assay based on a reaction between ATP+D-luciferin+oxygen catalyzed by luciferase to yield Oxyluciferin+AMP+PPi+$CO_2$+light. The emitted light is proportional to the amount of ATP present. Rather than a "flash" type signal, which has a very short half-life, this assay utilizes a proprietary "glow" technology that extends the signal half-life to 5 hr. In addition, a unique cell lysis reagent inhibits endogenous ATPases and therefore stabilizes cellular ATP by preventing its degradation to ADP. ATP is present in all-living cells and declines rapidly upon cell death. In addition, this assay in combination with the MTT assay provides an indicator of mitochondrial activity and energy status of the cell.

At the end of the 24-hr exposure period the medium was removed from the cells and the ATP cell lysis buffer added to each well. Plates were analyzed immediately or stored at –20° C. until needed. On the day of analysis, the plates were thawed and calibration curve prepared with ATP in the same liquid matrix as samples. ATP was quantified by adding ATP substrate solution and then reading luminescence on a Packard Fusion Luminescence or equivalent plate reader.

Intracellular Glutathione (GSH) Levels: Intracellular glutathione levels were determined essentially as described by Griffith (1980) with modifications. At the end of the exposure period, the medium was removed from the cells and meta-phosphoric acid (MPA) was added to each well. Plates were then shaken for 5 min at room temperature and stored at –20° C. until needed.

The sample plates were thawed just prior to analysis and centrifuged at >2000×g for at least 2 min. Sample aliquots were removed and transferred to a clean 96-well plate along with appropriate standard curve controls. Sample pH was neutralized just prior to analysis and each well received an aliquot of sodium phosphate reaction buffer containing EDTA, DTNB, NADPH, and glutathione reductase. The plates were mixed for 15-30 min at room temperature and glutathione content was determined calorimetrically with a Packard Fusion or equivalent reader at 415 nm.

Lipid Peroxidation Measured as 8-Isoprostane (8-ISO): 8-ISO levels were determined using an ELISA. 8-ISO is a member of a family of eicosanoids produced non-enzymatically by random oxidation of tissue phospholipids by oxygen radicals. Therefore, an increase in 8-ISO is an indirect measure of increased lipid peroxidation (Vacchiano and Tempel, 1994). At the end of the exposure period, plates were either analyzed immediately or stored at –80° C. until needed for analysis. Color development, which is indirectly proportional to the amount of 8-ISO present in the sample, was read on a Packard Fusion or equivalent plate reader at 415 nm.

Caspase 3 Procedure: Caspase 3 activity was determined using a caspase substrate (DEVD, Asp-Glu-Val-Asp) labeled with a fluorescent molecule, 7-Amino4-methylcoumarin (AMC). Caspase 3 cleaves the tetrapeptide between D and AMC, thus releasing the fluorogenic green AMC. Following the test article exposure to cells in 96-well plates, medium was aspirated from plates and PBS added to each well. Plates were stored at −80° C. to lyse cells and store samples until further analysis. On the day of analysis, plates were removed from freezer and thawed. Caspase buffer with fluorescent substrate was added to each well and incubated at room temperature for 1 hr. AMC release was measured in a spectrofluorometer at an excitation wavelength of 360 nm and an emission wavelength of 460 nm. Values are expressed as relative fluorescent units (RFU).

Lipidosis Procedure: After exposure period, the medium in each plate well was removed. Plates were treated with 1 µM Nile Red and incubated for 4 hr. Plates were washed and incubated overnight (8-16 hr). Fluorescence was measured using a Packard Fusion or equivalent plate reader at 535 nm excitation/580 nm emission.

bDNA Sample Collection and Storage: After 48 hr compound exposure in 96-well plates, 50 µL of stock lysis mixture was added to each 100 µL well. Plates were mixed using a DPC 5 Micromix plate shaker at 37° C. for 15-30 minutes to ensure complete lysis of cells. Cell lysis was confirmed using a Nikon inverted microscope. Plates were stored at −80° C. until further analysis.

bDNA Analysis (Day 1): All solutions were prepared fresh on the day of analysis. Quantigene® bDNA kit components were brought to room temperature prior to use. Chemicals not supplied by Genospectra were obtained from Sigma-Aldrich.

On the day of analysis, Target Probe Sets were prepared for probe gene sets by adding 25 µL of each probe set component (CE, LE, BL) to 425 µL stock lysis solution using the following probe set concentrations: CE (50 fmol/µL), LE (200 fmol/µL), BL (100 fmol/µL).

Cell lysis plates were removed from freezer storage and thawed. After thawing, 90 µL of cell lysate (48 hr) was added to each well of the Capture Plate. Next, 10 µL of the appropriate Target Probe Set (PS2) was added to each appropriate well of the Capture Plate. Plates were tightly sealed using a plate sealer and incubated at 53° C. for 16-20 hr (overnight).

bDNA Analysis (Day 2): Wash buffer was prepared in ultra-pure water using 0.1×Saline-Sodium Citrate (SSC) and 0.03% Lithium Lauryl Sulfate (LLS). Amplifier working solution was prepared by adding 10 µL Amplifier to 10 mL Amplifier Diluent per plate.

Plates were removed from incubator and washed three times with 300 µL wash buffer. Wash buffer was completely removed from plates by aspiration and 100 µL Amplifier working solution was added to each well. Plates were sealed and incubated at 46° C. for 1 hr.

Label Probe working solution was prepared by adding 10 µL Label Probe to 10 mL Label Probe Diluent per plate. Upon completion of plate incubation with Amplifier solution, plates were washed three times with 300 µL wash buffer. Wash buffer was completely removed from plates by aspiration and 100 µL Label Probe working solution was added to each well. Plates were sealed and incubated at 46° C. for 1 hr.

Substrate working solution was prepared by adding 30 µL of 10% Lithium Lauryl Sulfate to 10 mL Substrate solution per plate. Upon completion of plate incubation with Label Probe solution, plates were washed three times with 300 µL wash buffer. Wash buffer was completely removed from plates by aspiration and 100 µL Substrate working solution was added to each well. Plates were sealed and incubated at 47° C. for 30 minutes. Upon completion of last incubation, luminescence was measured using a Packard Fusion or equivalent plate reader with plate heater set to 46° C. Data were collected as relative light units (RLU) and expressed as fold change relative to controls after background subtract.

Dihydro-2',7'-dichloroflorescin-diacetate (DCFDA) for Monitoring Peroxide Formation: DCFDA (Sigma C-6827) was dissolved in DMSO at a concentration of 205 mM. The stock was diluted to 50 µM in phosphate buffered saline. Cells were preloaded with DCFDA for 1 hour prior to dosing with test compounds. Positive control wells were dosed with freshly prepared 300 µM t-Butyl hydroperoxide (tBHP). After compound exposure, the plates were washed with phosphate buffered saline and read at 485/530 in a Packard Fusion plate reader. Results were corrected for outliers (+/−2 s.d.) and expressed as fold increase over control values (n=7 per dose).

Solubility: The test compounds were prepared in DMSO and the appropriate amounts were then added to complete medium containing 10% bovine serum and 10% calf serum at 37° C. The samples were evaluated using a light scattering technique and a Nephaloskan instrument. A reading that was greater than or equal to 3 times background was considered the limit of solubility.

Assay Calculations

Cell Proliferation: After incubation, the test compound was removed and Triton X-100 solution containing propidium iodide is added. The plate was incubated and read on a fluorescent plate reader. Data was collected as relative fluorescent units (RFU). The blank was subtracted from the final well RFU. It represents the average of the first and last columns which contain no cells on that particular plate. The controls are untreated cells allowed to grow on the same plate. The compounds are represented by several separate RFU data points for each of the tested concentrations. The percent change relative to controls was calculated by dividing the average RFU by the control cell RFU and multiplying by 100.

Bromodexoyurine (BrDU) Incorporation: After incubation, the test compound/BrDU solution was removed and cells were fixed. A solution containing mouse monoclonal anti-BrDU (FITC) was added and fluorescence was measured. Data were collected as relative fluorescent units (RFU). The blank was subtracted from the final well RFU. It represents the average of the first and last columns which contain no cells on that particular plate. The controls are untreated cells allowed to grow on the same plate. The compounds are represented by several separate RFU data points for each of the tested concentrations. The percent change relative to controls was calculated by dividing the average RFU by the control cell RFU and multiplying by 100.

Membrane Leakage (α-Glutathione S-transferase and/or Adenylate Kinase): Leakage of Adenylate Kinase or α-GST from the cell into the culture medium was determined by collecting the culture medium at the end of the exposure period. Thus, the values measured represent total enzyme leakage lost over the exposure period. The control for 100% dead or maximum enzyme release was based on cells treated with 1 mM digitonin at the time of dosing. Percent dead cells relative to digitonin treated cells was determined and then subtracted from 100% to yield the percent live cells.

MTT Reductase Activity: At the end of the 24-hr exposure period the culture medium was removed and the remaining attached cells were assayed for their ability to reduce MTT. Viable cells will have the greatest amount of MTT reduction and hence the highest absorbance values. Percent control values were determined by dividing the mean absorbance/ fluorescence of the treatment group by the mean absorbance of the control group and multiplying by 100.

Intracellular ATP Levels: ATP levels in treated cells could be determined by using the regression coefficients obtained from the linear regression analysis of the calibration curve. Thus, values could be expressed as pmoles ATP/million cells. Background corrected luminescence was used to determine percent change relative to controls by dividing treated values by control values and multiplying by 100.

Intracellular Glutathione (GSH) Levels: The assay is based on the concept that all GSH is oxidized to GSSG by DTNB reagent. Two molecules of GSH are required to make one molecule of GSSG. Total GSH was determined by reducing GSSG to 2GSH with glutathione reductase. A standard curve was prepared with oxidized glutathione (GSSG) over a range of concentrations. These concentrations are then converted to glutathione equivalents (GSX) essentially by multiplying the GSSG standard concentrations by 2. The amount of GSX expressed as pmoles/well was determined using the standard curve and regression analysis. The final results can be expressed as pmoles GSX/mL by dividing total GSX by 0.05 mL, as a percent of control, or as total GSX (pmoles/well).

Lipid Peroxidation Measured as 8-Isoprostane (8-ISO): Background absorbance produced from Ellman's reagent is subtracted from all wells. Non-specific binding is subtracted from the maximum binding wells to give a corrected maximum binding expressed as Bo. The percent of bound (B) relative to maximum binding capacity (Bo) for all unknown samples and for standards was determined an expressed as (% B/Bo). The % B/Bo for standards was plotted against the log of 8-ISO added to yield the final standard curve. This curve was used to convert % B/Bo to pg 8-ISO/mL of sample.

Caspase Activity: After sample plates were completely thawed, the caspase substrate buffer mix was added to each plate. Plates were incubated at room temperature for 1hr, shielded from light. Plates were read using a in a spectrofluorometer at an excitation wavelength of 360 nm and an emission wavelength of 460 nm. Values were expressed as relative fluorescent units (RFU).

Lipidosis: Nile red incorporation was normalized to cell number and values were expressed as fold change relative to controls. Values are not considered significant unless >2-fold increase over controls.

Dihydro-2',7'-dichloroflorescin-diacetate (DCFDA) for Monitoring Peroxide Formation: Plates were read at 485/530 in a Packard Fusion plate reader or equivalent. Results were corrected for outliers (+/−2 s.d.) and expressed as fold increase over control values (n=7 per dose).

Criteria for the Acceptability and Interpretation of Assays

Assay Acceptance Criteria: The α-GST standard calibration curve fit should have an r-squared value $\geq 0.95$. The values for unknown samples must fall within the calibration curve. The α-GST standard O.D. values and negative control O.D. values should be within 15% of historical values. Values within a dose group that vary from the mean by more than ±1.4 standard deviations were omitted from the final mean calculation.

Data obtained from the propidium iodide assays were not associated with a calibration or standard curve. Control cells (high fluorescence values) and digitonin controls (low fluorescence values) were used as general indicators of assay performance. Values within a dose group that varied from the mean by more than ±2 standard deviations were omitted from the final mean calculation. For the CyQUANT® Cell Proliferation Assay, the calibration curve for cell number should have an r-squared value $\geq 0.92$. The values of unknown samples must fall within the calibration curve. It is not possible to dilute samples once the CyQUANT® reagents have been added. Therefore, in those instances where the unknown value was outside the calibration curve a value may be assigned, but it should be identified with an asterisk in the appropriate figure or table and considered an estimate of cell number. Values within a dose group that vary from the mean by more than ±2 standard deviations were omitted from the final mean calculation.

Data obtained from the MTT assays were not associated with a calibration or standard curve. Control cells (high absorbance values) and digitonin controls (low absorbance values) were used as general indicators of assay performance. Values within a dose group that varied from the mean by more than ±2 standard deviations were omitted from the final mean calculation.

ATP values can be reported either as a percent change relative to controls or as pmol of ATP per million cells. Relative change calculations are independent of a standard or calibration curve. Negative controls (medium only) and cells without drug and positive controls (cells with digitonin) are always included as indicators of assay function. If the results are reported as an actual amount of ATP per million cells then a calibration curve must be prepared. The slope, intercept, correlation coefficient, and raw lumin±escence values in each standard curve are compared to historical values for consistency. Correlation coefficients (r-squared) must be >0.97 in order for the curve to be considered valid. Unknown samples, within an exposure group, with luminescence values that vary from the mean by more than 2 standard deviations were omitted from the final mean calculation.

Total GSH is reported as pmols/well at each exposure concentration. Standard curves are prepared fresh for each set of analyses and the slope and intercepts monitored for changes in response and sensitivity. All standard curve data are maintained and routinely evaluated for trends and for historical comparison. Correlation coefficients must be >0.97 in order for the regression analysis to be considered valid for predicting the concentration of GSH in unknown samples.

8-Isoprostane is a measure of membrane specific lipid peroxidation. The assay is an ELISA format and values are expressed as picograms of 8-isoprostane/mL. Colorimetric values are converted to units of 8-isoprostane with regression coefficients obtained from standard curves and regression analysis. The slope, intercept, correlation coefficient, and standard response are maintained and evaluated historically as an indication of assay performance. Correlation coefficients must be >0.97 in order for the regression analysis to be considered valid for predicting the concentration of 8-isoprostane in unknown samples.

Key to Interpreting the Tox-Panel Data

The Tox-Panel assays were designed to provide information that could be used for the following: (1) to prioritize compounds based on a parameter of toxicity such as the exposure concentration that produces a half maximal response in a given assay ($TC_{50}$); (2) to obtain toxicity data relative to a reference compound of the same or similar drug class: for example, ketoconazole might be used as a reference compound when developing new azole antifungals; (3) to provide clues as to potential subcellular targets of toxicity; and (4) to provide a link between the exposure concentration that produces toxicity in vitro and the plasma concentration that first produces toxicity in vivo.

Figure 62:
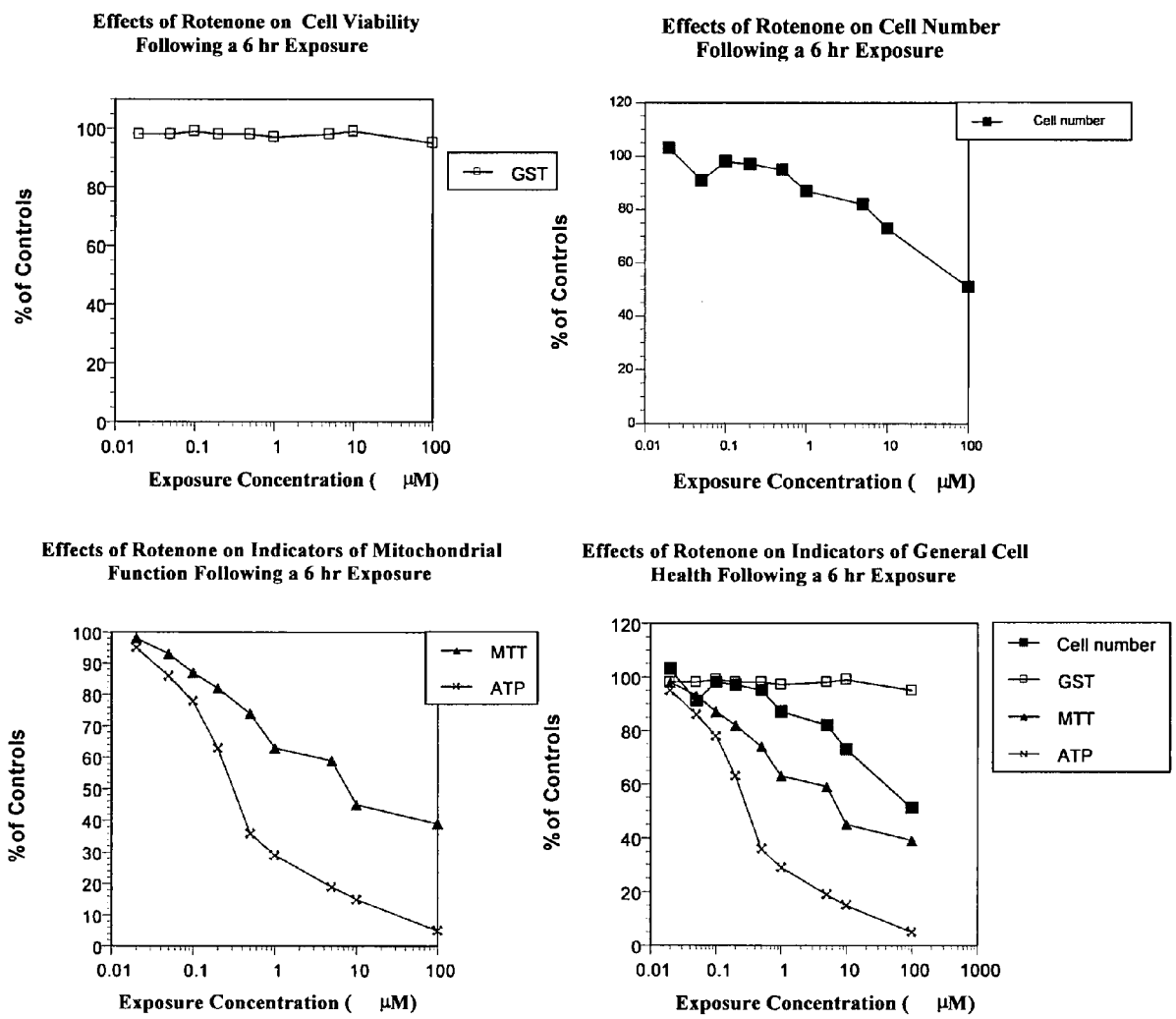
FIG. 62 illustrates concentration response analyses for Rotenone in H4IIE cells following a 6 hour exposure.

Example of General Toxicity Data: Referring now to FIG. 62, Rotenone is an extremely potent inhibitor of mitochondrial oxidative phosphorylation. Based on this mechanism of action, Rotenone is considered to be a very potent cytotoxic agent. In FIG. 62, the rat hepatoma cell line (H4IIE) was exposed to varying concentrations of rotenone. This example assumes that rotenone is a new drug candidate that has never been screened for toxicity. Rotenone was evaluated in the Tox-Panel, and the information obtained is shown in FIG. 62. After a 6 hr exposure, the upper left panel of FIG. 62 shows no cell death as determined by leakage of alpha-GST into the medium. If this were the only assay used to access toxicity, rotenone would be considered non-toxic.

In the upper right panel of FIG. 62, rotenone caused a reduction in cell number. These data alone are unclear because the reduction in cell number could be due to cell death or to a reduction in the rate of cell proliferation. When the data in the two upper panels of FIG. 62 are combined, it becomes clear that the reduction in cell number is not due to cell death and therefore must be due to a reduction in the rate of cell proliferation. In the lower left panel of FIG. 62, two markers of mitochondrial viability are shown, ATP and reduction of MTT. There is a dramatic exposure concentration dependent reduction in both ATP and MTT, with ATP being the most sensitive.

When all parameters are plotted together in the lower right panel of FIG. 62, a more complete profile of rotenone toxicity is seen. Rotenone was not acutely cytotoxic over the exposure period evaluated (6 hr); however, there were significant effects on mitochondrial function that occurred at low exposure concentrations. Thus, this compound has a significant effect on cellular ATP and this is most likely due to direct effects on mitochondrial function. The slowed rate of proliferation was due to reduced rate of proliferation caused by a reduction in cellular ATP.

Importance of Oxidative Stress Data: Tissue damage due to production of reactive oxygen species (ROS) occurs when highly reactive chemical species with unpaired electrons are generated both endogenously and by metabolism of parent chemicals. The most biologically significant free radical species are superoxide free radical anion ($O'_2{}^-$), hydroxyl radical (OH), and hydrogen peroxide ($H_2O_2$).

The cellular targets of these ROS are proteins, phospholipids (produces highly reactive aldehyde molecules), and DNA. The result of these interactions is membrane damage, enzyme malfunction, and hydroxylation of DNA, which can lead to mutagenesis.

Oxidative stress can also occur when a chemical is either a direct electrophile or is metabolized to an electrophilic entity. Electrophiles can produce oxidative damage indirectly by depleting cellular antioxidants such as glutathione (GSH) and vitamin E. Once depleted the cell would be considerably more susceptible to oxidant damage from endogenously produced ROS.

The potential clinical consequences of increased oxidative stress underscore the importance of evaluating changes in cellular oxidative stress using key biomarkers. The antioxidant defense mechanism of healthy cells can be divided into two primary categories: 1) Enzymatic antioxidant systems which would include superoxide dismutase, catalase, peroxidases, and glutathione reductase and 2) Non-enzymatic oxidants such as glutathione, vitamin E and vitamin A. Changes in ATP can also be indicative of oxidative or metabolic stress.

The toxicity panel of the present invention provides information on ATP, GSH/GSSG, and membrane lipid peroxidation. In addition, the DCFDA assay for measuring $H_2O_2$ is also available.

It is important to remember that oxidative stress is a normal part of cell death, and if these biomarkers correspond with changes in cell number or death, they are the result, not the cause, of the toxicity. Therefore, the most significant mechanistic information is obtained when ATP, GSH, or lipid peroxidation changes occur in a concentration dependant manner prior to changes in the general cell health biomarkers. When this profile is obtained the information strongly suggests an oxidative mechanism that would eventually lead to significant cytotoxicity.

Figure 63:
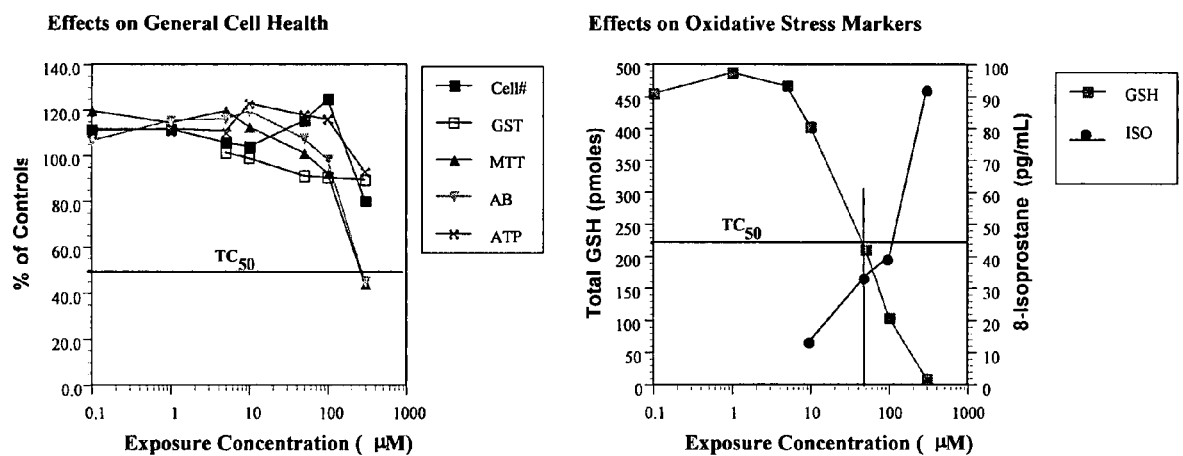
FIG. 63 illustrates concentration response analyses of the effects of Rotenone on general cell health and oxidative stress markers in H4IIE cells.

Example of Oxidative Stress: The left panel of FIG. 63 shows only modest effects on the general health biomarkers. MTT and AB are reduced, but only at the highest exposure concentrations. There was essentially no change in ATP levels at any exposure concentration. In contrast, the right panel of FIG. 63 shows a dramatic concentration dependent reduction in cellular GSH that occurred in the absence of measurable changes in cell number or cell death. In addition, there was a concomitant increase in membrane specific lipid peroxidation as measured by increases in 8-isoprostane. These data indicate that the compound tested causes significant changes in the cells oxidative state resulting in an increase of lipid peroxidation. These events would in all probability lead to significant cytotoxicity. This does not mean the compound above should be immediately dropped from further development. It does however provide a subcellular target and measurable biomarker of effect that can be monitored in vivo. If the plasma concentrations of the putative drug remain below 20 µM, it is possible that this compound would not produce harmful effects under therapeutic conditions. The mechanism of oxidative stress discovered in early screening could provide a cautionary flag that could be used to improve preclinical animal evaluations as well as human clinical evaluations. Idiosyncratic hepatotoxicity associated with many drugs may be linked to subtle alterations in key biochemical systems that control the metabolic and oxidative state of the cell.

Figure 64:
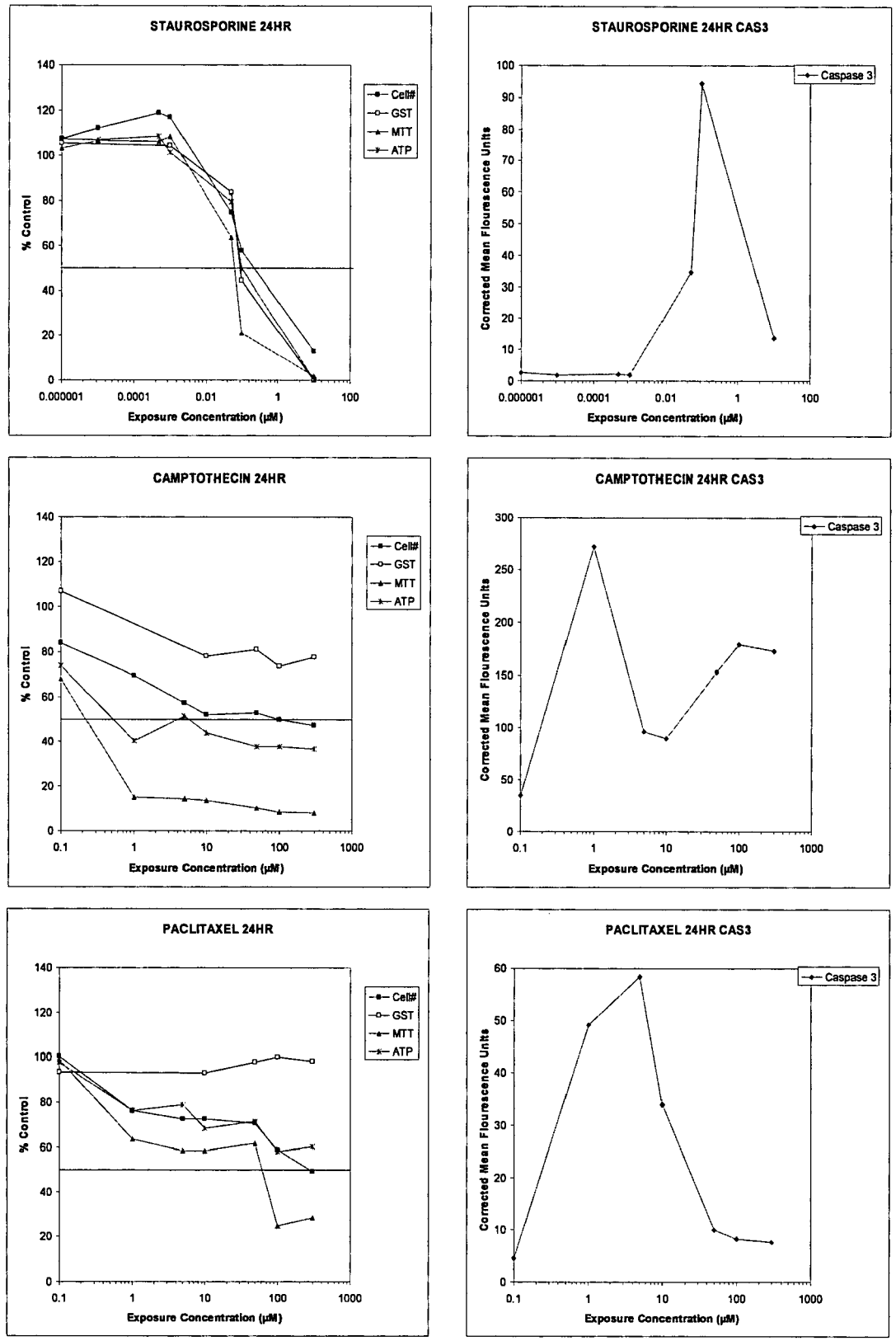
FIG. 64 illustrates concentration response analyses of the effects of Staurosporine, Camptothecin and Paclitaxel on general cell health and the apoptosis marker Caspase 3 in H4IIE cells following a 24 hour exposure.

Importance of Apoptosis Data: Apoptosis is a mode of cell death by which a cell can control its own fate. Apoptotic processes occur in development, differentiation, tumor deletion, and in response to exogenous stimuli. The morphologic and biochemical changes associated with apoptosis have been well described. There are multiple pathways that can initiate the process of apoptosis. One well characterized and committed step is activation of caspase 3. Therefore, caspase 3 activation has been included in the general health panel of assays as a marker for initiation of apoptosis. One way of assessing the significance of caspase 3 stimulation in vitro is to compare the test compounds to compounds that are capable of inducing apoptosis in vivo. Internal controls for apoptosis utilized herein include paclitaxel, camptothecin, and staurosporine. Significant increases in caspase 3 induction should be seen at exposures that produce cytotoxicity. These data can be seen in FIG. 64. A key factor when evaluating these compounds is the exposure concentration that produced a maximal induction and the magnitude of the response.

The apoptosis data is expressed in Table 2 as a ratio of the magnitude of response versus the exposure concentration that produced the response. The key to the maximal response data can be found below Table 2. By comparing the data in Table 2 for unknown compounds to the positive controls listed at the bottom of Table 2 and presented in graphic form below, the relative potency of each compound in Table 2 can be assessed.

Interpretation of Negative Cytotoxicity Data

In instances where no significant effects are detected in the Tox-Panel, it is important to evaluate all possible experimental or artifactual reasons for this result. For example, toxicity cannot be evaluated if a compound never comes in contact with the test system. Therefore, events such as solubility, protein binding, efflux via membrane transporters, and metabolism must be taken into account. Many of these issues have been evaluated in the current Tox-Panel system.

Solubility of the test compounds is evaluated in the dosing medium at 37° C. on the day of dosing, and these data are shown in Table 3.

The capacity of the rat hepatoma cell line (H4IIE) to metabolize xenobiotics has been evaluated by determining the constitutive activity of several key cytochrome P450 enzymes. This work has shown the existence of CYP1A, CYP2B, CYP2C, and CYP3A activity in the H4IIE cells. In addition, there is both glucuronide and glutathione conjugation capability.

P-glycoprotein (PgP) transport proteins are expressed in the bile canalicular membrane of normal liver. However, in neoplastic cells it is not uncommon to have expression of this transporter system in the plasma membrane. The H4IIE cells have a very active efflux pump activity in the plasma membrane. As a result, compounds that are substrates for this transporter may not accumulate inside the cell. The existence of these transporters was evaluated with the Calcein-AM assay and with known substrates of PgP. The results indicate that these cells have significant efflux pump activity. Therefore, compounds that show negative toxicity should be evaluated as potential substrates of PgP and compared to data shown in the PgP table of this example.

Example 2

In Vitro Metabolic and Toxicity Screening of Compounds in Rat and Dog Hepatocytes Species-Selector Analysis Test compounds were received and processed through the Species-Selector assay to identify potential differences in metabolic products and toxicity profiles in the rat as compared to the dog.

The Species Selector Assay was performed as follows:

Step 1: Analysis of metabolic activation: Species-specific formation of electrophiles was determined for all 10 compounds using isolated hepatic microsomes from dog and rat. Five compounds (COMP A, COMP B, COMP C, COMP D, and COMP E) that induced a differential response between the species were selected for metabolic stability and profiling.

Step 2: Analysis of metabolic stability: Metabolic stability for each of the five selected compounds was determined by measuring the metabolism of parent compound by LC/MS after incubation in isolated dog and rat hepatic microsomes.

Step 3: Analysis of metabolic profiles: The metabolic 'fingerprint' for each of the five compounds from Step 1 was obtained and compared to identify potential differences. LC/MS analysis of microsome reaction products was performed and the resulting chromatographic profiles compared. Two compounds (COMP B and COMP D) that displayed significant differences in their metabolite profiles were selected for toxicity profiling.

Step 4: Toxicity profiling in primary hepatocytes: Toxicity profiles were obtained for COMP B and COMP D in primary hepatocytes from dog and rat using a panel of 9 biochemical markers for cell health.

Results Summary

New drug candidates tested are typically evaluated in rat and dog safety studies to satisfy regulatory requirements for preparation of an IND. In some instances a test compound may be considered safe in once species while producing significant toxicity in the other. The ability to identify and understand the mechanisms underlying species-specific toxicity is essential for the efficient development of new drugs.

In many cases the reason for the species difference in toxicity is due to either the rate of metabolism, metabolic activation (defined as the formation of electrophilic intermediates), and the formation of stable but more toxic metabolites. The ability to identify potential species specific issues prior to performing in vivo studies would save development time, reduce expense, reduce animal usage, and provide key information that can be used to design more effective and robust animal studies.

The Species-Selector screen of the present invention is a multi-step process that involves a series of assays designed to evaluate metabolic activation, rates of metabolism, qualitative differences in the type of metabolite formed, and cell based toxicity across each test species.

In the first experiments, each compound was evaluated for potential metabolic activation. This assay measures cytochrome P450 (CYP) dependent formation of highly reactive electrophilic intermediates. The assay also identifies compounds that may have intrinsic electrophilic domains (e.g. the assay response appears independent of CYP activity). Each of the ten test compounds were evaluated for the formation of electrophilic intermediates in rat and dog induced microsomes (FIG. 65). By comparing the two bar graphs for rat and dog, it is clear that Compounds 17, 18, 29, 30, 39 and 40 had the most pronounced species differences in this assay.

Metabolic stability was determined for Compounds 17, 18, 29, 30, and 40. The rate of compound metabolism in rat and dog microsomes showed the greatest species related differences with Compounds 29, 30, and 40 (Table 6 and FIG. 66). Compound 17 showed good metabolic stability in rat with a slightly higher rat of metabolism in dog (FIG. 66). Compound 18 showed moderate stability in both species (FIG. 66). In terms of metabolic stability, Compounds 29 and 40 were metabolized at a higher rate in rat (FIG. 66), while Compound 30 showed the highest rate of metabolism in dog (FIG. 66).

Toxicity can be due to the type and quantity of metabolites formed. A qualitative analysis of the metabolite profiles for Compounds 18, 29, 30, and 40 can be seen in FIGS. 67-71. The metabolite profiles for Compound 17 were similar for both rat and dog (FIG. 67). The metabolite profile for Compound 18 shows considerably more metabolites are produced in rat than in dog (FIG. 68). The metabolite profile for Compound 29 was similar in both species although there may be some differences in relative abundance (FIG. 69). The metabolite profile for Compound 30 showed more metabolites in dog than in rat (FIG. 70).

Results from the metabolic activation assay combined with those from the metabolic stability assay and metabolite profiling were used to select two compounds for in vitro toxicity evaluation with primary hepatocytes from rat and dog. Compound 18 produced a P450 dependent metabolic activation in rat microsomes. Although there was depletion of GSH in dog microsomes this did not appear to be dependent on P450 (FIG. 65). There were no significant differences in metabolic stability between the two species (FIG. 66); however the compound was more extensively metabolized in rat with multiple metabolites observed as compared to dog where a single metabolite was measured.

Figure 73:
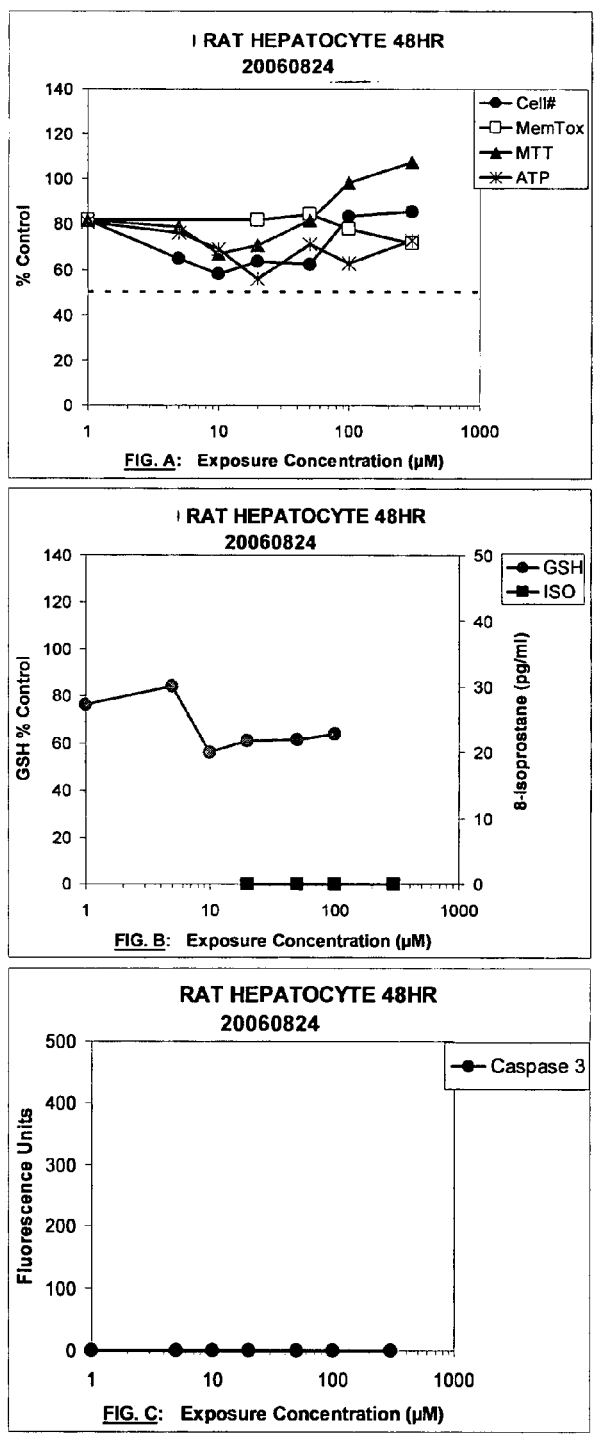
FIG. 73 illustrates concentration response analyses of Compound D in rat primary hepatocytes following a 48 hour exposure (after 24 hour induction with 50 μM PB plus 15 μM BNF).

In the cell based cytotoxicity evaluation Compound 18 was more acutely toxic in dog than rat primary hepatocytes based on the cell viability marker GST (FIG. 72 and 74). The formation of membrane lipid peroxides was also much more pronounced in dog than in rat (FIG. 72 and 74 middle graph) as measured by 8-isoprostane. Compound 18 should be evaluated at a shorter exposure time in order to identify the most sensitive subcellular targets. Compound 30 did not produce an acute toxicity in either species (FIGS. 73 and 75). There was a more pronounced depletion of GSH in rat which appears to be independent of P450.

Taken together these data indicate that Compound 18 would be more toxic in dog while the parent form of Compound 30 may be less toxic in dog due to more rapid rates of metabolism and similar metabolic profiles between the two species. However, Compound 30 is rapidly metabolized to an M+16 metabolite. If this metabolite has inherent toxicity it may become more apparent under in vivo dosing scenarios that could produce significant blood levels of this metabolite. Compound 30 metabolism should be evaluated in human microsomes to determine if metabolism in the dog is relevant to the human situation. These data would be valuable in determining the most relevant second species for toxicity studies.

Species specific toxicity can be due to metabolic stability (change in half-life or exposure), formation of reactive metabolites, and species specific targets of toxicity or a combination of these. In order to assess these possibilities all compounds should ideally be compared in the cell based toxicity screens.

Results

A. Step 1—Metabolic Activation

Test compounds were incubated in a phosphate-buffered solution containing reduced glutathione (GSH) and microsomes from Phenobarbital/β-Naphthoflavone induced rats. Reactions were initiated by addition of NADPH, and the disappearance of GSH was monitored using a fluorescent probe. Acetaminophen (APAP) was used as the positive control for metabolic activation and production of reactive intermediates. Reactions containing the P450 suicide inhibitor Aminobenzotriazole (ABT) and reactions minus NADPH were used as negative controls (see Table 5 and FIG. 65).

Analysis of Metabolic Activation Data and Selection of Compounds for Metabolic Stability and Profiling: The metabolic activation results for each compound were examined, and the five compounds (COMP A, COMP B, COMP C, COMP D and COMP E) demonstrating the greatest difference in activation between the two species were selected for subsequent analysis.

B. Step 2—Metabolic Stability

Metabolic stability was conducted using pooled microsomes form induced (BNF/PB) male rat (Sprague-Dawley) animals and induced (BNF/PB) male dog (Beagle) animals. The test compounds were incubated for 30 min at 37° C. at concentrations of 1 μM. Subsequent LC/MS analysis measured disappearance of the parent molecule. The data are expressed as percent of parent remaining. Positive controls for highly metabolized compounds were included for comparison. See Table 6 and FIG. 66.

C. Step 3—Metabolic Profiling

Samples from 0 and 60 minute microsomal incubations with 50 μM compound were analyzed by LC/MS on a Waters Alliance 2795 LC coupled to a Micromass Quattro micro MS (FIGS. 67-71). The first MS experiment was performed with ESI+/−ionization in full scan mode to observe the entire range of compounds present in each sample. The Total Ion Chromatograms (TIC) obtained for each 50 μM sample are displayed as the first trace in each of the bottom graphs of FIGS. 67-71. While these traces represent total ion chromatograms, further insights into the number and composition of the metabolites can be obtained from ion specific scans, probing for typically expected species such as addition of one or more oxygens to the parent molecule or mass. To observe potential metabolites, a second MS experiment was performed in Selected Ion Recording mode to enhance signal to noise for the metabolites of interest. Ion chromatograms from blank matrix samples (without compound), zero time incubations, and 60 minute incubations were generated to confirm the metabolic profiles for each species. Those species-specific profiles were then compared to present qualitative differences.

Analysis of Metabolic Stability and Profiling Data and Selection of Compounds for Toxicity Screening: The metabolic stability data revealed the metabolism (>40%) of COMP B, COMP C, COMP D and COMP E parent compound in reactions with rat microsomes, and metabolism (>35%) of COMP A, COMP B, COMP C, and COMP D parent compound in reactions with dog microsomes. COMP C and COMP E parent compound were metabolized to a greater extent in rat vs dog microsomes after 30 minutes, whereas COMP A and COMP D were metabolized to a greater extent in dog vs rat microsomes after 30 minutes. Similar amounts of COMP B parent (50%) remained after 30 minutes incubation in either species.

The metabolites produced in each species were examined by LC-MS analysis of microsomal reaction products. FIGS. 67-71 show the total ion chromatograms (top graphs on each page and top trace in bottom graphs) and selected ion chromatographs (bottom two graphs on each page) obtained for each compound. Similar profiles were observed in the total and selected ion chromatograms for masses corresponding to the parent mass +16(single oxygen) and parent mass +32 (two oxygens) for COMP A and COMP E compounds in rat as compared to dog (FIGS. 67 and 71).

Differences were observed in the total and selected ion chromatograms for compounds COMP B, COMP C and COMP D (FIGS. 68-70) in reactions with rat versus dog microsomes. For COMP B, multiple mono-oxygenated masses of the parent are observed at various retention times in the rat as compared to a single mono-oxygenated form in the dog. Three mono-oxygenated forms are seen in both rat and dog for the COMP C (M+16) compound but the relative abundance of two of these forms (at retention times between 4 and 4.5 minutes) are significantly different. Metabolites produced from COMP D showed marked differences when the M+16 and M+32 chromatograms are compared between rat and dog. A single oxygenated species is seen at a retention time of 3.69 minuets and this ion is greatly increased in reactions with dog versus rat microsomes. There are additional differences between the M+32 chromatograms for this compound.

Based on the stability and profiling results, COMP B and COMP D were chosen for toxicity profiling. COMP B was chosen because it showed similar metabolism rates between rat and dog, but the profiles for the metabolites produced were significantly different. COMP D was chosen because differences were seen in both stability and profiling experiments.

D. Step 4—Toxicity Screening in Primary Hepatocytes

Two compounds displaying species-specific differences in metabolic profiles were selected for toxicity analysis in primary rat (Sprague-Dawley) and dog (Beagle) hepatocytes. Hepatocytes were seeded by CellzDirect into 96-well plates, shipped overnight to the inventor, and maintained in medium containing 20% bovine serum. Following an equilibration period of 24 hr, the cells were treated with the P450 inducers (50 μM Phenobarbital (PB)+15 μM beta-Naphthoflavone (BNF)). After the 24 hr induction period, cells were treated with test compounds at concentrations of 0, 1, 5, 10, 20, 50, 100, and 300 μM for 48 hr at 37° C. in 5% $CO_2$. The cell supernatant or the cells themselves were harvested for biochemical analysis. General cytotoxicity was evaluated by monitoring membrane integrity, mitochondrial function, cell number, oxidative stress, and apoptosis. In addition to monitoring biochemical changes essential for cell health, solubility was also assessed. The means of each exposure group (n=3-7) were calculated for each assay performed.

The response of each assay must be compared to the change in cell number in order to ascertain whether the change was directly due to the test compound or the result of fewer cells. Thus, for correct interpretation of results, all data must be visually normalized to cell number within the graphs. For example, if a decrease in the mitochondrial markers track with loss of cell number, then the toxicity is likely not mitochondrial-specific but related to cell number. If the mitochondrial markers are decreased without a reduction in cell number, then the toxicity is likely specific to the mitochondria. In another example, if total glutathione (GSH) is decreased in the absence of decreased cell number, then the toxicity is likely glutathione related. Cell number and cell viability are key parameters for correct interpretation of results.

The results are summarized in Tables 7-9 and in FIGS. 72-75. Table 7 compares the test compound $TC_{50}$ values for each assay endpoint using rat and dog primary hepatocytes. Test compounds are rank-ordered from most to least toxic based on their $TC_{50}$ values and overall shape of the response curves. Assay response is continually monitored to assure reliable results. Table 8 summarizes oxidative stress and apoptosis data. Table 9 summarizes the solubility data.

Materials and Methods

Experimental Protocol for Toxicity Screening: The test compounds were provided by the sponsor and shipped to the inventor for testing. The compound was stored at 4° C. until needed. Dosing solutions were prepared in complete culture medium. Primary hepatocytes were used as the test system. Cells were received from CellzDirect, shipping medium was replaced with culture medium, and cells were given a 24 hr equilibration period. Following an equilibration period of 24 hr, the cells were treated with the P450 inducers (50 µM Phenobarbital (PB)+15 µM beta-Naphthoflavone (BNF)). After the 24 hr induction period, cells were treated with test compounds at concentrations of 0, 1, 5, 10, 20, 50, 100, and 300 µM. Solubility was determined by Nephalometry techniques immediately after dosing and prior to harvesting the cells at 48 hr. Following the exposure period, the cells or their supernatant (culture medium) were analyzed for changes in cell proliferation, membrane leakage, mitochondrial function, oxidative stress, and apoptosis. The resultant exposure concentration response curves were graphed and analyzed for determining the concentration that produced a half maximal response or $TC_{50}$.

Test and Control Articles: The test compounds were received dry or as a liquid and were used to prepare 20 mM stock solutions in DMSO. This stock was diluted in DMSO to prepare 0.2 mM stock solutions. Both the 20 mM and 0.2 mM stocks were used to prepare dosing solutions of 0, 1, 5, 10, 20, 50, 100, and 300 µM in culture medium. The final concentration of DMSO in the 0-100 µM solutions was 0.5% and at the 300 µM solution DMSO was 1.5%. The final dosing solutions in medium were prepared on the day prior to dosing. The solutions were wrapped in foil or shielded from light and stored at 4° C. until needed.

All experiments used dimethylsulfoxide (DMSO) as the test article solvent and the negative (solvent) control.

Negative controls of medium plus DMSO (0.5%) were included with and without cells. A positive control for complete cell death received 1 mM digitonin in medium on the day of dosing.

Reagents and Solutions: All chemicals used were reagent grade or better.

Test Systems: Rat and Dog Primary Hepatocytes: Primary hepatocytes were purchased from CellzDirect and received plated and sandwiched with Matrigel overlay. The culture medium used for these cells was Williams E medium with supplements and 20% bovine serum. Certified bovine serum was from In vitrogen.

Description of Experimental Setup and Biochemical Assays: Collagen-coated 96-well plates were seeded with 100,000 primary hepatocytes by CellzDirect, monitored overnight for attachment, and shipped the following day. Upon arrival, shipping medium was replaced with culture medium. Cells were dosed the following day after 24 hr equilibration time. Test compounds in medium were added to the plates after the equilibration period.

During method development experiments, it was determined that the 48 hr cell growth period for NRK cells allows cells to move into a stable growth phase prior to treatment. For rat primary hepatocytes, the 4 hr plating period allows cells to attach to the collagen base prior to treatment.

In previous studies, the effect of DMSO on cell number, MTT, and □-GST was evaluated at DMSO concentrations ranging from 0.05 to 4%. These studies showed no effects on any of the endpoints tested at concentrations below 2%. Finally, the ability of DMSO to enhance cell uptake and hence toxicity of a compound was also evaluated. No significant differences in toxicity were detected when a broad range of ketoconazole and amphotericin concentrations were tested at final DMSO concentrations of 0%, 0.5% and 1.5%.

Biochemical assays of cell number (i.e., cell proliferation), membrane leakage, tetrazolium dye reduction (MTT), intracellular ATP and Glutathione (GSH) levels, lipid peroxidation and caspase-3 were performed as described above in Example 1.

Solubility: The test compounds were prepared in DMSO and the appropriate amounts were then added to complete medium containing 10% bovine serum and 10% calf serum at 37° C. The samples were evaluated using a light scattering technique and a Nephaloskan instrument. A reading that was greater than or equal to 3 times background was considered the limit of solubility.

Metabolic Activation: Test compounds were incubated in a phosphate-buffered solution containing reduced glutathione (GSH) and microsomes from Phenobarbital/β-Naphthoflavone induced rats. Reaction was initiated by addition of NADPH, and disappearance of GSH was monitored using a fluorescent probe. Acetaminophen (APAP) was used as the positive control for metabolic activation and production of reactive intermediates. Reactions containing the P450 suicide inhibitor Aminobenzotriazole (ABT) and reactions minus NADPH were used as negative controls. Assays were performed in 96-well micro plates and fluorescence was read using a Packard FluoroCount reader with proper emission and excitation filters.

Metabolic Stability and Profiling by mass spectrometry: Metabolic stability was conducted using pooled male dog (beagle) microsomes and male rat (Sprague-Dawley) microsomes from induced (beta-Naphthoflavone/Phenobarbital, BNF/PB) animals. The test compounds were incubated for 30 min at 37° C. at concentrations of 1 and 10 µM. Subsequent analysis by mass spectrometry measured disappearance of the parent molecule. The data are expressed as percent of parent remaining. Positive controls for highly metabolized compounds were included for comparison.

For selected ion monitoring, the 50 µM reaction mixtures are incubated at 37° C. for 0 or 60 minutes, after which the reaction is quenched with acetonitrile, centrifuged and supernatant collected. Supernatant is concentrated with nitrogen gas, re-suspended in acetonitrile/$H_2O$ (50/50) and analyzed by LC/MS for metabolite appearance. Reaction mixtures without substrate are used for background determination. Duplicate incubations are run at each time-point.

The samples from the microsomal incubations are analyzed by LC/MS on a Waters Alliance 2795 LC coupled to a Micromass Quattro micro MS. The chromatography is performed on a Waters SymmetryShield RP8 5 um 3.0×150 mm column. Solvent A is water with 0.1% formic acid and Solvent B is acetonitrile with 0.07% formic acid. The gradient is programmed from 97% A to 5% A over 6 minutes. The first MS experiment is run with ESI+/−ionization in full scan mode to observe the entire range of compounds present in the samples. Additional MS experiments are performed in Selected Ion Recording mode to enhance signal to noise for the metabolites of interest. Ion chromatograms from blank matrix samples (without compound), zero time incubations, and 60 minute incubations are generated to confirm the metabolic profiles for each species.

Assay calculations and Criteria for Acceptability and Interpretation of Assays were performed as described in Example 1, except as described herein below.

Assay acceptance criteria: Data obtained from the WST-1 assays were not associated with a calibration or standard curve. Control cells (high fluorescence values) and digitonin controls (low fluorescence values) were used as general indicators of assay performance. Values within a dose group that varied from the mean by more than ±2 standard deviations were omitted from the final mean calculation.

Metabolic Activation: Data was collected from 96-well plates using a Packard FluoroCount reader with the appropriate excitation and emission wavelengths. Wells containing an assay mixture of reduced GSH, microsomes, NADPH, and fluorescent probe (minus compound) were used as controls. Data processing and calculations were performed using Microsoft Excel. Background fluorescence was subtracted from control and treated samples. Percent control values were determined by dividing the mean fluorescence value of the treatment group by the mean fluorescence value of the control group and multiplying by 100. Bar graph was prepared using Excel.

Metabolic Stability: The analysis measured disappearance of the parent molecule. The data were expressed as percent of parent remaining. Positive controls for highly metabolized compounds were included for comparison.

Example 3

In Vitro Toxicity Screenings of Compounds in Rat Hepatoma (H4IIE) Cell Line, Rat Primary Hepatocyte Cell Line, and Normal Rat Kidney (NRK) Cell Line: an Anti-Tumor Screen Three separate projects were carried out in series. The individual projects are presented in the order in which they were done. The bar graph in the third project summarizes the data showing cell selectivity.

A single compound was submitted for evaluation in a non-GLP general cytotoxicity screening platform. The compound was submitted, as a liquid and the dosing was based on a series of dilutions recommended by the sponsor. The dosing dilutions used in all experiments were 2000, 1000, 500, 100, 50, 10, and 1. The highest dilution represents the lowest exposure concentration and the lowest dilution the highest exposure concentration. The test compound was acidic in nature and was designed as an antitumor drug.

In the first experiment, the test compound was evaluated for toxicity using a rat hepatoma cell line. The results shown in the TABLE 10 and in FIG. 76A indicate that the compound was a potent cytotoxic agent. In order to separate toxicity related to the acidic nature of the compound from specific effects related to the compound itself, a series of experiments were done to evaluate the effects of pH on the test system. This information was related to the pH values of the actual dosing solutions. The pH values of the 2000, 1000, and 500 dosing solutions were near 7.0. The next highest exposure (100) dropped the pH to 3.7 a value considerably lower the test range of 7.5 to 6.0 (FIG. 77A). In FIG. 76A below nearly all cells were dead at the 500 dilution at 24 hr. This cytotoxic effect was not due to low pH as the 500 dilution had a pH of near 7.0 and the cells were stable at this pH. The extremely low pH values produced by the compound did have negative effects on mitochondrial markers (MTT and ATP) as shown in FIG. 77A. The oxidative stress markers and apoptotic markers had toxicity profiles consistent with the loss of cell viability.

In the second experiment, cyropreserved rat primary hepatocytes were used as the test system. These cells were purchased from XenoTech LLC of Kansas City, Kans. The data are summarized in TABLES 10B and 11B. The objective of this experiment was to evaluate the toxicity of the antitumor test compound on cells derived from normal tissues. The results of this experiment revealed that the cytotoxic effects of the test compound at dilutions within physiologic pH were selective for tumor cells. At the highest exposure concentration (dilution of 500) there were no changes in cell number or in acute cell death (FIG. 76B) after either 6 or 24 hr exposure. Again, the low pH inherent with this test material did produce effects on mitochondria as shown in FIG. 77B. However, these effects of pH were not observed at pHs of 7.0 and higher. Thus, the cytotoxicity of the test material must be due to the chemical mixture and not to the physical chemical changes conferred onto the test system.

The third experiment was done to evaluate the specificity and selectivity of the test compound in another non-tumor cell that was derived from normal rat kidney tissue. The results are summarized in TABLES 10C and 11C. In this experiment the test compound has no effect on cell number of acute cell death up to the 500 dilution after 6 and 24 hr of exposure (FIG. 76C and 77C). Significant effects were observed on mitochondrial markers at dilutions that dropped pH to 3.7. The bar graph in FIG. 82 summarizes these effects. Both non-tumor cell types showed no acute cytotoxicity at dilutions that maintained a pH near 7.0. In contrast the rat tumor cell line was sensitive to the test compound and cell death occurred at the 500 dilution and could not be attributed to low pH.

FIGS. 78-91 illustrate the positive controls Camptothecin and Rotenone in NRK cells at 6 and 24 hour exposures.

UNIQUE OBSERVATIONS AND COMMENTS RELATED TO TOXICITY: The anti tumor drug known as Comp A was evaluated in a previous study for cytotoxicity using a rat hepatoma derived cell line. Comp A was cytotoxic to the tumor cells at a dilution of 1:500. This dilution had a pH of approximately 7. In addition, there was a significant increase in the activity of caspase 3, a late stage marker of apoptosis. At higher exposures the pH dropped to levels below 5 and therefore effects on the cells at this extremely acidic pH could not be differentiated from desired effects of the drug itself. In the present experiment the objective was to evaluate Comp A cytotoxicity on non-tumor or cells derived from normal tissues. For this example, cryopreserved rat primary hepatocytes were obtained from a well established distributor. The dilutions of Comp A were the same as those used in the previous example. The lowest exposure concentrations (1:2000, 1:1000, and 1:500) did not produce acute cytotoxicty in the normal liver cells. There was however, a significant reduction in ATP and MTT indicating some stress on mitochondrial function (FIG. 76, 24 hr). The pH was again maintained at approximately 7. Again, the higher exposures had pH values well below 5. Experiments designed to evaluate the effects of pH on the cells revealed significant effects on mitochondrial function, but not cell death, at pHs below 6.5 (FIG. 77). These data also suggest that low pH can induce apoptosis. Thus, it is clear that a condition of extremely low pH would have direct effects on cell health. However, at the 1:500 exposure level all cells were viable in the normal liver cell model. This is in contrast to the effects observed in the tumor cell line where all markers of cell viability were at maximum reductions at the 1:500 dilution. These data indicate that the tumor cell line under conditions of near physiologic pH is considerably more sensitive to the cytotoxic effects of Comp A than are the non-tumor cells (see FIG. 82), based on cell number and membrane integrity. The Comp A drug does produce adverse effects on mitochondrial function, and that occurs in both cell types.

Materials and Methods were conducted as described in Example 1, except as described herein below.

Test System: Cell Lines: Rat hepatoma derived H4IIE cells were used as the test system. The culture medium used for these cells was Eagles Minimum Essential Medium with 10% FBS and 10% calf serum. Certified FBS and calf serum were from In vitrogen.

Experimental setup was the same as in Example 1, except that no DMSO was used.

Example 4

In vitro Toxicity Screening of Compound A (Protective Antigen: Lethal Factor) in SK-MEL28, Human Hepatocyte, HUVEC, C32, and NHEM Cells: Multiple Cell Screen to Identify Drug

Specificity and Species Sensitivity

The test compound consisted of two parts mixed in a constant ratio of 5:1. The final test mixture consisted of Test mix 1 and Test mix 2, which were received as frozen solutions. The test mixture was tested in a ratio of 5:1 COMP A in five different cell types which included the following: SK-MEL28, human hepatocytes, HUVEC, C32, and NHEM cells. Cells were seeded into 96-well plates and cultured in medium containing 10% bovine serum. Following an equilibration period of 48 hr, the cells were treated with the test compound mix at concentrations of COMP A (μg/mL)=(250:50), (125:25), (25:12.5), (12.5:2.5), (2.5:1.25), (1.25:0.25), and (0.25:0.05) for 24 hr (overnight) at 37° C. in 5% $CO_2$. Camptothecin and rotenone were included as positive control compounds because they produce measurable effects in all of the assays. Following an equilibration period of 4 hr, the cells were treated with the test compound mix at concentrations of COMP A (μg/mL)=(250:50), (125:25), (25:12.5), (12.5:2.5), (2.5:1.25), (1.25:0.25), and (0.25:0.05) for 24 hr (overnight) at 37° C. in 5% $CO_2$.

The cell supernatant or the cells themselves were harvested for biochemical analysis. General cytotoxicity was evaluated by monitoring membrane integrity, mitochondrial function, cell proliferation, oxidative stress, and apoptosis. In addition to monitoring biochemical changes essential for cell health, interaction with P-glycoprotein (PgP) and solubility were also assessed. The means of each exposure group (n=3-7) were calculated for each assay performed. Intra assay variation well to well was typically less than 10% with plate to plate variation typically less than 20%.

The response of each assay must be compared to the change in cell number in order to ascertain whether the change was directly due to the test compound or the result of fewer cells. Thus, for correct interpretation of results, all data must be visually normalized to cell number within the graphs. For example, if a decrease in the mitochondrial markers track with loss of cell number, then the toxicity is likely not mitochondrial-specific but related to cell number. If the mitochondrial markers are decreased without a reduction in cell number, then the toxicity is likely specific to the mitochondria. In another example, if total glutathione (GSH) is decreased in the absence of decreased cell number, then the toxicity is likely glutathione related. Cell number and cell viability are key parameters for correct interpretation of results.

The results are summarized in Tables 14-17 and in FIGS. 83-102. Table 14 compares the test compound $TC_{50}$ values for each assay endpoint. Test compounds are rank-ordered from most to least toxic based on their $TC_{50}$ values and overall shape of the response curves. The $C_{tox}$ value, or estimated sustained blood concentration where toxicity would first be expected to occur in a rat 14-day repeated dose study, is also included in this table. Negative and positive controls are included with every run. Assay response is continually monitored to assure reliable results. Camptothecin and rotenone were included as positive controls for all endpoints, while DMSO at 0.5% in culture medium was included as a negative control. Table 15 summarizes oxidative stress and apoptosis data, Table 16 summarizes the solubility data, and Table 17 provides information on interaction with PgP.

The $C_{tox}$ value was developed using 24 hr in vitro (H4IIE) toxicity data and was validated by retrospectively evaluating compounds across different classes of drugs in 14-day rat studies in which compounds were administered on a daily basis and pharmacokinetic data was available. These evaluations showed that the $C_{tox}$ value was an accurate prediction of in vivo toxicity. Thus, $C_{tox}$ values are only determined for the 24 hr in vitro results. In this example, $C_{tox}$ values could not be estimated due to low toxicity in most of the cell lines.

Summary of toxicity data from MTT and glutathione (GSH) assays across all cell types compared with positive cell data from the sponsor. The exposure concentration in all cases was PA: LF ration of 250:50 μg/mL. In an effort to maintain quality of data between laboratories, data was requested from the sponsor on SK-Mel 28 sensitivity. The MTT data obtained in this assay was essentially identical to the response reported by the sponsor. FIG. 83 also demonstrates varying degrees of sensitivity between cell types. Normal rat kidney cells (NRK) and human hepatocytes were the least sensitive. Note: the NRK cells and rat primary hepatocytes were tested in a previous project and are included in this summary graph for comparison purposes. SK-Mel28, NHEM, C32, and the rat primary hepatocytes were the most sensitive cell types and can be rank ordered from most to least sensitive as follows: Rat primary hepatocytes >NHEM=SK-Mel 28>C32>HUVEC>Human hepatocytes>NRK. Two key findings can be seen from these data. First human hepatocytes, and a proliferating cell line not derived from tumor tissue were the least sensitive. Human umbilical vein endothelial cells (HUVEC) were also resistant. The melanoma derived cell lines were sensitive to the cytotoxic properties of the test material. Interestingly, rat primary hepatocytes were the most sensitive. This finding indicates that the rat may be a sensitive species in terms of liver toxicity. In comparison, human primary hepatocytes were very resistant to toxicity. The exposure concentrations chosen for this study were high. As a result, many of the cells exhibited maximal effects at the lowest exposure concentration. An example can be seen in FIG. 84. The upper panel represents the high exposure concentration range and shows a maximal effect of about 50%. This is a typical cytostatic response pattern. When the dose range was extended into the lower concentrations (FIG. 84, lower panel), the full response curve could be described and an IC50 value determined.

As shown in FIG. 84, initial experiments using a high range of doses revealed a flat response at 50% for MTT (red triangles) with no effect on other markers of toxicity. MTT can be used to assess changes in cell number or mitochondrial function. The data shown in FIG. 84 reflect changes in cell number without acute toxicity because ATP levels were not affected by the test compound. Furthermore, the MTT assay proved to be a more sensitive marker for cell number than the propidium iodide assay (upper panel, circles). In order to define a dose-response relationship, the MTT assay was used to monitor change over a lower exposure range (FIG. 84B, lower panel). The lower end exposures used were as follows: 2.5/0.5, 1.25/0.25, 0.25/0.05, 0.125/0.025, 0.025/0.005, 0.0125/0.0025, 0.0025/0.0005 μg/mL COMP A. The IC50 value obtained from these data was 0.25/0.05. No effects on GSH (lower set of panels, circles) or Caspase 3 (lower set of panels, circles) were detected.

Experiments were also conducted to verify the relationship between exposure time and the observed cytostatic effects of the test compound. An additional assay was used to monitor cumulative change in DNA replication. The assay uses the thymidine analog BrdU to measure S-phase of cell replication and is considered to be the Gold Standard for cell proliferation. The data in FIG. 85 confirm that an increase in exposure time from 24 to 72 hr increased the cytostatic response (inhibition of cell proliferation) without an increase in acute cell death (See FIG. 89 for comparison to a known cytostatic drug). The BrdU assay paralleled the MTT and propidium iodide assays. The apparent lower sensitivity of the BrdU assay is a reflection of the experimental design not the assay. BrdU data represents a cumulative effect from the beginning of exposure while the other assays are measuring one is remaining at the end of either the 24 hr or 72 hr exposure period. Total glutathione levels were also reduced in this experiment. There was a trend toward increasing activity in caspase-3, a marker for cell apoptosis.

In FIG. 86, the effect of the test compound on human primary hepatocytes was examined. There were no detectable changes in any of the markers of cytotoxicity over the 35 hr exposure period.

FIG. 87 depicts the effects of the test material on a human umbilical vein endothelial cell line. There were no detectable changes measured in any of the acute toxicity markers (FIG. 87A, top panel). There was a significant increase in membrane lipid peroxidation as determined by 8-isoprostane.

The data presented in FIGS. 88 and 89 are similar to the response observed in SK-Mel 28 cells at the high exposure concentrations. MTT was the most sensitive marker to cell proliferation. Higher exposures actually produced a moderate increase in cells with a compensatory increase in ATP levels.

In FIGS. 90A and B, MTT was again the most sensitive assay at the high exposure concentrations. ATP increased in what was most likely a compensatory response. Total GSH was reduced at the highest exposures, and there was no cell death as determined by membrane leakage (open squares).

FIGS. 91 and 92 represent 24 and 72 hr cytotoxicity data following camptothecin exposure. In the top panel of FIG. 92, following a 24 hr exposure, the cells respond with a drop in MTT, cell number, and ATP. Cell proliferation as measured by the S-phase marker BrdU was undetectable after a 24 hr exposure to 5 and 10 μM. These data indicate that camptothecin inhibits cell proliferation prior to cell death. For multi-cell comparison, FIGS. 93-97 represent 24 hr cytotoxicity data following camptothecin exposure in human hepatocytes, HUVEC cells, C32 cells, and NHEM cells, respectively.

In FIG. 99, human primary hepatocytes were exposed to rotenone, an inhibitor of oxidative phosphorylation and ATP synthesis by mitochondria. These data provide a good example of ATP depletion and mitochondrial damage prior to acute cell death and loss of cells. For multi-cell comparison, FIGS. 97 and 98 represent 24 hr and 72 hr cytotoxicity data following rotenone exposure in SK-MEL28 cells, while FIGS. 100-102 represent 24 hr cytotoxicity data following rotenone exposure in HUVEC, C32 and NHEM cells, respectively.

Materials and Methods

All Materials and Methods, including Biochemical assay protocols, assay calculations, and Criteria for the Acceptability and Interpretation of Assays/Tox-Panel Data/Negative Cytotoxicity Data, were performed as described in Example 1, with the exceptions of those Materials and Methods described herein below.

Experimental Protocol: The test compounds were shipped on dry ice for testing. The compounds were stored frozen at −80° C. until needed. Dosing solutions were prepared in complete culture medium. SK-MEL28, human hepatocytes, HUVEC, C32, and NHEM cells were used as the test systems. Cells were seeded into 96-well plates and allowed to equilibrate for approximately 48 hr. Following the equilibration period the cells were exposed to the test compound mix at concentrations of COMP A (μg/mL)=(250:50), (125:25), (25: 12.5), (12.5:2.5), (2.5:1.25), (1.25:0.25), and (0.25:0.05). Solubility was determined by Nephalometry techniques immediately after dosing and prior to harvesting the cells at 24 hr. Following the exposure period, the cells or their supernatant (culture medium) were analyzed for changes in cell proliferation, membrane leakage, mitochondrial function, oxidative stress, and apoptosis. The resultant exposure concentration response curves were graphed and analyzed for determining the concentration that produced a half maximal response or $TC_{50}$.

Test and Control Articles: The test compounds were received as frozen solutions of 4.4 mg/mL Protective Antigen (PA) and 4.56 mg/mL Lethal Factor (LF) prepared in 5 mM HEPES, pH 7.4. The stock solution were used to prepare dosing solutions of COMP A (μg/mL) High Dose range= (250:50), (125:25), (25:12.5), (12.5:2.5), (2.5:1.25), (1.25: 0.25), and (0.25:0.05) in culture medium. In some experiments a low dose range was also included with COMP A ratios of (2.5:0.5), (1.25:0.25), (0.25:0.05), (0.125:0.025), 0.025:0.005), (0.0125:0.0025), 0.0025: 0.0005) μg/mL. The dosing solutions in medium were prepared on the day of dosing. The details of the preparation and dilutions can be found in the laboratory. A positive control for complete cell death received 1 mM digitonin in medium on the day of dosing.

Reagents and Solutions: All chemicals used were reagent grade or better. Cell culture supplies were from InVitrogen or Sigma/Aldrich.

Test Systems: SK-MEL28, human primary hepatocytes, HUVEC, C32, and NHEM were used as the test systems. The cell culture conditions for SK-Mel-28, HUVEC, and C32 cells were provided by the sponsor.

Culturing Conditions:

SK-Mel-28 cells. The cells were grown in RPMI 1640 medium with L-glutamine. The cells were cultured in the presence of penicillin and streptomycin at concentrations of 1% (v/v) in the final culture medium. Fetal bovine serum (FBS) was added to yield a final concentration of 5%. Serum and antibiotics were obtained from InVitrogen. The cells were seeded into 96-well culture plates at a density of 10,000 per well and allowed to equilibrate for 48 hr prior to dosing.

HUVEC cells: Normal human umbilical vein endothelial cells: Cells were purchased from Cambrex. The EGM-2 bullet kit was used for culture. The cells were grown in 1% fetal bovine serum (FBS). The cells were seeded into 96 well culture plates at a density of 10,000 per well and allowed to equilibrate for 48 hr prior to dosing.

C32 cells: Human amelanotic melanoma cells. Cells were grown in MEM with Earle's salts and L-glutamine. The media was supplemented with 1% penicillin and streptomycin, sodium pyruvate, essential amion acids, and 10% fetal bovine serum (FBS). Cells were seeded into 96-well culture plates and allowed to equilibrate for 48 hr prior to dosing.

NHEM cells: Normal human epidermal neonatal melanocytes. Cells were grown in media prepared by Cambrex in their MGM-4 bullet kit. The final serum concentration was 0.5% fetal bovine serum (FBS). These cells have extremely slow growth characteristics with doubling time of approximately 73 hr. These cells were seeded at a density of 12,500 per well and allowed to equilibrate for one week prior to dosing.

Rat Primary Hepatocytes: Cryopreserved cells were purchased from XenoTech LLC. (Kansas City, Kans.). The cells were seeded into 96-well plates at a density of 100,000 per well. The cells were allowed to equilibrate approximately 4 to 6 hr in seeding medium. During this time the cells formed a monolayer on the plate. After 4 to 6 hr the medium was removed and fresh culture medium containing 10% fetal bovine serum and test compound was added back to the wells.

Human Primary Hepatocytes: Cryopreserved cells were purchased from XenoTech, LLC, (Kansas City, Kans.). Cells were seeded into 96-well Biocoat plates at a density of 40,000 per well in seeding medium. The cells were allowed to equilibrate and form adherent monolayer over night. Following the equilibration period the medium was removed the fresh culture medium containing 10% fetal bovine serum and the test compound was added back to the wells.

For all cell types, the primary exposure time was 24 hr. In some instances, the exposure time was increased to 72 hr. When this occurred, both the 24 and 72 hr data were shown and clearly labeled.

Description of Experimental Setup and Biochemical Assays: Flat bottom 96-well plates were seeded with at the densities specified above under test systems. Collagen-coated 96-well plates were seeded with 100,000 rat primary hepatocytes 4 to 6 hr prior to dosing. Test compounds in medium were added to the plates after the equilibration period.

Solubility Assay: The test compounds were prepared in DMSO and the appropriate amounts were then added to complete medium containing 10% bovine serum at 37° C. The samples were evaluated using a light scattering technique and a Nephaloskan instrument. A reading that was greater than or equal to 3 times background was considered the limit of solubility.

Thus, in accordance with the present invention, there has been provided methods of determining a level of toxicity for a chemical compound, as well as methods of determining organ-specific and species-specific toxicities, that fully satisfies the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the invention.

REFERENCES

The following references, to the extent that they provide exemplary procedural or other details supplementary to those set forth herein, are specifically incorporated herein by reference.

Andrews, M. J., Garle, M. J., and Clothier, R. H. (1997). ATLA 25, 641-653.

Baldwin K M, Ernst S B, Mullin W J, Schrader L F, Herrick R E (1982). Exercise capacity and cardiac function of rats with drug-induced cardiac enlargement. J Appl Physiol. 52(3), 591-595.

Berridge M. V. and Tan, An S. (1993). Arch. Biochem. Biophys. 303, 474-482.

Chaiswing L, Cole M P, Ittarat W, Szweda L I, St Clair D K, Oberley T D (2005). Manganese superoxide dismutase and inducible nitric oxide synthase modify early oxidative events in acute adriamycin-induced mitochondrial toxicity. Molecular Cancer Therapeutics. 4(7), 1056-1064.

Christofferson T H E, Aplin M, Strom C C, Sheikh S P, Skott O, Busk P K, Haunso S, Nielsen L B (2006). Increased natriuretic peptide receptor A and C gene expression in rats with pressure-overload cardiac hypertrophy. American Journal of Physiology-Heart and Circulatory Physiology. 290, 1635-1641.

Davel A P, Kawamoto E M, Scavone C, Vassallo D V, Rossoni L V (2006). Changes in vascular reactivity following administration of isoproterenol for 1 week: a role for endothelial modulation. Br J Pharmacol. 148(5), 629-639.

Dent M R, Aroutiounova N, Dhalla N S, Tappia P S (2006). Losartan attenuates phospholipase C isozyme gene expression in hypertrophied hearts due to volume overload. J Cell Mol Med. 10(2), 470-479.

Esposito V, Palescandolo E, Spugnini E P, Montesarchio V, De Luca A, Cardillo I, Cortese G, Baldi A, Chirianni A (2006). Evaluation of antitumoral properties of the protease inhibitor indinavir in a murine model of hepatocarcinoma. Clin Cancer Res. 12(8), 2634-2639.

Fabiani R, De Bartolomeo A, Morozzi G (2005). Involvement of oxygen free radicals in the serum-mediated increase of benzoquinone genotoxicity. Environ Mol Mutagen. 46(3), 156-163.

Frohlich E D (1987). Potential mechanisms explaining the risk of left ventricular hypertrophy. Am J Cardiol. 59(2), 91A-97A.

Gervais M. Fornes P, Richer C, Nisato D, Giudicelli J F (2000). Effects of angiotensin II AT1-receptor blockade on coronary dynamics, function, and structure in post ischemic heart failure in rats. J Cardiovasc Pharmacol. 36(3), 329-337.

Gerwirtz D (1999). A critical evaluation of the mechanisms of action proposed for the antitumor effects of the anthracycline antibiotics adriamycin and daunorubicin. Biochem Pharmacol. 57, 727-741.

Goegan, P., Johnson, G. and Vincent, R. (1995). Toxicol. In vitro 9, 257-266.

Gonzalez A, Nunez A M, Granados M P, Pariente J A, Salido G M (2006). Ethanol impairs CCK-8-evoked amylase secretion through Ca2+-mediated ROS generation in mouse pancreatic acinar cells. Alcohol. 38(1), 51-57.

Grammer J B, Bleiziffer S, Monticelli F, Lange R, Bauernschmitt R (2006). Calcineurin and matrix protein expression in cardiac hypertrophy: Evidence for calcineurin B to control excessive hypertrophic signaling. Basic Res Cardiol. 101(4), 292-300.

Griffith, O. W. (1980) Determination of glutathione and glutathionedisulfide using glutathione reductase and 2-vinylpyridine. Anal. Biochem. 106, 207-212.

Harada M, Itoh H, Nakagawa O, Ogawa Y, Miyamoto Y, Kuwahara K, Ogawa E, Igaki T, Yamashita J, Masuda I, Yoshimasa T, Tanaka I, Saito Y, Nakao K (1997). Significance of ventricular myocytes and nonmyocytes interaction during cardiocyte hypertrophy: evidence for endothelin-1 as a paracrine hypertrophic factor from cardiac nonmyocytes. Circulation. 96(10), 3737-3744.

Hilfiker-Kleiner D, Hilfiker A, Castellazzi M, Wollert K C, Trautwein C, Schunkert H, Drexler H (2006). Jun D attenuates phenylephrine-mediated cardiomyocyte hypertrophy by negatively regulating AP-1 transcriptional activity. Cardiovascular Research. 71, 108-117.

Ho A K, Duffield R (2000). 6-Hydroxydopamine-induced developmental cardiac alterations in morphology, calmodulin content, and K(2+)-mediated [Ca(2+)](i)Transient of chicken cardiomyocytes. J Mol Cell Cardiol. 32(7), 1315-1326.

Horenstein M S, Vander Heide R S, L'Ecuyer, T J (2000). Molecular Basis of Anthracycline-Induced Cardiotoxicity and Its Prevention. Molecular Genetics and Metabolism. 71, 436-444.

Huveneers-oorsprong, M. B. M., Hoogenbroom, L. A. P., and Kuiper, H. A. (1997). Toxicol. in vitro. 11, 385-392.

Irukayama-Tomobe Y, Miyauchi T, Sakai S, Kasuya Y, Ogata T, Takanashi M, Iemitsu M, Sudo T, Goto K, Yamaguchi I, (2004). Endothelin-1-Induced Cardiac Hypertrophy Is Inhibited By Activation Of Peroxisome Proliferator-Activated Receptor-α Partly Via Blockade of c-Jun $NH_2$-Terminal Kinase Pathway. Circulation. 109, 904-910.

Kalender S, Kalender Y, Ates A, Yel M, Olcay E, Candan S (2002). Protective role of antioxidant vitamin E and catechin on idarubicin-induced cardiotoxicity in rats, Brazilian Journal of Medical and Biological Research. 35, 1379-1387.

King K L, Winer J, Phillips D M, Quach J, Williams P M, Mather J P (1998). Phenylephrine, Endothelin, Prostaglandin F and Leukemia Inhibitory Factor Induce Different Cardiac Hypertrophy Phenotypes In vitro. Endocrine. 9(1), 45-55.

Kontorinis N, Dieterich D T (2003). Toxicity of non-nucleoside analogue reverse transcriptase inhibitors, Semin Liver Dis. 23(2), 173-182.

Krauskopf A. (2002). British Journal of Pharmacology 135: 977-986.

Law W P, Dore G J, Duncombe C J, Mahanontharit A, Boyd M A, Ruxrungtham K, Lange J M, Phanuphak P, Cooper D A (2003). Risk of severe hepatotoxicity associated with antiretroviral therapy in the HIV-NAT Cohort, Thailand, 1996-2001. AIDS. 17(15), 2191-2199.

Lewis W, Dalakas M (1995). Mitochondrial toxicity of antiviral drugs. Nature Medicine. 1(5), 417-422.

Li H L, Huang Y, Zhang C N, Liu G, Wei Y S, Wang A B, Liu Y Q, Hui R T, Wei C, Williams G M, Liu D P, Liang C C (2006). Epigallocathechin-3 gallate inhibits cardiac hypertrophy through blocking reactive oxidative species-dependent and -independent signal pathways. Free Radic Biol Med. 40(10), 1756-1775.

Luodonpaa M, Vuolteenaho O, Sinikka E, Ruskoaho H (2001). Effects of arenomedullin on hypertrophic responses induced by angiotensin II, endothelin-1 and phenylephrine. Peptitdes. 22, 1859-1866.

Martin J L, Brown C E, Matthews-Davis N, Reardon J E (1994). Effects of Antiviral Nucleoside Analogs on Human DNA Polymerases and Mitochondrial DNA Synthesis. Antimicrobial Agents and Chemotherapy. 38(12), 2743-2749.

Martinez E, Blanco J L, Arnaiz J A, Perez-Cuevas J B, Mocroft A, Cruceta A, Marcos M A, Milinkovic A, Garcia-Viejo M A, Mallolas J, Carne X, Phillips A, Gatell J M (2001). Hepatotoxicity in HIV-1-infected patients receiving nevirapine-containing antiretroviral therapy. AIDS. 15(10), 1261-1268.

Mosmann, T. (1983). J Immunol. Meth. 65, 55-63.

Mracek T, Pecina P, Vojtiskova A, Kalous M, Sebesta 0, Houstek J (2006). Two components in pathogenic mechanism of mitochondrial ATPase deficiency: Energy deprivation and ROS production. Exp Gerontol. 41(7), 683-687.

Nakagawa O, Ogawa Y, Itoh H, Suga S, Komatsu Y, Kishimoto I, Nishino K, Yoshimasa T, Nakao K (1995). Rapid transcriptional activation and early mRNA turnover of brain natriuretic peptide in cardiocyte hypertrophy. Evidence for brain natriuretic peptide as an "emergency" cardiac hormone against ventricular overload. J Clin Invest. 96(3), 1280-1287.

Nishikimi T, Maeda N, Matsuoka H (2006). The role of natriuretic peptides in cardioprotection. Cardiovascular Research. 69, 318-328.

Olsson, T et al. (1983). Leakage of adenylate kinase from stored blood cells. J. Appl. Biochem. 5, 437-445.

Oldfield V, Plosker G L (2006). Lopinavir/Ritonavir: A Review of its Use in the Management of HIV Infection. Drugs. 66(9), 1275-1299.

Page, B. (1993). Inter. J. Oncol. 3, 473-476.

Paradis P, Dali-Youcef N, Paradis F W, Thibault G, Nemer M (2000). Overexpression of angiotensin II type I receptor in cardiomyocytes induces cardiac hypertrophy and remodeling. PNAS. 97(2), 931-936.

Perez-Elias M J, Moreno A, Moreno S, Lopez D, Antela A, Casado J L, Dronda F, Gutierrez C, Quereda C, Navas E, Abraira V, Rodriguez M A (2005). Higher virological effectiveness of NNRTI-based antiretroviral regimen containing nevirapine or efavirenz compared to a triple NRTI regimen as initial therapy in HIV-1-infected adults. HIV Clin Trials. 6(6), 312-319.

Pradelles, P., Grassi, J., and Maclouf, J. (1990) Enzyme immunoassays of eicosanoids using acetylcholinesterase. Methods of Enzymology. 187, 24-34.

Redi, H. (1995). Shock 3, 395-397.

Slater, T. F., Sawyer, G., and Strauli, U.(1963). Biochim. Biophys. Acta 77, 383-393.

Squirrell, D and Murphy, J. (1997). A Practical Guide to Industrial Uses of ATP-Luminescence in Rapid Microbiology: Rapid detection of very low number of micro-organisms using adenylate kinase as a cell marker. Cara Technology Ltd, Lingfield, Surrey, U K, 107-113.

Sriram D, Yogeeswari P, Myneedu N S, Saraswat V (2006). Abacavir prodrugs: Microwave-assisted synthesis and their evaluation of anti-HIV activities. Bioorganic and Medicinal Chemistry Letters. 16, 2127-2129.

Sulkowski M S, Thomas D L, Mehta S H, Chaisson R E, Moore R D (2002). Hepatotoxicity associated with nevirapine or efavirenz-containing antiretroviral therapy: role of hepatitis C and B infections. Hepatology. 36(2), 512-513.

Tiller P R, Romanyshyn L A (2002) Liquid chromatography/tandem mass spectrometric quantification with metabolite screening as a strategy to enhance the early drug discovery process. Rapid *Commun. Mass Spectrom.* 16:1225-1231.

Vacchiano, C. A. and Tempel, G. E. (1994) Role of nonenzymatically generated prostanoid, 8-iso-PGF2α in pulmonary oxygen toxicity. J. Appl. Physiol. 77, 2912-2917.

Vickers, A. E. (1994). Cell Biol. Toxicol. 10, 407-414.

von Hentig N, Muller A, Rottmann C, Lutz T, Klauke S, Kurowski M, Staszewski S, Harder S (2006). Pharmacokinetics and Tolerability of a Combination of Indinavir, Lopinavir and Ritonavir in Multiply Pretreated HIV-1 Infected Adults. Eur J Med Res. 11(6), 236-244.

Wilson, S. M., Barsoum, M. J., Wilson, B. W., and Pappone, P. A.(1999). Cell Prolif. 32, 131-14

TABLE 1

Summary of General Cytotoxicity (RAT CARDIOMYOCYTES)

| Compound Name/Number | Cell Number $TC_{50}$ (µM) | MemTox $TC_{50}$ (µM) | MTT $TC_{50}$ (µM) | ATP $TC_{50}$ (µM) | Predicted $C_{tox}$ (µM) |
|---|---|---|---|---|---|
| CLIENT Compound A CM 1 HR | ND | >300 | 276 | 185 | NA |
| CLIENT Compound A CM 3 HR | ND | >300 | 233 | 181 | NA |
| CLIENT Compound A CM 6 HR | ND | >300 | 187 | 163 | NA |
| CLIENT Compound A CM 24 HR | ND | >300 | 64 | 98 | NA |
| ADRIAMYCIN CM 1 HR | ND | >300 | >300 | >300 | NA |
| ADRIAMYCIN CM 3 HR | ND | >300 | 41 | 62 | NA |
| ADRIAMYCIN CM 6 HR | ND | 40 | 18 | 29 | NA |
| ADRIAMYCIN CM 24 HR | ND | 7 | 1 | 6 | NA |

TABLE 1-continued

| | | | | | |
|---|---|---|---|---|---|
| IDARUBICIN CM 24 HR | ND | <1 | <1 | 2 | NA |
| MITOXANTRONE CM 24 HR | ND | 2 | 1 | 2 | NA |
| DAUNORUBICIN CM 24 HR | ND | 4 | 6 | 9 | NA |
| PIRARUBICIN CM 24 HR | ND | 6 | 7 | 7 | NA |
| EPIRUBICIN CM 24 HR | ND | 35 | 16 | 19 | NA |
| RITONAVIR CM 24 HR | ND | 83 | 75 | 69 | NA |
| EFAVIRENZ CM 24 HR | ND | 69 | 79 | 75 | NA |
| LOPINAVIR CM 24 HR | ND | 76 | 72 | 72 | NA |
| DELAVIRDINE CM 24 HR | ND | 239 | 252 | 166 | NA |
| ABACAVIR CM 24 HR | ND | >300 | >300 | 165 | NA |
| INDINAVIR CM 24 HR | ND | >300 | >300 | >300 | NA |
| NEVIRAPINE CM 24 HR | ND | >300 | >300 | >300 | NA |
| AZT CM 24 HR | ND | >300 | >300 | >300 | NA |
| ROTENONE CM 24 HR | ND | 56 | 33 | 8 | NA |
| CAMPTOTHECIN CM 24 HR | 293 | >300 | >300 | >300 | NA |

Summary of General Cytotoxicity (H4IIE CELLS)
Ctox Ranking (μM) - Probability of in vivo Effects

| 1 | High | 20 | 21 | Moderate | 50 | 51 | Low | 300 |

| Compound Name/Number | Cell Number TC$_{50}$ (μM) | MemTox TC$_{50}$ (μM) | MTT TC$_{50}$ (μM) | ATP TC$_{50}$ (μM) | Predicted C$_{tox}$ (μM) |
|---|---|---|---|---|---|
| CLIENT Compound A H4IIE 24 HR | 236 | >300 | 163 | 164 | 60 |
| ADRIAMYCIN H4IIE 24 HR | 18 | 33 | 13 | 7 | 1 |
| IDARUBICIN H4IIE 24 HR | 4 | 30 | 3 | 2 | 1 |
| DAUNORUBICIN H4IIE 24 HR | 8 | 41 | 14 | 7 | 3 |
| PIRARUBICIN H4IIE 24 HR | 8 | 50 | 16 | 8 | 5 |
| DOXORUBICIN H4IIE 24 HR | 9 | 16 | 26 | 22 | 7 |
| EPIRUBICIN H4IIE 24 HR | 31 | 37 | 81 | 32 | 8 |
| MITOXANTRONE H4IIE 24 HR | <1 | >300 | >300 | 5 | 11 |
| EFAVIRENZ H4IIE 24 HR | 169 | 181 | 161 | 162 | 58 |
| RITONAVIR H4IIE 24 HR | >300 | >300 | 219 | 249 | 52 |
| DELAVIRDINE H4IIE 24 HR | >300 | >300 | 218 | 257 | 68 |
| LOPINAVIR H4IIE 24 HR | >300 | >300 | 184 | 195 | 60 |
| ABACAVIR H4IIE 24 HR | >300 | >300 | >300 | 154 | 65 |
| INDINAVIR H4IIE 24 HR | 300 | 300 | 300 | 300 | 90 |
| NEVIRAPINE H4IIE 24 HR | >300 | >300 | >300 | >300 | 100 |
| AZT H4IIE 24 HR | >300 | >300 | >300 | >300 | ND |
| ROTENONE H4IIE 24 HR | 0.04 | 100 | 0.07 | 0.04 | 0.03 |
| CAMPTOTHECIN H4IIE 24 HR | 4 | >300 | 1 | 1 | 0.1 |

CM = Rat Cardiomyocyte.
MemTox = Membrane permeability: AK = Adenylate kinase, GST = α-glutathione S-transferase (membrane leakage).
MTT = 3-[4,5-dimethylthiazol-2-yl]-2,5-diphenyltetrazolium bromide, ATP = adenosine triphosphate.
ND = Not determined, NA = Not applicable, NC = No change.
TC50 = concentration that produced a half-maximal response.
TC50 values were estimated from the graphs presented in FIGS. 1-46.
Ctox = Estimated sustained plasma concentration where toxicity would be expected to occur in vivo.
Blank boxes (line-out) = TC50 not achieved and therefore not determined.

TABLE 2

| Compound Name/Number | Total GSH TC$_{50}$ (μM) | Percent Change in Total GSH | Membrane Lipid Peroxidation | Caspase 3 Activity (Index/Dose) |
|---|---|---|---|---|
| Summary of Oxidative Stress and Apoptosis (RAT CARDIOMYOCYTES) | | | | |
| CLIENT Compound A CM 1 HR | >300 | −16.2 | 0 | NC |
| CLIENT Compound A CM 3 HR | 296 | −51.5 | 0 | NC |
| CLIENT Compound A CM 6 HR | 205 | −97.3 | 0 | NC |
| CLIENT Compound A CM 24 HR | 214 | −88.5 | 0 | NC |
| ADRIAMYCIN CM 1 HR | >300 | −19.3 | 0 | NC |
| ADRIAMYCIN CM 3 HR | 61 | −94.8 | 0 | NC |
| ADRIAMYCIN CM 6 HR | 23 | −96.2 | 0 | NC |
| ADRIAMYCIN CM 24 HR | 1 | −86.1 | 0 | NC |
| IDARUBICIN CM 24 HR | <1 | −100.0 | 0 | NC |
| MITOXANTRONE CM 24 HR | <1 | −100.0 | 0 | NC |
| DAUNORUBICIN CM 24 HR | <1 | −100.0 | 0 | 1/10 |
| PIRARUBICIN CM 24 HR | 6 | −96.3 | 0 | NC |
| EPIRUBICIN CM 24 HR | 13 | −100.0 | 0 | 1/20 |
| RITONAVIR CM 24 HR | 11 | −100.0 | 0 | NC |

TABLE 2-continued

| Compound Name/Number | Total GSH $TC_{50}$ (μM) | Percent Change in Total GSH | Membrane Lipid Peroxidation | Caspase 3 Activity (Index/Dose) |
|---|---|---|---|---|
| EFAVIRENZ CM 24 HR | 83 | −100.0 | 2 | NC |
| LOPINAVIR CM 24 HR | 69 | −91.7 | 0 | 1/100 |
| DELAVIRDINE CM 24 HR | >300 | −48.5 | 0 | 1/100 |
| ABACAVIR CM 24 HR | >300 | −37.7 | 2 | NC |
| INDINAVIR CM 24 HR | 71 | −89.2 | 1 | NC |
| NEVIRAPINE CM 24 HR | 251 | −58.6 | 1 | NC |
| AZT CM 24 HR | >300 | NC | 0 | NC |
| ROTENONE CM 24 HR | 7 | −80.8 | 3 | NC |
| CAMPTOTHECIN CM 24 HR | >300 | −31.5 | 0 | 6/300 |
| Summary of Oxidative Stress and Apoptosis (H4IIE CELLS) | | | | |
| CLIENT Compound A H4IIE 24 HR | 208 | −85.8 | 0 | NC |
| ADRIAMYCIN H4IIE 24 HR | 28 | −96.0 | 0 | 2/20 |
| IDARUBICIN H4IIE 24 HR | 4 | −100.0 | 0 | 10/5 |
| DAUNORUBICIN H4IIE 24 HR | 16 | −99.3 | 0 | 8/10 |
| PIRARUBICIN H4IIE 24 HR | 17 | −1.5 | 0 | 8/10 |
| DOXORUBICIN H4IIE 24 HR | 48 | −93.6 | 1 | 8/50 |
| EPIRUBICIN H4IIE 24 HR | 52 | −90.6 | 0 | 8/50 |
| MITOXANTRONE H4IIE 24 HR | 247 | −58.1 | 0 | 4/10 |
| EFAVIRENZ H4IIE 24 HR | 170 | −99.2 | 0 | NC |
| RITONAVIR H4IIE 24 HR | 92 | −79.7 | 0 | 1/300 |
| DELAVIRDINE H4IIE 24 HR | 96 | −73.9 | 1 | NC |
| LOPINAVIR H4IIE 24 HR | 99 | −70.3 | 0 | 1/300 |
| ABACAVIR H4IIE 24 HR | 213 | −63.1 | 0 | NC |
| INDINAVIR H4IIE 24 HR | 249 | −57.1 | 1 | NC |
| NEVIRAPINE H4IIE 24 HR | >300 | NC | 1 | NC |
| AZT H4IIE 24 HR | >300 | NC | 0 | NC |
| ROTENONE H4IIE 24 HR | 0.05 | −100.0 | 2 | 1/100 |
| CAMPTOTHECIN H4IIE 24 HR | 3 | −76.9 | 1 | 5/100 |

CM = Rat Cardiomyocyte.
GSH Data:
Decrease in Total GSH indicated by (−).
Increase in Total GSH indicated by (+).
Membrane Lipid Peroxidation Data:
0 = No Change,
1 = Modest increase with maximum values ≦15 pg/mL,
2 = Concentration related increase with maximum values ≧15 pg/mL,
3 = Concentration related increase with a maximum value ≧30 pg/mL.
Caspase 3 Data:
0-200 = 1, 200-400 = 2, 400-600 = 3, 600-800 = 4, 800-1000 = 5, 1000-1200 = 6, 1200-1400 = 7, 1400-1600 = 8, 1600-1800 = 9, 1800-2000 = 10.
ND = Not determined, NA = Not applicable, NC = No change.
TC50 = concentration that produced a half-maximal response.
TC50 values were estimated from the graphs presented in FIGS. 1-46.

TABLE 3

| Compound Name/Number | Highest Soluble Concentration Tested (μM) |
|---|---|
| Solubility Summary of Test Compounds in Culture Medium (RAT CARDIOMYOCYTES) | |
| CLIENT Compound A CM 1 HR | 300 |
| CLIENT Compound A CM 3 HR | 300 |
| CLIENT Compound A CM 6 HR | 300 |
| CLIENT Compound A CM 24 HR | 300 |
| ADRIAMYCIN CM 1 HR | 100 |
| ADRIAMYCIN CM 3 HR | 100 |
| ADRIAMYCIN CM 6 HR | 100 |
| ADRIAMYCIN CM 24 HR | 100 |
| IDARUBICIN CM 24 HR | 20 |
| MITOXANTRONE CM 24 HR | 300 |
| DAUNORUBICIN CM 24 HR | 100 |
| PIRARUBICIN CM 24 HR | 50 |
| EPIRUBICIN CM 24 HR | 300 |
| RITONAVIR CM 24 HR | 100 |
| EFAVIRENZ CM 24 HR | 300 |
| LOPINAVIR CM 24 HR | 50 |
| DELAVIRDINE CM 24 HR | 300 |
| ABACAVIR CM 24 HR | 300 |
| INDINAVIR CM 24 HR | 300 |
| NEVIRAPINE CM 24 HR | 300 |
| AZT CM 24 HR | 300 |
| ROTENONE CM 24 HR | 100 |
| CAMPTOTHECIN CM 24 HR | 10 |
| Solubility Summary of Test Compounds in Culture Medium (H4IIE CELLS) | |
| CLIENT Compound A H4IIE 24 HR | 300 |
| ADRIAMYCIN H4IIE 24 HR | 100 |
| IDARUBICIN H4IIE 24 HR | 20 |
| DAUNORUBICIN H4IIE 24 HR | 100 |
| PIRARUBICIN H4IIE 24 HR | 50 |
| DOXORUBICIN H4IIE 24 HR | 300 |
| EPIRUBICIN H4IIE 24 HR | 100 |
| MITOXANTRONE H4IIE 24 HR | 300 |
| EFAVIRENZ H4IIE 24 HR | 300 |
| RITONAVIR H4IIE 24 HR | 100 |
| DELAVIRDINE H4IIE 24 HR | 300 |
| LOPINAVIR H4IIE 24 HR | 50 |
| ABACAVIR H4IIE 24 HR | 300 |

TABLE 3-continued

| Compound Name/Number | Highest Soluble Concentration Tested (μM) |
| --- | --- |
| INDINAVIR H4IIE 24 HR | 300 |
| NEVIRAPINE H4IIE 24 HR | 300 |
| AZT H4IIE 24 HR | 300 |
| ROTENONE H4IIE 24 HR | 100 |
| CAMPTOTHECIN H4IIE 24 HR | 10 |

CM = Rat Cardiomyocyte.

Note:
The solubility values above represent the highest concentration tested at which the compound remained soluble. Solubility was assessed at 37° C. in the dosing medium, which contained 20% serum.

TABLE 4

Summary of P-glycoprotein (PgP) Binding (H4IIE CELLS)
The H4IIE cells possess high levels of PgP protein in the outer membrane. As a result compounds submitted for toxicity evaluations are also evaluated for their potential binding to PgP. Cells are incubated with and without cyclosporin A (CSA) (a PgP inhibitor) at a single exposure concentration (50 μM) and the difference in toxicity determined with the MTT assay. Compounds with increased toxicity in the presence of CSA have a high probability of binding to PgP proteins.

| Compound Name/Number | % Control (Compound) | % Control (Compound + CSA) | % Difference |
| --- | --- | --- | --- |
| CLIENT Compound A H4IIE 24 HR | 119.2 | 89.2 | 25.2 |
| ADRIAMYCIN H4IIE 24 HR | 8.0 | 0.0 | ND |
| IDARUBICIN H4IIE 24 HR | 0.8 | 0.0 | ND |
| DAUNORUBICIN H4IIE 24 HR | 9.3 | 5.5 | ND |
| PIRARUBICIN H4IIE 24 HR | 51.9 | 33.6 | 35.2 |
| DOXORUBICIN H4IIE 24 HR | 59.3 | 13.7 | 76.9 |
| EPIRUBICIN H4IIE 24 HR | 59.7 | 11.8 | 80.3 |
| MITOXANTRONE H4IIE 24 HR | 69.9 | 10.4 | 85.1 |
| EFAVIRENZ H4IIE 24 HR | 89.0 | 70.1 | 21.3 |
| RITONAVIR H4IIE 24 HR | 100.6 | 81.5 | 19.0 |
| DELAVIRDINE H4IIE 24 HR | 89.8 | 62.3 | 30.7 |
| LOPINAVIR H4IIE 24 HR | 98.0 | 82.1 | 16.2 |
| ABACAVIR H4IIE 24 HR | 97.6 | 104.8 | NC |
| INDINAVIR H4IIE 24 HR | 106.0 | 91.3 | 13.9 |
| NEVIRAPINE H4IIE 24 HR | 115.5 | 90.2 | 21.9 |
| AZT H4IIE 24 HR | 116.6 | 99.0 | NC |
| ROTENONE H4IIE 24 HR | 0.0 | 0.0 | ND |
| CAMPTOTHECIN H4IIE 24 HR | 23.6 | 26.0 | ND |

ND = Not determined (% control values <70% for compound are typically not determined because of high cytotoxicity).
NA = Not applicable.
NC = No change.
PgP Interaction Ranking (based on % Difference):
1-20% = Low interaction,
20-50% = Moderate interaction,
50-100% High interaction.

TABLE 5

Summary of Metabolic Activation

| Compound Name/Number | % Glutathione Remaining Rat Microsomes | % Glutathione Remaining Dog Microsomes |
| --- | --- | --- |
| Client Compounds | | |
| COMP A | 66.9 | 84.1 |
| COMP B | 58.5 | 47.4 |
| COMP C | 69.3 | 76.9 |
| 20 | 64.9 | 59.3 |
| COMP C | 46.3 | 67.8 |
| COMP D | 6.7 | 33.0 |
| 31 | 72.6 | 75.4 |
| 39 | 0.0 | 11.6 |
| COMP E | 96.6 | 76.9 |
| 41 | 84.9 | 84.4 |
| Controls | | |
| APAP 100 μM | 74.0 | 83.7 |
| APAP 1000 μM | 65.9 | 66.0 |

APAP = Acetaminophen.
NOTE:
Client compounds were analyzed at 100 μM.

TABLE 6

Summary of Metabolic Stability

| 1 μM Compound Name/Number | % Parent Remaining Rat Microsomes | % Parent Remaining Dog Microsomes |
| --- | --- | --- |
| COMP A | 82.0 | 63.5 |
| COMP B | 52.0 | 51.5 |
| COMP C | 13.5 | 56.5 |
| COMP D | 52.5 | 6.5 |
| COMP E | 33.5 | 89.5 |
| MIDAZOLAM | 0.0 | 0.0 |

TABLE 7

Summary of General Cytotoxicity: Client Compounds (48 HR Exposure)
Ctox Ranking (µM) - Probability of in vivo Effects

| 1 | High | 20 | 21 | Moderate | 50 | 51 | Low | 300 |
|---|------|----|----|----------|----|----|-----|-----|

| Compound Name/Number | Cell Number TC$_{50}$ (µM) | MemTox TC$_{50}$ (µM) | MTT TC$_{50}$ (µM) | ATP TC$_{50}$ (µM) | Predicted C$_{tox}$ (µM) |
|---|---|---|---|---|---|
| COMP B RAT PRIMARY HEPATOCYTE 48 HR | 10 | 79 | 8 | 7 | ND |
| COMP D RAT PRIMARY HEPATOCYTE 48 HR | >300 | >300 | >300 | >300 | ND |
| COMP B DOG PRIMARY HEPATOCYTE 48 HR | 8 | 6 | 8 | 7 | ND |
| COMP D DOG PRIMARY HEPATOCYTE 48 HR | >300 | >300 | >300 | >300 | ND |

MemTox = Membrane permeability: AK = Adenylate kinase, GST = α-glutathione S-transferase (membrane leakage).
MTT = 3-[4,5-dimethylthiazol-2-yl]-2,5-diphenyltetrazolium bromide, ATP = adenosine triphosphate.
ND = Not determined, NA = Not applicable, NC = No change.
TC50 = concentration that produced a half-maximal response.
TC50 values were estimated from the graphs presented in FIGS. 1-4.
Ctox = Estimated sustained plasma concentration where toxicity would be expected to occur in vivo.
Blank boxes (line-out) = TC50 not achieved and therefore not determined.

TABLE 8

Summary of Oxidative Stress and Apoptosis

| Compound Name/Number | Total GSH TC$_{50}$ (µM) | Percent Change in Total GSH | Membrane Lipid Peroxidation | Caspase 3 Activity (Index/Dose) |
|---|---|---|---|---|
| COMP B RAT PRIMARY HEPATOCYTE 48 HR | 8 | −71.4 | 0 | NC |
| COMP D RAT PRIMARY HEPATOCYTE 48 HR | >300 | −38.9 | 0 | NC |
| COMP B DOG PRIMARY HEPATOCYTE 48 HR | 8 | −91.0 | 3 | NC |
| COMP D DOG PRIMARY HEPATOCYTE 48 HR | >300 | NC | 0 | NC |

GSH Data:
Decrease in Total GSH indicated by (−).
Increase in Total GSH indicated by (+).
Membrane Lipid Peroxidation Data:
0 = No Change,
1 = Modest increase with maximum values ≦15 pg/mL,
2 = Concentration related increase with maximum values ≧15 pg/mL,
3 = Concentration related increase with a maximum value ≧30 pg/mL.
Caspase 3 Data:
0-200 = 1, 200-400 = 2, 400-600 = 3, 600-800 = 4, 800-1000 = 5, 1000-1200 = 6, 1200-1400 = 7, 1400-1600 = 8, 1600-1800 = 9, 1800-2000 = 10.
ND = Not determined, NA = Not applicable, NC = No change.
TC50 = concentration that produced a half-maximal response.
TC50 values were estimated from the graphs presented in FIGS. 1-4.

TABLE 9

Solubility Summary of Test Compounds in Culture Medium

| Compound Name/Number | Highest Soluble Concentration Tested (µM) |
|---|---|
| COMP B RAT PRIMARY HEPATOCYTE 48 HR | 20-50 (a) |
| COMP D RAT PRIMARY HEPATOCYTE 48 HR | 300 |
| COMP B DOG PRIMARY HEPATOCYTE 48 HR | 20-50 (a) |
| COMP D DOG PRIMARY HEPATOCYTE 48 HR | 300 |

Note:
The solubility values above represent the highest concentration tested at which the compound remained soluble. Solubility was assessed at 37° C. in the dosing medium, which contained 20% serum.
(a) Compound COMP B was soluble up to and including 20 µM at both 0 hr and 48 hr reads. The compound was borderline soluble (3× background) at 50 µM at both 0 hr and 48 hr reads.

TABLE 10A

Non-GLP In Vitro Toxicity Screening Results 24 hr Exposure

| Compound Number | Batch Number or Lot Number | Cell Number $TC_{50}$ (Dil.) | GST $TC_{50}$ (Dil.) | MTT $TC_{50}$ (Dil.) | Alamar Blue $TC_{50}$ (Dil.) | ATP $TC_{50}$ (Dil.) | Predicted $C_{tox}$ (Dil.) |
|---|---|---|---|---|---|---|---|
| COMP A | NA | 0.0016 (1:625) | 0.0016 (1:625) | 0.0016 (1:625) | ND | 0.0014 (1:714) | 0.001 (1:1000) |

TABLE 10B

Non-GLP In Vitro Toxicity Screening Results: 6 Hr and 24 Hr Exposures

| Compound Number | Batch Number or Lot Number | Cell Number $TC_{50}$ (Dil.) | GST $TC_{50}$ (Dil.) | MTT $TC_{50}$ (Dil.) | Alamar Blue $TC_{50}$ (Dil.) | ATP $TC_{50}$ (Dil.) | Predicted $C_{tox}$ (Dil.) |
|---|---|---|---|---|---|---|---|
| Comp A Rat Primary 6 Hr | NA | 0.009 (1:111) | 0.006 (1:167) | 0.004 (1:250) | ND | 0.006 (1:167) | ND |
| Comp A Rat Primary 24 Hr | NA | 0.007 (1:143) | 0.006 (1:167) | 0.004 (1:250) | ND | 0.002 (1:500) | ND |

| Compound Number | Batch Number or Lot Number | Cell Number $TC_{50}$ (pH) | GST $TC_{50}$ (pH) | MTT $TC_{50}$ (pH) | Alamar Blue $TC_{50}$ (pH) | ATP $TC_{50}$ (pH) | Predicted $C_{tox}$ (pH) |
|---|---|---|---|---|---|---|---|
| pH Test Rat Primary 6 Hr | NA | ND | ND | 6.2 | ND | 6.2 | ND |
| pH Test Rat Primary 24 Hr | NA | ND | ND | 6.2 | ND | 6.4 | ND |

TABLE 10C

Non-GLP In Vitro Toxicity Screening Results (24 Hr Exposure)

| Compound Number | Batch Number or Lot Number | Cell Number $TC_{50}$ (Dil.) | Mem Tox $TC_{50}$ (Dil.) | MTT $TC_{50}$ (Dil.) | ATP $TC_{50}$ (Dil.) | Predicted $C_{tox}$ (Dil.) |
|---|---|---|---|---|---|---|
| COMP A NRK 6 HR | NA | 0.049 (1:20) | 0.060 (1:17) | 0.040 (1:25) | 0.014 (1:71) | 0.009 (1:111) |
| COMP A NRK 24 HR | NA | 0.057 (1:18) | 0.044 (1:23) | 0.012 (1:83) | 0.006 (1:167) | 0.009 (1:111) |

| Compound Number | Batch Number or Lot Number | Cell Number $TC_{50}$ (pH) | Mem Tox $TC_{50}$ (pH) | MTT $TC_{50}$ (pH.) | ATP $TC_{50}$ (pH) | Predicted $C_{tox}$ (pH.) |
|---|---|---|---|---|---|---|
| PH TEST NRK 6 HR | NA | ND | 6.2 | 6.2 | 6.2 | 6.8 |
| PH TEST NRK 24 HR | NA | ND | 6.2 | 6.2 | 6.2 | 6.8 |

| Compound Number | Batch Number or Lot Number | Cell Number $TC_{50}$ (μM) | GST $TC_{50}$ (μM) | MTT $TC_{50}$ (μM) | ATP $TC_{50}$ (μM) | Predicted $C_{tox}$ (μM) |
|---|---|---|---|---|---|---|
| CAMPTOTHECIN NRK 6 HR | NA | ND | 300 | 300 | 300 | 0.1 |
| CAMPTOTHECIN NRK 24 HR | NA | ND | 100 | 100 | 9 | 0.1 |
| ROTENONE NRK 6 HR | NA | ND | 10 | 10 | 10 | 1 |

TABLE 10C-continued

Non-GLP In Vitro Toxicity Screening Results (24 Hr Exposure)

| | | | | | | |
|---|---|---|---|---|---|---|
| ROTENONE NRK 24 HR | NA | ND | 10 | 10 | 10 | 1 |

For Tables 10A-C:
GST = α-glutathione S-transferase (membrane permeability).
MTT = 3-[4,5-dimethylthiazol-2-yl]-2,5-diphenyltetrazolium bromide.
ATP = adenosine triphosphate.
ND = Not determined.
NA = Not applicable.
NC = No change.
Dil = Dilution.
TC50 = concentration that produced a half-maximal response.
TC50 values were estimated from the graphs presented in FIG. 1.
Ctox = Estimated sustained plasma concentration where toxicity would be expected to occur in vivo.
* = Ctox was based on the responses observed for two indicators of mitochondrial health. The true Ctox may be higher.
Exposure Concentrations (Dilutions):
2000 Dil. = 0.0005
1000 Dil. = 0.001
500 Dil. = 0.002
100 Dil. = 0.01
50 Dil. = 0.02
10 Dil. = 0.1
1 Dil. = 0.5

TABLE 11A

Non-GLP In Vitro Toxicity Screening Results For The Oxidative Stress-Cluster

| Compound Number | Batch Number or Lot Number | Total GSH TC50 (Dil.) | Percent Change in Total GSH | Membrane Lipid Peroxidation | Caspase 3 Activity Index/Dose |
|---|---|---|---|---|---|
| COMP A | NA | 0.0015 (1:667) | 100.0 | 1 | 3/0.002 (1:500) |

TABLE 11B

Non-GLP In Vitro Toxicity Screening Results For The Oxidative Stress and Apoptosis Clusters: 6 Hr and 24 Hr Exposures

| Compound Number | Batch Number or Lot Number | Total GSH TC50 (Dil.) | Percent Change in Total GSH | Membrane Lipid Peroxidation | Caspase 3 Activity Index/Dose (Dil.) |
|---|---|---|---|---|---|
| Comp A Rat Primary 6 Hr | NA | 0.002 (1:500) | −81.9 | 3 | 1/0.001 (1:1000) |
| Comp A Rat Primary 24 Hr | NA | 0.001 (1:1000) | −73.3 | 3 | 1/0.002 (1:500) |

| Compound Number | Batch Number or Lot Number | Total GSH TC50 (μM) | Percent Change in Total GSH | Membrane Lipid Peroxidation | Caspase 3 Activity Index/Dose (pH) |
|---|---|---|---|---|---|
| pH Test Rat Primary 6 Hr | NA | ND | ND | ND | 2/6.8 |
| pH Test Rat Primary 24 Hr | NA | ND | ND | ND | 1/6.8 |

TABLE 11C

Non-GLP In Vitro Toxicity Screening Results For The Oxidative
Stress and Apoptosis Panels: 6 Hr and 24 Hr Exposures

| Compound Number | Batch Number or Lot Number | Total GSH TC50 (Dil.) | Percent Change in Total GSH | Membrane Lipid Peroxidation | Caspase 3 Activity Index/Dose (Dil.) |
|---|---|---|---|---|---|
| COMP A NRK 6 HR | NA | 0 | 100.0 | 1 | NC |
| COMP A NRK 24 HR | NA | 0 | 100.0 | 3 | 2/0.01 |

| Compound Number | Batch Number or Lot Number | Total GSH TC50 (pH) | Percent Change in Total GSH | Membrane Lipid Peroxidation | Caspase 3 Activity Index/Dose (pH) |
|---|---|---|---|---|---|
| PH TEST NRK 6 HR | NA | ND | ND | ND | 1/6.0 |
| PH TEST NRK 24 HR | NA | ND | ND | ND | 1/6.0 |

| Compound Number | Batch Number or Lot Number | Total GSH TC50 (μM) | Percent Change in Total GSH | Membrane Lipid Peroxidation | Caspase 3 Activity Index/Dose (μM) |
|---|---|---|---|---|---|
| CAMPTOTHECIN NRK 6 HR | NA | ND | ND | ND | 3/100 |
| CAMPTOTHECIN NRK 24 HR | NA | ND | ND | ND | 10/300 |
| ROTENONE NRK 6 HR | NA | ND | ND | ND | NC |
| ROTENONE NRK 24 HR | NA | ND | ND | ND | 2/10 |

For Tables 11A-C:
Membrane Lipid Peroxidation data:
0 = No Change,
1 = Modest increase with maximum values $\leq$15 pg/mL,
2 = Concentration related increase with maximum values $\geq$15 pg/mL,
3 = Concentration related increase with a maximum value $\geq$30 pg/mL.
Caspase 3 Data:
0-20 = 1, 20-40 = 2, 40-60 = 3, 60-80 = 4, 80-100 = 5, 100-120 = 6, 120-140 = 7, 140-160 = 8, 160-180 = 9, 180-200 = 10.
ND = Not determined.
NA = Not applicable.
NC = No change.
Dil = Dilution.
TC50 = concentration that produced a half-maximal response.
TC50 values were estimated from the graphs presented in FIG. 1.

TABLE 12A

Solubility of the test compounds in culture media containing 20% serum

| Compound Number | Highest Soluble Concentration (Dil.) |
|---|---|
| COMP A | 0.002 (1:500) |

TABLE 12B

Solubility of the Test Compounds in Culture Media Containing 10% Serum

| Compound Number | Highest Soluble Concentration (Dil.) |
|---|---|
| Comp A Rat Primary 6 Hr | 0.002 (1:500) |
| Comp A Rat Primary 24 Hr | 0.002 (1:500) |

TABLE 12B-continued

Solubility of the Test Compounds in
Culture Media Containing 10% Serum

| Compound Number | Highest Soluble Concentration |
|---|---|
| | (pH) |
| pH Test Rat Primary 6 Hr | 6.5 |
| pH Test Rat Primary 24 Hr | 6.5 |

TABLE 12C

Solubility of the Test Compounds in
Culture Media Containing 20% Serum

| Compound Number | Highest Soluble Concentration |
|---|---|
| | (Dil.) |
| COMP A NRK 6 HR | 0.02 |
| COMP A NRK 24 HR | 0.01 |
| | (pH) |
| PH TEST NRK 6 HR | 6.0 |
| PH TEST NRK 24 HR | 6.0 |
| | ($\mu$M) |
| CAMPTOTHECIN NRK 6 HR | 50 |

TABLE 12C-continued

Solubility of the Test Compounds in
Culture Media Containing 20% Serum

| Compound Number | Highest Soluble Concentration |
|---|---|
| CAMPTOTHECIN NRK 24 HR | 50 |
| ROTENONE NRK 6 HR | 10 |
| ROTENONE NRK 24 HR | 10 |

Note for FIGS. 12A-C:
The solubility values above represent the highest concentration at which the compound remained soluble. Solubility was assessed at 37° C. in the dosing media, which contained 20% serum.

TABLE 13A

P-glycoprotein binding
The H4IIE cells possess high levels of PgP protein in the outer membrane. As a result compounds submitted to toxicity evaluations are also evaluated for their potential binding to PgP. Cells are incubated with and without cyclosporin A (CSA) (a PgP inhibitor) at a single exposure concentration (50 $\mu$M) and the difference in toxicity determined with the MTT assay. Compounds with increased toxicity in the presence of CSA have a high probability of binding to PgP proteins.

| Compound Number | Batch Number or Lot Number | % Control Compound | % Control Compound + CSA | % Difference |
|---|---|---|---|---|
| COMP A | NA | 6.6 | 6.3 | 3.5 |

TABLE 14

Summary of General Cytotoxicity

Ctox Ranking ($\mu$M) - Probability of in vivo Toxicity

| 1 | Toxic | 20 | 21 | Caution | 50 | 51 | Lowest Toxicity | 300 |

| Compound Name/Number | Cell Number $TC_{50}$ ($\mu$g/mL) | MemTox $TC_{50}$ ($\mu$g/mL) | MTT $TC_{50}$ ($\mu$g/mL) | BrdU $TC_{50}$ ($\mu$g/mL) | ATP $TC_{50}$ ($\mu$g/mL) | Predicted $C_{tox}$ ($\mu$g/mL) |
|---|---|---|---|---|---|---|
| COMP A; SK-MEL28 24 HR | — | — | (0.25:0.05) | ND | — | ND |
| COMP A (LOW); SK-MEL28 24 HR | — | — | — | — | — | (0.6:0.12) |
| COMP A (LOW); SK-MEL28 72 HR | (0.1:0.2) | — | (0.04:0.008) | (0.1:0.2) | (0.1:0.2) | ND |
| COMP A; HUMAN HEP 24 HR | — | — | — | ND | — | ND |
| COMP A; HUVEC 24 HR | — | — | — | ND | — | ND |
| COMP A; C32 24 HR | — | — | — | ND | — | ND |
| COMP A; NHEM 24 HR | — | — | — | ND | — | ND |

| Compound Name/Number | Cell Number $TC_{50}$ ($\mu$M) | MemTox $TC_{50}$ ($\mu$M) | MTT $TC_{50}$ ($\mu$M) | BrdU $TC_{50}$ ($\mu$M) | ATP $TC_{50}$ ($\mu$M) | Predicted $C_{tox}$ ($\mu$M) |
|---|---|---|---|---|---|---|
| CAMPTOTHECIN SK-MEL28 24 HR | — | — | 241 | ND | 293 | 0.1 |
| CAMPTOTHECIN #2 SK-MEL28 24 HR | — | — | 249 | 0.1 | — | 0.1 |
| CAMPTOTHECIN #2 SK-MEL28 72 HR | 0.1 | — | 0.1 | 0.2 | 0.1 | ND |
| CAMPTOTHECIN HUMAN HEP 24 HR | — | — | — | ND | — | 23 |
| CAMPTOTHECIN HUVEC 24 HR | 85 | 13 | 41 | ND | 40 | 0.1 |
| CAMPTOTHECIN C32 24 HR | — | — | 213 | ND | — | 0.1 |

TABLE 14-continued

Summary of General Cytotoxicity

| | | | | | | |
|---|---|---|---|---|---|---|
| CAMPTOTHECIN NHEM 24 HR | — | — | — | ND | — | 33 |
| ROTENONE; SK-MEL28 24 HR | — | — | — | ND | — | 1 |
| ROTENONE #2; SK-MEL28 24 HR | — | — | — | 9 | — | 0 |
| ROTENONE #2; SK-MEL28 72 HR | 1 | — | 0.2 | 44 | 2 | ND |
| ROTENONE; HUMAN HEP 24 HR | — | — | 3 | ND | 6 | 0.6 |
| ROTENONE; HUVEC 24 HR | — | — | — | ND | — | 0.1 |
| ROTENONE; C32 24 HR | — | — | — | ND | — | ND |
| ROTENONE; NHEM 24 HR | — | — | — | ND | — | 10 |

MemTox = Membrane permeability: AK = Adenylate kinase, GST = α-glutathione S-transferase (membrane leakage). MTT = 3-[4,5-dimethylthiazol-2-yl]-2,5-diphenyltetrazolium bromide, ATP = adenosine triphosphate.
ND = Not determined, NA = Not applicable, NC = No change.
TC50 = concentration that produced a half-maximal response. TC50 values were estimated from the graphs presented in FIGS. 68-87.
Ctox = Estimated sustained plasma concentration where toxicity would be expected to occur in vivo.

TABLE 15

Summary of Oxidative Stress and Apoptosis

| Compound Name/Number | Total GSH TC$_{50}$ | Percent Change in Total GSH | Membrane Lipid Peroxidation | Caspase 3 Activity (Index/Dose) |
|---|---|---|---|---|
| | (µg/mL) | | | |
| COMP A; SK-MEL28 24 HR | — | −30.6 | 0 | 1/(12.5:2.5) |
| COMP A (LOW); SK-MEL28 24 HR | — | −27.2 | 0 | 1/(1.25:0.25) |
| COMP A (LOW); SK-MEL28 72 HR | (0.1:0.02) | −79.4 | 0 | 1/(2.5:0.5) |
| COMP A; HUMAN HEP 24 HR | — | −23.7 | 0 | NC |
| COMP A; HUVEC 24 HR | (156:31) | −53.9 | 2 | NC |
| COMP A; C32 24 HR | — | NC | 0 | NC |
| COMP A; NHEM 24 HR | — | −30.4 | 1 | NC |
| | (µM) | | | |
| CAMPTOTHECIN; SK-MEL28 24 HR | — | −46.0 | 0 | 3/300 |
| CAMPTOTHECIN #2; SK-MEL28 24 HR | 10 | −57.9 | 0 | 3/100 |
| CAMPTOTHECIN #2 SK-MEL28 72 HR | 0.1 | −88.8 | 1 | 3/100 |
| CAMPTOTHECIN HUMAN HEP 24 HR | 44 | −69.9 | 1 | 3/100 |
| CAMPTOTHECIN; HUVEC 24 HR | 1 | −85.8 | 2 | 1/300 |
| CAMPTOTHECIN; C32 24 HR | 1 | −41.1 | 0 | 4/300 |
| CAMPTOTHECIN; NHEM 24 HR | — | NC | 1 | 3/300 |
| ROTENONE; SK-MEL28 24 HR | 9 | 52.8 | 3 | NC |
| ROTENONE #2; SK-MEL28 24 HR | 9 | 49.9 | 2 | NC |
| ROTENONE #2; SK-MEL28 72 HR | 0.1 | 85.1 | 3 | NC |
| ROTENONE; HUMAN HEP 24 HR | 1 | 95.9 | 0 | NC |
| ROTENONE; HUVEC 24 HR | 10 | 11.3 | 1 | NC |
| ROTENONE; C32 24 HR | 10 | 12.9 | 0 | NC |
| ROTENONE; NHEM 24 HR | — | NC | 2 | NC |

GSH Data: Decrease in Total GSH indicated by (−); Increase in Total GSH indicated by (+).
Membrane Lipid Peroxidation Data:
0 = No Change,
1 = Modest increase with maximum values ≦15 pg/mL,
2 = Concentration related increase with maximum values ≧15 pg/mL,
3 = Concentration related increase with a maximum value ≧30 pg/mL.
Caspase 3 Data:
0-200 = 1, 200-400 = 2, 400-600 = 3, 600-800 = 4, 800-1000 = 5, 1000-1200 = 6, 1200-1400 = 7, 1400-1600 = 8, 1600-1800 = 9, 1800-2000 = 10.
ND = Not determined, NA = Not applicable, NC = No change.
TC50 = concentration that produced a half-maximal response.
TC50 values were estimated from the graphs presented in FIGS. 1-19.
Blank boxes (line-out) = TC50 not achieved and therefore not determined.

TABLE 16

Solubility Summary of Test Compounds in Culture Medium

| Compound Name/Number | Highest Soluble Concentration |
|---|---|
| | (μg/mL) |
| COMP A; SK-MEL28 24 HR | (250:50) |
| COMP A (LOW); SK-MEL28 24 HR | (2.5:0.5) |
| COMP A (LOW); SK-MEL28 72 HR | (2.5:0.5) |
| COMP A; HUMAN HEP 24 HR | (250:50) |
| COMP A; HUVEC 24 HR | (250:50) |
| COMP A; C32 24 HR | (250:50) |
| COMP A; NHEM 24 HR | (250:50) |
| | (μM) |
| CAMPTOTHECIN; SK-MEL28 24 HR | 10 |
| CAMPTOTHECIN #2; SK-MEL28 24 HR | 10 |
| CAMPTOTHECIN #2; SK-MEL28 72 HR | 10 |
| CAMPTOTHECIN; HUMAN HEP 24 HR | 10 |
| CAMPTOTHECIN; HUVEC 24 HR | 10 |
| CAMPTOTHECIN; C32 24 HR | 10 |
| CAMPTOTHECIN; NHEM 24 HR | 10 |
| ROTENONE; SK-MEL28 24 HR | 10 |
| ROTENONE #2; SK-MEL28 24 HR | 100* |
| ROTENONE #2; SK-MEL28 72 HR | 100* |
| ROTENONE; HUMAN HEP 24 HR | 10 |
| ROTENONE; HUVEC 24 HR | 10 |
| ROTENONE; C32 24 HR | 10 |
| ROTENONE; NHEM 24 HR | 100* |

Note:
The solubility values above represent the highest concentration at which the compound remained soluble. Solubility was assessed at 37° C. in the dosing medium, which contained 20% serum. Red highlight indicates low solubility.
Note:
Rotenone exposures for SK-MEL28 (24, 72 hr) and NHEM (24 hr) were done up to and including 100 μM. All other Rotenone exposures in this group were done up to and including 10 μM.

TABLE 17

Summary of P-glycoprotein (PgP) Binding

| Compound Name/Number | % Control (Compound) | % Control (Compound + CSA) | % Difference |
|---|---|---|---|
| COMP A; SK-MEL28 24 HR | 48.2 | 42.3 | 12.3 |
| COMP A (LOW); SK-MEL28 24 HR | ND | ND | ND |
| COMP A (LOW); SK-MEL28 72 HR | ND | ND | ND |
| COMP A; HUMAN HEP 24 HR | 113.5 | 101.1 | NC |
| COMP A; HUVEC 24 HR | 70.5 | 88.3 | NC |
| COMP A; C32 24 HR | ND | ND | ND |
| COMP A; NHEM 24 HR | ND | ND | ND |
| CAMPTOTHECIN; SK-MEL28 24 HR | 56.5 | 63.3 | NC |
| CAMPTOTHECIN #2; SK-MEL28 24 HR | ND | ND | ND |
| CAMPTOTHECIN #2; SK-MEL28 72 HR | ND | ND | ND |
| CAMPTOTHECIN; HUMAN HEP 24 HR | 88.5 | 65.8 | 25.7 |
| CAMPTOTHECIN; HUVEC 24 HR | 29.4 | 18.0 | ND |
| CAMPTOTHECIN; C32 24 HR | ND | ND | ND |
| CAMPTOTHECIN; NHEM 24 HR | ND | ND | ND |
| ROTENONE; SK-MEL28 24 HR | 98.2 | 117.3 | NC |
| ROTENONE #2; SK-MEL28 24 HR | ND | ND | ND |
| ROTENONE #2; SK-MEL28 72 HR | ND | ND | ND |
| ROTENONE; HUMAN HEP 24 HR | 97.1 | 60.9 | 37.2 |
| ROTENONE; HUVEC 24 HR | 75.4 | 77.8 | NC |
| ROTENONE; C32 24 HR | ND | ND | ND |
| ROTENONE; NHEM 24 HR | ND | ND | ND |

The H4IIE cells possess high levels of PgP protein in the outer membrane. As a result compounds submitted for toxicity evaluations are also evaluated for their potential binding to PgP. Cells are incubated with and without cyclosporin A (CSA) (a PgP inhibitor) at a single exposure concentration (50 μM) and the difference in toxicity determined with the MTT assay. Compounds with increased toxicity in the presence of CSA have a high probability of binding to PgP proteins.
ND = Not determined (% control values <70% for compound are typically not determined because of high cytotoxicity).
NA = Not applicable.
NC = No change.
PgP Interaction Ranking (based on % Difference):
1-20% = Low interaction,
20-50% = Moderate interaction,
50-100% High interaction.

What is claimed is:

1. A method of determining a level of cardiac toxicity of a chemical compound comprising the steps of:
   (a) providing freshly isolated cardiomyocytes;
   (b) providing freshly isolated liver cells;
   (c) culturing the cardiomyocytes and liver cells in the presence of a plurality of concentrations of said chemical compound;
   (d) measuring two or more indicators of cell health at four or more concentrations of said chemical compound for the cardiomyocytes, wherein the two or more indicators of cell health are each independently selected from the group consisting of indicators of mitochondrial function, indicators of cell membrane integrity, indicators of cell mortality, and indicators of oxidative stress;
   (e) measuring two or more indicators of cell health at four or more concentrations of said chemical compound for the liver cells, wherein the two or more indicators of cell health are each independently selected from the group consisting of indicators of mitochondrial function, indicators of cell membrane integrity, indicators of cell mortality, and indicators of oxidative stress;
   (f) determining a level of toxicity of said chemical compound from the measurements taken in steps (d) and (e) by:
      (1) performing a concentration response analysis for each indicator of cell health from the measurements taken in step (d) for the cardiomyocytes;
      (2) performing a concentration response analysis for each indicator of cell health from the measurements taken in step (e) for the liver cells;
      (3) identifying, from the concentration response analyses of (1), the highest concentration of said chemical compound at which no measurable toxic effect was observed for each measured indicator of cell health for the cardiomyoctes;
      (4) identifying, from the concentration response analyses of (2), the highest concentration of said chemical compound at which no measurable toxic effect was observed for each measured indicator of cell health for the liver cells;

(5) selecting, as the toxic concentration ($C_{tox}$), a concentration less than or equal to the highest concentration of said chemical compound at which no measurable toxic effect was observed for all measured indicators of cell health in (3) for the cardiomyocytes, as a level of toxicity for the chemical compound in cardiac cells;

(6) selecting, as the toxic concentration ($C_{tox}$), a concentration less than or equal to the highest concentration of said chemical compound at which no measurable toxic effect was observed for all measured indicators of cell health in (4) for the liver cells, as a level of toxicity for the chemical compound in liver cells; and (g) determining that the chemical compound exhibits cardiac specific toxicity if the $C_{tox}$ calculated in (f)(5) is lower than the $C_{tox}$ calculated in (f)(6).

2. The method of claim 1 further comprising the step of measuring at least one indicator of cardiac-specific cell health at one or more concentrations of said chemical compound for the cardiomyocytes, wherein the at least one indicator of cardiac-specific cell health is selected from the group consisting of indicators of cardiac hypertrophy, indicators of QT interval prolongation, and indicators of cardiac cell physiology.

3. The method of claim 2, wherein the at least one indicator of cardiac-specific cell health is an indicator of cardiac hypertrophy, and wherein cardiac hypertrophy is monitored with an assay of expression of at least one cardiac hypertrophy marker.

4. The method of claim 3, wherein the at least one cardiac hypertrophy marker is selected from the group consisting of atrial natriuretic peptide (ANP), brain natriuretic peptide (BNP), skeletal α-actin, C-fos and C-jun.

5. The method of claim 2, wherein the at least one indicator of cardiac-specific cell health is an indicator of QT interval prolongation, and wherein QT interval prolongation is monitored with an hERG inhibition assay.

6. The method of claim 1, wherein at least one of the two or more indicators of cell health is an indicator of mitochondrial function, and wherein mitochondrial function is monitored with an assay selected from the group consisting of an ATP assay, an MTT assay, an Alamar Blue assay, and a Rhodamine 123 assay.

7. The method of claim 1, wherein at least one of the two or more indicators of cell health is an indicator of cell membrane integrity, and wherein cell membrane integrity is monitored with an assay selected from the group consisting of a glutathione S-transferase assay, lactate dehydrogenase assay, aspartyl aminotransferase assay, alanine aminotransferase assay, isocitrate dehydrogenase assay, sorbitol dehydrogenase assay, glutamate dehydrogenase assay, ornithine carbamyl transferase assay, γ-glutamyl transferase assay, alkaline phosphatase assay, and a Troponin I release assay.

8. The method of claim 1, wherein at least one of the two or more indicators of cell health is an indicator of cell mortality, and wherein cell mortality is monitored with an apoptosis assay.

9. The method of claim 1, wherein at least one of the two or more indicators of cell health is an indicator of oxidative stress, and wherein oxidative stress is monitored with an assay selected from the group consisting of a reduced glutathione assay, reactive oxygen species assay, reactive nitrogen species assay, and a lipid peroxidation assay.

10. The method of claim 1, further comprising determining a concentration of said compound that produces a half maximal toxic effect ($TC_{50}$) for each of said indicators of cell health.

11. The method of claim 1, wherein said plurality of concentrations of said chemical compound are selected from a concentration range from 0 micromolar and to about 300 micromolar.

12. The method of claim 1, wherein steps (1) and (2) comprise plotting the measurements for each said cell health indicator on a graph as a function of concentration for each said cell health indicators of the chemical compound.

13. The method of claim 1, wherein the measurements of each of said cell health indicators are expressed relative to a control measurement as a function of concentration of the chemical compound.

14. The method of claim 13, wherein the measurements of all of said cell health indicators are plotted on a single graph.

* * * * *

UNITED STATES PATENT AND TRADEMARK OFFICE
CERTIFICATE OF CORRECTION

PATENT NO.        : 7,615,361 B2                                                           Page 1 of 1
APPLICATION NO.   : 11/714526
DATED             : November 10, 2009
INVENTOR(S)       : James M. McKim It is certified that error appears in the above-identified patent and that said Letters Patent is hereby corrected as shown below:

In the Specification:
Column 3, line 56: After "whereas" delete "H4llE" and replace with -- H4IIE --

Column 34, line 55: Delete "calorimetrically" and replace with -- colorimetrically --

Signed and Sealed this

Fifth Day of January, 2010

David J. Kappos
*Director of the United States Patent and Trademark Office*